(12) United States Patent
Boyd et al.

(10) Patent No.: US 7,951,830 B2
(45) Date of Patent: *May 31, 2011

(54) COMPOUNDS EFFECTING GLUCOKINASE

(75) Inventors: Scott Boyd, Macclesfield (GB); Peter William Rodney Caulkett, Macclesfield (GB); Rodney Brian Hargreaves, Macclesfield (GB); Suzanne Saxon Bowker, Macclesfield (GB); Roger James, Congleton (GB); Clifford David Jones, Macclesfield (GB); Darren McKerrecher, Macclesfield (GB); Michael Howard Block, Waltham, MA (US); Craig Johnstone, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/363,899

(22) Filed: Feb. 2, 2009

(65) Prior Publication Data
US 2009/0227592 A1 Sep. 10, 2009

Related U.S. Application Data

(63) Continuation of application No. 12/024,561, filed on Feb. 1, 2008, now Pat. No. 7,524,957, which is a continuation of application No. 10/486,496, filed as application No. PCT/GB02/03745 on Aug. 15, 2002, now Pat. No. 7,390,908.

(30) Foreign Application Priority Data

Aug. 17, 2001 (SE) ........................................ 0102764

(51) Int. Cl.
A61K 31/425 (2006.01)
A61K 31/415 (2006.01)
A61K 31/496 (2006.01)
A61K 31/433 (2006.01)

(52) U.S. Cl. ................. 514/403; 514/252.1; 514/252.12; 514/336; 514/365; 514/373

(58) Field of Classification Search ............... 514/252.1, 514/252.12, 336, 365, 373, 403; 544/367, 544/405, 406, 238, 297, 336, 382; 546/269.7; 548/139, 161, 307.4, 372.1, 246, 128, 194; 564/123, 183
See application file for complete search history.

(56) References Cited

U.S. PATENT DOCUMENTS

| | | | |
|---|---|---|---|
| 2,750,393 A | 6/1956 | Elpern | |
| 2,967,194 A | 1/1961 | Hauptschein | |
| 3,917,625 A | 11/1975 | Lee et al. | |
| 3,950,351 A | 4/1976 | Rossignol et al. | |
| 4,009,174 A | 2/1977 | Cluzan et al. | |
| 4,105,785 A | 8/1978 | Mauvernay et al. | |
| 4,146,631 A | 3/1979 | Ford et al. | |
| 4,434,170 A | 2/1984 | Dostert et al. | |
| 4,474,792 A | 10/1984 | Erickson | |
| 4,634,783 A | 1/1987 | Fujii et al. | |
| 4,966,891 A | 10/1990 | Fujiu et al. | |
| 5,258,407 A | 11/1993 | Washburn et al. | |
| 5,273,986 A | 12/1993 | Holland et al. | |
| 5,399,702 A | 3/1995 | Holland et al. | |
| 5,466,715 A | 11/1995 | Washburn et al. | |
| 5,510,478 A | 4/1996 | Sabb | |
| 5,661,153 A | 8/1997 | Isobe et al. | |
| 5,672,750 A | 9/1997 | Perry | |
| 5,712,270 A | 1/1998 | Sabb | |
| 5,849,735 A | 12/1998 | Albright et al. | |
| 6,110,945 A | 8/2000 | Head et al. | |
| 6,197,798 B1 | 3/2001 | Fink et al. | |
| 6,200,995 B1 | 3/2001 | De la Brouse-Elwood et al. | |
| 6,207,693 B1 | 3/2001 | Setoi et al. | |
| 6,214,878 B1 | 4/2001 | Bernardon et al. | |
| 6,242,474 B1 | 6/2001 | Yamasaki et al. | |
| 6,255,335 B1 | 7/2001 | Himmler et al. | |
| 6,316,482 B1 | 11/2001 | Setoi et al. | |
| 6,320,050 B1 | 11/2001 | Bizzarro et al. | |
| 6,348,474 B1 | 2/2002 | Kayakiri et al. | |
| 6,369,229 B1 | 4/2002 | Head et al. | |
| 6,376,515 B2 | 4/2002 | Zhu et al. | |

(Continued)

FOREIGN PATENT DOCUMENTS

CA 2605738 11/2006

(Continued)

OTHER PUBLICATIONS

Wolff, M.E. "Burger's Medicinal Chemistry 4th Ed. Part I", Wiley: New York, 1979, 336-337.*

(Continued)

*Primary Examiner* — Shailendra Kumar
(74) *Attorney, Agent, or Firm* — Morgan Lewis & Bockius LLP

(57) ABSTRACT

The invention relates to the use of a compound of Formula (I) or a salt, solvate or prodrug thereof, wherein $R^1$, $R^2$, $R^3$, n and m are as described in the specification, in the preparation of a medicament for the treatment or prevention of a disease condition mediated through glucokinase (GLK), such as type 2 diabetes.

Formula (I)

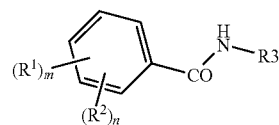

The invention also relates to a novel group of compounds of Formula (I) and to methods for preparing compounds of Formula (I).

11 Claims, No Drawings

U.S. PATENT DOCUMENTS

| | | |
|---|---|---|
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 7,390,908 B2* | 6/2008 | Boyd et al. .......... 548/195 |
| 7,524,957 B2* | 4/2009 | Boyd et al. .......... 544/405 |
| 2001/0027200 A1 | 10/2001 | De la Brouse-Elwood et al. |
| 2002/0002183 A1 | 1/2002 | Zhu et al. |
| 2002/0095044 A1 | 7/2002 | Jagtap et al. |
| 2003/0162690 A1 | 8/2003 | Zhu et al. |
| 2004/0014968 A1 | 1/2004 | Bizzarro et al. |
| 2004/0077555 A1 | 4/2004 | Ishihara et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 1/2005 |
| EP | 1600442 | 11/2005 |
| EP | 1702919 | 9/2006 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/051831 | 7/2002 |
| WO | WO 02/064545 | 8/2002 |
| WO | WO 02/079145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |

| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007041 | 1/2007 |
| WO | WO 2007/007042 | 1/2007 |
| WO | WO 2007/017649 | 2/2007 |
| WO | WO 2007/028135 | 3/2007 |
| WO | WO 2007/031739 | 3/2007 |
| WO | WO 2007/053657 | 5/2007 |
| WO | WO 2007/060448 | 5/2007 |
| WO | WO 2008/050101 | 5/2008 |
| WO | WO 2008/050117 | 5/2008 |
| WO | WO 2008/075073 | 6/2008 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Alvarez et al. "Evidence that glucokinase regulatory protein is expressed and interacts with glucokinase in rat brain" J. Neurochem. 80(1):45-53 (2002).
Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the pyrido[2,3-d]pyrimidine series" J. Org. Chem. 2(6):993-996 (1977).
Ando et al. "Fluoride salts on alumina as reagents or alkylation of phenols and alcohols" Bull. Chem. Soc. Jpn. 55 (8):2504-2507 (1982).
Atwell et al. "Potential antitumor agents. VI. Bisquaternary salts" J. Med. Chem. 11(2):295-300 (1968).
Baker et al. "Structure and synthesis of Pallescansin E utilising a modified Wadsworth-Emmons reaction" J. Chem. Soc., Perkin Trans. 1, 12:3087-3091 (1981).
Baker et al. "Synthesis of Pallescensin-E: Use of crown ether in the Wadsworth procedure olefin formation" Tetrahedron Letters 22:161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994) [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42(22)3514-3518 (1977).
Berl et al. "Induced fit selection of a barbiturate receptor from a dynamic structural and conformational/ configurational library" European J. Org. Chem. (11):3089-3094 (1999).
Berl et al. "Template-induced and molecular recognition directed hierarchical generation of supramolecular assemblies from molecular strands" Chem. Eur. J. 6(1)):1938-1946 (2000).
Bonina et al. "Synthesis and pharmacologic activity of 2-arylethenylthiazol-4-acetic and 4-carboxylic acids" II Farmaco 40(11):875-884 (1985).
Boucherle et al. "Recherches dans la serie des cetones polyphenoliques IV. Thiazoles" Chimica. Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002);CAS Registry No. 444923-81-3 (Jul. 9, 2002); CAS Registry No. 438222-80-1 (Jul. 9, 2002);CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002);CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].
Chemical Abstracts Service, Columbus, Ohio, US: CAS Registry No. 354767-51-4 (Sep. 5, 2001).
Chemical Abstracts Service, Columbus, Ohio, US: CAS Registry No. 354767-66-1 (Sep. 5, 2001).
Christesen et al. "The second activating glucokinase mutation (A456V):Implications or glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators(GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase—Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract No. 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111 (1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50—A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNA agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methylmorpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract No. 0377-OR, 67th Annual Scientific Sessions, American Diabetes Association, Chicago, IL (Jun. 22-26, 2007).

Leighton et al. "Small molecule glucokinase activators as novel anti-diabetic agents" Biochemical Society Transactions 33(Part 2):371-374 (2005).

Leighton, "Pre-clinical disease models—challenges and success stories"44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhumal Obshchei Khimii 27:3097-3107 (1957) (Translation enclosed).

Lith, "Evaluation of the effects on whole body glucose metabolism after single doses of X2000—A glucose lowering agent" Poster presentation, Master thesis in Pharmaceutical Bioscience, Goteborgs University (2008).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub Feb. 28, 2006.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328-7336 (1998).

Palmans "Extended-core discotic liquid crystals based on the intamolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Commun. 54:1675-1682 (1989).

Qian-Cutrone et al. "Glucolipsin A and B, two new glucokinase activators produced by *Streptomyces purpurogeniscleroticus* and *Nocardia vaccinii*" Journal of Antibiotics (Tokyo), 52(3):245-255 (1999).

Ralph et al. "Glucose Modulation of Glucokinase Activation by Small Molecules" Biochemistry 47(17):5028-5036 (2008).

Rivalle et al. "2,3 Disubstituted furans and pyrroles—XVIII: Synthesis and rearrangement of 4H-dihydro-9,10 benzo[4,5]cyclohepta[1,2-b]furannones-4" Tetrahedron 32(7):829-834 (1976).

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Sarabu et al., "Glucokinase activators as new type 2 diabetes therapeutic agents" Expert Opinion on Therapeutic Patents 18(7):759-768 (2008).

Schuit et al. "Glucose sensing in pancreatic β-Cells. A model for the study of other glucose-regulated cells in gut, pancreas, and hypothalamus" Diabetes 50:1-11 (2001).

Sekera et al. "No. 69.—Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Shorvon, "Pyrrolidone derivatives" Lancet 358(9296):1885-1892 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7):515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" J Am. Chem. Soc. 124(49):14759-14769 (2002).

Vanderstelt et al. "Synthesis and pharmacological properties of some derivatives of 5H-benzo[4,5] cyclohepta[1,2-b]pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulaton of hepatocyte glucose metabolism by pharmacological agents" Diabetologia, 47 Supp 1, A 214, 589 (2004).

West, Anthony R., "Solid State Chemistry and its Applications" Wiley, New York, pp. 358 and 365 (1988).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Wolff, Manfred E. "Burger's Medicinal Chemistry", 5th Edition, Part I, John Wiley & Sons, pp. 975-977 (1995).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

* cited by examiner

COMPOUNDS EFFECTING GLUCOKINASE

The present application is a Continuation of Application 12/024,561, filed Feb. 1, 2008, now U.S. Pat. No. 7,524,957, which is a Continuation of Application 10/486,496, filed Oct. 18, 2004, now U.S. Pat. No. 7,390,908, which is a National Phase Application of International Application No. PCT/GB02/03745, filed Aug. 15, 2002, which claims the benefit of Sweden Patent Application No. 0102764-8, filed Aug. 17, 2001, all of which are hereby incorporated by reference in their entirety.

The present invention relates to the use of a group of benzamide compounds in the preparation of a medicament for use in the treatment or prevention of a disease or medical condition mediated through glucokinase (GLK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said benzamide compound, a sub-group of novel compounds of said benzamide compounds, and the use of such a compound in the conditions described above.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Type 2 maturity-onset diabetes of the young (MODY-2), the diabetes is caused by GLK loss of function mutations [3, 4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is elevated in the post-absorptive state whereas F1P predominates in the post-prandial state. In contrast to the hepatocyte, the pancreatic β-cell expresses GLK in the absence of GLKRP. Therefore, β-cell GLK activity is regulated exclusively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act exclusively in the liver. However, compounds with either profile are predicted to be of therapeutic benefit in treating Type 2 diabetes as this disease is characterised by defective glucose utilisation in both tissues.

GLK and GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

In WO0058293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described in Example A. Compounds of the present invention may activate GLK directly or may activate GLK by inhibiting the interaction of GLKRP with GLK. The latter mechanism offers an important advantage over direct activators of GLK in that they will not cause the severe hypoglycaemic episodes predicted after direct stimulation. Many compounds of the present invention may show favourable selectivity compared to known GLK activators.

WO9622282, WO9622293, WO9622294, WO9622295, WO9749707 and WO9749708 disclose a number of intermediates used in the preparation of compounds useful as vasopressin agents which are structurally similar to those disclosed in the present invention. Structurally similar compounds are also disclosed in WO9641795 and JP8143565 (vasopressin antagonism), in JP8301760 (skin damage prevention) and in EP619116 (osetopathy).

WO01/12621 describes the preparation of as isoxazolylpyrimidines and related compounds as inhibitors of cJUN N-terminal kinases, and pharmaceutical compositions containing such compounds.

Cushman et al [Bioorg Med Chem Lett (1991) 1(4), 211-14] describe the synthesis of pyridine-containing stilbenes and amides and their evaluation as protein-tyrosine kinase inhibitors. Rogers et al [J Med Chem (1981) 24(11) 1284-7] describe mesoionic purinone analogs as inhibitors of cyclic-AMP phosphodiesterase.

WO00/26202 describes the preparation of 2-amino-thiazole derivatives as antitumour agents. GB 2331748 describes the preparation of insecticidal thiazole derivatives. WO96/36619 describes the preparation of aminothiazole derivatives as ameliorating agents for digestive tract movements. U.S. Pat. No. 5,466,715 and U.S. Pat. No. 5,258,407 describe the preparation of 3,4-disubstituted phenol immunostimulants. JP 58069812 describes hypoglycemic pharmaceuticals containing benzamide derivatives. U.S. Pat. No. 3,950,351 describes 2-benzamido-5-nitrothiazoles and Cavier et al [Eur J Med Chem—Chim Ther (1978) 13(6), 539-43] discuss the biological interest of these compounds.

We present as a feature of the invention the use of a compound of Formula (I) or a salt, solvate or pro-drug thereof, in the preparation of a medicament for use in the treatment or prevention of a disease or medical condition mediated through GLK:

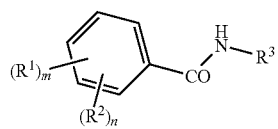

Formula (I)

wherein
m is 0, 1 or 2;
n is 0, 1, 2, 3 or 4;
and n+m>0;
each $R^1$ is independently selected from OH, —(CH$_2$)$_{1-4}$OH, —CH$_{3-a}$F$_a$, —(CH$_2$)$_{1-4}$CH$_{3-a}$F$_a$, —OCH$_{3-a}$F$_a$, halo, C$_{1-6}$alkyl, C$_{2-6}$alkenyl, C$_{2-6}$alkynyl, NH$_2$, —NH—C$_{1-4}$alkyl, —N-di-(C$_{1-4}$alkyl), CN, formyl, phenyl or heterocyclyl optionally substituted by C$_{1-6}$alkyl;
each $R^2$ is the group Y—X—
  wherein each X is a linker independently selected from: —O—Z—, —O—Z—O—Z—, —C(O)O—Z—, —OC(O)—Z—, —S—Z—, —SO—Z—, —SO$_2$—Z—, —N(R$^6$)—Z—, —N(R$^6$)SO$_2$—Z—, —SO$_2$N(R$^6$)—Z—, —CH=CH—Z—, —C≡C—Z—, —N(R$^6$)CO—Z—, —CON(R$^6$)—Z—, —C(O)N(R$^6$)S(O)$_2$—Z—, —S(O)$_2$N(R$^6$)C(O)—Z—, —C(O)—Z—, —Z—, —C(O)Z—O—Z—, —N(R$^6$)—C(O)—Z—O—Z—, —O—Z—N(R$^6$)—Z—, —O—C(O)—Z—O—Z— or a direct bond;
  each Z is independently a direct bond, C$_{2-6}$alkenylene or a group of the formula —(CH$_2$)$_p$—C(R$^{6a}$)$_2$—(CH$_2$)$_q$—;
  each Y is independently selected from aryl-Z$^1$—, heterocyclyl-Z$^1$—, C$_{3-7}$cycloalkyl-Z$^1$—, C$_{1-6}$alkyl, C$_{2-6}$alkenyl, C$_{2-6}$alkynyl, —(CH$_2$)$_{1-4}$CH$_{3-a}$F$_a$ or —CH(OH)CH$_{3-a}$F$_a$; wherein
    each Y is independently optionally substituted by up to 3 $R^4$ groups;
    each $R^4$ is independently selected from halo, —CH$_{3-a}$F$_a$, CN, NH$_2$, C$_{1-6}$alkyl, —OC$_{1-6}$alkyl, —COOH, —C(O)OC$_{1-6}$alkyl, OH or phenyl optionally substituted by C$_{1-6}$alkyl or —C(O)OC$_{1-6}$alkyl,
    or $R^5$—X$^1$—, where X$^1$ is independently as defined in X above and $R^5$ is selected from hydrogen, C$_{1-6}$alkyl, —CH$_{3-a}$F$_a$, phenyl, naphthyl, heterocyclyl or C$_{3-7}$cycloalkyl; and $R^5$ is optionally substituted by one or more substituents independently selected from: halo, C$_{1-6}$alkyl, —OC$_{1-6}$alkyl, —CH$_{3-a}$F$_a$, CN, OH, NH$_2$, COOH, or —C(O)OC$_{1-6}$alkyl,
    each $Z^1$ is independently a direct bond, C$_{2-6}$alkenylene or a group of the formula —(CH$_2$)$_p$—C(R$^{6a}$)$_2$—(CH$_2$)$_q$—;
$R^3$ is selected from phenyl or a heterocyclyl, and $R^3$ is optionally substituted by one or more $R^7$ groups;
$R^6$ is independently selected from hydrogen, C$_{1-6}$alkyl or —C$_{2-4}$alkyl-O—C$_{1-4}$alkyl;
$R^{6a}$ is independently selected from hydrogen, halo, C$_{1-6}$alkyl or —C$_{2-4}$alkyl-O—C$_{1-4}$alkyl;
each $R^7$ is independently selected from:
  C$_{1-6}$alkyl, C$_{2-6}$alkenyl, C$_{2-6}$alkynyl, (CH$_2$)$_{0-3}$aryl, (CH$_2$)$_{0-3}$heterocyclyl, (CH$_2$)$_{0-3}$C$_{3-7}$cycloalkyl, OH, C$_{1-6}$alkyl-OH, halo, C$_{1-6}$alkyl-halo, OC$_{1-6}$alkyl, (CH$_2$)$_{0-3}$S(O)$_{0-2}$R$^8$, SH, SO$_3$H, thioxo, NH$_2$, CN, (CH$_2$)$_{0-3}$NHSO$_2$R$^8$, (CH$_2$)$_{0-3}$COOH, (CH$_2$)$_{0-3}$—O—(CH$_2$)$_{0-3}$R$^8$, (CH$_2$)$_{0-3}$C(O)(CH$_2$)$_{0-3}$R$^8$, (CH$_2$)$_{0-3}$C(O)OR$^8$, (CH$_2$)$_{0-3}$C(O)NH$_2$, (CH$_2$)$_{0-3}$C(O)NH(CH$_2$)$_{0-3}$R$^8$, (CH$_2$)$_{0-3}$NH(CH$_2$)$_{0-3}$R$^8$, (CH$_2$)$_{0-3}$NHC(O)(CH$_2$)$_{0-3}$R$^8$; (CH$_2$)$_{0-3}$C(O)NHSO$_2$—R$^8$ and (CH$_2$)$_{0-3}$SO$_2$NHC(O)—R$^8$ wherein an alkyl chain, cycloalkyl ring or heterocyclyl ring within $R^7$ is optionally substituted by one of more substituents independently selected from: C$_{1-4}$alkyl, OH, halo, CN, NH$_2$, N—C$_{1-4}$alkylamino, N,N-di-C$_{1-4}$alkylamino and OC$_{1-4}$alkyl;
$R^8$ is selected from hydrogen, C$_{1-6}$alkyl, aryl, heterocyclyl, C$_{3-7}$cycloalkyl, OH, C$_{1-6}$alkyl-OH, COOH, C(O)OC$_{1-6}$alkyl, N(R$^6$)C$_{1-6}$ alkyl, OC$_{1-6}$ alkyl, C$_{0-6}$alkylOC(O)C$_{1-6}$ alkyl, C(OH)(C$_{1-6}$alkyl)C$_{1-6}$alkyl; wherein an alkyl chain or aryl, heterocyclyl or cycloalkyl ring within $R^8$ is optionally substituted by one of more substituents independently selected from: C$_{1-4}$alkyl, OH, halo, CN, NH$_2$, —NH—C$_{1-4}$alkyl, —N-di-(C$_{1-4}$alkyl) and OC$_{1-4}$alkyl;
each a is independently 1, 2 or 3;
p is an integer between 0 and 3;
q is an integer between 0 and 3;
and p+q<4.
provided that when $R^3$ is 2-pyridyl and X is other than —Z—, —C(O)—Z—O—Z—, —N((R$^6$)—C(O)—Z—O—Z— or —O—Z—N(R$^6$)—Z—, then $R^3$ cannot be mono-substituted at the 5-position with an $R^7$ group selected from COOH or C(O)OC$_{1-6}$alkyl.

For the avoidance of doubt the numbering in the above proviso is relative to the amide bond attached to the pyridine ring, thus $R^3$ in the proviso relates to a group of the following structure:

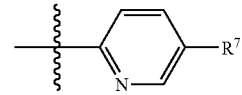

wherein

represents the point of attachment to the amide group in Formula (I).

According to a further feature of the invention there is provided the use of a compound of Formula (Ia) or a salt thereof in the preparation of a medicament for use in the treatment or prevention of a disease or medical condition mediated through GLK:

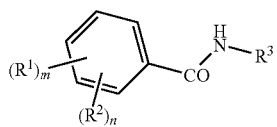

Formula (Ia)

wherein
m is 0, 1 or 2;
n is 0, 1, 2, 3 or 4;
and n+m>0;
each $R^1$ is independently selected from OH, $(CH_2)_{1-4}OH$, $CH_{3-a}F_a$, $(CH_2)_{1-4}CH_{3-a}F_a$, $OCH_{3-a}F_a$, halo, $C_{1-6}$ alkyl, $C_{2-6}$alkenyl, $C_{2-6}$alkynyl, $NH_2$, $N(C_{1-6}alkyl)C_{1-6}alkyl$, CN, phenyl or a heterocyclyl optionally substituted by $C_{1-6}$alkyl;
each $R^2$ is the group Y—X—
wherein each X is a linker independently selected from
—$O(CH_2)_{0-3}$—, —$(CH_2)_{0-3}O$—, —$C(O)O(CH_2)_{0-3}$—, —$S(CH_2)_{0-3}$—, —$SO(CH_2)_{0-3}$—, —$SO_2(CH_2)_{0-3}$—, —$NHSO_2$—, —$SO_2NH$—, —$N(CH_2)_{0-3}$—, —$N(CH_2)_{1-3}O(CH_2)_{0-3}$—, —$(CH_2)_{1-4}$—, —CH=CH$(CH_2)_{0-2}$—, —C≡C$(CH_2)_{0-2}$—, —NHCO—, —CONH—;
each Y is independently selected from phenyl$(CH_2)_{0-2}$, naphthyl$(CH_2)_{0-2}$, heterocyclyl$(CH_2)_{0-2}$, $C_{3-7}$cycloalkyl$(CH_2)_{0-2}$, $C_{1-6}$ alkyl, $OC_{1-6}$alkyl, $C_{2-6}$ alkenyl, $C_{2-6}$alkynyl, or $CH(OH)CH_{3-a}F_a$;
each Y is independently optionally substituted by one or more $R^4$ groups;
each $R^4$ is independently selected from halo, $CH_{3-a}F_a$, $OCH_{3-a}F_a$, CN, $NH_2$, $C_{1-6}$alkyl, $OC_{1-6}$alkyl, COOH, $(CH_2)_{0-3}COOH$, $O(CH_2)_{0-3}COOH$, $C(O)OC_{1-6}$alkyl, $C_{1-6}$alkyl$C(O)OC_{1-6}$alkyl, CO-phenyl, $CONH_2$, CONH-phenyl, $SO_2NH_2$, $SO_2C_{1-6}$alkyl, OH, or phenyl optionally substituted by one or more $R^5$ groups, or $R^{6b}$—X—;
$R^5$ is selected from hydrogen, $C_{1-6}$alkyl or $C(O)OC_{1-6}$alkyl,
$R^{6b}$ is selected from hydrogen, $C_{1-6}$alkyl, $CH_{3-a}F_a$ phenyl, naphthyl, heterocyclyl or $C_{3-7}$cycloalkyl; and $R^{6b}$ is optionally substituted by halo, $C_{1-6}$alkyl, $CH_{3-a}F_a$, CN, $NH_2$, COOH and $COOC_{1-6}$alkyl;
each a is independently 1, 2 or 3;
$R^3$ is selected from phenyl or a heterocyclyl, and $R^3$ is optionally substituted by one or more $R^7$ groups;
each $R^7$ is independently selected from:
$C_{1-6}$alkyl, $C_{2-6}$alkenyl, $C_{2-6}$alkynyl, heterocyclyl, $(CH_2)_{0-3}C_{3-7}$cycloalkyl, OH, $C_{1-6}$alkyl-OH, halo, $C_{1-6}$alkyl-halo, $OC_{1-6}$alkyl, $SC_{1-6}$alkyl, SH, $SO_3H$, $NH_2$, CN, NHCHO, $NSO_2C_{1-6}$alkyl, $(CH_2)_{0-3}COOH$, $(CH_2)_{0-3}C(O)OC_{1-6}$alkyl, $(CH_2)_{0-3}CONH_2$, $(CH_2)_{0-3}CON(CH_2)_{0-3}R^8$, $(CH_2)_{0-3}NH(CH_2)_{0-3}R^8$, $(CH_2)_{0-3}NHC(O)(CH_2)_{0-3}R^8$;
$R^8$ is selected from hydrogen, $C_{1-6}$alkyl, $C_{3-7}$cycloalkyl, OH, $C_{1-6}$alkyl-OH, COOH, $C(O)OC_{1-6}$alkyl, $N(C_{0-6}alkyl)C_{1-6}$ alkyl, $O(C_{0-6}$ alkyl$)C_{1-6}$alkyl, $C_{0-6}$alkylOC(O)$C_{1-6}$alkyl, $C(OH)(C_{1-6}alkyl)C_{1-6}$alkyl;

provided that when $R^3$ is pyridine, then $R^7$ is other than COOH or $COOC_{1-6}$alkyl.

According to a further feature of the invention there is provided a compound of Formula (Ib) or a salt, solvate or pro-drug thereof;

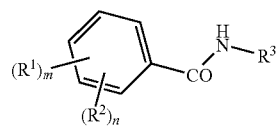

Formula (Ib)

wherein
m is 0, 1 or 2;
n is 1, 2 or 3;
and n+m is 2 or 3;
each $R^1$ is independently selected from OH, —$(CH_2)_{1-4}$OH, —$CH_{3-a}F_a$, —$(CH_2)_{1-4}CH_{3-a}F_a$, —$OCH_{3-a}F_a$, halo, $OCH_3$, $C_2H_5O$, $CH_3C(O)O$—, $C_{1-6}$alkyl, $C_{2-6}$alkenyl, $C_{2-6}$alkynyl, —NH—$C_{1-4}$alkyl, —N-di-($C_{1-4}$ alkyl), CN, formyl, phenyl or heterocyclyl optionally substituted by $C_{1-6}$alkyl;
each $R^2$ is the group Y—X—
with the proviso that Y—X— cannot be $CH_3O$, $C_2H_5O$ or $CH_3C(O)O$—;
wherein each X is a linker independently selected from:
—O—Z—, —O—Z—O—Z—, —C(O)O—Z—, —OC(O)—Z—, —S—Z—, —SO—Z—, —$SO_2$—Z—, —N($R^6$)—Z—, —N($R^6$)$SO_2$—Z—, —$SO_2$N($R^6$)—Z—, —CH=CH—Z—, —C≡C—Z—, —N($R^6$)CO—Z—, —CON($R^6$)—Z—, —C(O)N($R^6$)S(O)$_2$—Z—, —S(O)$_2$N($R^6$)C(O)—Z—, —C(O)—Z—, —Z—, —C(O)—Z—O—Z—, —N($R^6$)—C(O)—Z—O—Z—, —O—Z—N($R^6$)—Z—, —O—C(O)—Z—O—Z— or a direct bond except where Z is $C_{1-6}$alkyl;
each Z is independently a direct bond, $C_{2-6}$alkenylene or a group of the formula —$(CH_2)_p$—C($R^{6a}$)$_2$—$(CH_2)_q$—;
each Y is independently selected from aryl-$Z^1$—, heterocyclyl-$Z^1$—, $C_{3-7}$cycloalkyl-$Z^1$—, $C_{1-6}$alkyl, $C_{2-6}$alkenyl, $C_{2-6}$alkynyl, —$(CH_2)_{1-4}CH_{3-a}F_a$ or —$CH(OH)CH_{3-a}F_a$; wherein
each Y is independently optionally substituted by up to 3 $R^4$ groups;
each $R^4$ is independently selected from halo, —$CH_{3-a}F_a$, CN, $NH_2$, $C_{1-4}$alkyl, —$OC_{1-6}$alkyl, —COOH, —$C(O)OC_{1-6}$alkyl, OH or phenyl optionally substituted by $C_{1-6}$alkyl or —$C(O)OC_{1-6}$alkyl,
or $R^5$—$X^1$—, where $X^1$ is independently as defined in X above and $R^5$ is selected from hydrogen, $C_{1-6}$alkyl, —$CH_{3-a}F_a$, phenyl, naphthyl, heterocyclyl or $C_{3-7}$cycloalkyl; and $R^5$ is optionally substituted by one or more substituents independently selected from: halo, $C_{1-6}$alkyl, —$OC_{1-6}$alkyl, —$CH_{3-a}F_a$, CN, OH, $NH_2$, COOH, or —$C(O)OC_{1-6}$alkyl,
each $Z^1$ is independently a direct bond, $C_{2-6}$alkenylene or a group of the formula —$(CH_2)_p$—C($R^{6a}$)$_2$—$(CH_2)_q$—;
$R^3$ is heterocyclyl, wherein the atom at the two position of the heterocyclyl ring relative to the amide group, to which $R^3$ is attached, is a heteroatom and when the atom at the two position of the heterocyclyl ring relative to the amide group is nitrogen, this is an sp² hybridised nitrogen, and R³ is optionally substituted by up to 2 R⁷ groups;

$R^6$ is independently selected from hydrogen, $C_{1-6}$alkyl or —$C_{2-4}$alkyl-O—$C_{1-4}$alkyl;

$R^{6a}$ is independently selected from hydrogen, halo, $C_{1-6}$alkyl or —$C_{2-4}$alkyl-O—$C_{1-4}$alkyl;

each $R^7$ is independently selected from:

$C_{1-6}$alkyl, $C_{2-6}$alkenyl, $C_{2-6}$alkynyl, $(CH_2)_{0-3}$aryl, $(CH_2)_{0-3}$heterocyclyl, $(CH_2)_{0-3}C_{3-7}$cycloalkyl, OH, $C_{1-6}$alkyl-OH, halo, $C_{1-6}$alkyl-halo, OC$_{1-6}$alkyl, $(CH_2)_{0-3}S(O)_{0-2}R^8$, SH, SO$_3$H, thioxo, NH$_2$, CN, $(CH_2)_{0-3}$NHSO$_2R^8$, $(CH_2)_{0-3}$COOH, $(CH_2)_{0-3}$—O—$(CH_2)_{0-3}R^8$, $(CH_2)_{0-3}C(O)(CH_2)_{0-3}R^8$, $(CH_2)_{0-3}C(O)OR^8$, $(CH_2)_{0-3}C(O)NH_2$, $(CH_2)_{0-3}C(O)NH(CH_2)_{0-3}R^8$, $(CH_2)_{0-3}NH(CH_2)_{0-3}R^8$, $(CH_2)_{0-3}NHC(O)(CH_2)_{0-3}R^8$; $(CH_2)_{0-3}C(O)NHSO_2$—$R^8$ and $(CH_2)_{0-3}SO_2NHC(O)$—$R^8$ wherein an alkyl chain, cycloalkyl ring or heterocyclyl ring within $R^7$ is optionally substituted by one of more substituents independently selected from: $C_{1-4}$alkyl, OH, halo, CN, NH$_2$, N—$C_{1-4}$alkylamino, N,N-di-$C_{1-4}$alkylamino and OC$_{1-4}$alkyl;

$R^8$ is selected from hydrogen, $C_{1-6}$alkyl, aryl, heterocyclyl, $C_{3-7}$cycloalkyl, OH, $C_{1-6}$alkyl-OH, COOH, C(O)OC$_{1-6}$alkyl, N(R$^6$)C$_{1-6}$alkyl, OC$_{1-6}$alkyl, C$_{0-6}$alkylOC(O)C$_{1-6}$alkyl, C(OH)(C$_{1-6}$alkyl)C$_{1-6}$alkyl; wherein an alkyl chain or aryl, heterocyclyl or cycloalkyl ring within $R^8$ is optionally substituted by one of more substituents independently selected from: $C_{1-4}$alkyl, OH, halo, CN, NH$_2$, —NH—$C_{1-4}$alkyl, —N-di-($C_{1-4}$alkyl) and OC$_{1-4}$alkyl;

each a is independently 1, 2 or 3;

p is an integer between 0 and 3;

q is an integer between 0 and 3;

and p+q<4.

provided that (i) when $R^3$ is 2-pyridyl and X is other than —Z—, —C(O)—Z—O—Z—, —N((R$^6$)—C(O)—Z—O—Z— or —O—Z—N(R$^6$)—Z—, then $R^3$ cannot be mono-substituted at the 5-position with an $R^7$ group selected from COOH or C(O)OC$_{1-6}$alkyl;

(ii) positions 3,5 on the phenyl ring (to which R¹ and R² are attached) relative to the amide bond must be substituted and at least one of the groups at position 3 and 5 is an $R^2$ group;

(iii) an unbranched, unsubstituted $C_{1-6}$alkyl chain cannot exceed $C_6$alkyl in length;

(iv) when n is 2 or 3 then only one X group can be —NHC(O)—;

(v) when $R^3$ is pyridyl and $R^7$ is halo or methyl then the phenyl ring to which $R^2$ is attached cannot be substituted by an $R^2$ group at the 2-position relative to the amide bond wherein X is —C(O)NH— and Y is optionally substituted phenyl, optionally substituted thienyl or optionally substituted pyridyl;

(vi) when n+m is 2, m is 0 or m is 1 and R¹ is OH, n is 1 and X is —NHC(O)— or n is 2 and X is independently selected from —C(O)NH—, —NHC(O)—, —O—, —S(O$_2$)NH— or a direct bond wherein one X group is —NHC(O)—, Y is selected from phenyl, cyclohexyl, 4,5-dihydro-5-oxo-pyrazolyl, thienyl, 1,3-dihydro-1,3-dioxo-isoindolinyl, 2-oxo-1-benzopyran or pyridyl and Y is optionally substituted by R⁴ then $R^3$ cannot be unsubstituted thiazole, 4,5-dihydro-5-oxo-pyrazolyl substituted by trichlorophenyl, 4,5,6,7-tetrahydro-benzo[b]thiophene substituted by ethoxycarbonyl or pyridyl optionally independently mono or di-substituted by methyl, ethoxy or propylcarbonylamino; and (vii) when n+m is 3, m is 0 or 2, R¹ is independently selected from methyl, methoxy or hydroxy, n is 1, 2 or 3, X is independently selected from —O—, —S(O$_2$)NH—, —C(O)—, —S(O$_2$)—, —CH$_2$— or a direct bond, Y is selected from pyrrolidinyl, morpholino, phenyl, tetrazolyl or propyl wherein Y is optionally substituted by R⁴ and R⁴ is selected from di-hydroxy, methoxy, $C_{1-4}$alkyl then $R^3$ cannot be unsubstituted tetrazolyl, unsubstituted thiazolyl or thiazolyl substituted by ethoxycarbonylmethyl.

For the avoidance of doubt $C_6$alkyl is —CH$_2$—CH$_2$—CH$_2$—CH$_2$—CH$_2$—CH$_3$.

For the avoidance of doubt examples of R³ wherein R³ is heterocyclyl and the atom at the two position of the R³ heterocyclyl ring, relative to the amide group to which R³ is attached, is an sp² hybridised nitrogen include:

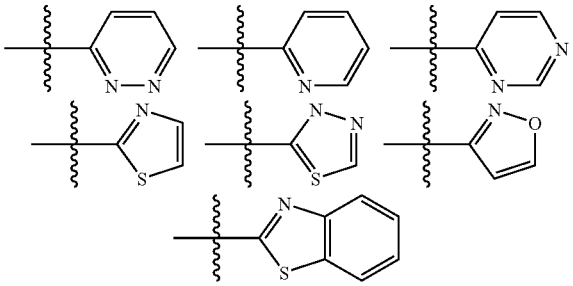

wherein

represents the point of attachment to the amide group.

According to a further feature of the invention there is provided a compound of Formula (Ic) or a salt thereof;

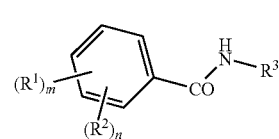

Formula (Ic)

wherein m is 0, 1 or 2;

n is 0, 1, 2, 3 or 4;

and n+m>0;

each R¹ is independently selected from OH, (CH$_2$)$_{1-4}$OH, CH$_{3-a}$F$_a$, (CH$_2$)$_{1-4}$CH$_{3-a}$F$_a$, OCH$_{3-a}$F$_a$, halo, C$_{1-6}$ alkyl, C$_{2-6}$alkenyl, C$_{2-6}$alkynyl, NH$_2$, N(C$_{1-6}$alkyl)$_{C2-6}$alkyl, CN, phenyl or a heterocyclyl optionally substituted by C$_{1-6}$alkyl;

each R² is the group Y—X— wherein each X is a linker independently selected from —O(CH$_2$)$_{0-3}$—, —(CH$_2$)$_{0-3}$O—, —C(O)O(CH$_2$)$_{0-3}$—, —S(CH$_2$)$_{0-3}$—, —SO(CH$_2$)$_{0-3}$—, —O$_2$(CH$_2$)$_{0-3}$—, —NHSO$_2$—, —SO$_2$NH—, —N(CH$_2$)$_{0-3}$—, —N(CH$_2$)$_{1-3}$O(CH$_2$)$_{0-3}$, —(CH$_2$)$_{1-4}$—, —CH=CH(CH$_2$)$_{0-2}$—, —C≡C(CH$_2$)$_{0-2}$—, —NHCO—, —CONH—;

each Y is independently selected from phenyl($CH_2$)$_{0-2}$, naphthyl($CH_2$)$_{0-2}$, heterocyclyl($CH_2$)$_{0-2}$, $C_{3-7}$ cycloalkyl($CH_2$)$_{0-2}$, $C_{2-6}$ alkyl, $C_{2-6}$ alkenyl, $C_{2-6}$alkynyl, or $CH(OH)CH_{3-a}F_a$;

each Y is independently optionally substituted by one or more $R^4$ groups;

each $R^4$ is independently selected from halo, $CH_{3-a}F_a$, $OCH_{3-a}F_a$, CN, $NH_2$, $C_{1-6}$alkyl, $OC_{1-6}$alkyl, COOH, $(CH_2)_{0-3}$COOH, $O(CH_2)_{0-3}$COOH, $C(O)OC_{1-6}$alkyl, $C_{1-6}$alkylC(O)$OC_{1-6}$alkyl, CO-phenyl, $CONH_2$, CONH-phenyl, $SO_2NH_2$, $SO_2C_{1-6}$alkyl, OH, or phenyl optionally substituted by one or more $R^5$ groups, or $R^{6b}$—X—;

$R^5$ is selected from hydrogen, $C_{1-6}$alkyl or $C(O)OC_{1-6}$alkyl, $R^{6b}$ is selected from hydrogen, $C_{1-6}$alkyl, $CH_{3-a}F_a$ phenyl, naphthyl, heterocyclyl or $C_{3-7}$cycloalkyl; and $R^{6b}$ is optionally substituted by halo, $C_{1-6}$alkyl, $CH_{3-a}F_a$, CN, $NH_2$, COOH and $COOC_{1-6}$alkyl;

each a is independently 1, 2 or 3;

$R^3$ is a heterocyclyl, and $R^3$ is optionally substituted by one or more $R^7$ groups;

each $R^7$ is independently selected from:

$C_{1-6}$alkyl, $C_{2-6}$alkenyl, $C_{2-6}$alkynyl, heterocyclyl, $(CH_2)_{0-3}C_{3-7}$cycloalkyl, OH, $C_{1-6}$alkyl-OH, halo, $C_{1-6}$alkyl-halo, $OC_{1-6}$alkyl, $SC_{1-6}$alkyl, SH, $SO_3H$, $NH_2$, CN, NHCHO, $NSO_2C_{1-6}$alkyl, $(CH_2)_{0-3}$COOH, $(CH_2)_{0-3}C(O)OC_{1-6}$alkyl, $(CH_2)_{0-3}CONH_2$, $(CH_2)_{0-3}CON(CH_2)_{0-3}R^8$, $(CH_2)_{0-3}NH(CH_2)_{0-3}R^8$, $(CH_2)_{0-3}NHC(O)(CH_2)_{0-3}R^8$;

$R^8$ is selected from hydrogen, $C_{1-6}$alkyl, $C_{3-7}$cycloalkyl, OH, $C_{1-6}$alkyl-OH, COOH, $C(O)OC_{1-6}$alkyl, $N(C_{0-6}$ alkyl)$C_{1-6}$ alkyl, $O(C_{0-6}$ alkyl)$C_{1-6}$alkyl, $C_{0-6}$alkylOC(O)$C_{1-6}$alkyl, $C(OH)(C_{1-6}$alkyl)$C_{1-6}$alkyl;

provided that (i) when $R^3$ is thiazole and $R^7$ is nitro, then at least one $R^2$ group is other than —O-propene;

(ii) when $R^3$ is pyrimidine or pyridine, then $R^1$ is other than OH;

(iii) when $R^3$ is pyridine, then $R^7$ is other than COOH or $COOC_{1-6}$alkyl.

A further feature of the invention is a compound of Formula (Id) or a salt, solvate of pro-drug thereof;

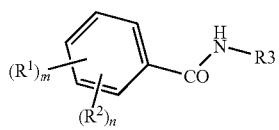

Formula (Id)

wherein $R^3$ is phenyl, optionally substituted by one or more $R^7$ groups;

m, n, $R^1$, $R^2$, X, Y, $R^4$, $R^5$, $R^6$, $R^7$, $R^8$, and a are as defined above for a Compound of Formula (I).

Compounds of Formula (I), (Ia), (Ib), (Ic), or (Id) may form salts which are within the ambit of the invention. Pharmaceutically acceptable salts are preferred although other salts may be useful in, for example, isolating or purifying compounds.

When m is 2, each $R^1$ group may be the same or different; preferably both $R^1$ groups are the same. When n is 2, 3 or 4, each $R^2$ group may be the same or different to any other $R^2$ group; preferably at least two $R^2$ groups are different. The $R^1$ and/or $R^2$ group(s) may be attached at the –2, –3, –4, –5 or –6 positions.

The term "aryl" refers to phenyl, naphthyl or a partially saturated bicyclic carbocyclic ring containing between 8 and 12 carbon atoms, preferably between 8 and 10 carbon atoms. Example of partially saturated bicyclic carbocyclic ring include: 1,2,3,4-tetrahydronaphthyl, indanyl, indenyl, 1,2,4a, 5,8,8a-hexahydronaphthyyl or 1,3a-dihydropentalene.

The term "halo" includes chloro, bromo, fluoro and iodo; preferably chloro, bromo and fluoro; most preferably fluoro.

The expression "—$CH_{3-a}F_a$" wherein a is an integer between 1 and 3 refers to a methyl group in which 1, 2 or all 3 hydrogen are replaced by a fluorine atom. Examples include: trifluoromethyl, difluoromethyl and fluoromethyl An analogous notation is used with reference to the group —$(CH_2)_{1-4}CH_{3-a}F_a$, examples include: 2,2-difluoroethyl and 3,3,3-trifluoropropyl.

In this specification the term "alkyl" includes both straight and branched chain alkyl groups. For example, "$C_{1-4}$alkyl" includes propyl, isopropyl and t-butyl. For the avoidance of doubt, an alkyl chain can be joined to the rest of the molecule at the end of the alkyl chain or in the middle of an alkyl chain, i.e. the definition of "alkyl" includes the following structures:

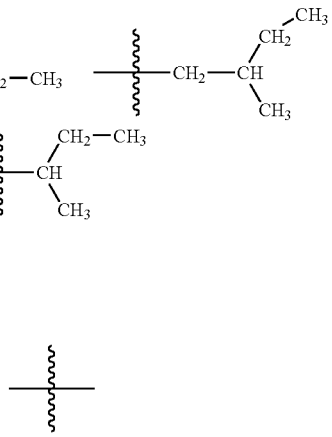

wherein represents the point of attachment to the rest of the molecule.

A "heterocyclyl" is a saturated, partially saturated or unsaturated, monocyclic or fused bicyclic ring containing 3-12 atoms of which at least one atom is chosen from nitrogen, sulphur or oxygen, wherein a —$CH_2$— group can optionally be replaced by a —C(O)— or sulphur atoms in a heterocyclic ring may be oxidised to S(O) or $S(O)_2$. A 'heterocyclyl ring may, unless otherwise specified, be carbon or nitrogen linked, unless linking via nitrogen leads to a charged quaternary nitrogen.

Preferably a "heterocyclyl" is a saturated, partially saturated or unsaturated, monocyclic or fused bicyclic ring wherein each ring contains 5 or 6 atoms of which 1 to 3 atoms are nitrogen, sulphur or oxygen, which may, unless otherwise specified, be carbon or nitrogen linked, wherein a —$CH_2$— group can optionally be replaced by a —C(O)— or sulphur atoms in a heterocyclic ring may be oxidised to S(O) or $S(O)_2$ groups.

Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, isoxazolyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiazolyl, thiadiazolyl, isothiazolyl, 1,2,4-triazolyl, 1,2,3-triazolyl, pyranyl, indolyl, pyrimidyl, thiazolyl, pyrazinyl, pyridazinyl, pyridyl, 4-pyridonyl, quinolyl and 1-isoquinolonyl.

Preferably the term "heterocyclyl" refers to monocyclic heterocyclic rings with 5— or 6-membered systems, such as isoxazolyl, pyrrolidinyl, 2-pyrrolidonyl, 2,5-dioxopyrrolidinyl, morpholino, tetrahydrofuranyl, piperidyl, piperazinyl, thiomorpholino, tetrahydropyranyl, thienyl, imidazolyl, 1,2,4-triazolyl, 1,3,4-triazolyl, indolyl, thiazolyl, thiadiazolyl, pyrazinyl, pyridazinyl and pyridyl.

Preferred examples of 5/6 and 6/6 bicyclic ring systems include benzofuranyl, benzimidazolyl, benzthiophenyl, benzthiazolyl, benzisothiazolyl, benzoxazolyl, benzisoxazolyl, pyridoimidazolyl, pyrimidoimidazolyl, quinolinyl, isoquinolinyl, quinoxalinyl, quinazolinyl, phthalazinyl, cinnolinyl and naphthyridinyl.

The term "cycloalkyl" refers to a saturated carbocyclic ring containing between 3 to 12 carbon atoms, preferably between 3 and 7 carbon atoms. Examples of $C_{3-7}$cycloalkyl include cycloheptyl, cyclohexyl, cyclopentyl, cyclobutyl or cyclopropyl. Preferably cyclopropyl, cyclopentyl or cyclohexyl.

Examples of $C_{1-6}$alkyl include methyl, ethyl, propyl, isopropyl, sec-butyl, tert-butyl and 2-ethyl-butyl; examples of $C_{1-6}$alkyl-OH include hydroxymethylen and hydroxyethylene; examples of $C_{1-6}$alkyl-halo include chloromethylene, fluoromethylene, chloroethylene and fluoroethylene; examples of $C_{2-6}$alkenyl include: ethenyl, 2-propenyl, 2-butenyl, or 2-methyl-2-butenyl; examples of $C_{2-6}$alkynyl include: ethynyl, 2-propynyl, 2-butynyl, or 2-methyl-2-butynyl, examples of —O$C_{1-4}$alkyl include methoxy, ethoxy, propoxy and tert-butoxy; examples of —C(O)O$C_{1-6}$alkyl include methoxycarbonyl, ethoxycarbonyl and tert-butyloxycarbonyl; examples of —NH—$C_{1-4}$alkyl include:

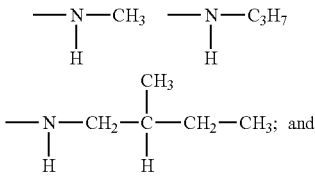

examples of —N-di-($C_{1-4}$alkyl):

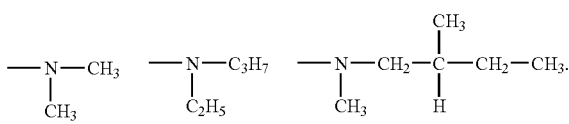

For the avoidance of doubt, in the definition of linker group 'X', the right hand side of the group is attached to the phenyl ring and the left hand side is bound to 'Y'. The same orientation applies to the linker group '$X^1$', thus the right hand side of '$X^1$' is attached to Y and the left hand side is attached to '$R^5$'.

It is to be understood that, insofar as certain of the compounds of Formula (I), (Ia), (Ib), (Ic) and (Id) defined above or compounds of Formula (II) to (IIk) defined below may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

Preferred compounds of Formula (I), (Ia), (Ib), (Ic), and (Id) above, and of compounds of Formula (II) to (IIk) below are those wherein any one or more of the following apply:

(1) m is 0 or 1;
n is 1 or 2; preferably n is 2;
most preferably m is 0 and n is 2.

(2) The $R^1$ and/or $R^2$ group(s) are attached at the 2-position and/or the 3-position and/or the 5-position; when n+m is 3, the groups are preferably at the 2-, 3- and 5-positions; when n+m is 2, the groups are preferably at the 2- and 5— or the 3- and 5-positions; most preferably there are two groups in total, substituted at the 3- and 5-positions.

(3) each $R^1$ is independently selected from OH, formyl, $CH_{3-a}F_a$ (preferably $CF_3$), $OCH_{3-a}F_a$, halo, $C_{1-6}$alkyl, $NH_2$, CN, $(CH_2)_{1-4}OH$ or a heterocyclyl optionally substituted by $C_{1-6}$alkyl;

Preferably $R^1$ is selected from:
OH, formyl, $CH_{3-a}F_a$ (preferably $CF_3$), $OCH_{3-a}F_a$ (preferably $OCF_3$), halo, $C_{1-4}$ alkyl (preferably methyl), $NH_2$, CN and $(CH_2)_{1-4}OH$;

Most preferably $R^1$ is selected from:
OH, formyl, $NH_2$, halo (preferably chloro) or $(CH_2)_{1-4}OH$.

(4) each $R^2$ is the group Y—X—
wherein each X is independently selected from:
—Z—, —CH=CH—Z—, —O—Z—, —C(O)—Z—, —C(O)O—Z—, —OC(O)—Z—, —C(O)—Z—O—Z—, —O—C(O)—Z—O—Z—, —S—Z—, —SO—Z—, —SO_2—Z—, —N(R^6)—Z—, —N(R^6)CO—Z—, —CON(R^6)—Z—, —N(R^6)—C(O)—Z—O—Z—, —SO_2N(R^6)—Z—, —N(R^6)SO_2—Z— or —O—Z—N(R^6)—Z—;

preferably each X is selected from:
—Z—, —CH=CH—Z—, —O—Z—, —C(O)—Z—, —C(O)O—Z—, —C(O)—Z—O—Z—, —O—C(O)—Z—O—Z—, —N(R^6)—Z—, —N(R^6)CO—Z—, —N(R^6)—C(O)—Z—O—Z— or —O—Z—N(R^6)—Z—;

further preferably each X is selected from:
—Z—, —CH=CH—Z—, —O—Z—, —C(O)—Z—, —C(O)O—Z—, —C(O)—Z—O—Z—, —N(R^6)—Z—, or —N(R^6)CO—Z—;

Most preferably each X is selected from:
—CH=CH—Z—, —O—Z— or —C(O)—Z—.

each Z is independently selected from:
a direct bond, —$(CH_2)_{1-2}$, or a group of the formula —$(CH_2)_p$—$C(R^{6a})_2$—$(CH_2)_q$—, wherein $R^{6a}$ is independently selected from hydrogen and $C_{1-4}$alkyl;

preferably a direct bond, —$(CH_2)_{1-2}$— or a group of the formula —$(CH_2)_p$—$C(R^{6a})_2$—$(CH_2)_q$—, wherein $R^{6a}$ is independently selected from hydrogen and $C_{1-4}$alkyl and p and q are independently 0 or 1;

more preferably a direct bond, —$CH_2$— or —$C(CH_3)_2$—.
and each Y is independently selected from:

$C_{1-6}$alkyl, $C_{2-6}$alkenyl, aryl-$Z^1$—, heterocyclyl-$Z^1$—, $C_{3-7}$cycloalkyl($CH_2$)$_{0-2}$, —($CH_2$)$_{1-4}$$CH_{3-a}F_a$;

preferably each Y is selected from:
$C_{1-6}$alkyl (preferably a branched chain $C_{2-6}$ alkyl such as isopropyl, isobutyl, etc), $C_{2-6}$alkenyl, phenyl-$Z^1$— or heterocyclyl-$Z^1$—, Most preferably each Y is selected from:
—$CH_3$, —$C_2H_5$, prop-2-yl, iso-propyl, 1-methyl-propyl, 2-methyl-propyl, allyl, phenyl, 2-ethyl-butyl, phenyl-$Z^1$—, cyclopropyl-$Z^1$—, cyclopentyl-$Z^1$—, morpholino-$Z^1$—, piperidinyl-$Z^1$—, piperazinyl-$Z^1$—, pyrrolidinyl-$Z^1$—, tetrahydro-2H-pyranyl-$Z^1$—, isoxazolyl-$Z^1$—, oxazolyl-$Z^1$—, pyridyl-$Z^1$—, thiazolyl-$Z^1$—, thienyl-$Z^1$— or isoindolinyl-$Z^1$—, each $Z^1$ is independently selected from:
a direct bond, —($CH_2$)$_{1-2}$—, or a group of the formula —($CH_2$)$_p$—C($R^{6a}$)$_2$—($CH_2$)$_q$—, wherein $R^{6a}$ is independently selected from hydrogen and $C_{1-4}$alkyl;

preferably a direct bond, —($CH_2$)$_{1-2}$— or a group of the formula —($CH_2$)$_p$—C($R^{6a}$)$_2$—($CH_2$)$_q$—, wherein $R^{6a}$ is independently selected from hydrogen and $C_{1-2}$alkyl and p and q are independently 0 or 1;

further preferably a direct bond, —$CH_2$—, —$CH_2$—CH($CH_3$)— or —($CH_2$)$_2$—;

most preferably a direct bond, —$CH_2$— or —($CH_2$)$_2$— wherein in each of the above Y is independently optionally substituted by $R^4$.

(5) each $R^2$ is the group Y—X—, Z within the definition of X is a direct bond and $Z^1$ within the definition of Y is a group of the formula —($CH_2$)$_p$—C($R^{6a}$)$_2$—($CH_2$)$_q$—, (6) each $R^4$ is independently selected from
halo, $CH_{3-a}F_a$ (ideally $CF_3$), $OCH_{3-a}F_a$ (ideally $OCF_3$), CN, $C_{1-6}$alkyl, $OC_{1-6}$alkyl, COOH, C(O)OC$_{1-6}$alkyl, ($CH_2$)$_{0-3}$COOH, O($CH_2$)$_{0-3}$COOH, CO-phenyl, CONH$_2$, CONH-phenyl, $SO_2NH_2$, $SO_2C_{1-6}$alkyl, OH, or phenyl optionally substituted by one or more $R^5$ groups where $R^5$ is selected from hydrogen, $C_{1-6}$alkyl or C(O)OC$_{1-6}$alkyl;

Preferably each $R^4$ is selected from
halo, CN, $C_{1-6}$alkyl, $OC_{1-6}$alkyl or COOH.

(7) each $R^5$ is selected from:
$C_{1-6}$alkyl, phenyl, heterocyclyl or $C_{3-7}$cycloalkyl;
Preferably each $R^5$ is selected from:
$C_{1-6}$alkyl, tetrahydrofuranyl, imidazolyl, isoxazolyl, pyrazinyl, pyrimidinyl, thienyl, 1,3-benzodioxol, cyclopropyl, cyclobutyl, cyclopentyl or cyclohexyl;
Most preferably each $R^5$ is selected from:
$CH_3$, $C_2H_5$, prop-2-yl, tetrahydrofuranyl, imidazolyl, isoxazolyl, pyrazinyl, pyrimidinyl, thienyl, 1,3-benzodioxolyl or cyclopentyl;

(8) each $X^1$ is independently selected from:
a direct bond, —Z—, —O—C(O)—Z—, —C(O)—O—Z—, —C(O)—Z—, —N($R^6$)—C(O)—Z—, —C(O)—N($R^6$)—Z—, —S(O$_2$)—Z—, —N($R^6$)SO$_2$—Z— or —SO$_2$N($R^6$)—Z—;

Preferably each $X^1$ is independently selected from:
a direct bond, —Z—, —O—C(O)—Z—, —C(O)—Z—, N($R^6$)—C(O)—Z— or —S(O$_2$)—Z—;

Most preferably each $X^1$ is independently selected from:
a direct bond, —$CH_2$—, —O—C(O)—, —C(O)—, —N($CH_3$)—C(O)—$CH_2$— or —S(O)$_2$—;

(9) optional substituents on $R^5$ are independently selected from:
OH, CN, $NH_2$, $C_{1-6}$alkyl, $OC_{1-6}$alkyl or halo;
Preferably optional substituents on $R^5$ are independently selected from:
OH, $C_{1-6}$alkyl, $OC_{1-6}$alkyl or halo;

Most preferably optional substituents on $R^5$ are independently selected from:
OH, $CH_3$, t-butyl, $OCH_3$, chloro or fluoro;

(10) $R^3$ is a heterocyclyl (preferably a nitrogen-containing heterocyclyl group), optionally substituted by one or more $R^7$ groups;

Preferably $R^3$ is a heterocyclyl selected from the following:

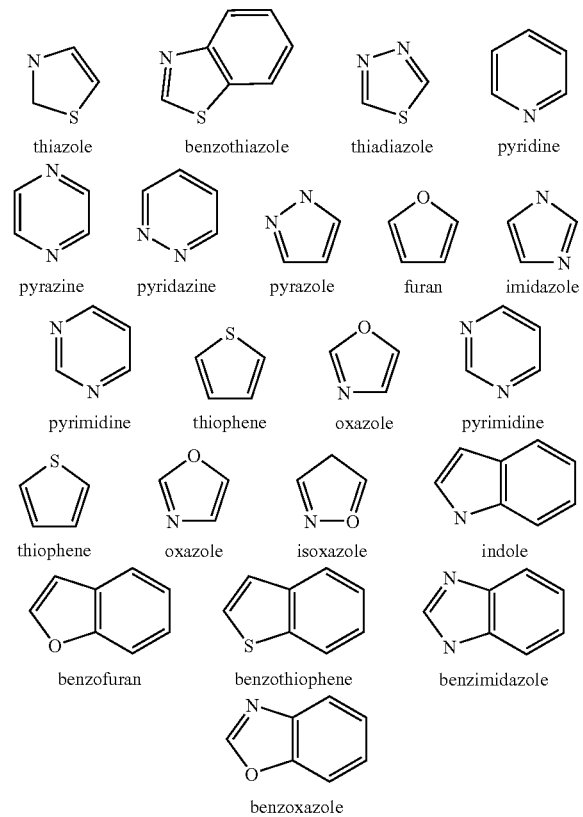

More preferably $R^3$ is selected from:
thiazole, thiadiazole, pyridine, pyrazine, pyridazine, pyrazole, pyrimidine, isoxazole, furan, benzothiazole, benzimidazole and benzoxazole.

Further preferably $R^3$ is selected from:
thiazole, benzothiazole, thiadiazole, pyridine, pyrazine, pyridazine, pyrazole, imidazole, pyrimidine, oxazole and indole.

Most preferably $R^3$ is selected from:
pyridine, thiazole or thiadiazole.

In a further embodiment of the invention, $R^3$ is selected from:
benzothiazole, thiazole, thiadiazole, pyridine, pyrazine, pyridazine, pyrazole, pyrimidine, isoxazole and furan.

(11) $R^3$ is not substituted or is substituted by one $R^7$ group.
(12) each $R^7$ is independently selected from:
OH, CN, $NH_2$, $SO_3H$, thioxo, halo, $C_{1-6}$alkyl, $C_{1-6}$alkyl-OH, O—$C_{1-6}$alkyl, $C_{1-6}$alkyl-halo, ($CH_2$)$_{0-3}$COOH, ($CH_2$)$_{0-3}$C(O)OR$^8$, ($CH_2$)$_{0-3}$NH($CH_2$)$_{0-3}$R$^8$, ($CH_2$)$_{0-3}$NHC(O)($CH_2$)$_{0-3}$R$^8$, ($CH_2$)$_{0-3}$C(O)NH($CH_2$)$_{0-3}$R$^8$, —($CH_2$)$_{0-3}$S(O)$_{0-2}$R$^8$, —($CH_2$)$_{0-3}$N($R^6$)SO$_2$R$^8$, ($CH_2$)$_{0-3}$C(O)N($R^6$)S(O)$_2$R$^8$ or ($CH_2$)$_{0-3}$heterocyclyl;

preferably $R^7$ is selected from:
OH, CN, $NH_2$, $SO_3H$, thioxo, halo, $C_{1-4}$alkyl, $C_{1-4}$alkyl-OH, O—$C_{1-4}$alkyl, $C_{1-4}$alkyl-halo, ($CH_2$)$_{0-1}$COOH, $(CH_2)_{0-1}C(O)OR^8$, $(CH_2)_{0-1}NH(CH_2)_{0-2}R^8$, $(CH_2)_{0-1}NHC(O)(CH_2)_{0-2}R^8$, $(CH_2)_{0-1}C(O)NH(CH_2)_{0-2}R^8$, —$(CH_2)_{0-2}S(O)_{0-2}R^8$, —$(CH_2)_{0-1}N(R^6)SO_2R^8$, $(CH_2)_{0-1}C(O)N(R^6)S(O)_2R^8$ or $(CH_2)_{0-1}$heterocyclyl (preferably the heterocyclyl is selected from furanyl, morpholino, 5-oxo-oxadiazolyl or tetrazolyl);

further preferably $R^7$ is selected from:

COOH, $C(O)OC_{1-6}$alkyl, $(CH_2)_{0-1}C(O)NH(CH_2)_{0-2}R^8$, $(CH_2)_{0-3}C(O)NHSO_2$—$R^8$ or $(CH_2)_{0-3}SO_2NHC(O)$—$R^8$;

most preferably $R^7$ is selected from:

COOH, $C(O)OC_{1-6}$alkyl or $(CH_2)_{0-1}C(O)NH(CH_2)_{0-2}R^8$,

(13) $R^8$ is selected from:

hydrogen, OH, COOH, $C_{1-6}$alkyl, O—$C_{1-6}$alkyl, —C(O)—O—$C_{1-6}$alkyl, $C_{0-6}$alkylOC(O)$C_{1-6}$alkyl, $N(R^6)C_{1-6}$alkyl, aryl, heterocyclyl or $C_{3-7}$cycloalkyl;

Preferably $R^8$ is selected from:

hydrogen, OH, COOH, $CH_3$, isopropyl, 2-methyl-butyl, pent-3-yl, —O—$CH_3$, —C(O)—O—$C_2H_5$, —$CH_2$—O—C(O)—$CH_3$, —$CH_2$—O—C(O)—$C_2H_5$, —$C(CH_3)_2$—O—C(O)—$CH_3$, NH-isopropyl, NH-t-butyl, $N(CH_3)$—$CH_3$, phenyl, isoxazolyl, pyrazolyl, pyridyl, thienyl, cyclopropyl or cyclobutyl;

(14) Preferred optional substituents on $R^8$ are independently selected from:

OH, CN, $NH_2$, halo or $C_{1-6}$alkyl;

More preferred optional substituents on $R^8$ are independently selected from:

OH, halo or $C_{1-6}$alkyl;

More preferred optional substituents on $R^8$ are independently selected from:

OH, chloro, fluoro and $CH_3$.

For example, particularly preferred compounds of the invention are those wherein:

m is 0 and n is 2, the two $R^2$ groups are attached at the 2- and 5— or the 3- and 5-positions (ideally the 3- and 5-positions), and X is —$O(CH_2)_{0-2}$— (ideally —$OCH_2$—); or m is 0 and n is 2, the two $R^2$ groups are attached at the 2- and 5— or the 3- and 5-positions (ideally the 3- and 5-positions), X is —$O(CH_2)_{0-2}$— (ideally —O— or —$OCH_2$—), and Y is benzyl optionally substituted by halo (such as fluoro or chloro, ideally fluoro) or $C_{1-6}$alkyl; or m is 0 and n is 2, the two $R^2$ groups are attached at the 2- and 5— or the 3- and 5-positions (ideally the 3- and 5-positions), X is —$O(CH_2)_{0-2}$— (ideally —O— or —$OCH_2$—), and $R^3$ is a heterocyclyl optionally substituted by $R^7$; or m is 0 and n is 2, the two $R^2$ groups are attached at the 2- and 5— or the 3- and 5-positions (ideally the 3- and 5-positions), X is —O— or —$O(CH_2)_{0-2}$— (ideally —O— or —$OCH_2$—), Y is phenyl optionally substituted by halo (such as fluoro or chloro, ideally fluoro) or $C_{1-6}$alkyl, and $R^3$ is a heterocyclyl optionally substituted by $R^7$; or m is 1 and n is 1, the $R^1$ and $R^2$ groups are attached at the 2- and 5— or the 3- and 5-positions (ideally the 3- and 5-positions), $R^1$ is halo (such as fluoro, chloro), and X is —O$(CH_2)_{0-2}$-(ideally —O— or —$OCH_2$—).

According to a further feature of the invention there is provided the following preferred groups of compounds of the invention:

(I) a compound of Formula (II)

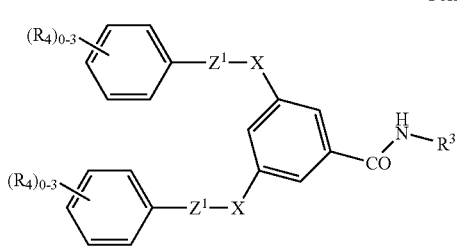

Formula (II)

wherein:

X, $Z^1$, $R^3$ and $R^4$ are as defined above in a compound of Formula (I);

or a salt, solvate or pro-drug thereof.

(II) a compound of Formula (IIa)

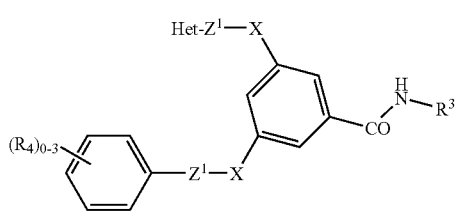

Formula (IIa)

wherein:

Het is a monocyclic heterocyclyl, optionally substituted with up to 3 groups selected from $R^4$ and, X, $Z^1$, $R^3$ and $R^4$ are as defined above in a compound of Formula (I);

or a salt, solvate or pro-drug thereof.

(III) a compound of Formula (IIb)

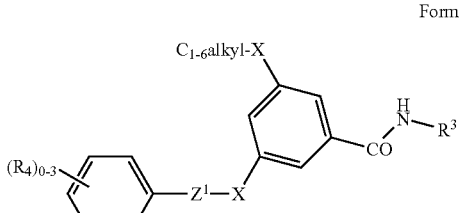

Formula (IIb)

wherein:

the $C_{1-6}$alkyl group is optionally substituted with up to 3 groups selected from $R^4$, preferably unsubstituted;

the $C_{1-6}$alkyl group optionally contains a double bond, preferably the $C_{1-6}$alkyl group does not contains a double bond; and X, $Z^1$, $R^3$ and $R^4$ are as defined above in a compound of Formula (I);

or a salt, solvate or pro-drug thereof.

(IV) a compound of Formula (IIc)

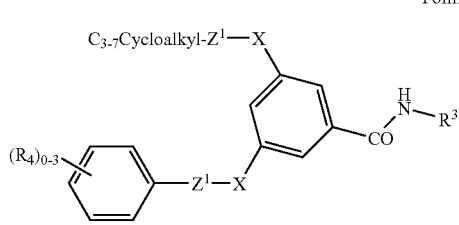

Formula (IIc)

wherein:
the $C_{3-7}$cycloalkyl group is optionally substituted with up to 3 groups selected from $R^4$, and
X, $Z^1$, $R^3$ and $R^4$ are as defined above in a compound of Formula (I);
or a salt, solvate or pro-drug thereof.

(V) a compound of Formula (IId)

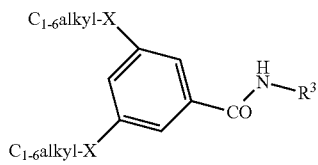

Formula (IId)

wherein:
the $C_{1-6}$alkyl groups are independently optionally substituted with up to 3 groups selected from $R^4$, preferably one of the $C_{1-6}$alkyl groups is unsubstituted,
the $C_{1-6}$alkyl groups independently optionally contain a double bond, preferably only one of the $C_{1-6}$alkyl groups contain a double bond, preferably neither of the $C_{1-6}$alkyl group contains a double bond, and
X, $R^3$ and $R^4$ are as defined above in a compound of Formula (I);
or a salt, solvate or pro-drug thereof.

(VI) a compound of Formula (IIe)

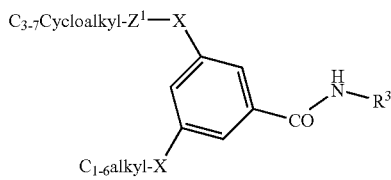

Formula (IIe)

wherein:
the $C_{3-7}$cycloalkyl and $C_{1-6}$alkyl groups are independently optionally substituted with up to 3 groups selected from $R^4$, preferably the $C_{1-6}$alkyl group is unsubstituted;
the $C_{1-6}$alkyl group optionally contains a double bond, preferably the $C_{1-6}$alkyl group does not contains a double bond; and
X, $Z^1$, $R^3$ and $R^4$ are as defined above in a compound of Formula (I);
or a salt, solvate or pro-drug thereof.

(VII) a compound of Formula (IIf)

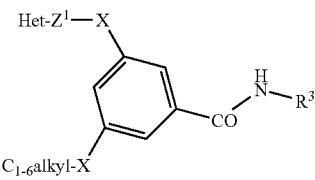

Formula (IIf)

wherein:
Het is a monocyclic heterocyclyl,
the Het and $C_{1-6}$alkyl groups are independently optionally substituted with up to 3 groups selected from $R^4$, preferably the $C_{1-6}$alkyl group is unsubstituted;
the $C_{1-6}$alkyl group optionally contains a double bond, preferably the $C_{1-6}$alkyl group does not contains a double bond; and
X, $Z^1$, $R^3$ and $R^4$ are as defined above in a compound of Formula (I);
or a salt, solvate or pro-drug thereof.

A further preferred group of compounds of group (VII) comprise compounds of Formula (IIf) wherein:
Het is a saturated monocyclic heterocyclyl;
X is —Z—, preferably —$CH_2$—;
$R^4$ is a group of $R^5$—$X^1$—;
$X^1$ is as defined for a compound of Formula (I);
$R^5$ is $C_{1-6}$alkyl, phenyl, heterocyclyl, each of which is optionally substituted as defined for a compound of Formula (I);

(VIII) a compound of Formula (IIg)

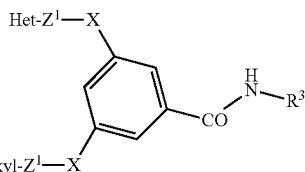

Formula (IIg)

wherein:
Het is a monocyclic heterocyclyl,
the Het and $C_{3-7}$cycloalkyl groups are independently optionally substituted with up to 3 groups selected from $R^4$, and
X, $Z^1$, $R^3$ and $R^4$ are as defined above in a compound of Formula (I);
or a salt, solvate or pro-drug thereof.

(IX) a compound of Formula (IIh)

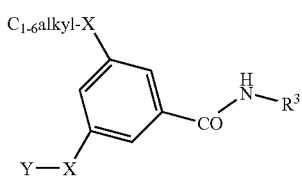

Formula (IIh)

wherein:
Y is aryl-$Z^1$—, wherein aryl is preferably a partially saturated bicyclic carbocyclic ring;
Y and the $C_{1-6}$alkyl group are independently optionally substituted with up to 3 groups selected from $R^4$, preferably the $C_{1-6}$alkyl group is unsubstituted, the $C_{1-6}$alkyl group optionally contains a double bond, preferably the $C_{1-6}$alkyl group does not contains a double bond; and $X$, $Z^1$, $R^3$ and $R^4$ are as defined above in a compound of Formula (I);

or a salt, solvate or pro-drug thereof.

(X) a compound of Formula (IIj)

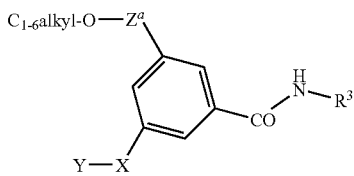

Formula (IIj)

wherein:

$X$ is selected from $-SO_2N(R^6)-Z-$ or $-N(R^6)SO_2-Z-$, preferably $X$ is $-SO_2N(R^6)-Z-$;

$Z$ is as described above, preferably $Z$ is propylene, ethylene or methylene, more preferably $Z$ is methylene;

$Z^a$ is selected from a direct bond or a group of the formula $-(CH_2)_p-C(R^{6a})_2-(CH_2)_q-$; preferably $Z^a$ is selected from $C_{1-2}$alkylene or a direct bond; preferably $Z^a$ is a direct bond;

$R^{6a}$ is selected from: $C_{1-4}$alkyl or hydrogen, preferably methyl or hydrogen;

$Y$ is selected from aryl-$Z^1-$ or heterocyclyl-$Z^1-$;

$Y$ and the $C_{1-6}$alkyl group are independently optionally substituted with up to 3 groups selected from $R^4$, the $C_{1-6}$alkyl group optionally contains a double bond, preferably the $C_{1-6}$alkyl group does not contain a double bond, and $Z^1$, $R^3$ and $R^4$ are as defined above in a compound of Formula (I);

or a salt, solvate or pro-drug thereof.

(XI) a compound of Formula (IIk)

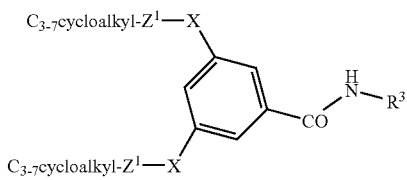

Formula (IIk)

wherein:

the $C_{3-7}$cycloalkyl groups are independently optionally substituted with up to 3 groups selected from $R^4$, and $X$, $Z^1$, $R^3$ and $R^4$ are as defined above in a compound of Formula (I);

or a salt, solvate or pro-drug thereof.

A further preferred groups of compounds of the invention in either of groups (I)-(XI) above is wherein:

$X$ is independently selected from: $-O-Z-$, $SO_2N(R^6)-Z-$ or $-N(R^6)-Z-$;

$Z$ is a direct bond or $-CH_2-$;

$Z^1$ is selected from a direct bond, $-CH_2-$, $-(CH_2)_2-$ or

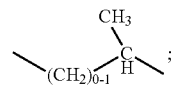

and $R^3$ is as defined above in a compound of Formula (I);

or a salt, solvate or pro-drug thereof.

A further preferred groups of compounds of the invention in either of groups (I)-(XI) above is wherein:

$R^3$ is substituted by at least one $R^7$ group (preferably one $R^7$ group);

$R^7$ is a group of the formula $(CH_2)_{0-3}NH(CH_2)_{0-3}R^8$, $(CH_2)_{0-3}N(R^6)S(O)_2R^8$ or $(CH_2)_{0-3}$heterocyclyl (preferably 5-oxo-1,2,4-oxadiaxol-3-yl or -tetrazol-5-yl);

$R^3$, $R^6$ and $R^8$ are as defined above in a compound of Formula (I);

or a salt, solvate or pro-drug thereof.

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen;

c) H. Bundgaard, Chapter 5 "Design and Application of Prodrugs", by H. Bundgaard p. 113-191 (1991);

d) H. Bundgaard, Advanced Drug Delivery Reviews, 8, 1-38 (1992);

e) H. Bundgaard, et al., Journal of Pharmaceutical Sciences, 77, 285 (1988); and f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$ alkanoyloxymethyl esters for example pivaloyloxymethyl, phthalidyl esters, $C_3$ to $C_8$cycloalkoxycarbonyloxy $C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)- N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

A further feature of the invention is a pharmaceutical composition comprising a compound of Formula (I) to (Id) or (II) to (IIk) as defined above, or a salt, solvate or prodrug thereof, together with a pharmaceutically-acceptable diluent or carrier.

According to another aspect of the invention there is provided a compound of Formula (Ib) to (Id), or (II) to (IIk) as defined above for use as a medicament;
provided that when $R^3$ is 2-pyridyl and X is other than —Z—, —C(O)—Z—O—Z—, —N(($R^6$))—C(O)—Z—O—Z— or —O—Z—N($R^6$)—Z—, then $R^3$ cannot be mono-substituted at the 4-position with an $R^7$ group selected from COOH or C(O)OC$_{1-6}$alkyl.

Further according to the invention there is provided a compound of Formula (Ib) to (Id), or (II) to (IIk) for use in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (Ib) to (Id), or (II) to (IIk), or salt, solvate or pro-drug thereof, to a mammal in need of such treatment.

Specific disease which may be treated by the compound or composition of the invention include: blood glucose lowering in Diabetes Mellitus type 2 without a serious risk of hypoglycaemia (and potential to treat type 1), dyslipidemea, obesity, insulin resistance, metabolic syndrome X, impaired glucose tolerance.

As discussed above, thus the GLK/GLKRP system can be described as a potential "Diabesity" target (of benefit in both Diabetes and Obesity). Thus, according to another aspect of the invention there if provided the use of a compound of Formula (Ib) to (Id), or (II) to (IIk), or salt, solvate or pro-drug thereof, in the preparation of a medicament for use in the combined treatment or prevention of diabetes and obesity.

According to another aspect of the invention there if provided the use of a compound of Formula (Ib) to (Id), or (II) to (IIk), or salt, solvate or pro-drug thereof, in the preparation of a medicament for use in the treatment or prevention of obesity.

According to a further aspect of the invention there is provided a method for the combined treatment of obesity and diabetes by administering an effective amount of a compound of Formula (Ib) to (Id), or (II) to (IIk), or salt, solvate or pro-drug thereof, to a mammal in need of such treatment.

According to a further aspect of the invention there is provided a method for the treatment of obesity by administering an effective amount of a compound of Formula (Ib) to (Id), or (II) to (IIk), or salt, solvate or pro-drug thereof, to a mammal in need of such treatment.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I), (Ia), (Ib), (Ic) or (Id) will naturally vary according to the nature and severity of the conditions, the age and sex of the animal or patient and the route of administration, according to well known principles of medicine.

In using a compound of the Formula (I), (Ia), (Ib), (Ic) or (Id) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, eg pravastatin); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, β blockers (eg atenolol, inderal); ACE inhibitors (eg lisinopril); Calcium antagonists (eg. nifedipine); Angiotensin receptor antagonists (eg candesartan), α antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts, solvates and prodrugs thereof.

A compound of the invention, or a salt thereof, may be prepared by any process known to be applicable to the preparation of such compounds or structurally related compounds. Such processes are illustrated by the following representative schemes (Routes 1-18) in which variable groups have any of the meanings defined for formula (I) unless stated otherwise. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

The condensation of an acid with a heterocyclic amine (Route 1) is used in the preparation of compounds of the invention or in the preparation of intermediates to the final products. One or more further reactions (such as ester hydrolysis, Routes 2a and 2b) may then be performed on these intermediates. The amide-forming reaction (Route 1) is best accomplished via the acid chloride, which is usually prepared using oxalyl chloride. However, alternative methods for acid chloride formation (such as resin-bound triphenyl phosphine with carbon tetrachloride and dichloromethane) may also be employed. Additionally, alternative methods of amide-bond formation (such as a peptide coupling agent such as EDC or HATU, with or without additives such as DIPEA or DMAP) may be used.

The remaining preparative routes (Routes 2-18) consist of further manipulation of the compound with the amide bond in place. Further preparative routes are summarise in Routes 19-29. Examples of routes 1-29 are provided in the examples below. Reagents and conditions given are only for illustration and alternative methods may generally be employed.

Route 1

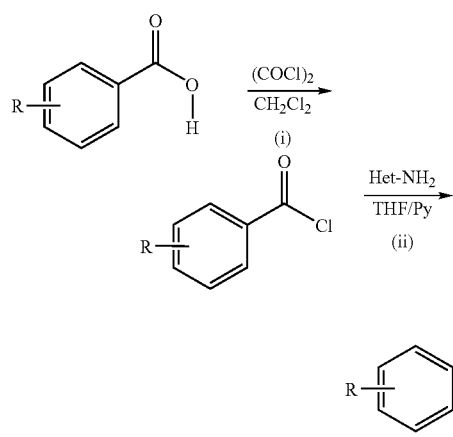

Other amide forming reactions include:
1a: Oxalyl chloride in the presence of a suitable solvent or base;
1b: coupling reagents such as HATU or EDAC in the presence of a suitable solvent or base; and
1c: POCl3/Pyridine, according to Dirk T. S. Rijkers, Hans P. H. M. Adams, H. Coenraad Hemker, Godefridus I. Tesser; Tetrahedron, 1995, 51(41), pp 11235-11250.

Route 2a and 2b

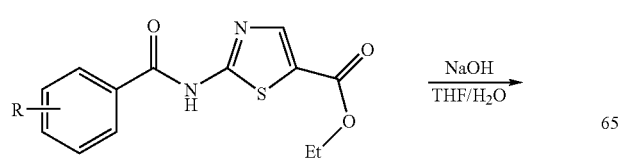

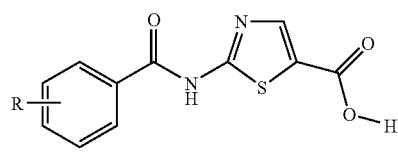

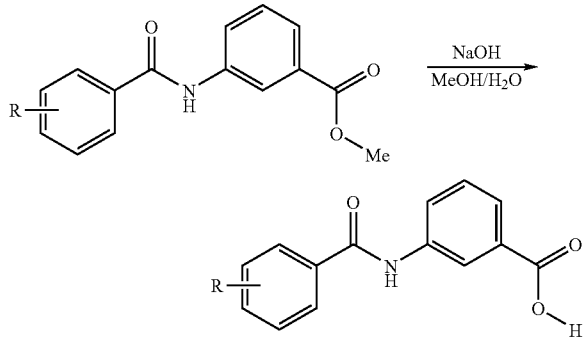

Route 3

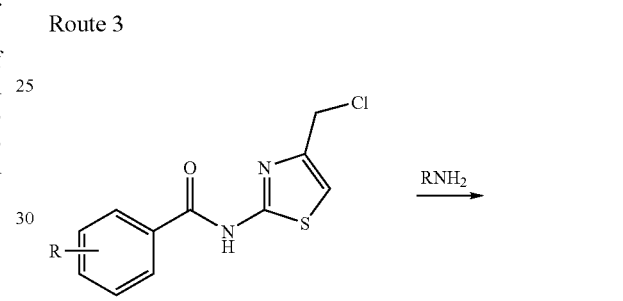

Route 4

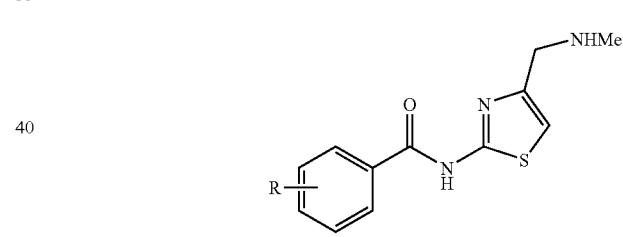

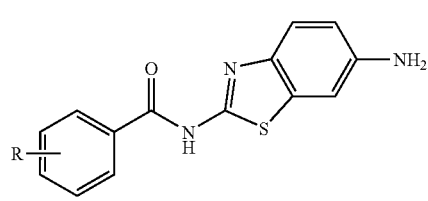

Route 5
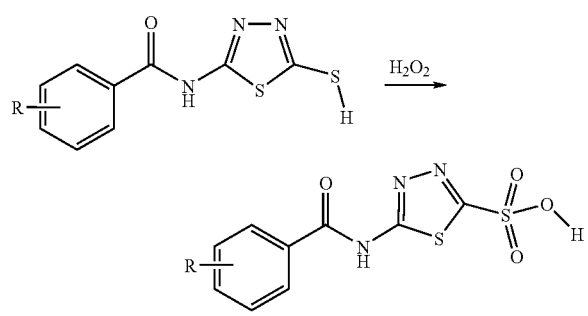
Route 6
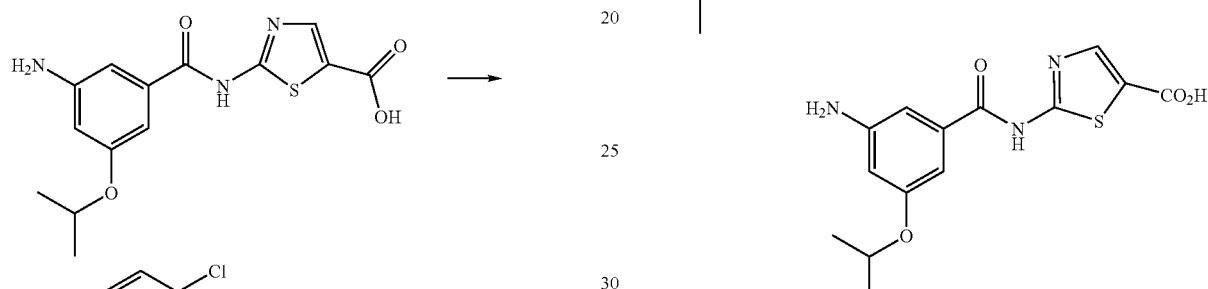
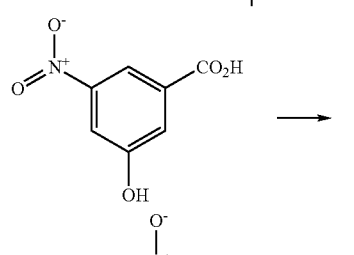
-continued
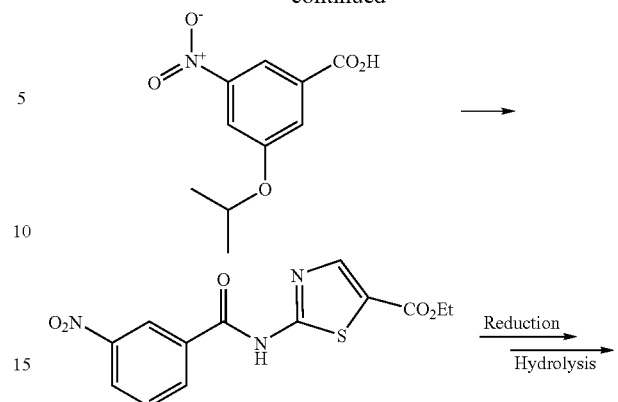
Route 7
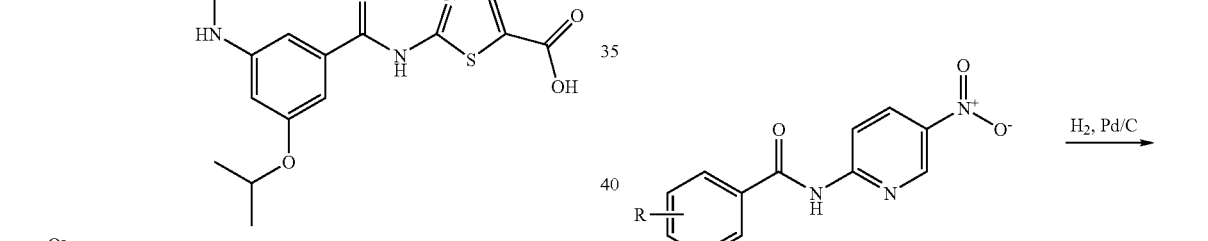
Route 7b:
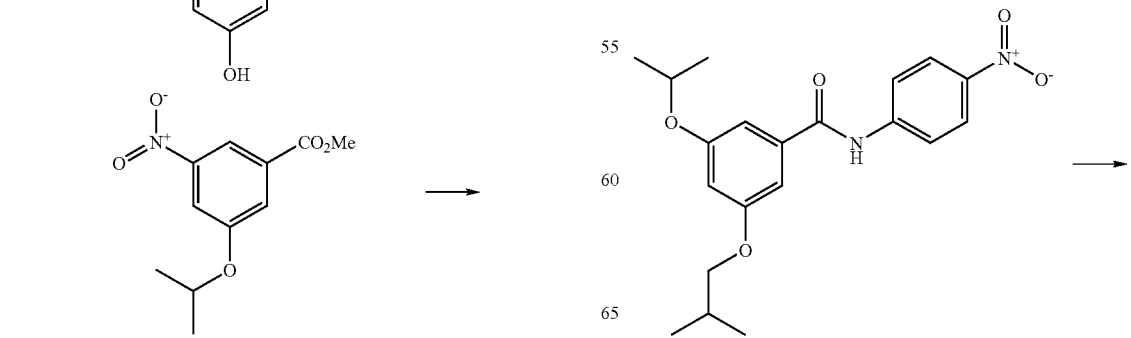

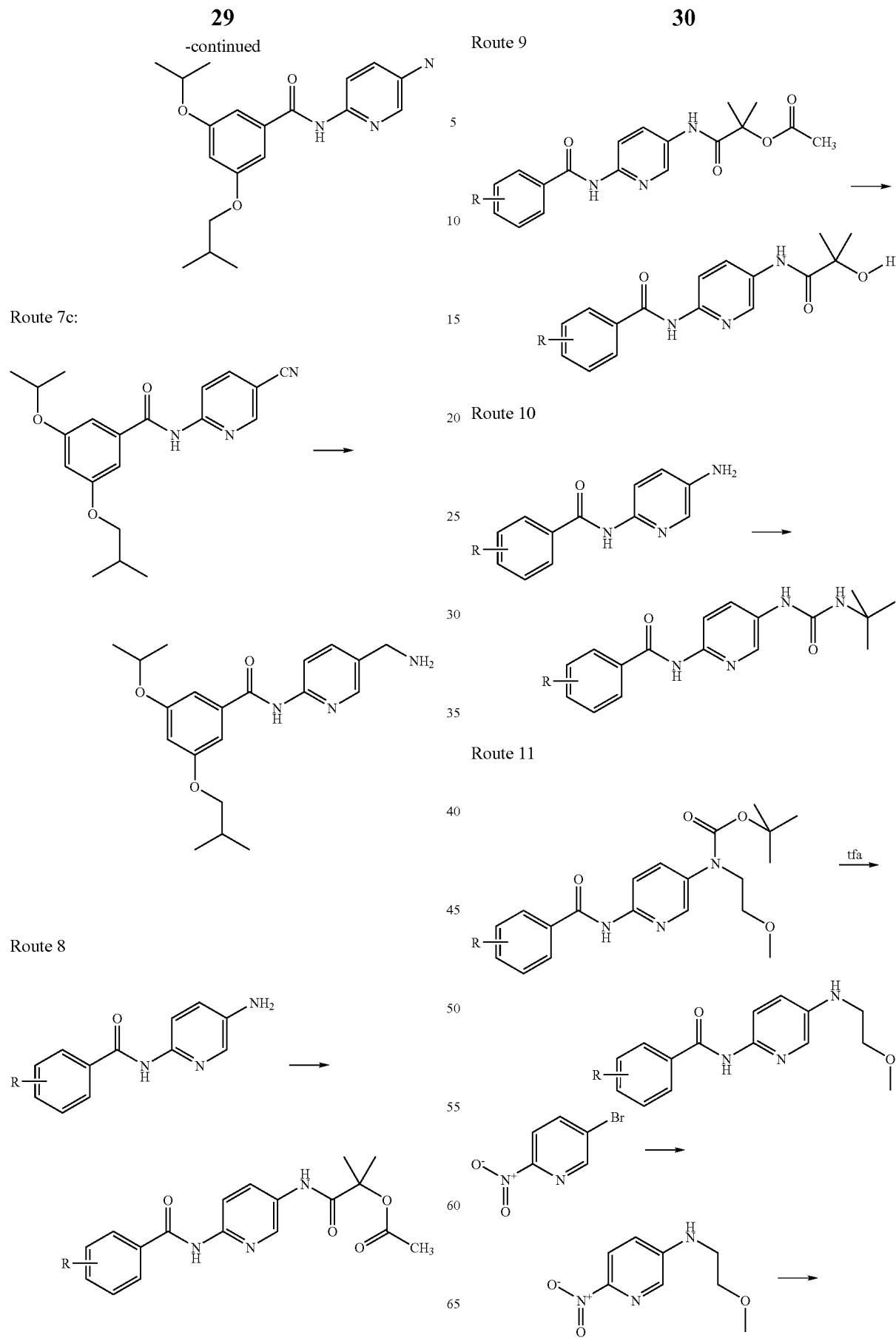

31
-continued
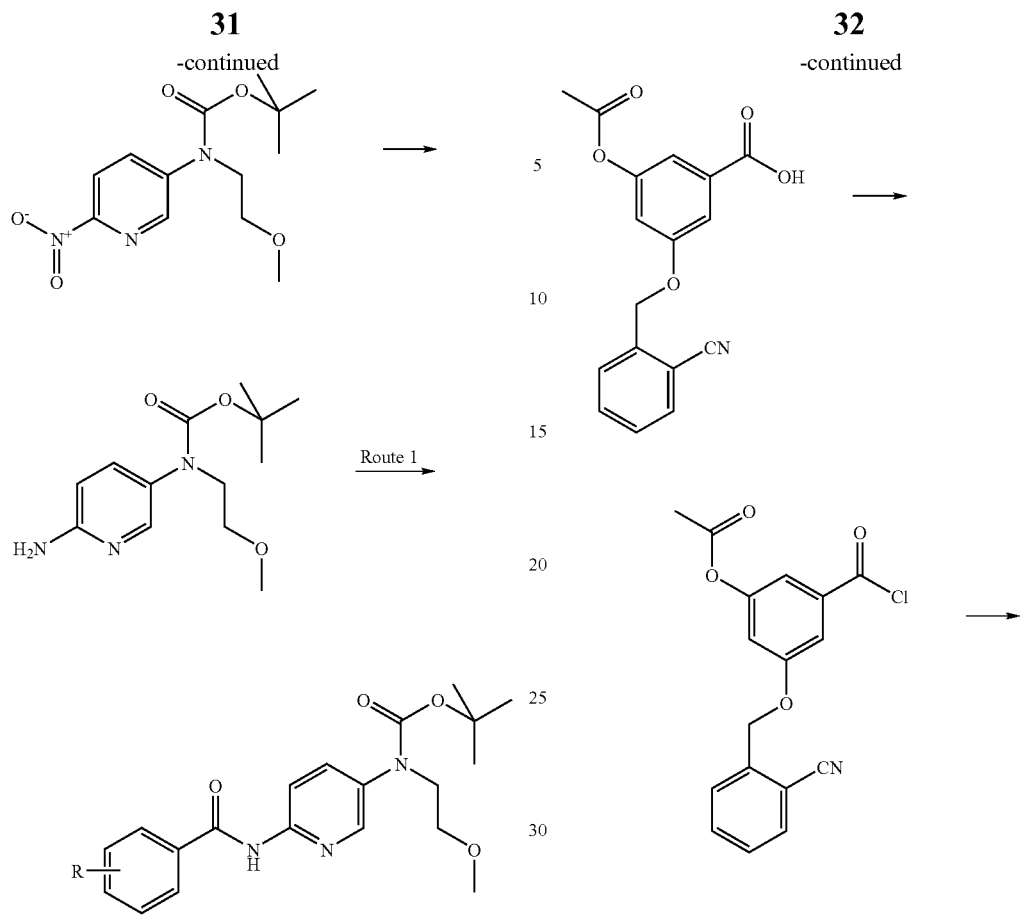
Route 12
32
-continued
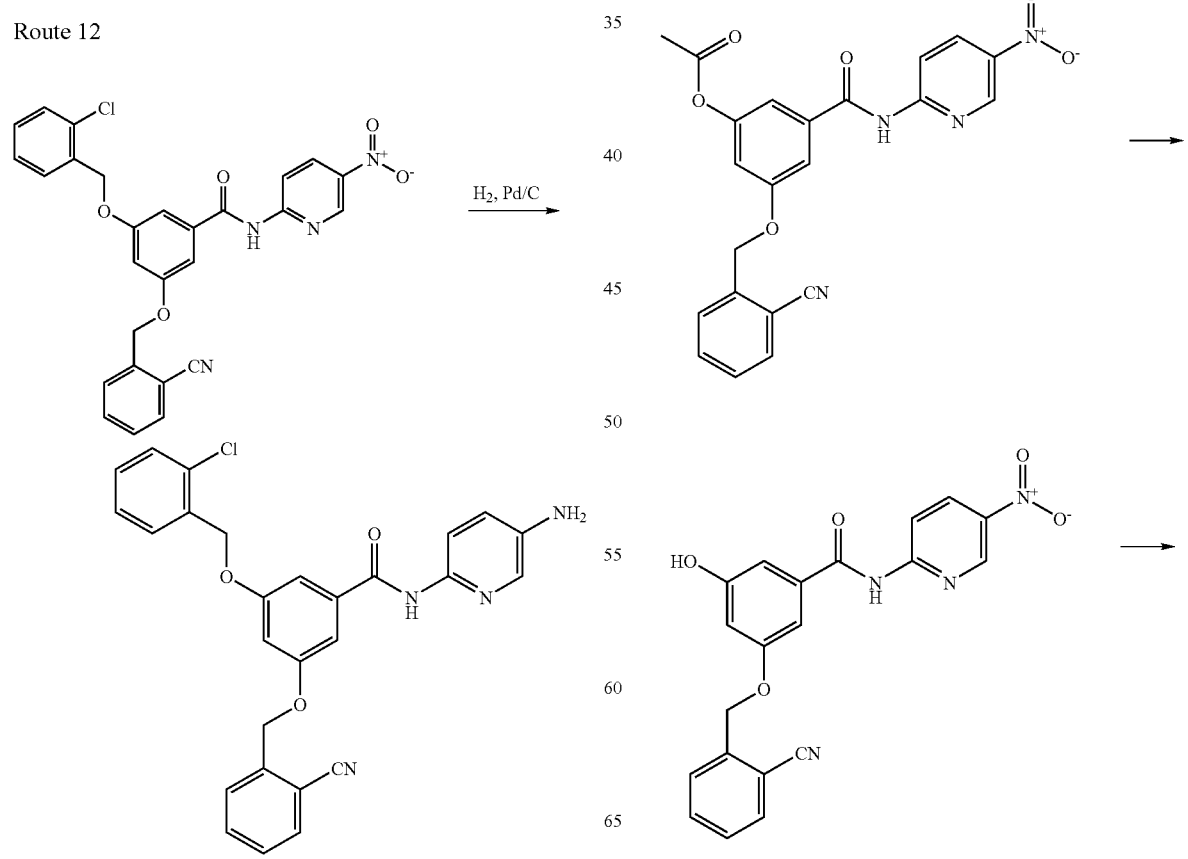

33
-continued
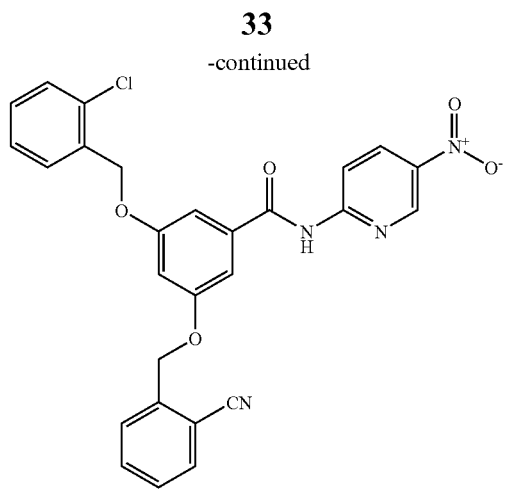
Route 13
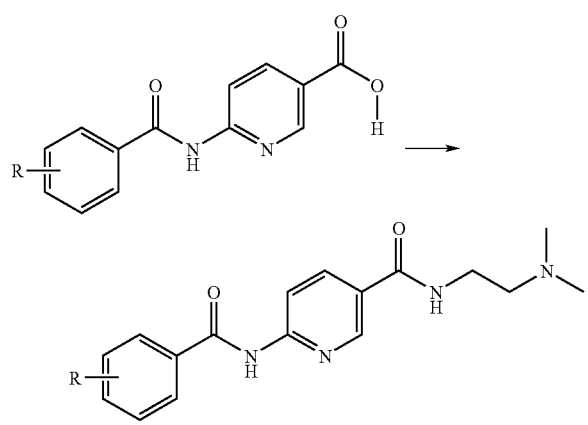
Route 14
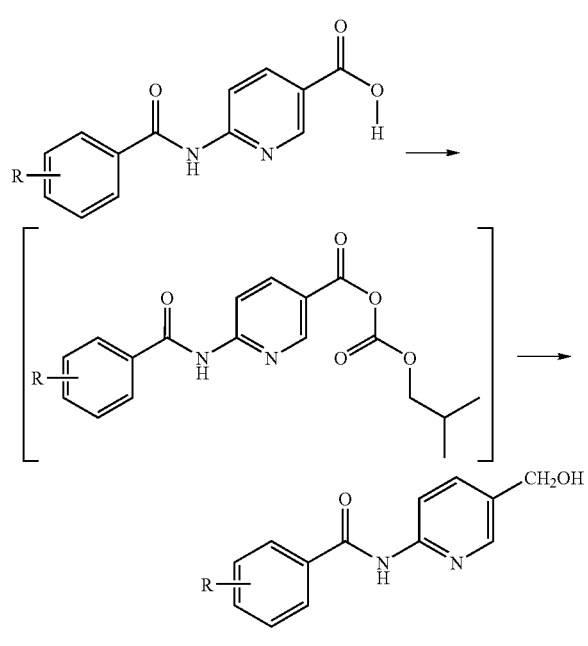
34
Route 15
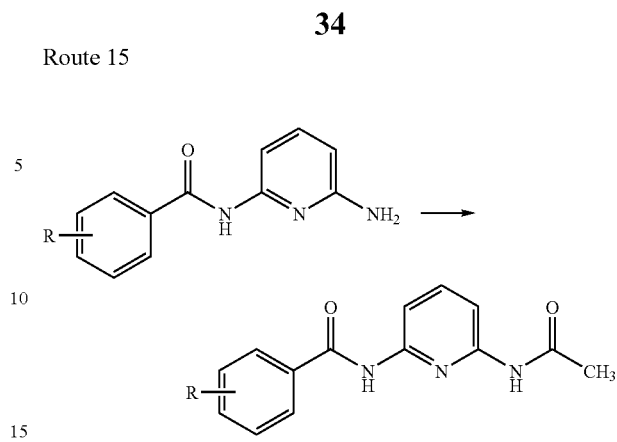
Route 16
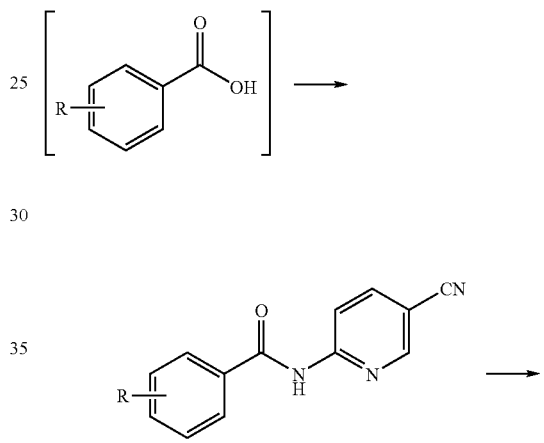
Route 17
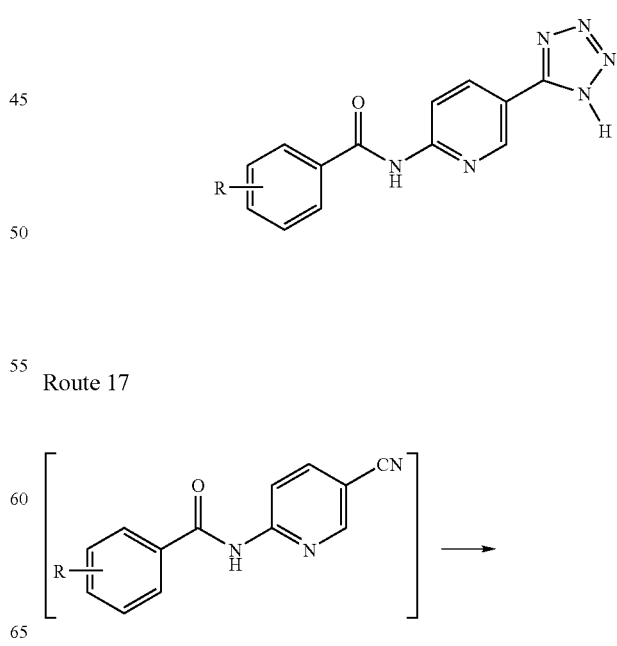

35 -continued
Route 18
36
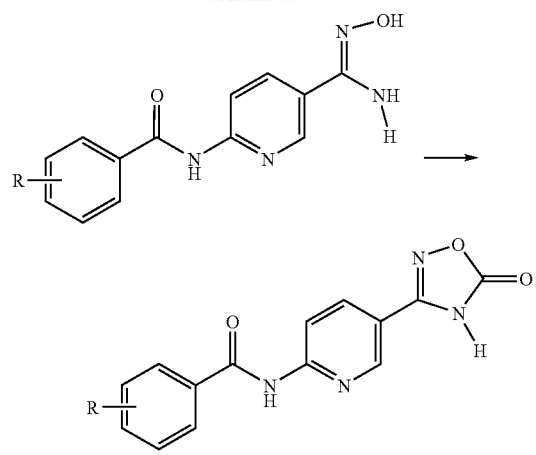
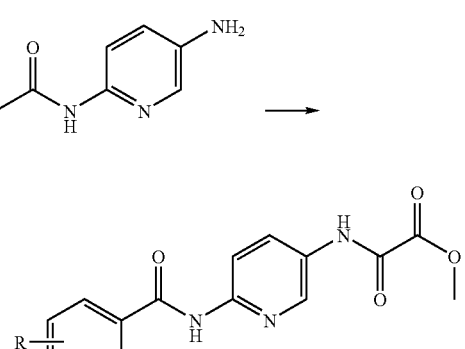
Route 19:
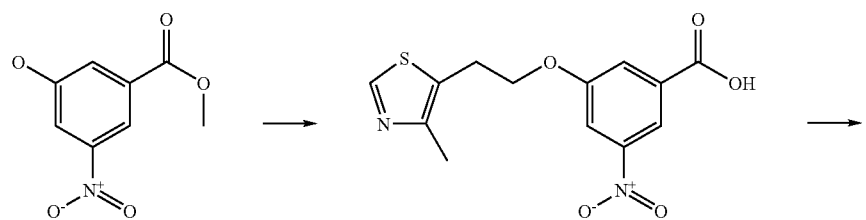
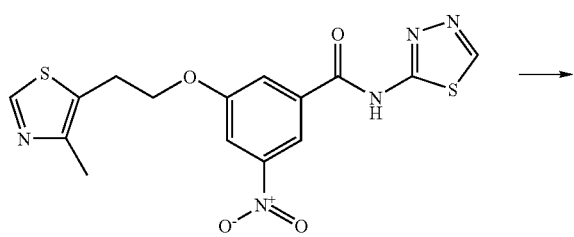
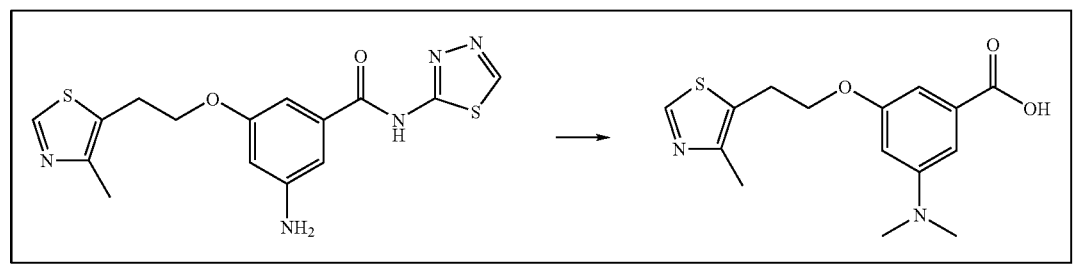

Route 20:
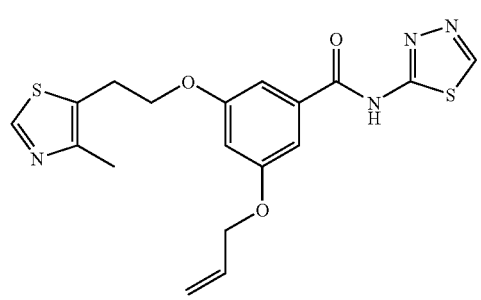
↓
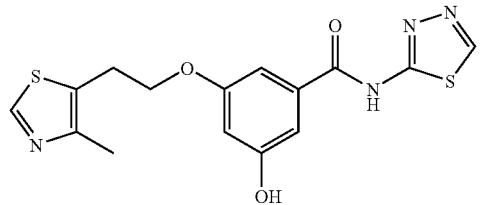
Route 21:
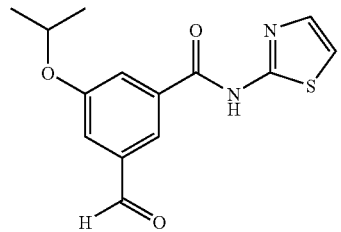
↓
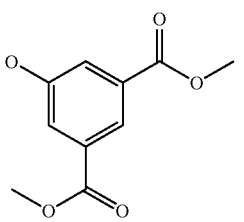
Route 22:
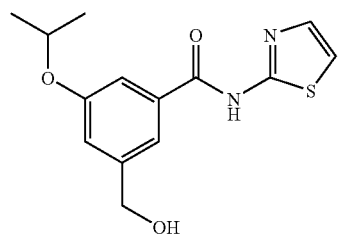
-continued
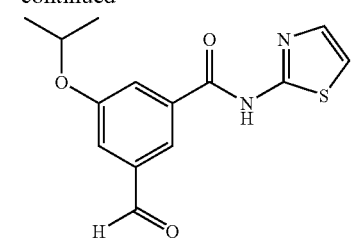
Route 23:
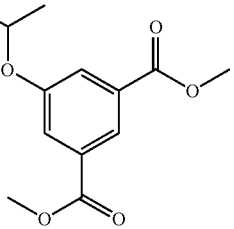
↓
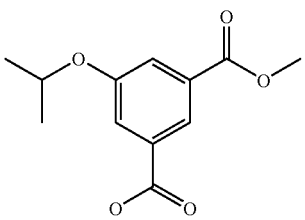
↓
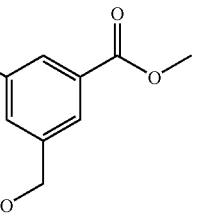
↓
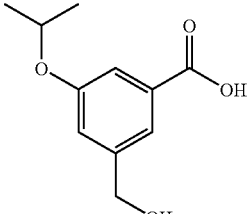
↓
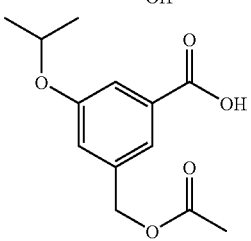
↓

Route 26:
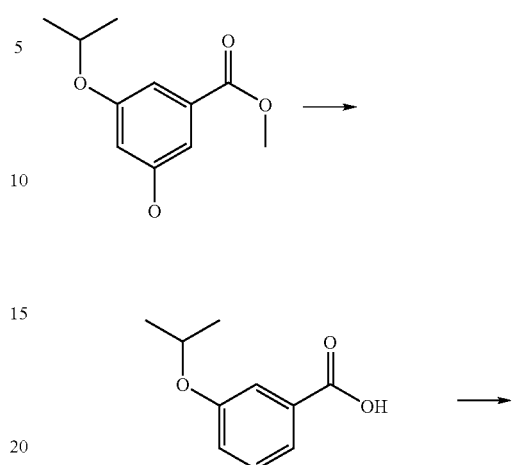
Route 24:
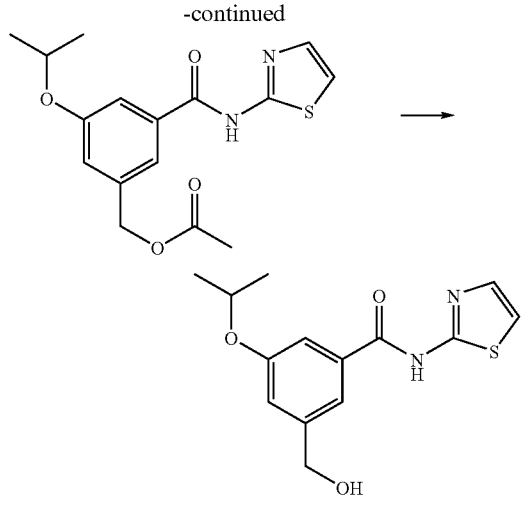
Route 25:
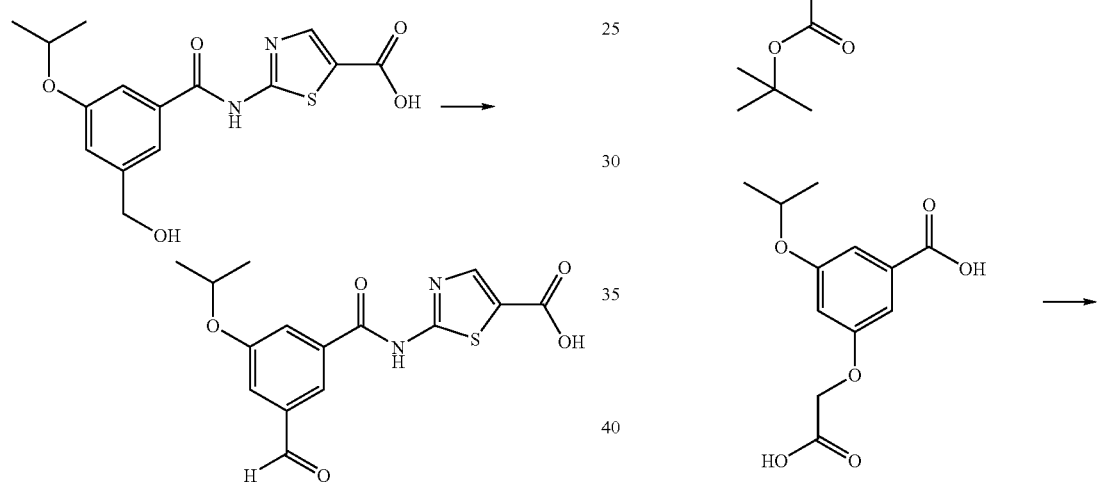
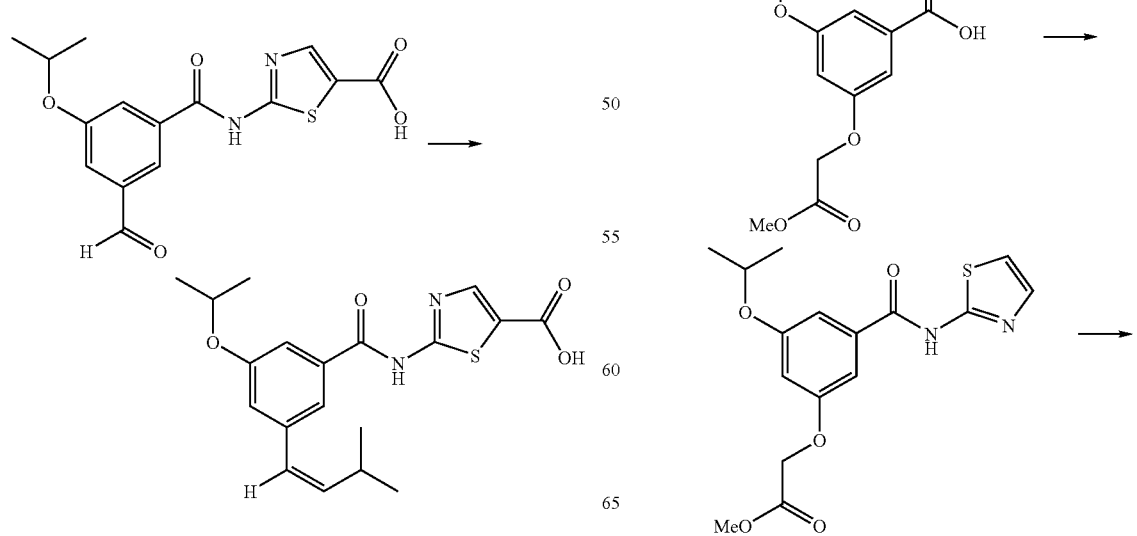

-continued
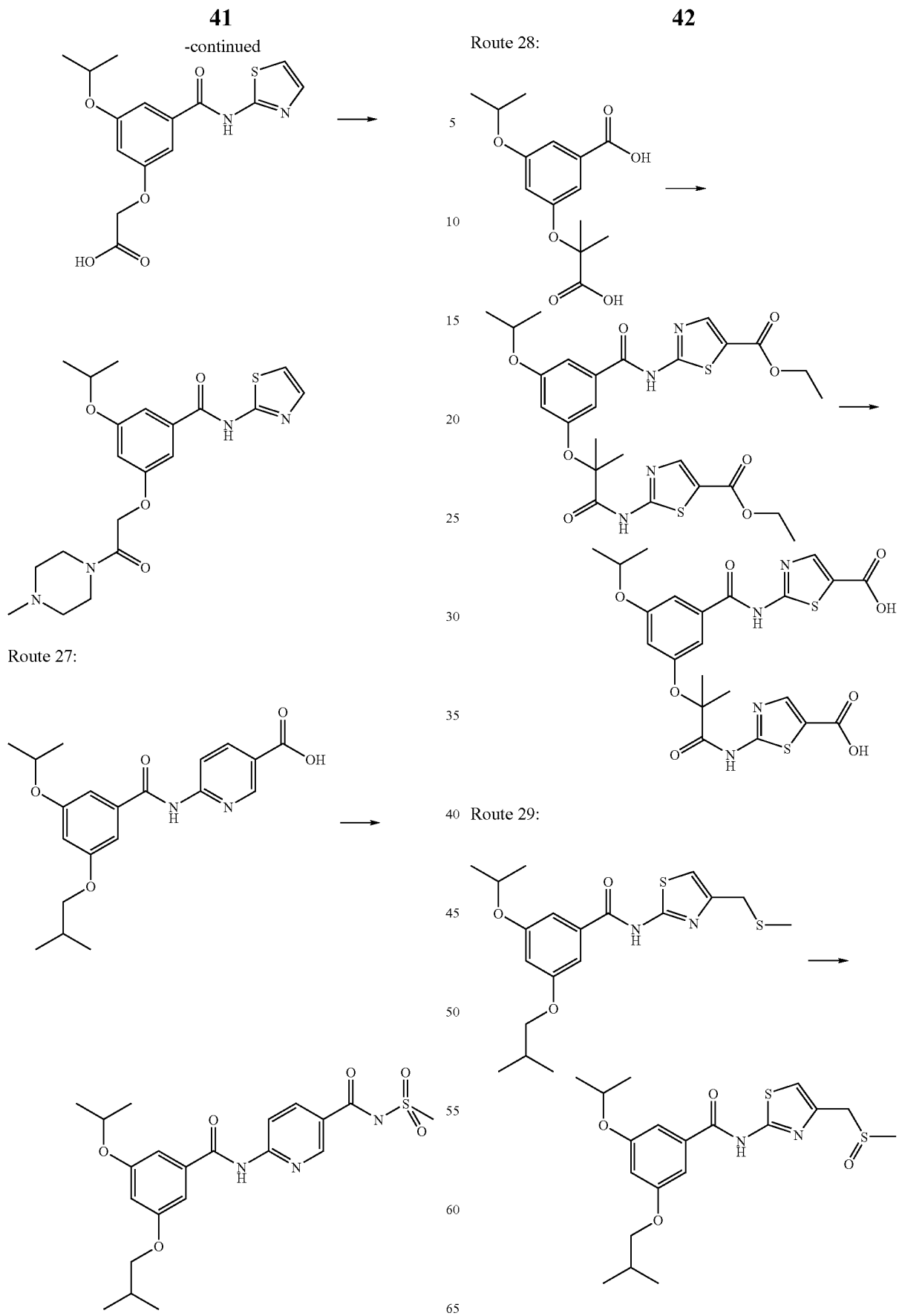
Route 27:
Route 28:
Route 29:
Processes for the synthesis of compounds of Formula (I) are provided as a further feature of the invention. Thus, according to a further aspect of the invention there is provided a process for the preparation of a compound of Formula (I) which comprises:

(a) reaction of a compound of Formula (IIIa) with a compound of Formula (IIIb),

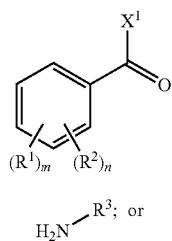

Formula (IIIa)

H$_2$N—R$^3$; or

Formula (IIIb)

wherein X$^1$ is a leaving group (b) for compounds of Formula (I) wherein R$^3$ is substituted with —(CH$_2$)$_{0-3}$COOH, de-protection of a compound of Formula (IIIc),

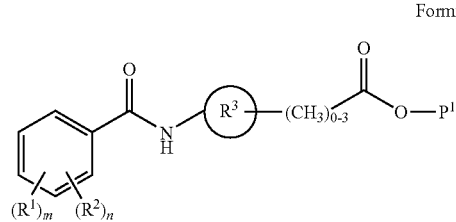

Formula (IIIc)

wherein P$^1$ is a protecting group;

(c) for compounds of Formula (I) wherein n is 1, 2, 3 or 4, reaction of a compound of Formula (IIId) with a compound of Formula (IIIe),

Y—X″

Formula (IIId)

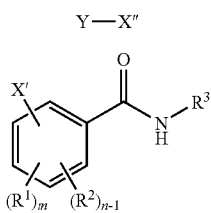

Formula (IIIe)

wherein X′ and X″ comprises groups which when reacted together form the group X;

(d) for a compound of Formula (I) wherein n is 1, 2, 3 or 4 and X or X$^1$ is —SO—Z— or —SO$_2$—Z—, oxidation of the corresponding compound of Formula (I) wherein X or X$^1$ respectively is —S—Z—;

(e) reaction of a compound of Formula (IIIf) with a compound of Formula (IIIg),

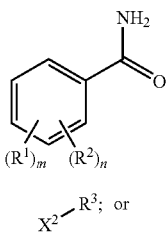

Formula (IIIf)

X$^2$—R$^3$; or

Formula (IIIg)

wherein X$^2$ is a leaving group and thereafter, if necessary:
i) converting a compound of Formula (I) into another compound of Formula (I);
ii) removing any protecting groups;
iii) forming a salt, pro-drug or solvate thereof.

Specific reaction conditions for the above reactions are as follows:

Process a)—as described above for Route 1);
Process b)—as described above for Route 2);
Process c)—examples of this process are as follows:
  (i) to form a group when X is —O—Z—, X′ is a group of formula HO—Z— and X″ is a leaving group (alternatively X′ is a group of formula L$^2$—Z—wherein L is a leaving group and X″ is a hydroxyl group), compounds of Formula (IIId) and (IIIe) are reacted together in a suitable solvent, such as DMF or THF, with a base such as sodium hydride or potassium tert-butoxide, at a temperature in the range 0 to 100° C., optionally using metal catalysis such as palladium on carbon or cuprous iodide;
  (ii) to form a group when X is N(R$^6$)—Z—, X′ is a group of formula H—(R$^6$)N—Z— and X″ is a leaving group (alternatively X′ is a group of formula L$^2$—Z— wherein L$^2$ is a leaving group and X″ is a group or formula —N(R$^6$)—H), compounds of Formula (IIId) and (IIIe) are reacted together in a suitable solvent such as THF, an alcohol or acetonitrile, using a reducing agent such as sodium cyano borohydride or sodium trisacetoxyborohydride at room temperature;
  (iii) to form a group when X is —SO$_2$N(R$^6$)—Z—, X′ is a group of formula H—N(R$^6$)—Z— wherein L$^2$ is a leaving group and X″ is an activated sulphonyl group such as a group of formula —SO$_2$—Cl, compounds of Formula (IIId) and (IIIe) are reacted together in a suitable solvent such as methylene chloride, THF or pyridine, in the presence of a base such as triethylamine or pyridine at room temperature;
  (iv) to form a group when X is —N(R$^6$)SO$_2$—Z—, X′ is an activated sulphonyl group such as a group of formula C$_1$—SO$_2$—Z— group and X″ is a group of formula —N(R$^6$)—L$^2$ wherein L$^2$ is a leaving group, compounds of Formula (IIId) and (IIIe) are reacted together in a suitable solvent such as methylene chloride, THF or pyridine, in the presence of a base such as triethylamine or pyridine at room temperature;
  (v) to form a group when X is —C(O)N(R$^6$)—Z—, X′ is a group of formula H—N(R$^6$)—Z— wherein L$^2$ is a leaving group and X″ is an activated carbonyl group such as a group of formula —C(O)—Cl, compounds of Formula (IIId) and (IIIe) are reacted together in a suitable solvent such as THF or methylene chloride, in the presence of a base such as triethylamine or pyridine at room temperature;
  (vi) to form a group when X is —N(R$^6$)C(O)—Z—, X′ is an activated carbonyl group such as a group of formula Cl—C(O)—Z— group and X" is a group of formula —N(R⁶)—L² wherein L² is a leaving group, compounds of Formula (IIId) and (IIIe) are reacted together in a suitable solvent such as THF or methylene chloride, in the presence of a base such as triethylamine or pyridine at room temperature;

(vii) to form a group when X is —CH=CH—Z—, a Wittag reaction or a Wadsworth-Emmans Horner reaction can be used. For example, X' terminates in an aldehyde group and Y—X" is a phosphine derivative of the formula Y—C—H—P⁺PH₃ which can be reacted together in a strong base such as sodium hydride or potassium tert-butoxide, in a suitable solvent such as THF at a temperature between room temperature and 100° C.

Process d)—the oxidization of a compound of Formula (I) wherein X or X¹ is —S—Z— is well known in the art, for example, reaction with metachloroperbenzoic acid (MCPBA) is the presence of a suitable solvent such as dichloromethane at ambient temperature. If an excess of MCPBA is used a compound of Formula (I) wherein X is —S(O₂)— is obtained.

Process e)—reaction of a Formula (IIIf) with a compound of Formula (IIIg) can be performed in a polar solvent, such as DMF or a non-polar solvent such as THF with a strong base, such as sodium hydride or potassium tert-butoxide at a temperature between 0 and 100° C., optionally using metal catalysis, such as palladium on carbon or cuprous iodide.

During the preparation process, it may be advantageous to use a protecting group for a functional group within R². Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/siloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Silica gel 60, 0.040-0.063 mm, 230-400 mesh); and (vi) Biotage cartridges refer to pre-packed silica cartridges (from 40 g up to 400 g), eluted using a biotage pump and fraction collector system; Biotage UK Ltd, Hertford, Herts, UK.

| Abbreviations | |
|---|---|
| ADDP | azodicarbonyl)dipiperidine; |
| DCM | dichloromethane; |
| DEAD | diethyldiazocarboxylate; |
| DIAD | di-i-propyl azodicarboxylate; |
| DIPEA | di-isopropylethylamine |
| DMSO | dimethyl sulphoxide; |
| DMF | dimethylformamide; |
| DtAD | di-t-butyl azodicarboxylate; |
| EDAC/EDC | 1-(3-dimethylaminopropyl)-3-ethylcarbodiimide hydrochloride; |
| HATU | O—(7-azabenzotriazol-1-yl)—N,N,N',N'-tetramethyluronium hexafluorophosphate; |
| LCMS | liquid chromatography/mass spectroscopy; |
| MPLC | medium pressure liquid chromatography; |
| RT | room temperature; and |
| THF | tetrahydrofuran. |

Generic Methods for Alkylation of Mono- and Di-Hydroxy Benzoate Esters:
The following generic alkylation methods are referred to in the Examples below.

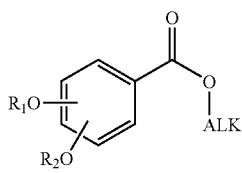

Generic Method A—Synthesis of Symmetrical Diethers (R1=R2)

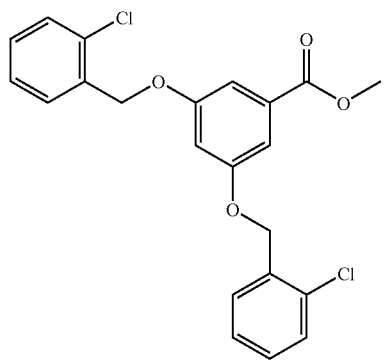

Compound (a)

Methyl 3,5-dihydroxybenzoate (74.1 g, 0.44M) was dissolved in dimethylformamide (400 ml), potassium carbonate (152 g, 1.10M) added, stirred for 15 mins then 2-chlorobenzylchloride (117 ml, 0.92M) added and heated at 100° C. under an argon atmosphere. After 3 hrs the reaction mixture was cooled to ambient temperature, concentrated in vacuo, diluted with water (800 ml), extracted with ethyl acetate (2×600 ml). The organic extracts were washed with brine (300 ml), dried (MgSO$_4$), filtered, concentrated in vacuo to yield a brown oil which was triturated with diethyl ether/isohexane to give compound (a) as an off-white solid (195 g, 100%); $^1$H nmr (d6-DMSO, δ values): 3.81 (3H, s); 5.18 (4H, s); 6.98 (1H, m); 7.16 (1H, d); 7.36 (4H, m); 7.50 (2H, m); 7.58 (2H, m).

Generic Method B—Synthesis of Unsymmetrical Diethers (R1=/R2)

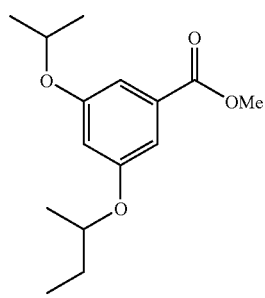

Compound (b)

Methyl 3,5-dihydroxybenzoate (16.8 g, 0.1 mol) was dissolved in dimethylformamide (180 ml), powdered potassium carbonate (27.6 g, 0.2 mol) added, followed by 2-iodopropane (10 ml, 0.1 mol), and the resulting suspension stirred overnight at ambient temperature under an argon atmosphere. The reaction mixture was diluted with water (1l) and extracted with diethyl ether (2×200 ml). The organic extracts were washed sequentially with water and brine, dried (MgSO$_4$), filtered and concentrated in vacuo to yield a pale golden oil which was triturated with toluene and filtered to remove unreacted ether starting material. The filtrate was concentrated in vacuo and the residue chromatographed (2×90 g Biotage cartridges, eluting with isohexane containing ethyl acetate (10% v/v increasing to 15% v/v) to give methyl 3-hydroxy 5-isopropyloxy benzoate as a colourless solid (5.3 g, 25%); $^1$H nmr (d6-DMSO, δ values): 1.2 (6H, d); 3.8 (3H, s); 4.6 (1H, hept); 6.55 (1H, m); 6.85 (1H, m); 6.95 (1H, m); 9.8 (1H, s).

Methyl 3-hydroxy 5-isopropyloxy benzoate (1.5 g, 7.2 mmol) was dissolved in dimethylformamide (10 ml), potassium carbonate (2.5 g, 18 mmol) added, followed by 2-bromobutane (1.2 ml, 11 mmol), and the resulting suspension stirred for 7 hours at 80 deg C. under an argon atmosphere. The reaction mixture was cooled to ambient temperature, diluted with hexane/ethyl acetate (1:1 v/v) and washed sequentially with water and brine, dried (MgSO$_4$), filtered and concentrated in vacuo to yield a colourless oil which was chromatographed (flash column on silica (20 g), eluting with isohexane containing ethyl acetate (5% v/v) to give methyl 3-(2-butyloxy) 5-isopropyloxy benzoate as a colourless oil (1.06 g); $^1$H nmr (d6-DMSO, δ values): 0.9 (3H, t); 1.2 (3H, d+6H, d); 1.6 (2h, m); 3.85 (3H, s); 4.4 (1H, hept); 4.55 (1H, hept); 6.7 (1H, m); 7.0 (2H, m); m/z 267 (M+H)$^+$.

Generic Method C—Synthesis of Unsymmetrical Diethers (R1≠/R2):

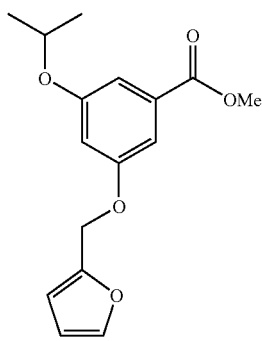

Compound (c)

Methyl 3-hydroxy 5-isopropyloxy benzoate (0.5 g, 2.4 mmol) was dissolved in dichloromethane (10 ml) and cooled to 0 deg C. whilst stirring under an argon atmosphere; the solution was treated sequentially with triphenyl phosphine (Polymer supported, 1.19 g, 3.6 mmol), furfuryl alcohol (0.23 ml, 2.7 mmol) and di-t-butyl azodicarboxylate (DtAD, 0.082 g, 3.5 mmol) added dropwise in dichloromethane (4 ml), and the resulting solution stirred for 1.5 hours. The reaction was monitored by hplc and further reagents were added until the starting phenol was consumed—total reagents added were triphenyl phosphine (Polymer supported, 2.38 g, 3 eq), furfuryl alcohol (0.53 ml, 2.5 eq) and DtAD (1.64 g, 3 eq). The reaction mixture was concentrated in vacuo and purified by chromatography (flash column on silica, eluting with isohexane containing ethyl acetate (5% v/v) to give methyl 3-(2-furyl methoxy) 5-isopropyloxy benzoate as a colourless oil, (0.225 g); $^1$H nmr (d6-DMSO, δ values): 1.25 (6H, d); 3.85 (3H, s); 4.65 (1H, hept); 5.1 (2H, s); 6.45 (1H, m); 6.6 (1H, m); 6.85 (1H, m); 7.05 (1H, m); 7.15 (1H, m) 7.75 (1H, m).

Generic Method D—Synthesis of Unsymmetrical Diethers:

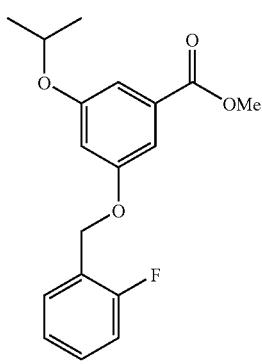

Compound (d)

Di-i-propyl azodicarboxylate (DIAD, 0.74 ml, 3.7 mM) was added to methyl (5-isopropoxy-3-methanol)-benzoate (0.56 g, 2.5 mM), triphenylphosphine (0.98 g, 3.7 mM) and 2-fluorophenol (0.24 ml, 2.7 mM) in DCM (40 ml) under argon at ambient temperature. After 10 mins concentrated, purified on silica gel (10-15% EtOAc/iso-hexane) gave the title compound as a pale yellow oil, which solidified under high-vacuum (0.71 g, 90%); $^1$H NMR δ (d$_6$-DMSO): 1.26 (d, 6H), 3.82 (s, 3H), 4.64 (m, 1H), 5.21 (s, 2H), 6.92 (m, 1H), 7.09 (m, 1H), 7.16-7.26 (m, 3H), 7.35 (s, 1H), 7.58 (s, 1H).

The above generic methods are for illustration only; it will be appreciated that alternative conditions that may optionally be used include: use of alternative solvents (such as acetone or tetrahydrofuran), alternative stoichiometries of reagents, alternative reaction temperatures and alternative methods of purification.

All analytical data (NMR and/or MS) were consistent with the proposed structures.

EXAMPLE A

Route 1: 2-[3,5-Di-(2-chlorobenzyloxy)benzoyl)amino]-thiazole

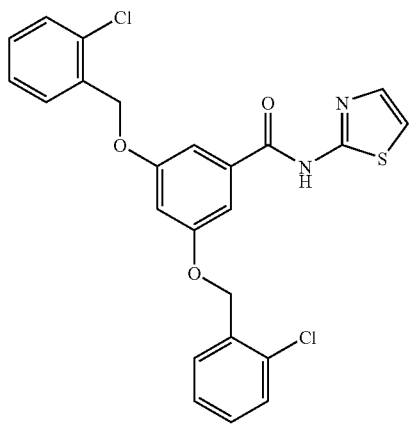

Diisopropylethylamine (DIPEA, 0.34 ml, 2.0 mM) then N,N-dimethylaminopyridine (DMAP, 12 mg, 0.1 mM) were added to a solution of 2-aminothiazole (0.10 g, 1.0 mM) and 3,5-di-(2-chlorobenzyloxy)benzoic acid chloride (0.42 g, 1.0 mM) in dichloromethane (10 ml) under argon at ambient temperature. After 80 mins the reaction mixture was filtered, washed with dichloromethane and dried under high vacuum to give the title compound as a colourless solid (0.20 g, 41%); $^1$H NMR δ (d$_6$-DMSO): 5.24 (4H, s); 6.93 (1H, s); 7.26 (1H, d); 7.36-7.43 (6H, m); 7.50 (2H, m); 7.55 (1H, d); 7.61 (2H, m); 12.60 (1H, br s).

Alternative conditions that may optionally be used include: use of an alternative solvent, such as tetrahydrofuran; use of pyridine as solvent, with or without the addition of DMAP or DIPEA; dissolving the acid chloride component in the solvent of choice, and adding the amine component to it.

The requisite 3,5-Di-(2-chlorobenzyloxy)benzoic acid chloride starting material, compound (c), was prepared as follows:

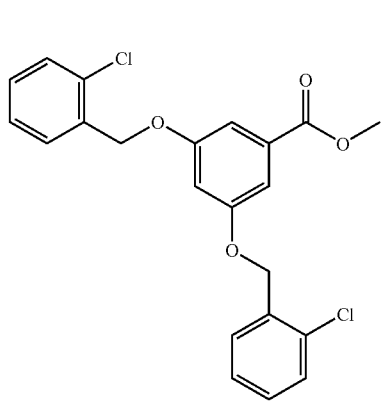

Compound (a)

Methyl 3,5-dihydroxybenzoate (74.1 g, 0.44M) was dissolved in dimethylformamide (400 ml), potassium carbonate (152 g, 1.10M) added, stirred for 15 mins then 2-chlorobenzylchloride (117 ml, 0.92M) added and heated at 100° C. under an argon atmosphere. After 3 hrs the reaction mixture was cooled to ambient temperature, concentrated in vacuo, diluted with water (800 ml), extracted with ethyl acetate (2×600 ml). The organic extracts were washed with brine (300 ml), dried (MgSO$_4$), filtered, concentrated in vacuo to yield a brown oil which was triturated with diethyl ether/isohexane to give compound (a) as an off-white solid (195 g, 100%); $^1$H nmr (d6-DMSO, δ values): 3.81 (3H, s); 5.18 (4H, s); 6.98 (1H, m); 7.16 (1H, d); 7.36 (4H, m); 7.50 (2H, m); 7.58 (2H, m).

Compound (b)

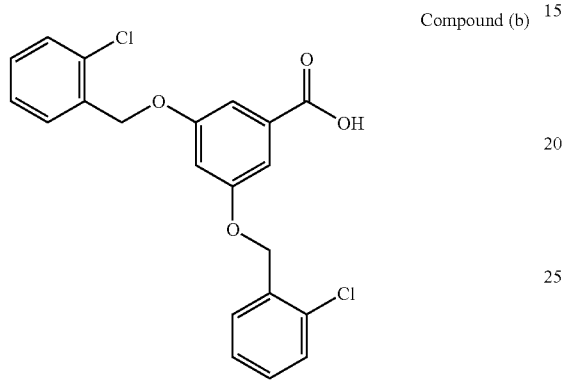

2M Sodium hydroxide (700 ml, 1.40M) was added to a solution of compound (a), methyl 3,5-di-(2-chlorobenzyloxy)benzoate, (195 g, 0.45M) in methanol (600 ml)/tetrahydrofuran 15 (150 ml) and stirred for 6 hrs at 55° C. The organics were then removed in vacuo, acidified to pH 3-4 with concentrated hydrochloric acid, the precipitate filtered, washed with water and dried under high-vacuum at 60° C. Compound (b) was obtained as a colourless solid (0.2/3NaCl) (199 g, 100%); $^1$H nmr (d6-DMSO, δ values): 5.18 (4H, s); 6.93 (1H, m); 7.15 (1H, d); 7.37 (4H, m); 7.49 (2H, m); 7.58 (2H, m).

Compound (c)

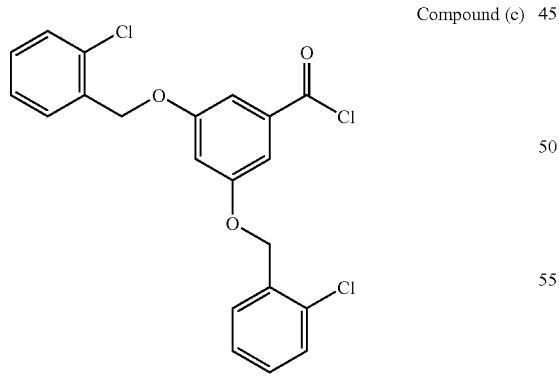

Oxalyl chloride (7.91 ml, 91 mM) was added to a suspension of compound (b), 3,5-di-(2-chlorobenzyloxy)benzoic acid.⅔NaCl (18.3 g, 45.4 mM) in dichloromethane (500 ml) containing dimethylformamide (4 drops) under argon at ambient temperature. After 16 hrs the reaction mixture was filtered under argon, concentrated in vacuo then azeotroped with toluene (2×) to give the title compound as an off-white solid (17.5 g, 100%); $^1$H nmr (d6-DMSO, δ values): 5.18 (4H, s); 6.94 (1H, m); 7.16 (1H, d); 7.35 (4H, m); 7.50 (2H, m); 7.58 (2H, m).

EXAMPLE B

Route 2a: 2-[3,5-di-(2-chlorobenzyloxy)benzoyl]aminothiazole-5-carboxylic acid

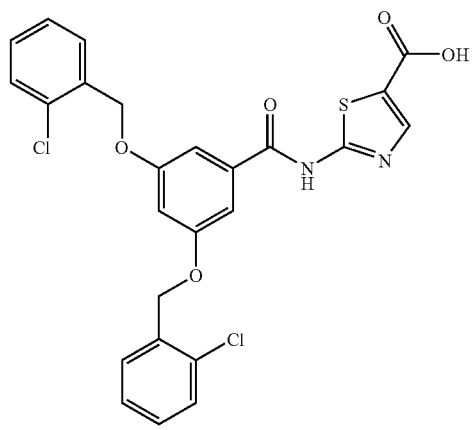

A solution of ethyl 2-[3,5-di-(2-chlorobenzyloxy)benzoyl]aminothiazole-5-carboxylate (158 mg, 0.28 mmol) in THF (2 ml) was treated with sodium hydroxide solution (0.57 ml of 2M, 1.4 mmol), and the reaction stirred at 40-50 deg C., until complete hydrolysis was achieved (with tlc monitoring, approximate reaction time 2 hrs). The resulting solution was cooled, diluted with water (5 ml) and acidified to pH1 using c.HCl. The precipitate thus formed was filtered off, washed (water) and dried to give the title compound as a colourless solid, 130 mg, $^1$H NMR δ (d$_6$-DMSO): 5.25 (4H, s); 7.0 (1H, s); 7.4 (6H, m); 7.5 (2H, m); 7.6 (2H, m); 8.2 (1H, d).

The requisite starting material was prepared by a route analogous to that given in Example A.

EXAMPLE C

Route 2b: [3,5-di-(2-chlorobenzyloxy)benzoyl]aminobenzene-3-carboxylic acid

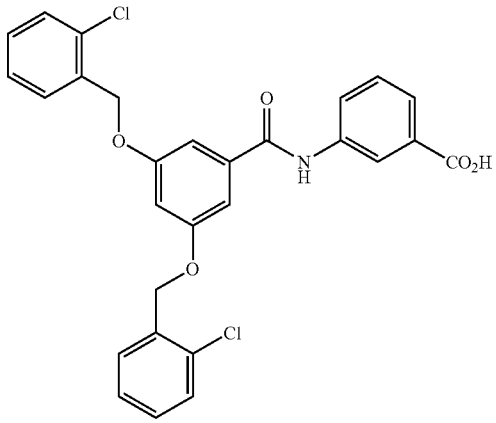

A suspension of methyl [3,5-di-(2-chlorobenzyloxy)benzoyl]aminobenzene-3-carboxylate (455 mg, 1.04 mmol) in THF was treated with sodium hydroxide solution (0.85 ml of 2M, 1.7 mmol), and the reaction stirred at ambient temperature, with tlc monitoring. Methanol (3 drops) and further additions of sodium hydroxide solution (2×0.85 ml of 2M, 3.4 mmol) were made, until complete hydrolysis was achieved. The resulting solution was diluted with water (30 ml) and acidified to pH1 (2M HCl); the precipitate thus formed was filtered off, washed (water) and dried to give the title compound as a colourless solid, 328 mg, $^1$H NMR δ (d$_6$-DMSO): 5.25 (4H, s); 7.0 (1H, s); 7.4 (6H, m); 7.5 (2H, m); 7.6 (2H, m); 8.2 (1H, d).

The requisite methyl ester starting material was prepared by a method analogous to that given in Example A.

EXAMPLE D

Route 3: 2-[3,5-Di-(2-chlorobenzyloxy)benzoyl]amino-4-methyl aminomethyl thiazole

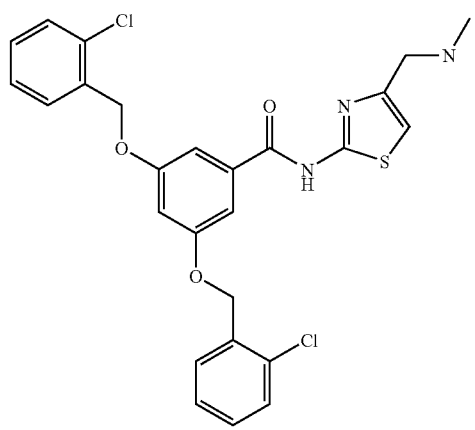

2-[3,5-Di-(2-chlorobenzyloxy)benzoyl)amino]-4-chloromethylthiazole (56 mg, 0.10 mM) was dissolved in 33% methylamine in methylated spirit (4 ml) and stirred at ambient temperature for 16 hrs. The reaction mixture was concentrated in vacuo, triturated with methanol, filtered and dried under high-vacuum to give the title compound as a colourless solid (30 mg, 57%); $^1$H nmr (d6-DMSO, δ values): 2.63 (3H, m); 4.16 (2H, m); 5.24 (4H, s); 6.99 (1H, s); 7.38-7.44 (7H, m); 7.52 (2H, m); 7.62 (2H, m); 9.06 (1H, br s); 12.75 (1H, br s).

2-[3,5-Di-(2-chlorobenzyloxy)benzoyl)amino]-4-chloromethylthiazole was prepared from 3,5-di-(2-chlorobenzyloxy)benzoyl chloride (prepared according to the method described in Example A) and 2-amino 4-chloromethyl-thiazole (JACS, 1946, 68, 2155; prepared by route 1 described in Example A).

EXAMPLE E

Route 4: 2-[3,5-Di-(2-chlorobenzyloxy)benzoyl)amino]-6-aminobenzothiazole

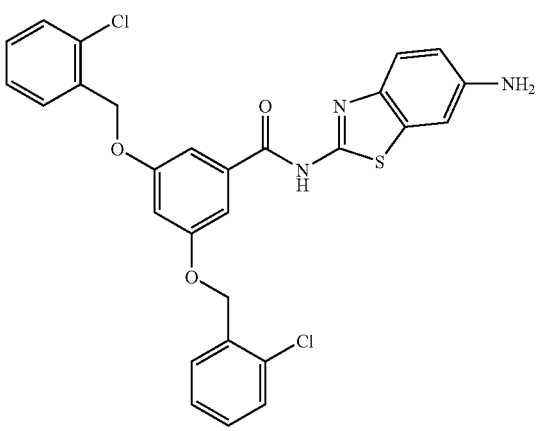

2-[3,5-Di-(2-chlorobenzyloxy)benzoyl)amino]-6-nitrobenzothiazole (235 mg, 0.40 mM) was dissolved in ethyl acetate (40 ml), ethanol (20 ml) and dimethylformamide (5 ml). 5% Palladium on carbon (46 mg) was added under an argon atmosphere then the reaction mixture stirred under a hydrogen atmosphere for 16 hrs. The reaction mixture was filtered through celite, concentrated in vacuo, triturated with methanol to give the title compound as a pale yellow solid (140 mg, 63%); $^1$H nmr (d6-DMSO, δ values): 5.19 (2H, br s); 5.23 (4H, s); 6.72 (1H, dd); 6.93 (1H, m); 7.03 (1H, m); 7.35-7.44 (7H, m); 7.51 (2H, m); 7.61 (2H, m); 12.46 (1H, br s).

2-[3,5-Di-(2-chlorobenzyloxy)benzoyl)amino]-6-nitrobenzothiazole was prepared from 3,5-di-(2-chlorobenzyloxy)benzoyl chloride (prepared according to the method described in Example A) and 2-amino-6-nitrobenzothiazole (prepared by route 1 described in Example A). $^1$H nmr (d6-DMSO, δ values): 5.27 (4H, s); 7.03 (1H, s); 7.38-7.46 (4H, m); 7.49-7.55 (4H, m); 7.65 (2H, m); 7.93 (1H, d); 8.30 (1H, dd); 9.09 (1H, m); 13.28 (1H, br s).

EXAMPLE F

Route 5: 5-[3,5-Di-(2-chlorobenzyloxy)benzoyl)amino]-[1,3,4]thiadiazole-2-sulfonic acid

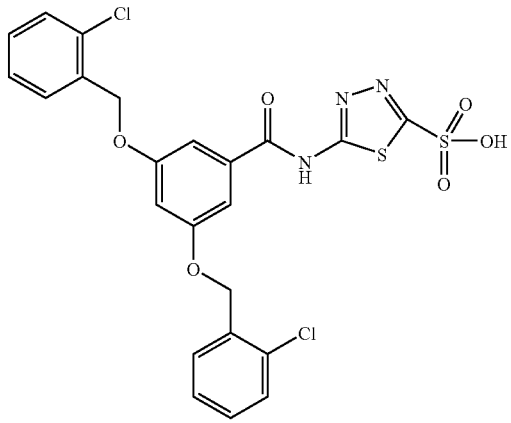

5-[3,5-Di-(2-chlorobenzyloxy)benzoyl)amino]-[1,3,4]
thiadiazole-2-thiol (200 mg, 0.38 mM) was suspended in 2M
NaOH (5 ml), cooled (ice bath) and 30% aqueous hydrogen
peroxide (0.16 ml, 1.54 mM) added dropwise then allowed to
warm to ambient temperature. After 40 hrs the reaction mixture was filtered, washed with water then methanol and dried
under high-vacuum to give the title compound as a colourless
solid (122 mg, 57%); $^1$H nmr (d6-DMSO, δ values): 5.20 (4H,
s); 6.68 (1H, m); 7.37 (4H, m); 7.45 (2H, m); 7.50 (2H, m);
7.62 (2H, m). MS (M–H$^+$)$^-$ 564, 566.

5-[3,5-Di-(2-chlorobenzyloxy)benzoyl)amino]-[1,3,4]
thiadiazole-2-thiol was prepared from 3,5-di-(2-chlorobenzyloxy)benzoyl chloride and 5-amino-[1,3,4]thiadiazole-2-thiol (Maybridge) by route 1 as described in Example A. $^1$H
nmr (d$_6$-DMSO, δ values): 5.21 (4H, s); 6.98 (1H, m); 7.34-
7.40 (6H, m); 7.50 (2H, m); 7.59 (2H, m). MS (M–H$^+$)$^-$ 516,
518.

EXAMPLE G

Route 6: 2-[(3-isopropyloxy-5-(2-chlorobenzylamino)benzoyl)amino]-5-thiazolecarboxylic acid

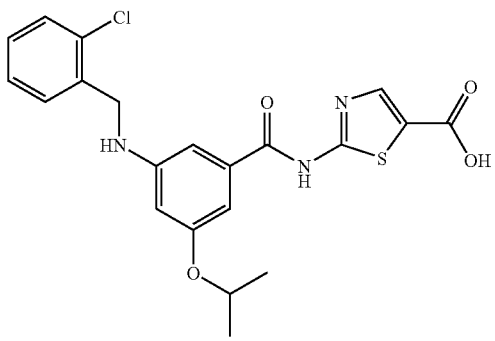

2-Chlorobenzaldehyde (0.012 ml, 0.11 mM) was added to
2-[(3-isopropoxy-5-aminobenzoyl)amino]-5-thiazolecarboxylic acid (29 mg 0.09 mM) and 4A molecular sieves (90
mg) in methanol under an inert atmosphere at room temperature. After 1 hr sodium cyanoborohydride (7 mg, 0.11 mM)
was added and the reaction mixture stirred for 16 hrs. The
reaction mixture was filtered, concentrated in vacuo, the residue stirred with water then extracted with ethyl acetate (3×10
ml). The organic extracts were washed with brine (20 ml),
dried (MgSO$_4$), filtered and concentrated in vacuo to give the
title compound as a pale yellow solid (22 mg, 55%); $^1$H nmr
(d6-DMSO, δ values): 1.22 (6H, d); 4.36 (2H, m); 4.58 (1H,
m); 6.24 (1H, s); 6.47 (1H, m); 6.84 (2H, m); 7.26 (3H, m);
7.37 (2H, m); 7.45 (1H, m); 7.76 (1H, br s). MS [M-CO$_2$H]$^-$
400, 402.

2-[(3-isopropyloxy-5-aminobenzoyl)amino]-5-thiazolecarboxylic acid was prepared as follows:

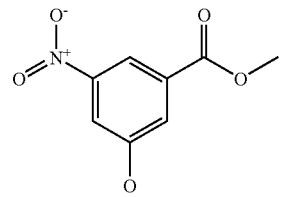

Compound (d)

3-Nitro-5-hydroxy benzoic acid (6.1 g, 33.3 mM) was dissolved in methanol (150 ml), concentrated sulfuric acid (2.0
ml) was added, and the solution stirred at room temperature
for 5 days. The reaction mixture was concentrated in vacuo,
saturated aqueous sodium hydrogencarbonate (60 ml) added
cautiously and the aqueous layer extracted with ethyl acetate
(200 ml). The organic layer was washed with brine (80 ml),
dried (MgSO$_4$), filtered and concentrated in vacuo to give
compound (d) as a pale yellow solid (6.0 g, 91%); $^1$H nmr
(d6-DMSO, δ values): 3.85 (3H, s); 7.67 (1H, m); 7.75 (1H,
m); 8.05 (1H, m); 10.88 (1H, br s).

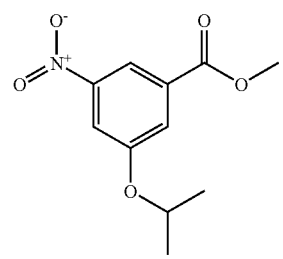

Compound (e)

2-Iodopropane (0.54 ml, 5.4 mM) was added to a solution
of methyl 3-nitro-5-hydroxy benzoate (1.06 g, 5.4 mM) and
potassium carbonate (1.12 g, 8.1 mM) in dimethylformamide
(15 ml) under an argon atmosphere at room temperature. The
reaction mixture was heated at 60° C. for 1 hr then additional
2-iodopropane (0.32 ml, 3.2 mM) added and heating continued for a further 1 hr. The reaction mixture was then concentrated in vacuo, water (50 ml) and ethyl acetate (100 ml)
added. The organic layer was separated and washed with
brine (40 ml), dried (MgSO$_4$) filtered, concentrated in vacuo
to give compound (e) as a mobile brown oil; $^1$H nmr (d6-
DMSO, δ values): 1.30 (6H, s); 3.90 (3H, s); 4.84 (1H, m);
7.76 (1H, m); 7.89 (1H, m); 8.16 (1H, m).

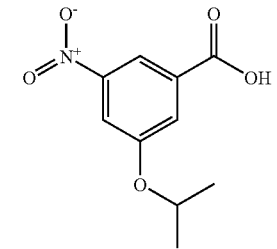

Compound (f)

2M Sodium hydroxide (12.3 ml, 24.7 mM) was added to a
solution of methyl (3-nitro-5-isopropoxy)benzoic acid (1.18
g, 4.9 mM) in methanol (60 ml) and stirred for 5 hrs at room
temperature. The reaction mixture was then concentrated in
vacuo, acidified to pH 1-2 with 2M hydrochloric acid, the precipitate filtered, washed with water and dried under high-vacuum over silica gel. Compound (f) was obtained as an off-white solid (1.04 g, 94%); $^1$H nmr (d6-DMSO, δ values): 1.30 (6H, s); 4.81 (1H, m); 7.74 (1H, m); 7.85 (1H, m); 8.14 (1H, m). MS (M−H$^+$)$^-$ 224.

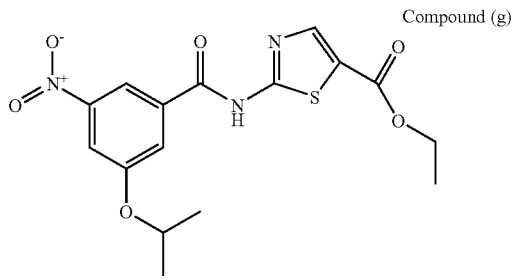

Compound (g)

Oxalyl chloride (0.75 ml, 8.6 mM) was added to 3-nitro-5-isopropoxy benzoic acid (1.03 g, 4.3 mM) in dichloromethane (50 ml) containing dimethylformamide (2 drops) under an argon atmosphere at room temperature. After 3 hrs the reaction mixture was concentrated in vacuo and azeotroped with toluene to give an orange oil which was dissolved in dichloromethane (40 ml). Ethyl 2-aminothiazole-5-carboxylate (0.89 g, 5.1 mM), diisopropylethylamine (1.77 g, 10.3 mM) and N,N-dimethylaminopyridine (50 mg, 0.43 mM) were added and stirred for 1 hr under an argon atmosphere. After which the reaction mixture was concentrated in vacuo then the pale brown residue purified on silica gel using 15 to 20% ethyl acetate/isohexane as eluant. Compound (g) was obtained as a pale yellow solid (1.56 g, 92%); $^1$H nmr (d6-DMSO, δ values): 1.32 (6H, d); 4.88 (1H, m); 7.87 (1H, s); 8.05 (1H, s); 8.14 (1H, s); 8.45 (1H, s).

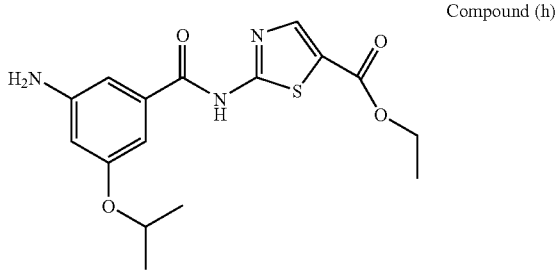

Compound (h)

10% Palladium on carbon (20 mg) was added under an argon atmosphere to a solution of ethyl 2-[(3-isopropoxy-5-nitro)benzoylamino]-5-thiazolecarboxylate (209 mg, 0.53 mM) in ethyl acetate (35 ml). Hydrogen gas was introduced and the reaction mixture stirred vigorously for 18 hrs before filtering through celite and concentration in vacuo to give compound (h) as pale yellow solid (160 mg, 83%); $^1$H nmr (d6-DMSO, δ values): 1.25 (6H, d); 1.29 (3H, t); 4.28 (2H, q); 4.58 (1H, m); 5.31 (2H, br s); 6.33 (1H, m); 6.81 (1H, m); 6.87 (1H, s); 8.17 (1H, s).

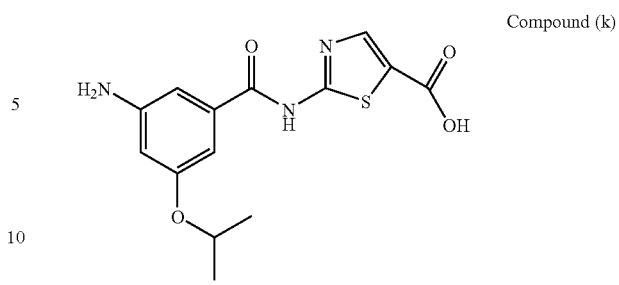

Compound (k)

2M Sodium hydroxide (0.3 ml, 0.57 mM) was added to a solution of ethyl 2-[(3-isopropoxy-5-amino)benzoylamino]-5-thiazolecarboxylate (40 mg, 0.11 mM) in tetrahydrofuran (1.2 ml)/methanol (0.5 ml) and heated at 50° C. for 5 hrs then at room temperature overnight. The reaction mixture was then concentrated in vacuo, acidified to pH 4-5 with 2M hydrochloric acid, the precipitate filtered, washed with water and dried under high-vacuum over silica gel. Compound (k) was obtained as a red-brown solid (35 mg, 100%); $^1$H nmr (d6-DMSO, δ values): 1.27 (6H, d); 4.63 (1H, m); 6.58 (1H, s); 7.05 (1H, s); 7.16 (1H, s); 8.14 (1H, s).

EXAMPLE H

Route 7:
2-[(3,5-dibenzyloxybenzoyl)amino]-5-aminopyridine

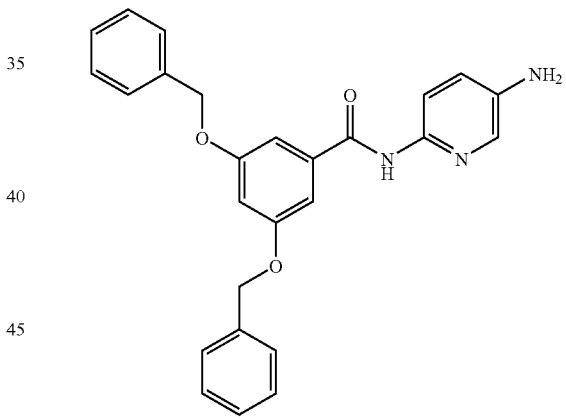

To a stirred solution of 2-[(3,5-dibenzyloxybenzoyl)amino]-5-nitropyridine (910 mg) in DMF (6 ml) was added Zinc dust (1300 mg) and a solution of ferric chloride hexahydrate (1700 mg) in water (6 ml). The resulting mixture was stirred at 120° C. for three hours. Allowed to cool to ambient temperature. The mixture was extracted with ethyl acetate. The extract was washed with water (50 ml), brine (50 ml), dried over MgSO4, then volatile material was removed by evaporation to leave a solid, which was dried under high vacuum for 24 hours at 100° C. to give the title compound (518 mg) as a solid, $^1$H NMR δ (d$_6$-DMSO): 5.17 (m, 6H), 6.80 (s, 1H), 7.00 (d, 1H), 7.26 to 7.46 (m, 12H), 7.71 (s, 1H), 7.78 (d, 1H), 10.28 (br s, 1H). MS ES$^+$ 426.52 (M+H)$^+$.

The requisite 6-[(3,5-dibenzyloxybenzoyl)amino]-3-nitropyridine starting material was prepared by a method analogous to that given in Example A (route 1), starting from 2-amino-5-nitropyridine; $^1$H NMR δ (d$_6$-DMSO): 5.18 (s, 4H), 6.90 (s, 1H), 7.29-7.50 (m, 12H), 8.42 (d, 1H), 8.64 (d, 1H), 9.23 (s, 1H), 11.46 (brs, 1H). MS ES+ 456.12 (M+H)+.

EXAMPLE I

Route 8: N-{6-[3,5-dibenzyloxybenzoyl)amino]-pyridin-3-yl}-2-acetoxy-2-methyl-propionamide

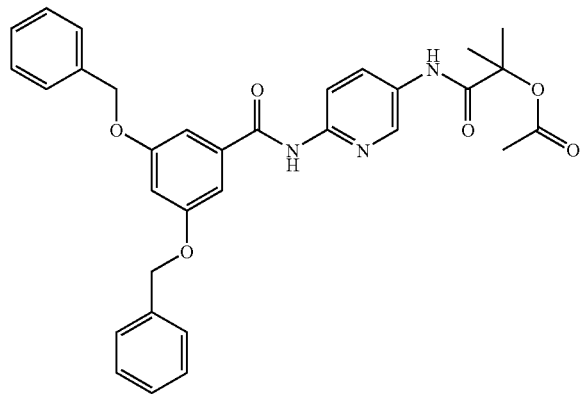

To a stirred solution of 2-[(3,5-dibenzyloxybenzoyl)amino]-5-aminopyridine (200 mg) in THF (2 ml) and pyridine (2 ml) was added a solution of 2-acetoxyisobutyryl chloride (98 mg) in THF (1 ml). The mixture was stirred at ambient temperature for 16 hours. Volatile material was removed by evaporation. The residue was dissolved in ethyl acetate (50 ml), washed with water (25 ml), brine (25 ml), dried over MgSO$_4$. Volatile material was removed by evaporation to leave a gum which was triturated under ether to give the title compound (211 mg) as a solid, $^1$H NMR δ (d$_6$-DMSO): 1.55 (s, 6H), 2.08 (s, 3H), 5.18 (s, 4H), 6.85 (s, 1H), 7.29 to 7.50 (m, 12H), 7.98 (dd, 1H), 8.13 (d, 1H), 8.61 (s, 1H), 9.70 (s, 1H), 10.72 (s, 1H). MS ES− 552.22 (M−H)−.

EXAMPLE J

Route 9: N-{6-[(3,5-dibenzyloxybenzoyl)amino]-pyridin-3-yl}-2-hydroxy-2-methyl-propionamide

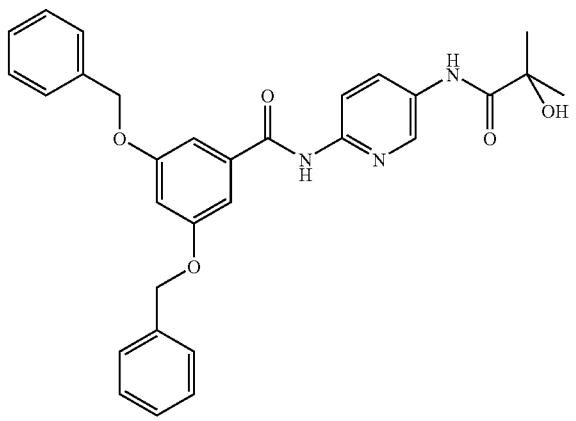

To a stirred suspension of N-{6-[(3,5-dibenzyloxybenzoyl)amino]-pyridin-3-yl}-2-acetoxy-2-methyl-propionamide (158 mg) in methanol (10 ml) was added a solution of LiOH.H2O (30 mg) in water (1 ml) and THF (3 ml). The mixture was stirred at ambient temperature for 20 hours. Volatile material was removed by evaporation. To the residue was added water (10 ml). Made acidic with 2M hydrochloric acid. Precipitate filtered off, washed with ethyl acetate, and dried under high vacuum to give the title compound (120 mg) as a solid, $^1$H NMR δ d$_6$-DMSO): 1.35 (s, 6H), 5.18 (s, 4H), 6.88 (s, 1H), 7.28 to 7.48 (m, 12H), 8.08 (d, 1H), 8.22 (d, 1H), 8.82 (s, 1H), 9.90 (s, 1H), 10.96 (s, 1H). MS ES+ 512.16 (M+H)+.

EXAMPLE K

Route 10: 3,5-dibenzyloxy-N-(5-{[(tert-butylamino)carbonyl]amino}pyridin-2-yl)benzamide

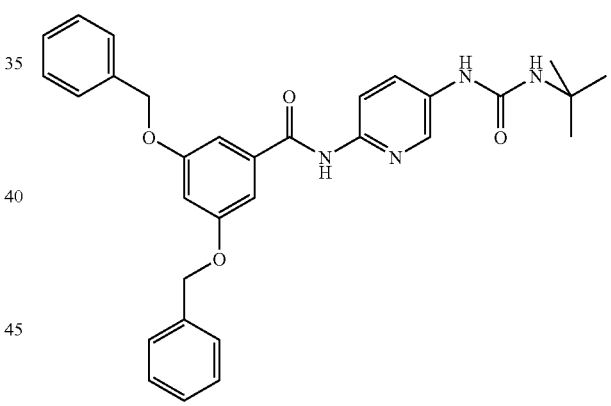

A solution of tert-butyl isocyanate (51 mg) in THF (5 ml) was treated with 2-[(3,5-dibenzyloxybenzoyl)amino]-5-aminopyridine (212 mg), and stirred at ambient temperature for 24 hours. More tert-butyl isocyanate (0.34 ml) added, and stirring continued at ambient temperature for a further 4 days. Volatile material was removed by evaporation and the residue was triturated under methanol to give the title compound (159 mg) as a solid, $^1$H NMR δ (d$_6$-DMSO): 1.30 (s, 9H), 5.18 (s, 4H), 6.09 (s, 1H), 6.85 (s, 1H), 7.32 to 7.50 (m, 12H), 7.78

(dd, 1H), 8.04 (d, 1H), 8.38 (s, 1H), 8.44 (s, 1H), 10.65 (s, 1H). MS ES+ 525.61 (M+H)+.

EXAMPLE L

Route 11: 3,5-di(2-cyanobenzyloxy)-N-[5-{(2-methoxyethyl)amino]pyridin-2-yl}benzamide

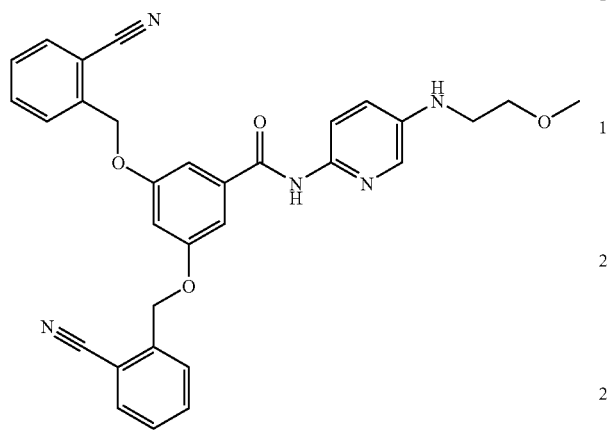

To a stirred solution of tert-butyl 6-({3,5-di(2-cyanobenzyloxy)benzoyl}amino)pyridin-3-yl(2-methoxyethyl)carbamate (237 mg) in dichloromethane (10 ml) was added trifluoroacetic acid (3 ml). The solution was stirred at ambient temperature for three hours. Volatile material was removed by evaporation. The residue was diluted in DCM (100 ml), washed with 2M sodium Hydroxide (50 ml), brine (50 ml), dried over MgSO4. Volatile material was removed by evaporation to give the title compound (190 mg) as a foam, 1H NMR δ (d6-DMSO): 3.22 (t, 2H), 3.28 (2, 3H), 3.50 (t, 2H), 5.31 (s, 4H), 6.92 (s, 1H), 7.12 (dd, 1H), 7.34 (s, 2H), 7.57 (m, 2H), 7.75 (m, 5H), 7.82 (d, 1H), 7.91 (d, 2H), 10.49 (br s, 1H). MS ES+ 534.41 (M+H)+.

The requisite starting materials were prepared as follows:

Preparation of tert-butyl 2-nitropyridin-5-yl(2-methoxyethyl)carbamate

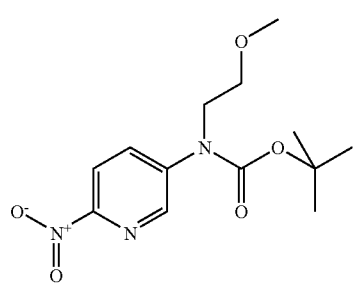

To a suspension of Cs2CO3 (1430 mg) in toluene was added 2-nitro-5-bromopyridine (406 mg), Pd(Ac)2 (44 mg), 1,1-bis(diphenylphosphino)ferrocene (322 mg) and 2-methyloxyethyl amine (0.26 ml). The mixture was stirred at 85° C., under Nitrogen, for 16 hours. Allowed to cool to ambient temperature. Diluted with ethyl acetate (100 ml), and filtered through a celite plug. Volatile material was removed by evaporation, the residue was purified by flash chromatography on silica, eluted with 50-100% ethyl acetate in hexane to give a solid which was added to a solution of di-tert-butyl-dicarbonate (436 mg) and N-dimethyl-aminopyridine (cat) in THF (10 ml). The solution was stirred for 14 hours at 75° C. Allowed to cool to ambient temperature, then the volatile material was removed by evaporation. The residue was dissolved in ethyl acetate (100 ml), washed with water (50 ml), brine (50 ml), dried over MgSO4. Volatile material was removed by evaporation, the residue was purified by flash chromatography on silica, eluted with 20-40% ethyl acetate in hexane to give the title compound (359 mg) as a gum, 1H NMR δ (CDCL3): 1.49 (s, 9H), 3.33 (s, 6H), 3.62 (t, 2H), 3.86 (t, 2H), 8.06 (dd, 1H), 8.21 (d, 1H), 8.65 (s, 1H). MS ES+ 298.35 (M+H)+.

Preparation of tert-butyl 2-aminopyridin-5-yl(2-methoxyethyl)carbamate

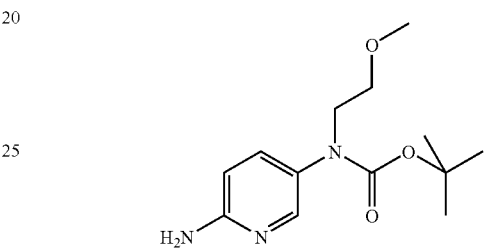

To a solution of tert-butyl 2-(6-nitropyridin-3-yl)-4-methoxybutanoate (350 mg) in ethanol (20 ml) and ethyl acetate (20 ml) was added 10% Palladium on carbon (100 mg). The suspension was stirred at ambient temperature for 16 hours under Hydrogen. Filtered through celite, then volatile material removed by evaporation to give the title compound (299 mg) as a solid, 1H NMR δ (d6-DMSO): 1.32 (brs, 9H), 3.18 (s, 3H), 3.34 (t, 2H), 3.56 (t, 2H), 5.84 (s, 2H), 6.37 (d, 1H), 7.17 (dd, 1H), 7.70 (d, 1H). MS ES+ 268.34 (M+H)+.

EXAMPLE M

Route 12: N-(5-aminopyridin-2-yl)-3-[(2-chlorobenzyl)oxy]-5-[(2-cyanobenzyl)oxy]benzamide

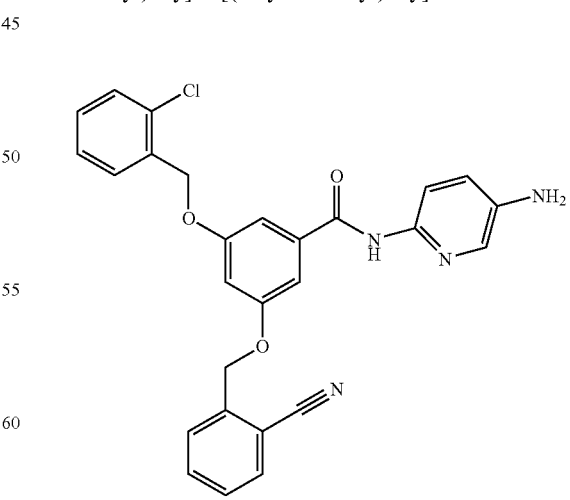

The title compound was prepared from N-(5-nitropyridin-2-yl)-3-[(2-chlorobenzyl)oxy]-5-[(2-cyanobenzyl)oxy]benzamide using a method similar to that described in Route 7.

The requisite starting materials were prepared as follows:

Preparation of 3-{[(5-nitropyridin-2-yl)amino]carbonyl}-5-[(2-cyanobenzyl)oxy]phenyl acetate

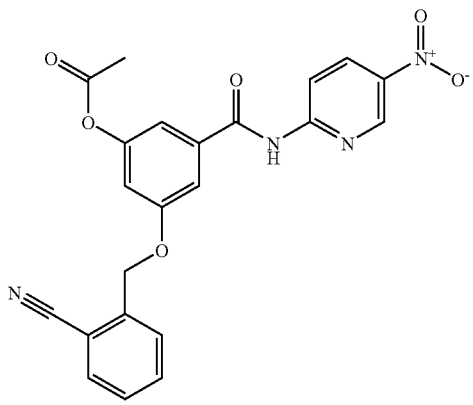

To a stirred solution of 3-acetoxy,5-(2-cyanobenzyloxy) benzoic acid (8760 mg) in THF (100 ml) was added Oxalyl chloride (3.6 ml) and DMF (0.5 ml). The mixture was stirred at ambient temperature for 3 hours. Volatile material was removed by evaporation. The residue was dissolved in a mixture of THF (60 ml) and pyridine (40 ml). 2-amino-5-nitropyridine (3919 mg) added. The stirred mixture was heated to 55° C. for 16 hours. Volatile material was removed by evaporation to leave a gum which was purified by flash chromatography on silica eluted with 1-5% ethyl acetate in hexane to give the title compound (6200 mg) as a solid, $^1$H NMR δ (d$_6$-DMSO): 2.29 (s, 3H), 5.37 (s, 2H), 7.17 (s, 1H), 7.45 (s, 1H), 7.58 (m, 1H), 7.70 (s, 1H), 7.76 (m, 2H), 7.92 (d, 1H), 8.40 (d, 1H), 8.65 (dm, 1H), 9.21 (m, 1H), 11.57 (s, 1H). MS ES$^+$ 433.48 (M+H)$^+$.

Preparation of N-(5-nitropyridin-2-yl)-3-[(2-cyanobenzyl)oxy]-5-hydroxybenzamide

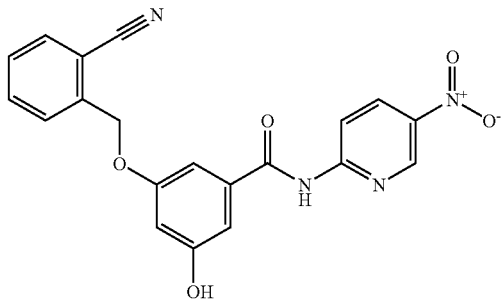

A suspension of 3-{[(5-nitropyridin-2-yl)amino]carbonyl}-5-[(2-cyanobenzyl)oxy]phenyl acetate (5710 mg) in THF (35 ml) was treated with 25% NaOMe in methanol (6 ml). Stirred at ambient temperature for 30 minutes. Acidified with 2m hydrochloric acid (25 ml), then extracted with ethyl acetate (100 ml). The extract was washed with water (50 ml), brine (50 ml), dried over MgSO$_4$. Volatile material was removed by evaporation to give a solid. This was washed with hot methanol to give the title compound (4358 mg) as a solid, LCMS rt=2.38 min (90.5%). ES$^+$ 391.45 (M+H)$^+$.

Preparation of N-(5-nitropyridin-2-yl)-3-[(2-chlorobenzyl)oxy]-5-[(2-cyanobenzyl)oxy]benzamide

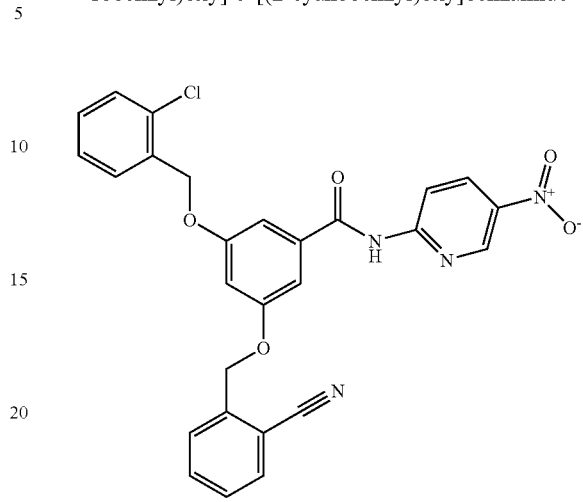

A solution of N-(5-nitropyridin-2-yl)-3-[(2-cyanobenzyl)oxy]-5-hydroxybenzamide (195 mg) in DMF (3 ml) was treated with Ag$_2$CO$_3$ (165 mg) and 2-Chlorobenzyl bromide (0.073 ml). Heated to 85° C. and stirred for 17 hours under Nitrogen. Allowed to cool to ambient temperature. Water (25 ml) added. Extracted with ethyl acetate (50 ml), washed with brine (25 ml), dried over MgSO$_4$. Volatile material was removed by evaporation to give a solid, which was purified by flash chromatography on silica eluted with 0-5% ethyl acetate in dichloromethane to give the title compound (43 mg) as a solid, $^1$H NMR δ (d$_6$-DMSO): 5.20 (s, 2H), 5.33 (s, 2H), 6.96 (s, 1H), 7.40 (m, 5H), 7.57 (m, 2H), 7.72 (m, 2H), 7.90 (d, 1H), 8.40 (d, 1H), 8.64 (dd, 1H), 9.22 (s, 1H), 11.50 (s, 1H). LCMS rt=3.27 min (97.4%), ES$^+$ 515.50 (M+H)$^+$.

EXAMPLE N

Route 13: 6-{[3,5-Di-(benzyloxy)benzoyl]amino}-N-[2-(dimethylamino)ethyl]nicotinamide

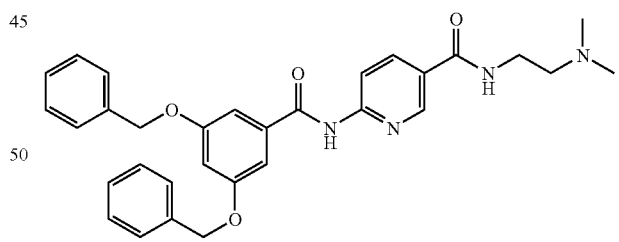

Diisopropylethylamine (DIPEA, 0.23 ml, 1.3 mM) then 1-(3-dimethylaminopropyl)-3-ethyl-carbodiimide (EDC, 126 mg, 0.66 mM) were added to a solution of 2-dimethylaminoethylamine (0.57 ml, 0.53 mM) and 6-{[3,5-Di-(benzyloxy)benzoyl]amino}nicotinic acid (0.20 g, 0.44 mM) in dichloromethane (10 ml) under argon at ambient temperature. After 16 hours the reaction mixture was evaporated in vacuo and then chromatographed on SiO$_2$ using a gradient elution of 10 to 25% methanol in dichloromethane. The fractions containing product were evaporated to give a cream solid (0.052 g, 25%); $^1$H NMR δ (d$_6$-DMSO): 2.67 (6H, s); 3.11 (2H, m); 3.62 (2H, m); 5.18 (4H, s); 6.88 (1H, s); 7.27-7.52 (12H, br m); 8.18-8.36 (2H, m); 8.90 (1H, s); 10.20 (1H, br s).

EXAMPLE O

Route 14: 2-[3,5-Di-(2-chlorobenzyloxy)benzoylamino]-5-hydroxymethyl pyridine

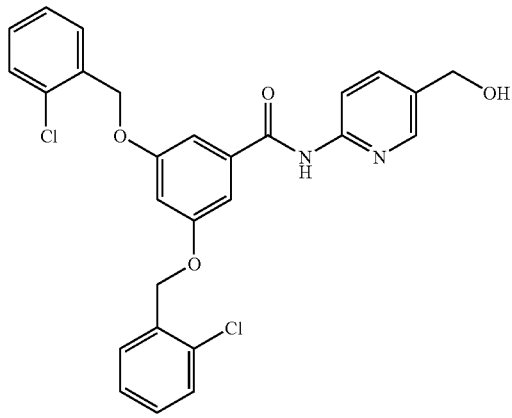

To a cold (−15 degC.) solution of 2-[3,5-Di-(2-chlorobenzyloxy)benzoyl)amino]-pyridine-5-carboxylic acid (305 mg, 0.59 mmol) in dimethoxy ethane (5 ml) was added 4-methyl morpholine (80 μl, 1 eq) and isobutyl chloroformate (76 μl, 1.02 eq). The reaction mixture was stirred at −15 deg C. for 15 mins and then filtered; the residue was washed with dimethoxy ethane (5×1 ml). The filtrate and washings were cooled to −15 deg C. and treated with a suspension of sodium borohydride (22 mg, 1 eq) in water (1 ml). After the effervescence had ceased, water (50 ml) and ethyl acetate (30 ml) were added; the reaction mixture was evaporated to dryness and the residue absorbed onto silica. The required compound was isolated by flash chromatography (eluting with 5% methanol in dichloromethane) to give the title compound as a colourless solid (97 mg), $^1$H NMR δ (d$_6$-DMSO): 4.5 (1H, d), 5.25 (s, 4H), 6.9 (s, 1H), 7.40 (m, 6H), 7.5 (m, 2H), 7.6 (m, 2H), 7.75 (dd, 1H), 8.10 (d, 1H), 8.3 (s, 1H), 10.8 (br s, 1H); LCMS rt=3.25 min (100%), ES$^+$ 509 (M+H)$^+$.

EXAMPLE P

Route 15: N-{6-[3,5-di-(2-chlorobenzyloxybenzoyl)amino]-pyridin-2-yl}-2-acetamide

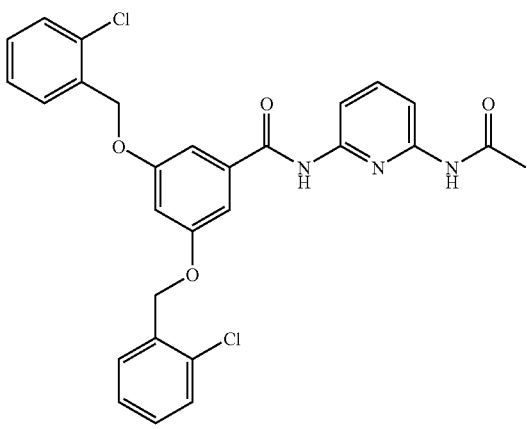

To a solution of 2-[(3,5-di-(2-chlorobenzyloxybenzoyl)amino]-6-aminopyridine (220 mg, 0.45 mmol) in tetrahydrofuran (4 ml) was added pyridine (43 mg, 0.54 mmol) and acetyl chloride (42 mg, 0.54 mmol), and the reaction mixture stirred at ambient temperature for 16 hours. The reaction mixture was diluted with diethyl ether and washed successively with water, 1M citric acid, and water; the solution was dried over magnesium sulfate and the solvent removed in vacuo to give a yellow solid (154 mg). Trituration with methanol gave the title compound (75 mg), $^1$H NMR δ (d$_6$-DMSO): 3.3 (3H, s), 5.25 (s, 4H), 6.95 (s, 1H), 7.3 (d, 2H), 7.4 (m, 4H), 7.5 (m, 2H), 7.6 (m, 2H), 7.7 (m, 1H), 7.8 (m, 2H), 10.14 (br s, 1H), 10.36 (br s, 1H); ES$^+$ 536/538 (M+H)$^+$.

The starting material, 2-[(3,5-di-(2-chlorobenzyloxybenzoyl)amino]-6-aminopyridine, is exemplified herein as Example number 106.

EXAMPLE Q

Route 16: 3,5-bis(benzyloxy)-N-[5-(1H-tetrazol-5-yl)pyridin-2-yl]benzamide

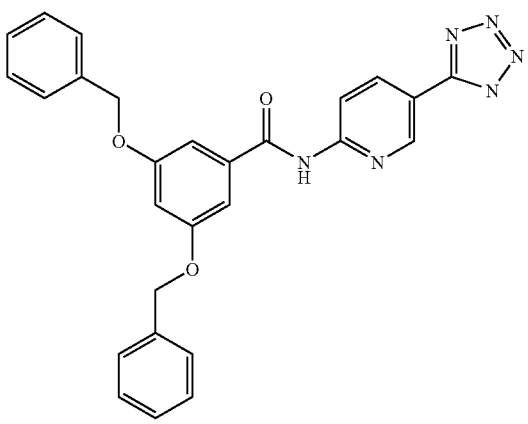

Tributyltin azide (156 μL, 0.57 mmol) was added to a suspension of 3,5-bis(benzyloxy)-N-(5-cyanopyridin-2-yl)benzamide (180 mg, 0.41 mmol) in toluene (3 mL). The mixture was heated at reflux for 16 hours. The suspension was cooled and partitioned between ethyl acetate and hydrochloric acid (1M). The organic layer was concentrated in vacuo and the residue was purified by MPLC on silica MPLC (eluting with 1% methanol/DCM to 15% methanol/DCM). The tetrazole was obtained as a colourless solid (113 mg, 57%). $^1$H NMR δ (d$_6$-DMSO): 5.19 (4H, s); 6.88 (1H, s); 7.26-7.48 (12H, m); 8.40 (1H, d); 8.46 (1H, dd); 9.04 (1H, s); 11.13 (1H, br s); m/z (LCMS; ESI+) 479 (MH$^+$).

The requisite starting material was prepared as follows:

Preparation of 3,5-bis(benzyloxy)-N-(5-cyanopyridin-2-yl)benzamide

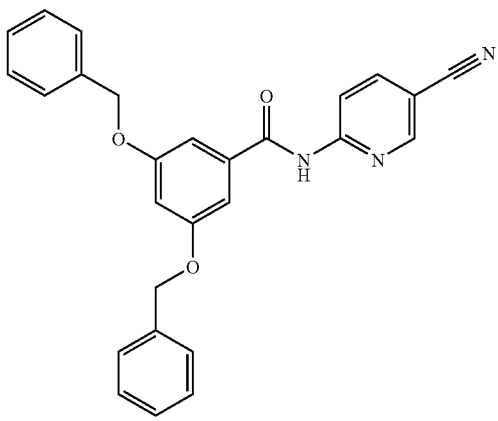

The title compound was prepared as described in Example A (route 1), starting from 2-amino-5-cyanopyridine and 3,5-bis(benzyloxy)benzoyl chloride, $^1$H NMR δ (d$_6$-DMSO): 5.19 (4H, s); 6.89 (1H, m); 7.26-7.46 (12H, m); 8.27 (1H, dd); 8.33 (1H, d); 8.84 (1H, s); 11.23 (1H, br s); m/z (LCMS; ESI+) 436 (MH$^+$).

The requisite 2-amino-5-cyanopyridine starting material may be purchased (Bionet Research, and other suppliers), or may be prepared according to the method given in WO95/06034.

EXAMPLE R

Route 17: 3,5-bis(benzyloxy)-N-[5-(5-oxo-4,5-dihydro-1,2,4-oxadiazol-3-yl)pyridin-2-yl]benzamide

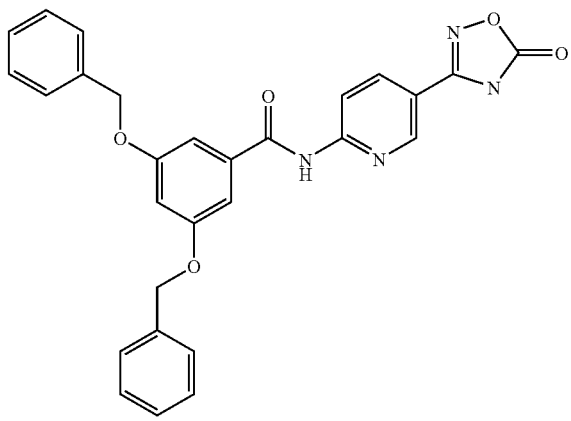

Ethyl chloroformate (32 μL, 0.33 mmol) was added to a solution of 3,5-bis(benzyloxy)-N-{5-[(hydroxyamino)(imino)methyl]pyridin-2-yl}benzamide (140 mg, 0.30 mmol) in pyridine (5 mL). This solution was heated at reflux overnight. The mixture was cooled and concentrated under reduced pressure. DCM and methanol were used to dissolve the remaining material and the solution was washed with water. The organic solution was concentrated under reduced pressure and the residue was purified on silica by MPLC (eluting firstly with 5% methanol/DCM then 10% methanol/DCM). The title compound was obtained as a colourless solid (103 mg, 70%). $^1$H NMR δ (d$_6$-DMSO): 5.19 (4H, s); 6.87 (1H, s); 7.28-7.46 (12H, m); 8.21 (1H, dd); 8.38 (1H, d); 8.79 (1H, s); 11.14 (1H, br s); m/z (LCMS; ESI+) 495 (MH$^+$).

The requisite staring material was prepared as follows:

Preparation of 3,5-bis(benzyloxy)-N-{5-[(hydroxyamino)(imino)methyl]pyridin-2-yl}benzamide

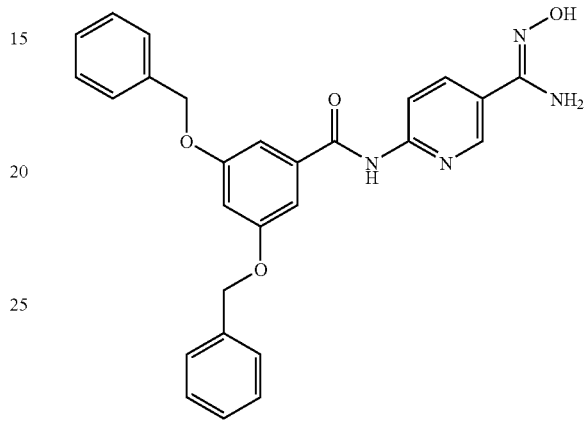

A mixture of 3,5-bis(benzyloxy)-N-(5-cyanopyridin-2-yl)benzamide (212 mg, 0.49 mmol), triethylamine (170 μL, 1.22 mmol) and hydroxylamine hydrochloride (85 mg, 1.22 mmol) in ethanol (5 mL) was heated at reflux overnight. The mixture was cooled and concentrated under reduced pressure. The residue was purified by MPLC on silica eluting with 5% methanol/DCM then 15% methanol/DCM. The title compound was obtained as a colourless solid (171 mg, 75%). $^1$H NMR δ (d$_6$-DMSO): 5.19 (4H, s); 5.92 (2H, s), 6.87 (1H, s); 7.28-7.48 (12H, m); 8.06 (1H, dd); 8.17 (1H, d), 8.65 (1H, s); 9.68 (1H, s); 10.85 (1H, br s); m/z (LCMS; ESI+) 469 (MH$^+$).

The requisite 3,5-bis(benzyloxy)-N-(5-cyanopyridin-2-yl)benzamide was prepared as described in Example P (route 15).

EXAMPLE S

Route 18: [(2-{[3,5-bis(benzyloxy)benzoyl]amino}pyridin-5-yl)amino](oxo)acetic acid

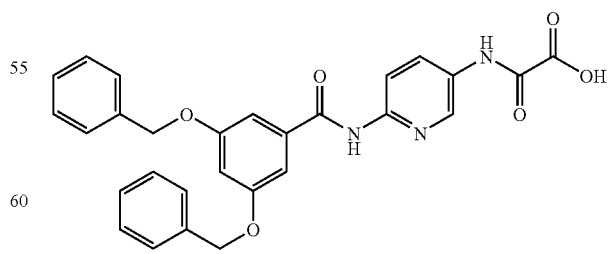

Methyl oxalyl chloride (37 μL, 0.4 mmol) was added to a mixture of N-(5-aminopyridin-2-yl)-3,5-bis(benzyloxy)benzamide (150 mg, 0.36 mmol) and triethylamine in DCM (5 mL). The mixture was stirred for 1 hour under an atmosphere of nitrogen. The solution was diluted with DCM and washed with water. The organics were concentrated under reduced pressure and the residue was purified on silica by MPLC (eluting with 1% methanol/DCM to 15% methanol/DCM) to give a colourless solid (110 mg). This material was dissolved in THF (2 mL). Water (3 mL) and sodium hydroxide (0.5 mL, 2M, 1 mmol) were added. The mixture was stirred for 1 hour before being acidified with hydrochloric acid (2M) and diluted with water. The resulting precipitate was isolated by filtration, washed with water and dried in vacuo. The title compound was obtained as a colourless solid (88 mg, 50%). $^1$H NMR δ (d$_6$-DMSO): 5.18 (4H, s); 6.88 (1H, s); 7.30-7.50 (12H, m); 8.17 (2H, s); 8.79 (1H, s); 10.79 (1H, s); 10.93 (1H, br s); m/z (LCMS; ESI+) 498 (MH$^+$).

The requisite starting material was prepared according to Example H (route 7).

EXAMPLE T

By analogous methods to those described above the following compounds, Example numbers T$_1$ to T$_{20}$, were also made.

Compound T$_9$ was prepared by Route 1b (multi-parallel synthesis), as follows. To the appropriate acid (6.0 mmol) in dichloromethane (25 mls) was added 1 drop of dimethylformamide and the mixture stirred at room temperature under argon. The oxalyl chloride (0.867 mls) was added to the acid and stirred at room temperature for 2 hrs. The solvent was removed in Genevac DD4, and resulting residue azeotroped with dichloromethane (3×10 mls), then dried high vacuum for 2 hrs. The resulting acid chloride was then dissolved in THF (30 mls) and 5 mls of the solution was added to one of the set of six amines in THF/Pyridine (5 mls). The resulting mixture was stirred overnight at room temperature, diluted with ethyl acetate (5 mls). The resulting solution was transferred to the Allex automated extractor and washed with water (2×5 mls), sodium hydrogen carbonate (5 mls), 1M citric acid (5 mls), brine (5 mls) dried (magnesium sulphate) and evaporated in Genevac DD4. The resulting gum was triturated with methanol (1-2 mls) and the resulting solid filtered, washed methanol and air-dried.

| Example | Structure | Route | NMR |
|---|---|---|---|
| 1 | 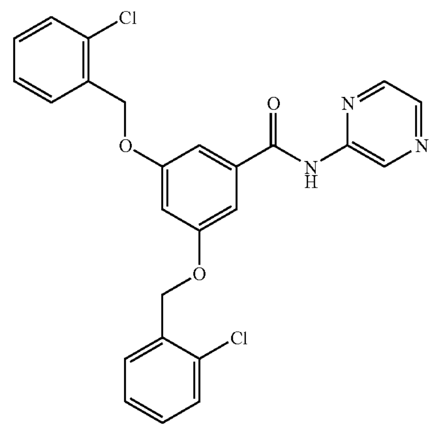 | 1 | 1H NMR d (d6-DMSO): 5.26 (4H, s); 6.96 (1H, m); 7.38-7.45 (6H, m); 7.53 (2H, m); 7.62 (2H, m); 8.43 (1H, d); 8.49 (1H, m); 9.42 (1H, m); 11.13 (1H, s). |
| 2 | 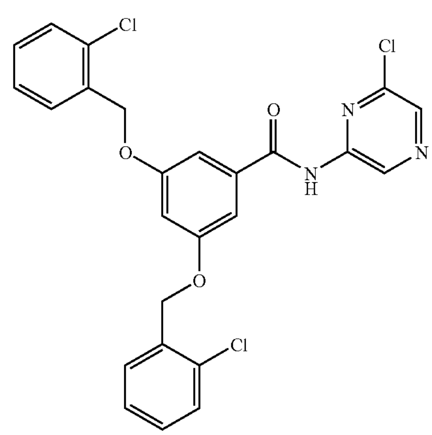 | 1 | 1H NMR d (d6-DMSO): 5.25 (4H, s); 6.97 (1H, m); 7.38-7.45 (6H, m); 7.53 (2H, m); 7.63 (2H, m); 8.64 (1H, d); 9.26 (1H, d); 11.33 (1H, s). |

| Example | Structure | Route | NMR |
|---|---|---|---|
| 3 | 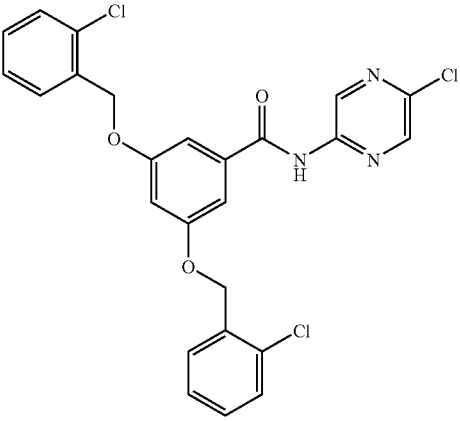 | 1 | 1H NMR d (d6-DMSO): 5.24 (4H, s); 6.95 (1H, s); 7.35-7.40 (6H, m); 7.50 (2H, m); 7.60 (2H, m); 8.61 (1H, s); 9.22 (1H, s); 11.25 (1H, br s). |
| 4 | 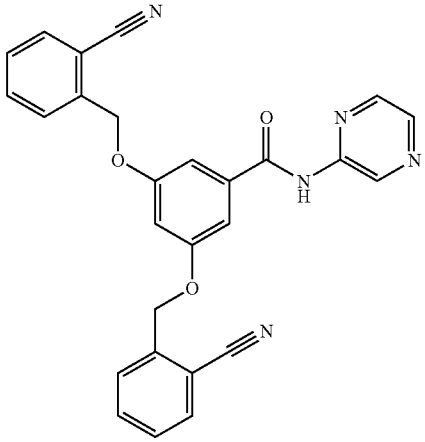 | 1 | 1H NMR d (d6-DMSO): 5.36 (4H, s); 7.00 (1H, m); 7.44 (2H, d); 7.55-7.64 (2H, m); 7.77 (4H, m); 7.93 (2H, d); 8.43 (1H, d); 8.49 (1H, m); 9.43 (1H, s); 11.17 (1H, s). |
| 5 | 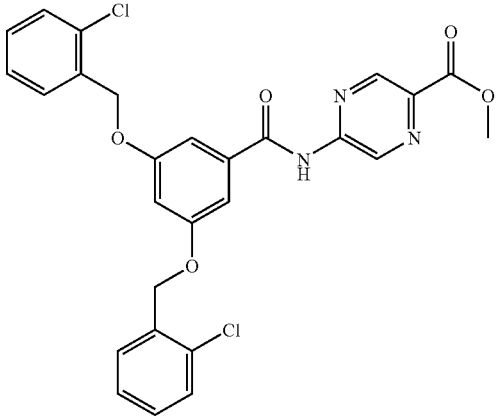 | 1 | 1H NMR d (d6-DMSO): 3.90 (3H, s); 5.24 (4H, s), 6.97 (1H, m), 7.39 (6H, m); 7.50 (2H, m); 7.60 (2H, m); 9.02 (1H, s); 9.52 (1H, s); 11.54 (1H, br s). |

| Example | Structure | Route | NMR |
|---|---|---|---|
| 6 | 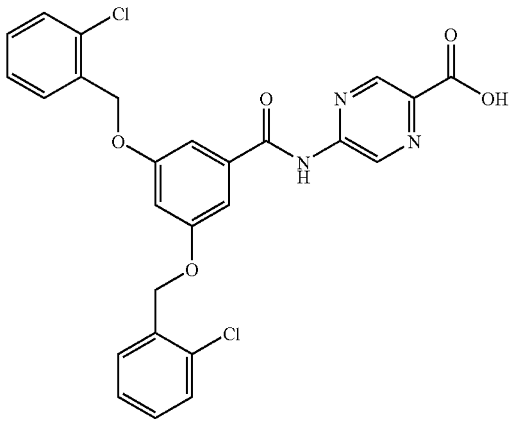 | 2 | 1H NMR d (d6-DMSO): 5.24 (4H, s); 6.96 (1H, m); 7.39 (6H, m); 7.51 (2H, m); 7.62 (2H, m); 8.98 (1H, s); 9.48 (1H, s); 11.44 (1H, br s). |
| 7 | 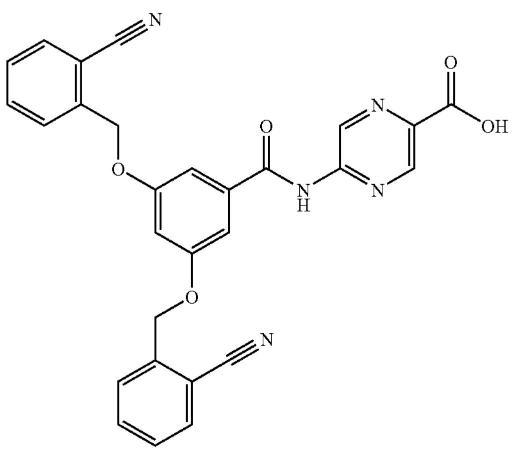 | 2* | 1H NMR d (d6-DMSO): 5.34 (4H, s); 7.00 (1H, s); 7.57 (2H, m); 7.75 (4H, m); 7.91 (2H, d); 9.00 (1H, s); 9.52 (1H, s); 11.53 (1H, s); 13.43, (1H br s). |
| 8 | 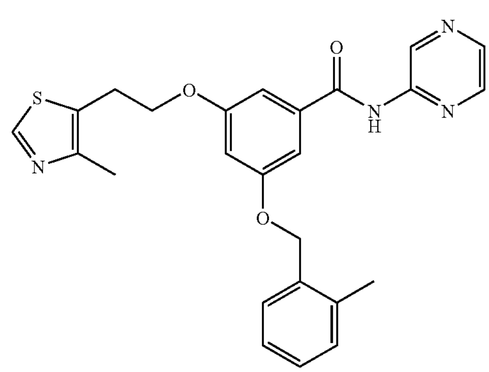 | 1 | 1H NMR d (d6-DMSO): 2.29 (3H, s); 2.33 (3H, s); 3.24 (m, 2H); 4.21 (2H, t); 5.12 (2H, s); 6.80 (1H, m); 7.21 (4H, m); 7.31 (1H, m); 7.40 (2H, m); 8.39 (1H, m); 8.45 (1H, m); 8.82 (1H, s); 9.38 (1H, s); 11.06 (1H, br s). |
| 9 | 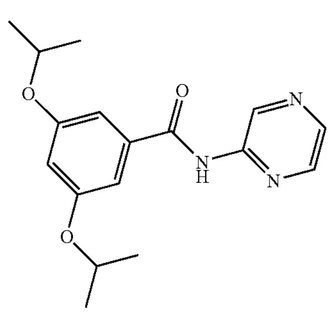 | 1b | $^1$H NMR d (d$_6$-DMSO): 1.25 (d, 12H), 4.7 (hept, 2H), 6.6 (d, 1H), 7.2 (d, 2H), 8.4 (d, 1H), 8.45 (t, 1H), 9.4 (s, 1H), 11.0 (br s, 1H). |

-continued

| Example | Structure | Route | | NMR |
|---|---|---|---|---|
| 10 | 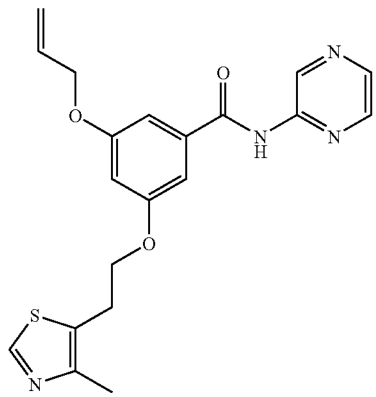 | 1 | | ¹H NMR δ (d₆-DMSO): 2.37 (s, 3H), 3.24 (t, 2H), 4.23 (t, 2H), 4.65 (d, 2H), 5.28 (d, 1H), 5.42 (d, 1H), 6.05 (m, 1H), 6.75 (s, 1H), 7.23 (s, 2H), 8.43 (s, 1H), 8.84 (s, 1H), 9.40 (s, 1H), 11.07 (br s, 1H). |
| 11 | 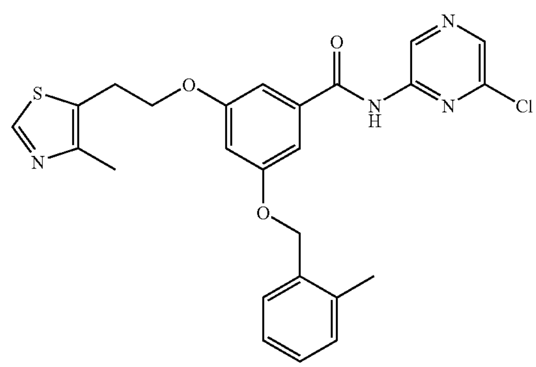 | 1 | | ¹H NMR δ (d₆-DMSO): 2.32 (s, 3H), 2.35 (s, 3H), 3.21 (t, 2H), 4.21 (t, 2H), 5.13 (s, 2H), 6.81 (s, 1H), 7.14-7.26 (m, 4H), 7.32 (1H, s), 7.41 (1H, d), 8.51 (s, 1H), 8.81 (s, 1H), 9.39 (s, 1H), 11.34 (brs, 1H). |
| 12 | 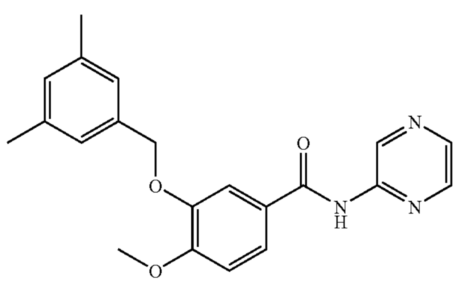 | 1 | 364 | ¹H NMR δ (d₆-DMSO): 2.12 (s, 6H), 3.81 (s, 3H), 5.05 (s, 2H), 6.95 (s, 1H), 7.05 (s, 2H), 7.1 (s, 1H), 7.72 (d, 1H), 7.78 (s, 1H), 8.36 (d, 1H), 8.43 (s, 1H), 9.4 (s, 1H), 10.92 (br s, 1H) |
| 13 | 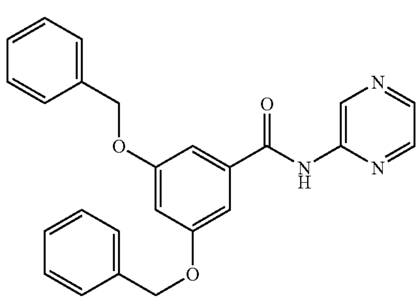 | 1b | 412 410 | |
| 14 | 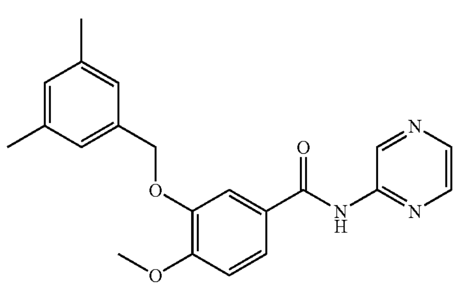 | 1b | 330 | |

-continued
| Example | Structure | Route | NMR |
|---|---|---|---|
| 15 | 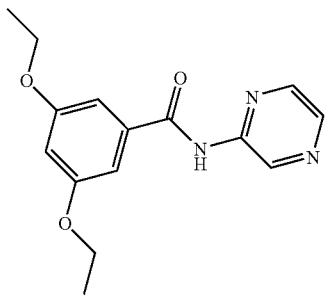 | 1b | 288 |
| 16 | 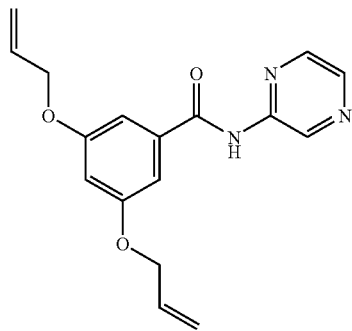 | 1b | 312 |
| 17 | 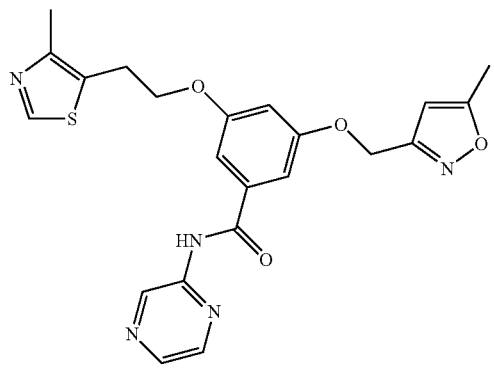 | 1b | 452 |
| 18 | 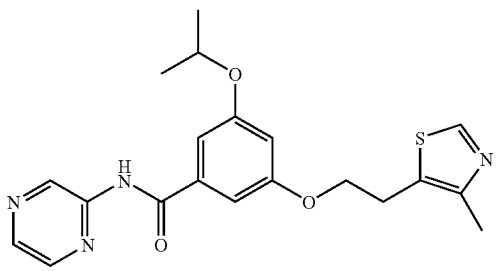 | 1b | 400 |

-continued

| Example | Structure | Route | | | NMR |
|---|---|---|---|---|---|
| 19 | 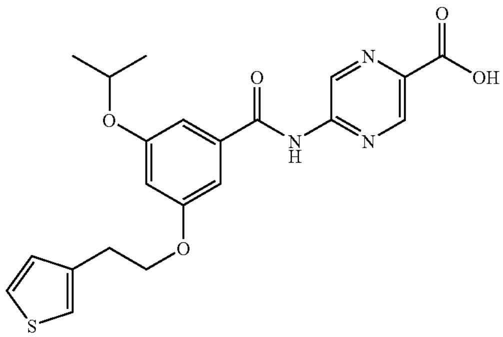 | 2a, 1c | 428 | 426 | δ_H (500 MHz, DMSO-d_6) 1.28 (6H, d), 3.07 (2H, t), 4.26 (2H, t), 4.70 (1H, m), 6.71 (1H, m), 7.12 (1H, m), 7.24 (2H, m), 7.30 (1H, m), 7.46 (1H, m), 8.98 (1H, d), 9.48 (1H, d), 11.33 (1H, s), 13.24 (1H, br s). |
| 20 | 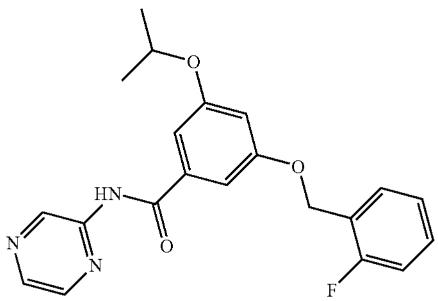 | 1a | 382 | | |

*For Example 7, the ester intermediate was prepared by route 1:

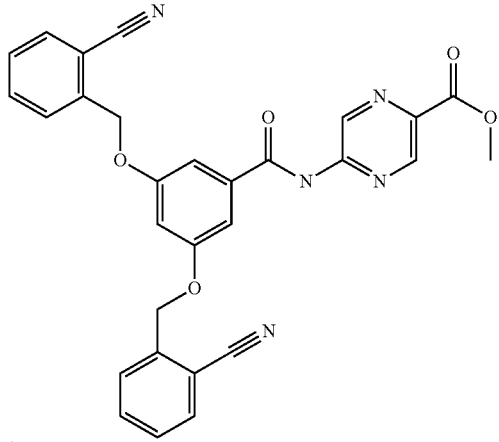

$^1$H NMR δ (d_6-DMSO): 3.90 (3H, s); 5.34 (4H, s); 7.01 (1H, s); 7.43 (2H, s); 7.58 (2H, m); 7.74 (4H, m); 7.91 (2H, d); 9.02 (IH. s); 9.52 (1H, s); 11.57 (IH, br s).

EXAMPLE U

2-[3-{2-(4-methyl thiazol-5-yl)ethoxy}-5-dimethylamino]benzoylamino]-[1,3,4]-thiadiazole (Route 19)

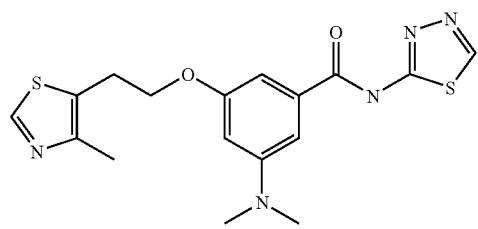

Formaldehyde (37% in water) (0.033 ml, 0.44 mM) was added to 2-[3-{2-(4-methyl thiazol-5-yl)ethoxy}-5-amino] benzoylamino]-[1,3,4]-thiadiazole (27 mg 0.074 mM) and 4A molecular sieves (0.2 g) in methanol (4 ml)/acetonitrile (3 ml)/g.AcOH (2 drops) under an inert atmosphere at room temperature. After 150 mins sodium cyanoborohydride (7 mg, 0.12 mM) was added and the reaction mixture stirred for 40 hrs. The reaction mixture was filtered, concentrated in vacuo, the residue acidified with 2M HCl to precipitate a colourless solid. Purified on silica gel (50 to 75% EtOAc/isohexane) gave the title compound as a colourless solid (25 mg, 85%); $^1$H NMR δ (d_6-DMSO): 2.35 (s, 3H), 2.93 (s, 6H), 3.22 (m, 2H), 4.19 (m, 2H), 6.41 (m, 1H), 6.98 (m, 1H), 7.06 (m, 1H), 8.80 (s, 1H), 9.17 (s, 1H).

The requisite 2-[3-{2-(4-methyl thiazol-5-yl)ethoxy}-5-amino]benzoylamino]-[1,3,4]-thiadiazole starting material was prepared as follows:

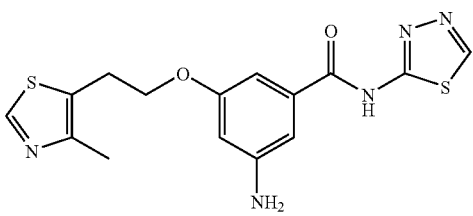

10% Palladium on carbon (80 mg) was added under an argon atmosphere to a solution of 2-[3-{2-(4-methyl thiazol-5-yl)ethoxy}-5-nitro]benzoylamino]-[1,3,4]-thiadiazole (0.38 g, 0.99 mM) in ethyl acetate (40 ml). Hydrogen gas was introduced and the reaction mixture stirred vigorously for 18 hrs before filtering through celite, concentration in vacuo and replacement of the catalyst (80 mg). After stirring under hydrogen gas for a further 18 hrs a final catalyst change was carried out. After which the crude aniline was purified on silica gel (1% to 4% MeOH/DCM) to give 2-[3-{2-(4-methyl thiazol-5-yl)ethoxy}-5-amino]benzoylamino]-[1,3,4]-thiadiazole as a colourless solid (0.1 g, 28%); MS (M−H$^+$)$^−$ 360.

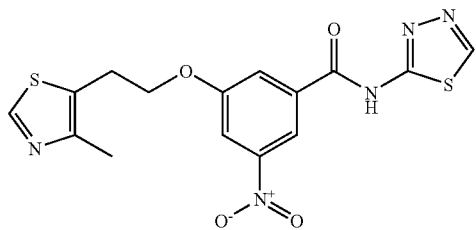

Oxalyl chloride (0.20 ml, 2.35 mM) was added to 3-{2-(4-methyl thiazol-5-yl)ethoxy}-5-nitro benzoic acid (0.72 g, 2 mM) in dichloromethane (30 ml) containing DMF (2 drops) under an argon atmosphere at room temperature. After 3 hrs the reaction mixture was concentrated in vacuo and azeotroped with toluene to give an off-white solid. The acid chloride and 2-amino-[1,3,4]-thiadiazole (0.19 g, 1.9 mM) were dissolved in DCM (20 ml) then DIPEA (0.96 ml, 5.6 mM) and DMAP (0.04 g, 0.3 mM) added. After stirring overnight under argon the reaction mixture was concentrated, purified on silica gel (50% to 75% to 100% EtOAc/iso-hexane) gave a pale yellow solid which was triturated with MeOH to give 2-[3-{2-(4-methyl thiazol-5-yl)ethoxy}-5-nitro]benzoylamino]-[1,3,4]-thiadiazole as a colourless solid (0.30 g, 48%); $^1$H NMR δ (d$_6$-DMSO): 2.37 (s, 3H), 3.26 (t, 2H), 4.35 (t, 2H), 7.89 (m, 1H), 8.09 (s, 1H), 8.47 (s, 1H), 8.81 (s, 1H), 9.24 (s, 1H).

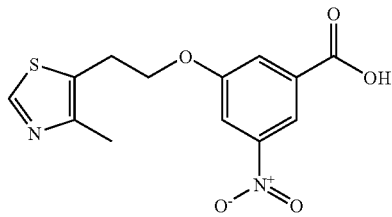

DIAD (3.16 ml, 16.1 mM) was added to a stirred solution of methyl 3-nitro-5-hydroxy benzoate (2.11 g, 10.7 mM), 4-(2-hydroxy ethyl)-5-methylthiazole (1.55 ml, 12.8 mM), and triphenylphosphine (4.21 g, 16.1 mM) in THF (50 ml) under an argon atmosphere at room temperature. After 1 hr reaction mixture concentrated in vacuo, residue triturated with diethyl ether to give a colourless solid (triphenylphosphine oxide). Diethyl ether conc. to give a dark brown gum, purification on silica gel (50% to 75% EtOAc/iso-hexane) gave the product contaminated with reduced DIAD and triphenylphosphine oxide (6.8 g). The crude product was dissolved/suspended in MeOH (80 ml), 2M NaOH (20 ml, 40 mM) added, heated at 65° C. for 4 hrs then cooled and concentrated. The residue was diluted with water (140 ml)/2M NaOH (40 ml), the precipitated triphenylphosphine oxide filtered, then acidified with c.HCl to pH1-2. The precipitate was filtered, washed with water, dried under high-vacuum to give 3-{2-(4-methyl thiazol-5-yl)ethoxy}-5-nitro benzoic acid as a colourless solid (3.12 g, 79% over 2 steps); $^1$H NMR δ (d$_6$-DMSO): 2.39 (s, 3H), 3.23 (t, 2H), 4.35 (t, 2H), 7.78 (s, 1H), 7.90 (m, 1H), 8.22 (s, 1H), 8.93 (s, 1H).

EXAMPLE V

2-[3-{2-(4-methyl thiazol-5-yl)ethoxy}-5-hydroxy]benzoylamino]-[1,3,4]-thiadiazole (Route 20)

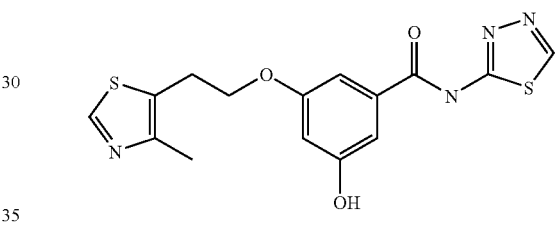

A solution of 2-[3-{2-(4-methyl thiazol-5-yl)ethoxy}-5-allyloxy]benzoylamino]-[1,3,4]-thiadiazole (1.1 g, 2.7 mmol) in tetrahydrofuran (40 ml) was stirred under an argon atmosphere and treated with Meldrum's acid (0.79 g, 5.4 mmol) and tetrakis(triphenyl phosphine) palladium (0) (825 mg, 0.7 mmol, 0.25 eq) and the resulting yellow solution stirred at ambient temperature for 2 hours. Sequential triturations with dichloromethane and hot tetrahydrofuran gave 2-[3-{2-(4-methyl thiazol-5-yl)ethoxy}-5-hydroxy]benzoylamino]-[1,3,4]-thiadiazole as a colourless solid (0.59 g, 59%), $^1$H NMR δ (d$_6$-DMSO): 2.35 (s, 3H), 3.2 (t, 2H), 4.2 (t, 2H), 6.55 (m, 1H), 7.05 (s, 1H), 7.2 (s, 1H), 8.81 (s, 1H), 9.2 (s, 1H), 9.8 (br s, 1H); m/z 363 (M+H)+, 361 (M−H)−.

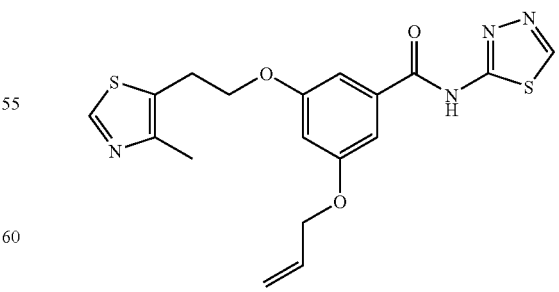

The requisite 2-[3-{2-(4-methyl thiazol-5-yl)ethoxy}-5-allyloxy]benzoylamino]-[1,3,4]-thiadiazole starting material was prepared according to the appropriate generic alkylation method, and the resulting benzoic acid coupled with 1,3,4-thiadiazole according to Route 1. The analytical data on all intermediates was consistent with the proposed structures.

EXAMPLE W 2-(3-isopropoxy-5-dimethylaminomethyl)benzoyl aminothiazole (Route 21)

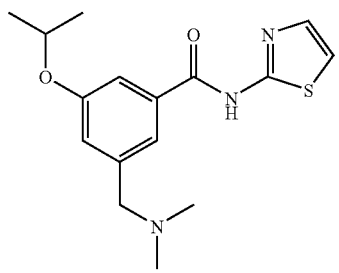

A solution of 2-(3-isopropoxy-5-formyl)benzoyl aminothiazole (0.11 g, 0.39 mmol) in dichloromethane was treated with dimethylamine (0.074 ml of an approx. 5.6M solution in ethanol, 0.41 mmol, 1.1 eq) and stirred under argon for 10 mins. To the solution was added sodium tris-acetoxy borohydride (0.11 g, 0.53 mmol, 1.4 eq), and the resulting mixture stirred overnight at ambient temperature. Further reagents were then added (same quantities as before) and the mixture again stirred overnight at ambient temperature. The solution was treated with saturated sodium bicarbonate solution (10 ml) and stirred for 20 mins; it was then extracted twice with dichloromethane, the organic extracts dried over magnesium sulfate and evaporated in vacuo to give the product as a colourless oil. This was dissolved in ethyl acetate and the solution treated with an ethereal solution of HCl (excess of 1M); the precipitate thus formed was filtered under argon and washed with diethyl ether to give 2-(3-isopropoxy-5-dimethylaminomethyl)benzoyl aminothiazole hydrochloride as a colourless solid (0.1 g, 72%), $^1$H NMR δ (d$_6$-DMSO): 1.31 (d, 6H), 2.71 (s, 6H), 4.26 (m, 2H), 4.76 (m, 1H), 7.29 (d, 1H), 7.42 (m, 1H), 7.55 (d, 1H), 7.70 (s, 1H), 10.66 (bs, 1H).

The requisite starting material was prepared as follows:

EXAMPLE X 2-(3-isopropoxy-5-formyl)benzoyl aminothiazole (Route 22):

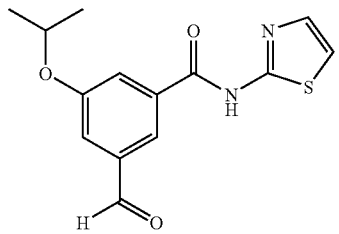

A solution of 2-(3-isopropoxy-5-hydroxymethyl)benzoyl aminothiazole (0.115 g, 0.39 mmol) in tetrahydrofuran (8 ml) was treated with manganese dioxide (0.27 g, 3.1 mmol, 8 eq) and the resulting suspension stirred overnight at ambient temperature; additional oxidant (0.1 g portions) was added until all the starting material was consumed (tlc). The suspension was filtered, the residue washed well with ethyl acetate, and the combined filtrate and washings evaporated in vacuo to give the product as a pale yellow solid, $^1$H NMR δ (d$_6$-DMSO): 1.31 (d, 6H), 4.82 (m, 1H), 7.26 (d, 1H), 7.56 (d, 1H), 7.59 (s, 1H), 7.94 (d, 1H), 8.15 (s, 1H), 10.00 (s, 1H), 12.77 (bs, 1H).

The requisite starting material was prepared as follows:

EXAMPLE Y 2-(3-isopropoxy-5-hydroxymethyl)benzoyl aminothiazole (Route 23)

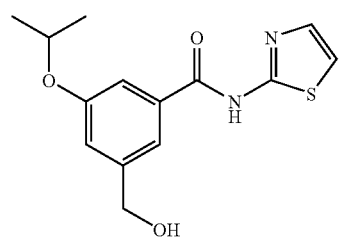

Standard ester cleavage of 2-(3-isopropoxy-5-acetoxymethyl)benzoyl aminothiazole (0.15 g, 0.46 mM) using 2M NaOH/THF/MeOH for 1 hour gave 2-(3-isopropoxy-5-hydroxymethyl)benzoyl aminothiazole as a colourless solid (0.149 g, 100%); $^1$H NMR δ (d$_6$-DMSO): 1.28 (d, 6H), 4.51 (s, 2H), 4.71 (m, 1H), 7.05 (s, 1H), 7.25 (d, 1H), 7.50 (s, 1H), 7.53 (d, 1H), 7.58 (s, 1H), 12.50 (bs, 1H).

The requisite 2-(3-isopropoxy-5-acetoxymethyl)benzoyl aminothiazole was prepared by a standard coupling between 3-isopropoxy-5-acetoxymethyl benzoyl chloride and 2-aminothiazole according to Route 1, to give the title compound as a pale yellow oil, δ (d$_6$-DMSO): 1.3 (d, 6H), 2.1 (s, 3H), 4.75 (hept, 1H), 5.1 (s, 2H), 7.15 (s, 1H), 7.25 (d, 1H), 7.65 (d, 1H), 7.6 (m, 2H), 12.6 (bs, 1H).

The requisite 3-isopropoxy-5-acetoxymethyl benzoic acid was prepared as follows:

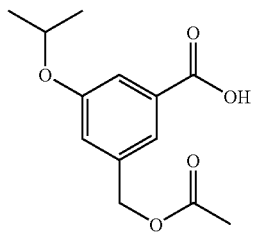

A solution of 3-isopropoxy-5-hydroxymethyl benzoic acid (0.77 g, 3.7 mmol) in dichloromethane (20 ml) was cooled (ice-bath) and stirred under argon; pyridine (1.18 ml, 14.6 mmol, 4 eq) was added followed dropwise by acetyl chloride (0.55 ml, 7.7 mmol, 2.1 eq). The mixture was stirred for 5 mins, then allowed to warm to ambient temperature over 90 mins. Water (20 ml) was added, the mixture stirred for 2 hrs, then allowed to stand overnight. The organic layer was separated, the aqueous portion washed with dichloromethane, and the dichloromethane fractions combined and evaporated. The resulting pale yellow oil was dissolved in ethyl acetate and the solution washed with 0.05M aqueous HCl (20 ml); the organic layer was separated, dried over magnesium sulfate and evaporated in vacuo to give the product as a pale yellow solid, $^1$H NMR δ (d$_6$-DMSO): 1.25 (d, 6H), 2.06 (s, 3H), 4.65 (hept, 1H), 5.05 (s, 2H), 7.12 (s, 1H), 7.31 (d, 1H), 7.46 (s, 1H).

The requisite 3-isopropoxy-5-hydroxymethyl benzoic acid starting material was prepared as follows:

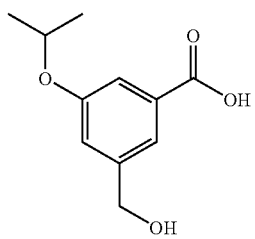

Standard 2M NaOH/THF/MeOH cleavage of methyl 3-isopropoxy-5-hydroxymethyl benzoate (1.12 g, 5.0 mM) gave the title compound as a colourless solid (0.98 g, 94%); $^1$H NMR δ (d$_6$-DMSO): 1.25 (d, 6H), 4.47 (s, 2H), 4.60 (m, 1H), 5.23 (bs, 1H), 7.06 (s, 1H), 7.24 (s, 1H), 7.45 (s, 1H).

The requisite methyl 3-isopropoxy-5-hydroxymethyl benzoate starting material was prepared as follows:

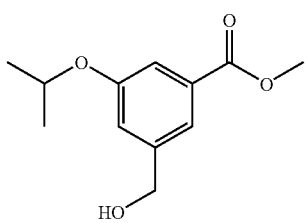

Mono-methyl-5-isopropoxy-isophthalate (5.15 g, 21.6 mM) was dissolved in THF (180 ml), cooled to 2° C. and borane:THF complex (72 ml of 1.5M solution in THF, 0.11 mM) added dropwise over 15 mins, maintaining an internal temperature of <5° C. After 15 mins the reaction mixture was warmed to ambient temperature, stirred for 3 hrs before cooling (ice bath) and quenching with pieces of ice. When no further reaction observed brine (150 ml)/diethyl ether (150 ml) added. The organic layer was removed, aqueous extracted with additional diethyl ether (1×100 ml), combined organics washed with brine (1×100 ml), dried (MgSO$_4$), filtered and concentrated. Purified on silica gel (20-25% EtOAc/isohexane) to give the title compound as a colourless solid (3.57 g, 74%); $^1$H NMR δ (d$_6$-DMSO): 1.26 (d, 6H), 3.82 (s, 3H), 4.50 (d, 2H), 4.63 (m, 1H), 5.26 (t, 1H (—OH)), 7.10 (s, 1H), 7.25 (s, 1H), 7.47 (s, 1H).

The requisite mono-methyl-5-isopropoxy-isophthalate starting material was prepared as follows:

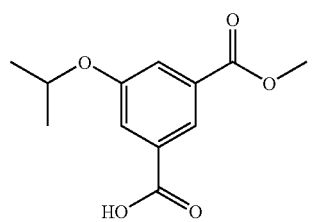

2M NaOH (1.03 g, 25.9 mM) in methanol (9 ml) was added to a solution of dimethyl-5-isopropoxy-isophthalate (5.68 g, 22.5 mM) in acetone (45 ml) and stirred at ambient temperature overnight. The reaction mixture was concentrated, acidified (2M HCl) to pH 1-2, filtered, washed with water and dried under high vacuum to give 14279/66/1 as a colourless solid (5.25 g, 98%) (contains 15-20% diacid); MS (M–H$^+$)$^-$ 237.

The requisite dimethyl-5-isopropoxy-isophthalate starting material was prepared as follows:

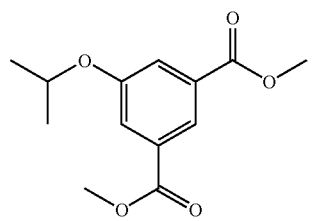

Dimethyl-5-hydroxy-isophthalate (5.2 g, 24.6 mM), potassium carbonate (4.07 g, 29.5 mM), potassium iodide (0.82 g, 4.9 mM) and 2-bromopropane (2.4 ml, 25.8 mM) in DMF (50 ml) was heated at 90° C. for 3 hrs, after which additional 2-bromopropane (2.4 ml), potassium carbonate (2.2 g) was added, heated for a further 4 hrs then cooled to room temperature and concentrated. EtOAc (150 ml) was added then washed with water, brine, dried (MgSO$_4$), filtered and concentrated to give a pale yellow oil which solidified on standing (6.0 g, 97%); MS (MH$^+$) 253.

EXAMPLE Z 2-(3-isopropoxy-5-formyl)benzoyl aminothiazole-5-carboxylic acid (Route 24)

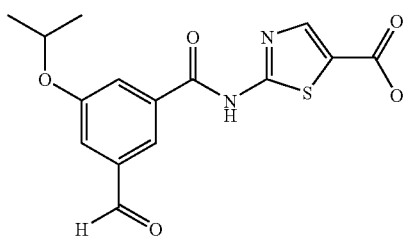

A solution of 2-(3-isopropoxy-5-hydroxymethyl)benzoyl aminothiazole-5-carboxylic acid (0.42 g, 1.25 mmol) in tetrahydrofuran (50 ml) was treated with Dess-Martin periodinane (DMP, 0.58 g, 1.37 mmol, 1.1 eq) and stirred at ambient temperature for 90 mins. The solvent was removed in vacuo, and the residue treated with dichloromethane and filtered. The residue was partitioned between ethyl acetate and sat'd sodium bicarbonate solution containing sodium thiosulfate solution (ca 7 eq of 2.1 M), and the resulting 2-phase mixture stirred vigorously before being acidified to ca pH6. The title compound was isolated by filtration as a colourless solid, (0.145 g, 35%), $^1$H NMR δ ($d_6$-DMSO): 1.32 (d, 6H), 4.79 (m, 1H), 7.62 (m, 1H), 7.92 (m, 1H), 8.13 (s, 1H), 8.18 (s, 1H), 10.03 (s, 1H).

The requisite 2-(3-isopropoxy-5-hydroxymethyl)benzoyl aminothiazole-5-carboxylic acid starting material was prepared according to the procedure given in Route 2a and is exemplified as Example II$_{81}$.

EXAMPLE AA

Z-{2-[3-isopropoxy-5-(3-methyl-but-1-enyl)]benzoyl aminothiazole-5-carboxylic acid}

(Route 25)

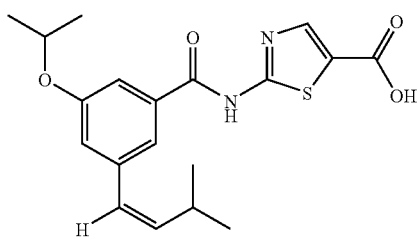

A solution of iso-butyl triphenyl phosphonium bromide (0.45 g, 1.13 mmol, 3.1 eq) in tetrahydrofuran (20 ml) was treated with potassium t-butoxide (1.1 ml of 1M in tetrahydrofuran, 1.13 mmol, 3.1 eq) and stirred at 0 deg C. under argon. To this was added 2-(3-isopropoxy-5-formyl)benzoyl aminothiazole-5-carboxylic acid (0.122 g, 0.36 mmol), and the resulting solution stirred for 100 mins, allowing to warm to ambient temperature. Water was added and the solvent removed in vacuo; the residue was partitioned between water and ethyl acetate and the layers separated. The aqueous portion was neutralised (2M HCl) and extracted twice with ethyl acetate; the organic extracts were dried (MgSO$_4$), filtered and concentrated and the residue purified by chromatography on silica gel (10 g Bondelut cartridge, eluting with dichloromethane containing methanol, 10% v/v) to give the title compound as a colourless solid (0.012 g, 9%); $^1$H NMR δ ($d_6$-DMSO): 1.01 (d, 6H), 1.29 (d, 6H), 2.81 (m, 1H), 4.72 (m, 1H), 6.53 (dd, 1H), 6.29 (d, 1H), 6.97 (s, 1H), 7.50 (s, 1H), 7.53 (s, 1H), 8.11 (s, 1H), 8.18 (s, 1H).

The requisite 2-(3-isopropoxy-5-formyl)benzoyl aminothiazole-5-carboxylic acid was prepared according to the procedure given under Example Z (Route 24); see Example II$_{89}$.

EXAMPLE BB

2-[3-isopropoxy-5-(4-methyl-1-piperidinocarbonyl-methyleneoxy)]benzoyl aminothiazole (Route 26)

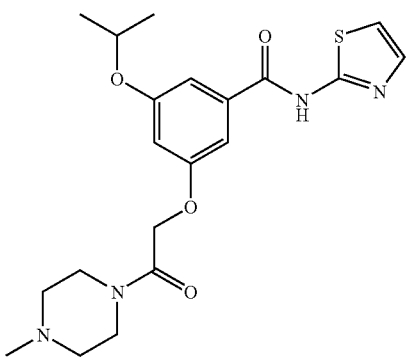

This was prepared by a standard acid chloride coupling (Example A, Route 1), starting from 2-(3-isopropoxy-5-carboxymethylene oxy)benzoyl aminothiazole, to give the title compound, $^1$H NMR δ ($d_6$-DMSO): 1.28 (d, 6H), 2.18 (s, 3H), 2.24 (m, 2H), 2.32 (m, 2H), 3.44 (ap t, 4H), 4.65 (m, 1H), 4.85 (s, 2H), 6.68 (apt, 1H), 7.19 (m, 1H), 7.24 (ap d, 2H), 7.55 (ap d, 1H), 12.45 (bs, 1H); m/z 419 (M+H)$^+$, 417 (M−H)$^−$.

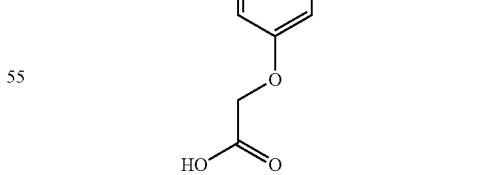

The requisite 2-(3-isopropoxy-5-carboxymethylene oxy) benzoyl aminothiazole was prepared from 2-(3-isopropoxy-5-methoxycarbonylmethylene oxy)benzoyl aminothiazole by standard ester hydrolysis (Route 2a); $^1$H NMR δ ($d_6$-DMSO): 1.28 (d, 6H), 4.69 (m, 1H), 4.73 (s, 2H), 6.66 (ap t, 1H), 7.22 (s, 1H), 7.27 (ap d, 2H), 7.53 (ap d, 1H); m/z 337.31 (M+H)$^+$ 335.27 (M−H)$^−$

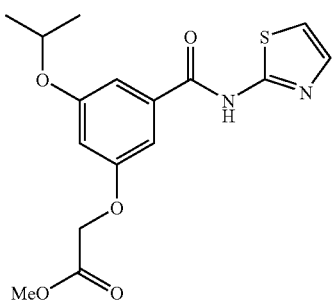

The requisite 2-(3-isopropoxy-5-methoxycarbonylmethylene oxy)benzoyl aminothiazole starting material was prepared from 3-isopropoxy-5-(methoxycarbonyl)methoxybenzoic acid and 2-aminothiazole (48% isolated yield) by a standard acid chloride coupling (Route 1); $^1$H NMR δ (d$_6$-DMSO): 1.27 (d, 6H), 3.70 (s, 3H), 4.71 (m, 1H), 4.86 (s, 2H), 6.99 (t, 1H), 7.23 (t, 1H), 7.26-7.27 (m, 2H), 12.53 (s, 1H); m/z 351.31 (M+H)$^+$, 349.28 (M−H)$^−$

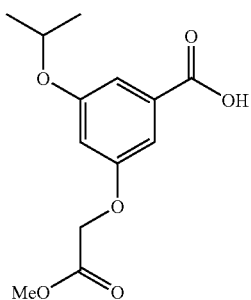

The requisite starting material was prepared from 3-isopropoxy-5-(methoxycarbonyl methylene oxy)benzoic acid was prepared by monoesterification of 3-isopropoxy-5-(carboxymethylene oxy)benzoic acid (78% isolated yield) using the conditions of Ram and Charles, *Tetrahedron* 1997, 53 (21), pp. 7335-7340: $^1$H NMR δ (d$_6$-DMSO): 1.25 (d, 6H), 3.69 (s, 3H), 4.65 (m, 1H), 4.83 (s, 2H), 6.71 (ap t, 1H), 6.98 (s, 1H), 7.01 (s, 1H), 12.97 (bs, 1H); m/z 554.27 (2M+NH4)$^+$, 267.26 (M−H)$^−$ 3-isopropoxy-5-(carboxymethoxy)benzoic acid

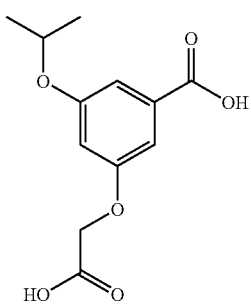

The title compound was prepared from methyl (3-isopropoxy-5-(t-butyloxylcarbonyl)methoxy)benzoate (56% isolated yield) using standard hydrolysis method 2a. $^1$H NMR δ (d$_6$-DMSO): 1.25 (d, 6H), 4.62 (m, 1H), 4.69 (s, 2H), 6.67 (ap t, 1H), 6.96 (s, 1H), 7.02 (s, 1H), 12.95 (bs, 1H); m/z 253.27 (M−H)$^−$

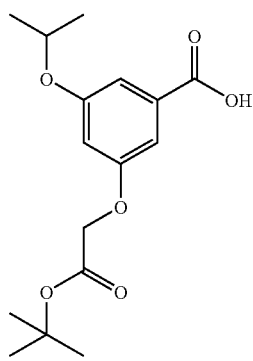

The requisite methyl (3-isopropoxy-5-(t-butyloxylcarbonyl)methoxy)benzoate was prepared according to generic Alkylation Method B. The analytical data on all intermediates was consistent with the proposed structures.

EXAMPLE CC 3-amino-6-(3-isobutyloxy-5-isopropyloxy benzoyl)aminopyridine (Route 7b)

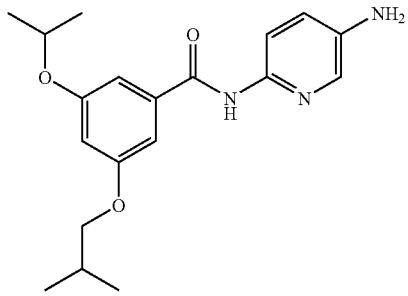

To a solution of 2-(3-isobutoxy-5-isopropoxybenzoyl)amino-5-nitropyridine (1.74 g, 4.66 mmol) in ethanol (20 ml) was added 10% Pd/C under an inert atmosphere. The reaction mixture was placed under a hydrogen atmosphere and stirred vigorously for 16 h. The reaction mixture was flooded with argon, and then diluted with water (20 ml) and acidified with 2M HCl (5 ml). The suspension was filtered through celite, and the filtrate evaporated in vacuo. The residue was partitioned between ethyl acetate (25 ml) and saturated sodium bicarbonate (25 ml), and the organic extract dried over MgSO$_4$. Evaporation in vacuo afforded the title compound as a brown solid (1.30 g, 81%).

$^1$H NMR δ (d$_6$-DMSO): 0.97 (d, 6H), 1.26 (d, 6H), 2.00 (m, 1H), 3.78 (d, 2H), 4.69 (m, 1H), 5.12 (s, 2H), 6.58 (t, 1H), 6.99 (dd, 1H), 7.1 (ap d, 2H), 7.73-7.78 (m, 2H), 10.24 (bs, 1H); m/z 344.41 (M+H)$^+$

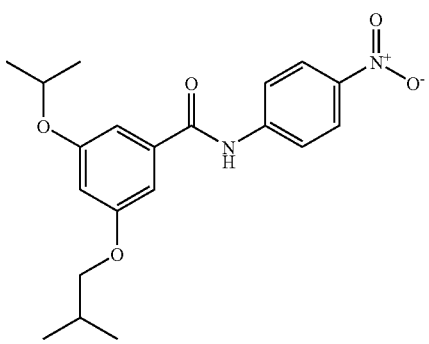

The requisite 2-(3-isobutyloxy-5-isopropyloxy)benzoyl amino-5-nitropyridine was prepared according to Route 1 (see Example 10 in Pyridine table); $^1$H NMR δ (d$_6$-DMSO): 0.98 (d, 6H), 1.27 (d, 6H), 2.01 (m, 1H), 3.60 (d, 2H), 4.71 (m, 1H), 6.67 (ap t, 1H), 7.17 (ap d, 2H), 8.39 (d, 1H), 8.63 (dd, 1H), 9.20 (d, 1H), 11.43 (bs, 1H); m/z 374 (M+H)$^+$, 372 (M−H)$^−$.

EXAMPLE DD

2-[(3-isobutyloxy-5-isopropyloxy)benzoyl]amino-5-(N-methylsulfonyl)-carboxamido pyridine (Route 27)

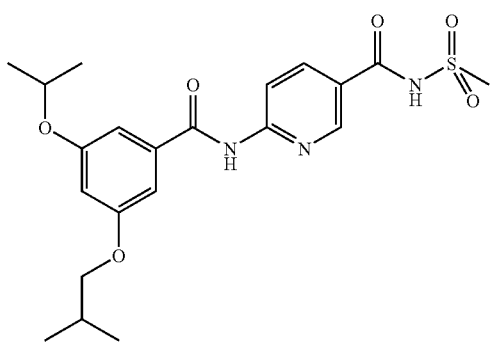

2-[(3-isobutyloxy-5-isopropyloxy)benzoyl]aminopyridine-5-carboxylic acid (95 mg, 0.255 mmol) was stirred with EDC (59 mg, 0.306 mmol), DMAP (37 mg, 0.306 mmol) and methanesulfonamide (36 mg, 0.378 mmol) in DCM (3 ml) under an inert atmosphere for 16 h. The reaction mixture was diluted with further DCM (10 ml) and extracted with water (2×5 ml). 1M citric acid (5 ml) and brine (5 ml). Filtration through a PTFE membrane and evaporation in vacuo afforded the title compound as a colourless crystalline solid (90 mg, 79%). $^1$H NMR δ (d$_6$-DMSO): 0.97 (d, 6H), 1.26 (d, 6H), 2.03 (m, 1H), 3.01 (s, 3H), 3.79 (d, 2H), 4.70 (m, 1H), 6.63 (ap t, 1H), 7.14 (ap d, 2H), 7.70 (dd, 1H), 8.12 (d, 1H), 8.34 (ap d, 1H), (9.83, s, 1H), 10.81 (bs, 1H);

m/z 422.37 (M+H)+, 420.30 (M−H)−

The requisite 2-[(3-isobutyloxy-5-isopropyloxy)benzoyl]aminopyridine-5-carboxylic acid starting material was prepared from methyl 2-[(3-isobutyloxy-5-isopropyloxy)benzoyl]aminopyridine-5-carboxylate by standard hydrolysis (Route 2a); The requisite methyl 2-(3-isobutyloxy-5-isopropyloxy)benzoyl aminopyridine-5-carboxylate was prepared by standard acid chloride coupling (Route 1);

EXAMPLE EE

2-{3-isopropyloxy-5-[1-methyl-1-(5-carboxy-thiazol-2-yl aminocarbonyl)]ethoxy benzoyl}aminothiazole-5-carboxylic acid (Route 28)

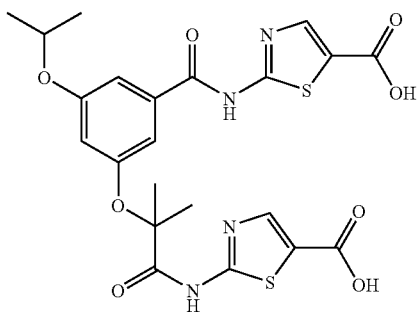

Ethyl 2-{3-isopropyloxy-5-[1-methyl-1-(5-ethoxycarbonyl-thiazol-2-yl aminocarbonyl)]ethoxy benzoyl}aminothiazole-5-carboxylate was hydrolysed by a standard method according to Example B Route 2a to give 2-{3-isopropyloxy-5-[1-methyl-1-(5-carboxy-thiazol-2-yl aminocarbonyl)]ethoxy benzoyl}aminothiazole-5-carboxylic acid, $^1$H NMR δ (d$_6$-DMSO): 1.22 (d, 6H), 1.61 (s, 6H), 4.58-4.64 (m, 1H), 6.62 (s, 1H), 7.19 (s, 1H), 7.40 (s, 1H), 8.05 (s, 1H), 8.12 (s, 1H), m/z 533 (M−H)$^−$.

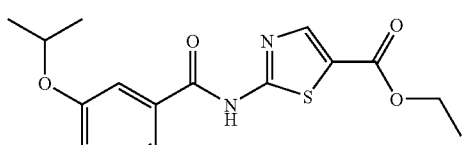

The requisite ethyl 2-{3-isopropyloxy-5-[1-methyl-1-(5-ethoxycarbonyl-thiazol-2-yl aminocarbonyl)]ethoxy benzoyl}aminothiazole-5-carboxylate starting material was prepared by a standard acid chloride method according to Example A Route 1, starting from 3-isopropyloxy-5-[(1-methyl-1-carboxy)ethoxy]benzoic acid.

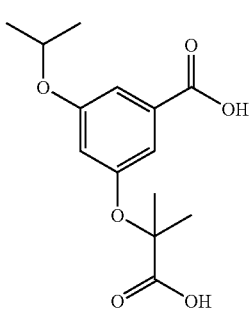

The requisite 3-isopropyloxy-5-[(1-methyl-1-carboxy) ethoxy]benzoic acid. starting material was prepared according to the procedure described by Corey et al, JACS 91 p 4782 (1969), starting from methyl 3-isopropyloxy-5-hydroxy benzoate. The methyl ester was hydrolysed under the reaction conditions, and the product was isolated by extraction into aqueous sodium bicarbonate solution followed by acidification and extraction into ethyl acetate. The organic extracts were dried (MgSO$_4$), filtered and concentrated in vacuo to give the crude product as a pale yellow solid. Recrystallisation from hexane gave the title compound as a colourless solid; $^1$H NMR δ (d$_6$-DMSO): 1.15 (d, 6H), 1.5 (s, 6H), 4.55 (hept, 1H), 6.55 (dd, 1H), 6.95 (m, 1H), 7.05 (m, 1H), 13.0 (br s, 1H); m/z 283 (M+H)$^+$, 281 (M+H)$^-$.

EXAMPLE FF

By analogous methods to those described above the following pyridazine compounds, Example numbers FF$_1$ to FF$_5$, were also made.

| Example | Structure | Route | (M + H)+ | (M − H)− | NMR |
|---|---|---|---|---|---|
| 1 | 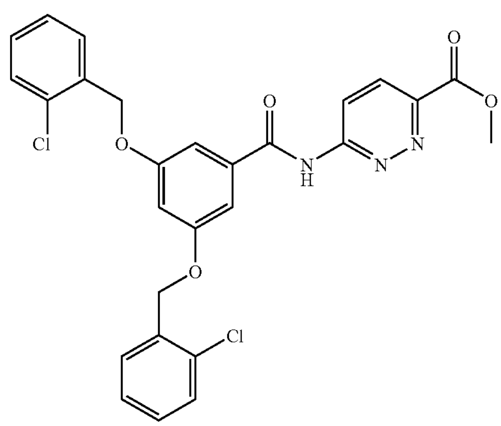 | 1 | | | 1H NMR d (d6-DMSO): 3.95 (3H, s); 5.25 (4H, s); 6.95 (1H, s); 7.4 (6H, m); 7.5 (2H, m); 7.65 (2H, m); 8.25 (1H, d); 8.6 (1H, d); 11.85 (1H, br s). |
| 2 | 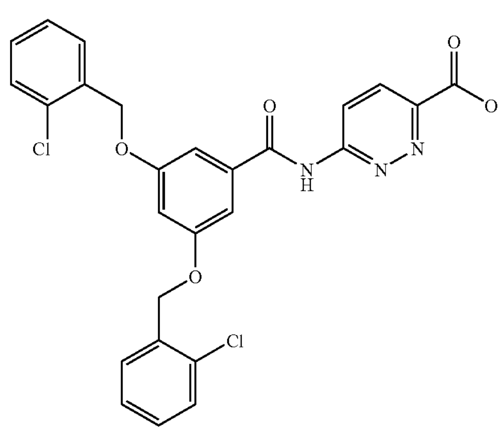 | 2 | 524/526 | 522 | 1H NMR d (d6-DMSO): 2.0 (1H, s); 5.25 (4H, s); 6.95 (1H, s); 7.4 (6H, m); 7.5 (2H, m); 7.6 (2H, m); 8.25 (1H, d); 8.55 (1H, d); 11.8 (1H, br s). MS and NMR contained signals due to acid starting material (~20 mol%); NMR contained signals due to ethyl acetate, (~33 mol%) |

| Example | Structure | Route | (M + H)+ | (M − H)− | NMR |
|---|---|---|---|---|---|
| 3 | 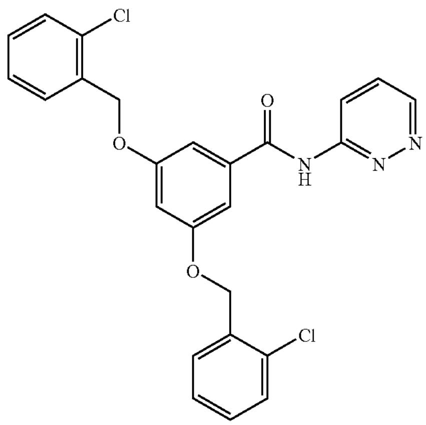 | 1 | | | 1H NMR d (d6-DMSO): 5.24 (4H, s); 6.93 (1H, m); 7.37 (6H, m); 7.50 (2H, m); 7.61 (2H, m); 7.71 (1H, dd); 8.36 (1H, d); 9.00 (1H, d). |
| 4 | 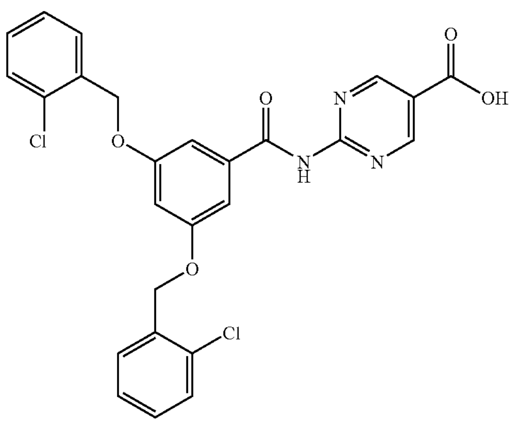 | 2* | 524/526 | 522/524 | $^1$H NMR δ (d$_6$-DMSO): 5.2 (4H, s); 6.95 (1H, m); 7.15 (1H, s); 7.3 (1H, d); 7.4 (4H, m); 7.5 (2H, m); 7.6 (2H, m); 9.1 (2H, s); 11.35 (1H, br s); the spectrum also contains signals due to acid starting material (~40 mol%) |
| 5 | 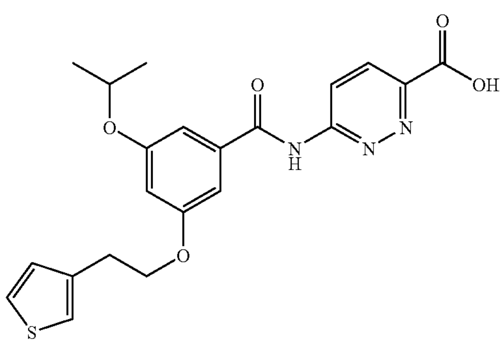 | 2a, 1c (c) | 428 | | δ$_H$ (300 MHz, DMSO-d$_6$) 1.29 (6H, d), 3.08 (2H, t), 4.30 (2H, t), 4.74 (1H, m), 6.73 (1H, s), 7.13 (1H, m), 7.24 (1H, s), 7.27 (1H, s), 7.34 (1H, m), 7.52 (1H, m), 8.25 (1H, d), 8.56 (1H, d), 11.75 (1H, s), 13.66 (1H, br s). |

*For Example 15, the ester intermediate was prepared by route 1 and is exemplified as Example 12:

| Example | Structure | Route | (M + H)+ | (M − H)− | NMR |
|---------|-----------|-------|----------|----------|-----|
| | (structure: methyl 6-[[3,5-bis[(2-chlorobenzyl)oxy]benzoyl]amino]pyridazine-3-carboxylate) | | | | |

EXAMPLE GG

By analogous methods to those described above the following compounds, Example numbers $GG_1$ to $GG_7$, were also made.

| Example | Structure | Route | (M + H)+ | (M − H)− | NMR |
|---------|-----------|-------|----------|----------|-----|
| 1 | (structure: 5-[[3,5-bis[(2-chlorobenzyl)oxy]benzoyl]amino]furan-2-carboxylic acid) | 2* | | | 1H NMR d (d6-DMSO): 5.22 (4H, s); 6.54 (1H, d); 6.93 (1H, d); 7.27 (1H, d); 7.32-7.44 (6H, m); 7.53 (2H, m); 7.63 (2H, m); 11.85 (1H, s); 12.86 (1H, br s). |
| 2 | (structure: 3,5-bis[(2-chlorobenzyl)oxy]-N-(1-methylpyrazol-3-yl)benzamide) | | | | 1H NMR d (d6-DMSO): 3.75 (3H, s); 5.21 (4H, s); 6.55 (1H, d); 6.86 (1H, m); 7.31 (1H, m); 7.38 (4H, m); 7.38 (2H, m); 7.56 (1H, m); 7.59 (2H, m); 10.80 (1H, br s). |

-continued

| Example | Structure | Route | (M + H)+ | (M − H)− | NMR |
|---|---|---|---|---|---|
| 3 | 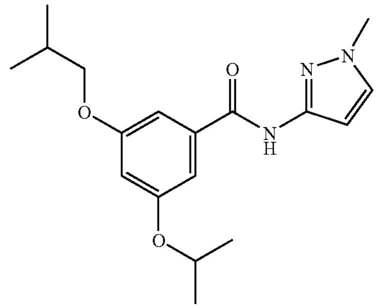 | 1a | 331 | | |
| 4 | 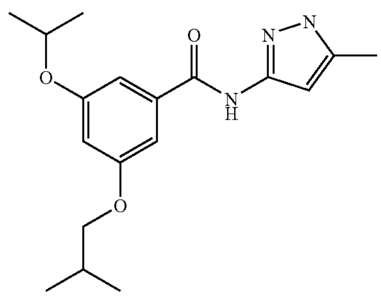 | 1a | 332.53 | 330.51 | $\delta_H$ (300 MHz, CDCl$_3$) 1.02 (6H, d), 1.36 (6H, d), 2.08 (1H, m), 2.30 (3H, s), 3.75 (d, 2H), 4.60 (1H, hept), 6.66 (2H, m), 7.08 (2H, m), 9.85 (1H, br s). |
| 5 | 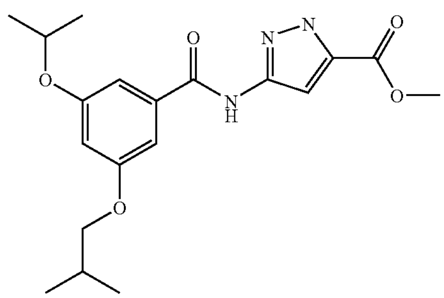 | 1a | 376.47 | 374.45 | $\delta_H$ (300 MHz, DMSO-d$_6$) 0.98 (6H, d), 1.27 (6H, d), 2.02 (1H, m), 3.80 (2H, d), 3.84 (3H, s), 4.68 (1H, hept), 6.62 (1H, s), 7.12 (3H, m), 10.95 (1H, br s), 13.65 (1H, br s). |
| 6 | 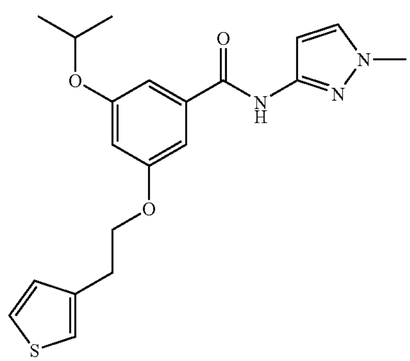 | 1b (HATU) | 386.47 | | $\delta_H$ (300 MHz, CDCl$_3$) 1.35 (6H, d), 3.13 (2H, t), 3.72 (3H, s), 4.16 (2H, t), 4.53 (1H, hept), 6.60 (1H, s), 6.83 (1H, s), 7.00 (4H, m) 7.28 (2H, m), 8.98 (1H, br s). |

| Example | Structure | Route | (M + H)+ | (M − H)− | NMR |
|---|---|---|---|---|---|
| 7 | 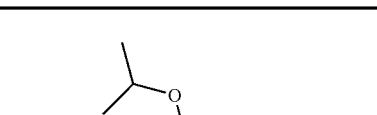 | 1a | 384 | | |
*For GG₁, the ester intermediate was prepared by route 1:
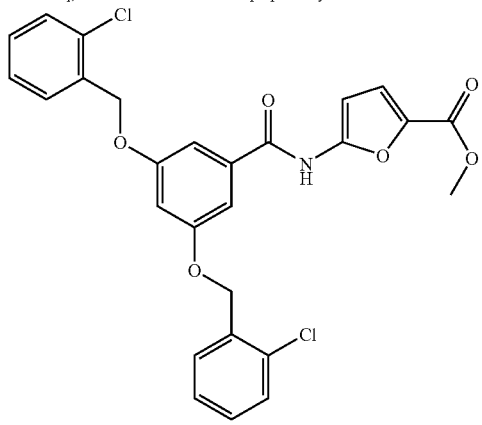
¹H NMR δ(d6-DMSO): 3.80 (3H, s); 5.23 (1H, m); 6.61 (1H, d); 6.95 (1H, s); 7.33-7.43 (7H, m); 7.50-7.55 (2H, m); 7.60-7.63 (2H, m); 11.90 (IH, br s).
EXAMPLE HH
By analogous methods to those described above the following compounds, Example numbers HH₁ to HH₃₃, were also made.
| Example | Structure | Route | (M + H)+ | (M − H)− | NMR |
|---|---|---|---|---|---|
| 1 | 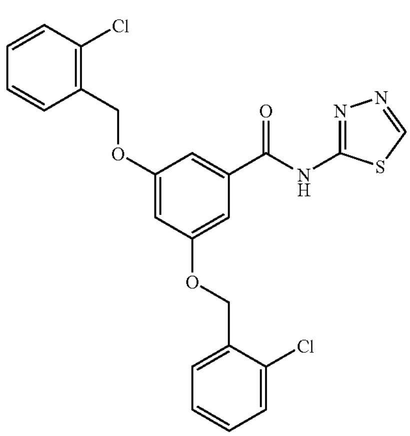 | 1 | 484 | | 1H NMR d (d6-DMSO): 5.26 (4H, s); 7.02 (1H, s); 7.40 (4H, m); 7.46 (2H, m); 7.54 (2H, m); 7.63 (2H, m); 9.24 (1H, s); 13.08 (1H, br s). |

-continued

| Example | Structure | Route | (M + H)+ | (M − H)− | NMR |
|---|---|---|---|---|---|
| 2 | 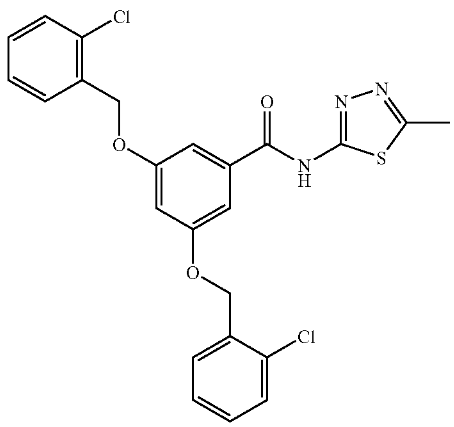 | 1 | | | 1H NMR d (d6-DMSO): 2.63 (3H, s); 5.24 (4H, s); 6.96 (1H, s); 7.35-7.45 (6H, m); 7.51 (2H, m); 7.61 (2H, m); 12.84 (1H, br s). |
| 3 | 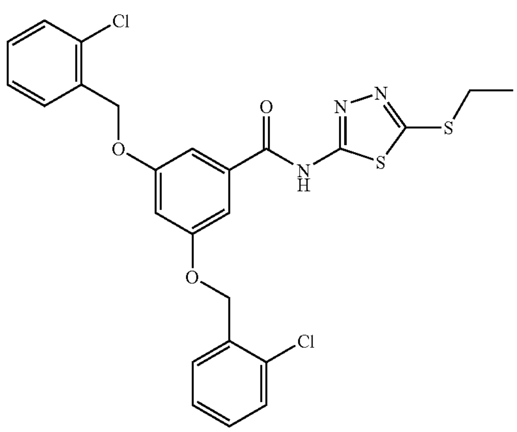 | 1 | | | 1H NMR d (d6-DMSO): 1.38 (3H, t), 3.25 (2H, q); 5.25 (4H, s); 6.97 (1H, s); 7.41 (6H, m); 7.54 (2H, m); 7.64 (2H, m); 13.13 (1H, br s). |
| 4 | 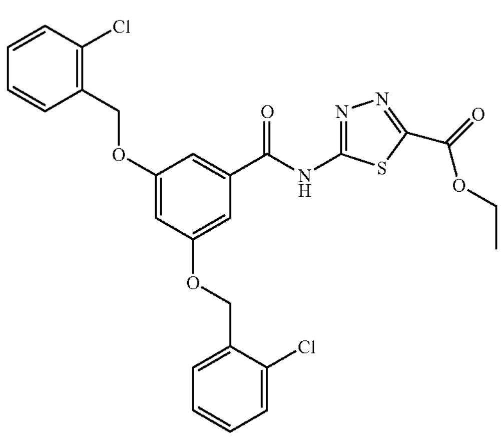 | 1 | | | 1H NMR d (d6-DMSO): 1.32 (3H, t), 4.32 (2H, q); 5.20 (4H, s); 6.78 (1H, s); 7.39 (4H, m); 7.46 (2H, m); 7.53 (2H, m); 7.64 (2H, m). |

| Example | Structure | Route | (M + H)+ | (M − H)− | NMR |
|---|---|---|---|---|---|
| 5 | 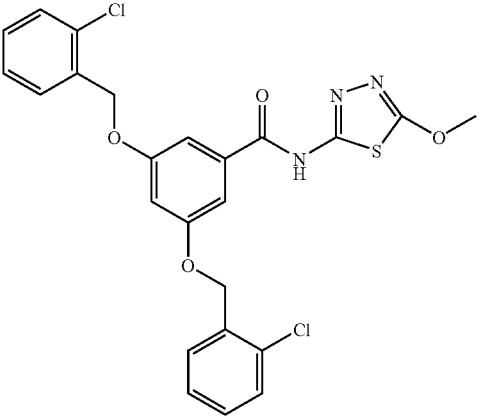 | 1 | | | 1H NMR d (d6-DMSO): 4.20 (3H, s); 5.28 (4H, s); 6.98 (1H, s); 7.42 (6H, m); 7.53 (2H, m); 7.62 (2H, m); 12.78 (1H, br s). |
| 6 | 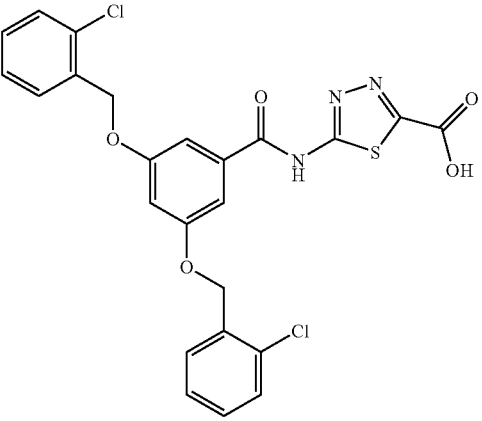 | 2 | | 530, 532 | 1H NMR d (d6-DMSO): 5.24 (4H, s); 6.96 (1H, s); 7.37 (4H, m); 7.33 (2H, m); 7.53 (2H, m); 7.62 (2H, m). |
| 7 | 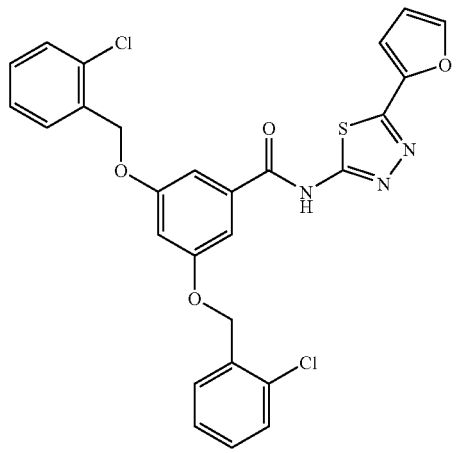 | 1 | | | 1H NMR d (d6-DMSO): 5.25 (4H, s); 6.74 (1H, m); 6.99 (1H, s); 7.23 (1H, m); 7.41 (4H, m); 7.49 (2H, m); 7.53 (2H, m); 7.65 (2H, m); 7.97 (1H, s); 13.20 (1H, br s). |

-continued

| Example | Structure | Route | (M + H)+ | (M − H)− | NMR |
|---|---|---|---|---|---|
| 8 | 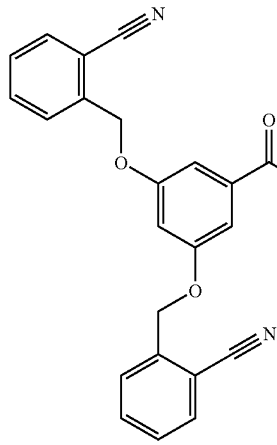 | 1 | | | 1H NMR d (d6-DMSO): 5.34 (4H, s); 7.03 (1H, s); 7.49 (2H, m); 7.57 (2H, m); 7.75 (4H, m); 7.91 (2H, d); 9.22 (1H, s); 13.06 (1H, br s). |
| 9 | 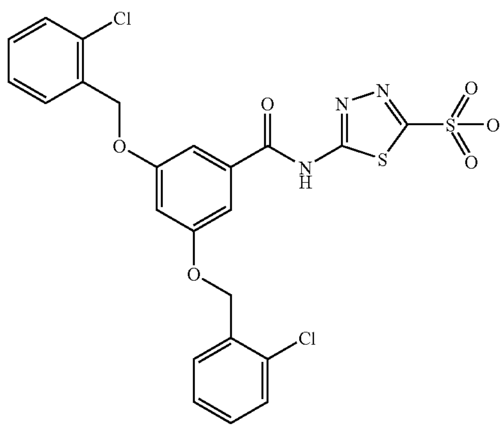 | 19 | | 564, 566 | 1H NMR d (d6-DMSO): 5.20 (4H, s); 6.68 (1H, m); 7.37 (4H, m); 7.45 (2H, m); 7.50 (2H, m); 7.62 (2H, m). |
| 10 | 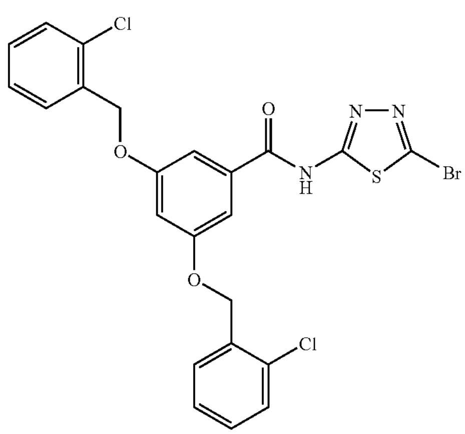 | 1 | 566 | 564, 566 | 1H NMR d (d6-DMSO): 5.22 (4H, s); 6.99 (1H, m); 7.39 (4H, m); 7.45 (2H, m); 7.51 (2H, m); 7.60 (2H, m); 13.34 (1H, br s). |

-continued

| Example | Structure | Route | (M + H)+ | (M − H)− | NMR |
|---------|-----------|-------|----------|----------|-----|
| 11 | 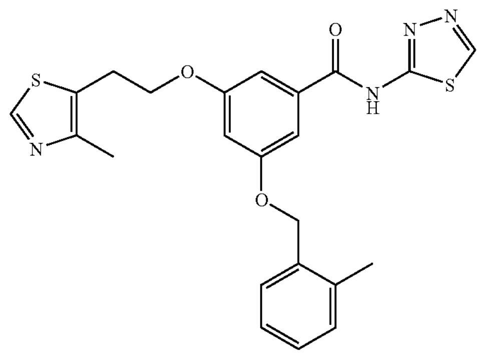 | 1 | | | 1H NMR d (d6-DMSO): 2.33 (3H, s), 2.37 (3H, s); 3.25 (2H, m); 4.21 (2H, t); 5.14 (2H, s); 6.84 (1H, m); 7.22 (3H, m); 7.31 (1H, s); 7.40 (2H, m); 8.83 (1H, s); 9.21 (1H, s); 12.99 (1H, br s). |
| 12 | 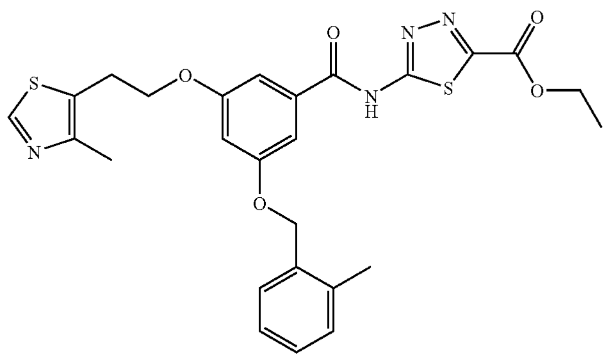 | 1 | | | 1H NMR d (d6-DMSO): 1.33 (3H, t); 2.32 (3H, s), 2.35 (3H, s); 3.22 (2H, m); 4.21 (2H, t); 4.40 (2H, q); 5.13 (2H, s); 6.87 (1H, m); 7.22 (3H, m); 7.33 (1H, m); 7.41 (2H, m); 8.82 (1H, s); 13.46 (1H, br s). |
| 13 | 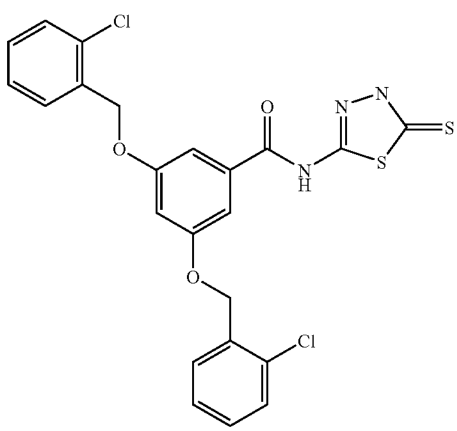 | | | 516, 518 | 1H NMR d (d6-DMSO): 5.21 (4H, s); 6.98 (1H, m); 7.34-7.40 (6H, m); 7.50 (2H, m); 7.59 (2H, m). |
| 14 | 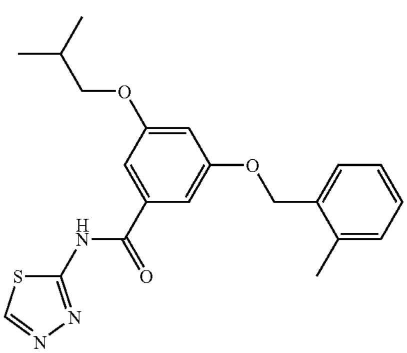 | | | 398 | $^1$H NMR δ (d$_6$-DMSO): 1.0 (d, 6H), 2.0 (hept, 1H), 2.35 (s, 3H), 3.8 (d, 2H), 5.2 (s, 2H), 6.85 (d, 1H), 7.15-7.25 (m, 3H), 7.30 (d, 1H), 7.4 (2H, m), 9.2 (s, 1H), 11.6 (br s, 1H). |

-continued

| Example | Structure | Route | (M + H)+ | (M − H)− | NMR |
|---|---|---|---|---|---|
| 15 | 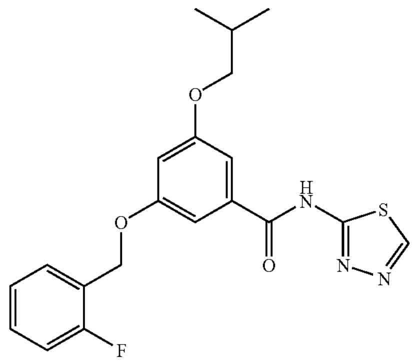 | | | 402 | ¹H NMR δ (d₆-DMSO): 1.0 (d, 6H), 2.0 (hept, 1H), 3.8 (d, 2H), 5.2 (s, 2H), 6.85 (s, 1H), 7.2-7.3 (m, 2H), 7.35 (s, 1H), 7.4 (m, 2H), 7.6 (t, 1H), 9.2 (s, 1H), 13.0 (br s, 1H). |
| 16 | 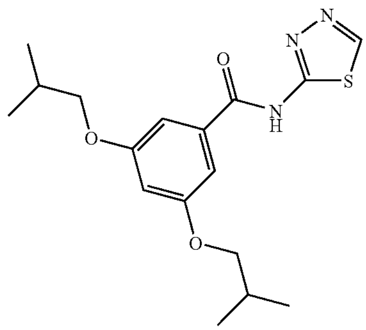 | | | 350 | |
| 17 | 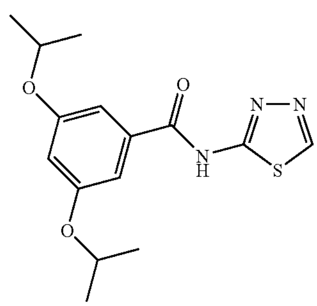 | | | 322 | ¹H NMR δ (d₆-DMSO): 1.3 (d, 12H), 4.7 (hept, 2H), 6.65 (s, 1H), 7.25 (s, 2H), 9.2 (s, 1H), 12.95 (br s, 1H). |
| 18 | 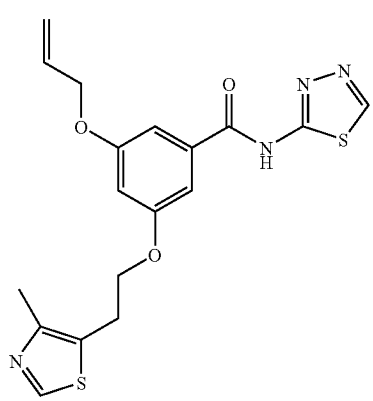 | | | | ¹H NMR δ (d₆-DMSO): 2.34 (s, 3H), 3.23 (t, 2H), 4.21 (t, 2H), 4.62 (d, 2H), 5.26 (d, 1H), 5.40 (d, 1H), 6.05 (m, 1H), 6.75 (s, 1H), 7.31 (s, 2H), 8.83 (s, 1H), 9.20 (s, 1H), 12.48 (br s, 1H). |

| Example | Structure | Route | (M + H)+ | (M − H)− | NMR |
|---|---|---|---|---|---|
| 19 | 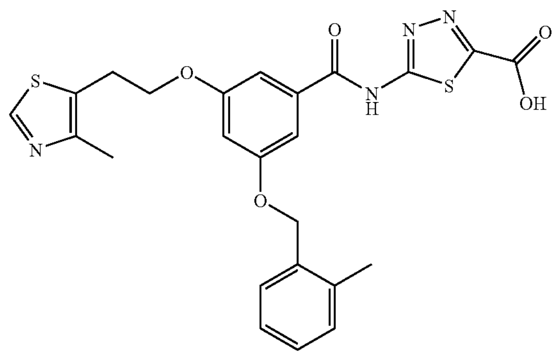 | | | | ¹H NMR δ (d₆-DMSO): 2.31 (s, 3H), 2.34 (s, 3H), 3.22 (t, 2H), 4.21 (t, 2H), 5.13 (s, 2H), 6.84 (s, 1H), 7.15-7.25 (m, 3H), 7.26 (1H, m), 7.39 (2H, m), 8.81 (s, 1H). |
| 20 | 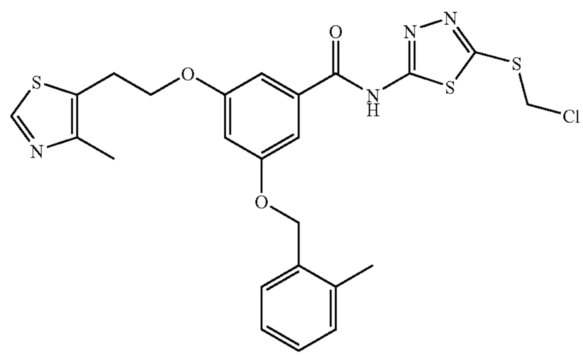 | | | | ¹H NMR δ (d₆-DMSO): 2.37 (s, 3H), 2.42 (s, 3H), 3.29 (t, 2H), 4.29 (t, 2H), 5.21 (s, 2H), 5.58 (s, 2H); 6.92 (s, 1H), 7.22-7.31 (m, 3H), 7.40 (1H, bs), 7.47 (2H, m), 8.90 (s, 1H). MS ES⁺ 547.2, 549.1 (M + H)⁺. |
| 21 | 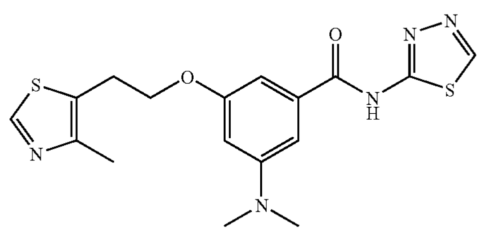 | 19 | | | ¹H NMR δ (d₆-DMSO): 2.35 (s, 3H), 2.93 (s, 6H), 3.22 (m, 2H), 4.19 (m, 2H), 6.41 (m, 1H), 6.98 (m, 1H), 7.06 (m, 1H), 8.80 (s, 1H), 9.17 (s, 1H). |
| 22 | 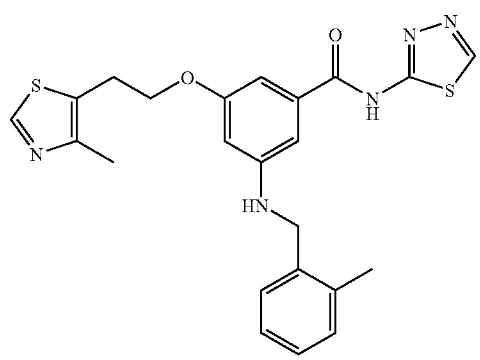 | 19 | | | ¹H NMR δ (d₆-DMSO): 2.58 (m, 6H), 3.43 (t, 2H), 4.37 (t, 2H), 4.50 (d, 2H), 6.41 (m, 1H), 6.61 (m, 1H), 7.16 (m, 2H), 7.34-7.45 (m, 3H), 7.50 (m, 1H), 9.05 (s, 1H), 9.42 (s, 1H). |
| 23 | 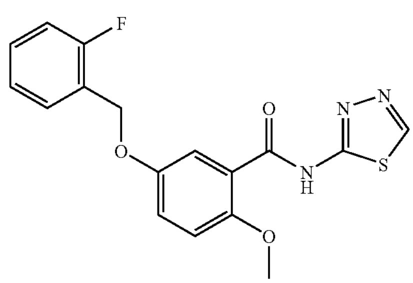 | 1 | | 358 | ¹H NMR δ (d₆-DMSO): 3.81 (s, 3H), 5.15 (s, 2H), 7.18 (t, 1H), 7.2-7.3 (m, 3H), 7.38 (d, 1H), 7.39-7.43 (m, 1H), 7.55 (t, 1H), 12.27 (br s, 1H) |

-continued

| Example | Structure | Route | (M + H)+ | (M − H)− | NMR |
|---|---|---|---|---|---|
| 24 | 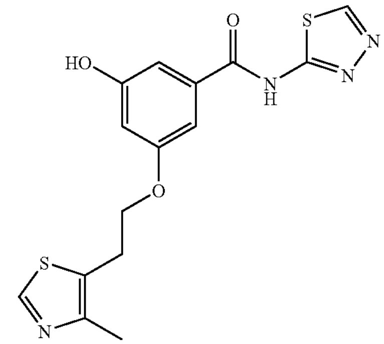 | 20 | 363 | 361 | ¹H NMR δ (d₆-DMSO): 2.35 (s, 3H), 3.2 (t, 2H), 4.2 (t, 2H), 6.55 (m, 1H), 7.05 (s, 1H), 7.2 (s, 1H), 8.81 (s, 1H), 9.2 (s, 1H), 9.8 (br s, 1H). |
| 25 | 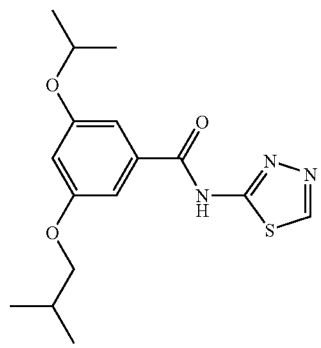 | 1b | 336 | | |
| 26 | 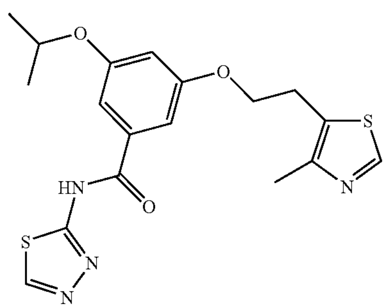 | 1b | 405 | | |
| 27 | 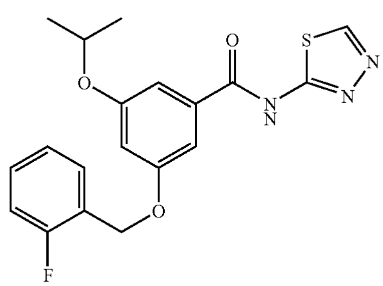 | 2a, 1c (b) | 388 | 386 | δ$_H$ (500 MHz, DMSO-d₆) 1.27 (6H, d), 4.73 (1H, m), 5.21 (2H, s), 6.82 (1H, s), 7.20-7.31 (3H, br m), 7.36-7.47 (2H, brm), 7.58 (1H, t), 9.23 (1H, s), 12.97 (1H, br s). |
| 28 | 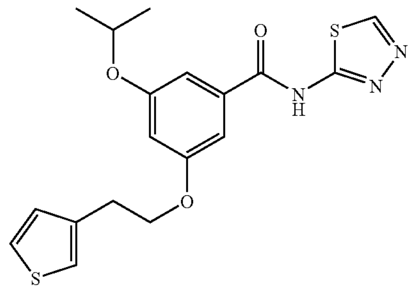 | 2a, 1c (b) | 389 | | δ$_H$ (500 MHz, DMSO-d₆) 1.28 (6H, d), 3.06 (2H, t), 4.27 (2H, t), 4.72 (1H, m), 6.72 (1H, s), 7.12 (1H, d), 7.26 (1H, s), 7.31 (2H, m), 7.48 (1H, m), 9.20 (1H, s). |

-continued

| Example | Structure | Route | (M + H)+ | (M − H)− | NMR |
|---|---|---|---|---|---|
| 29 | 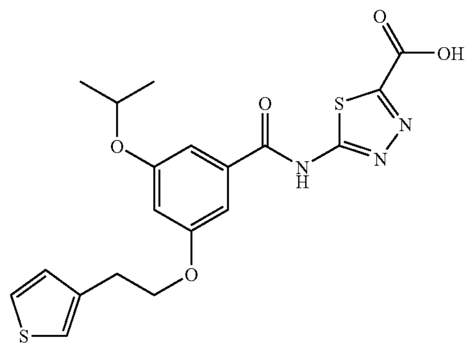 | 2a, 1a (d) | 434 | | δ$_H$ (300 MHz, DMSO-d$_6$) 1.26 (6H, d), 3.07 (2H, t), 4.15 (2H, t), 4.70 (1H, m), 6.68 (1H, s), 7.11 (1H, d), 7.22-7.34 (3H, br m), 7.47 (1H, m). |
| 30 | 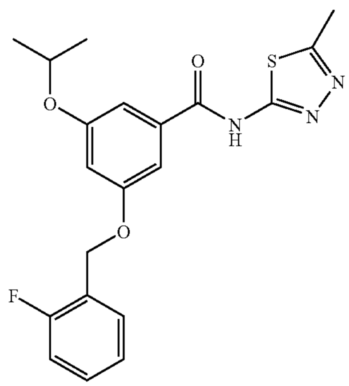 | 1b (HATU) | 402.42 | 400.39 | δ$_H$ (300 MHz, DMSO-d$_6$) 1.27 (6H, d), 2.63 (3H, s), 4.70 (1H, hept), 5.20 (2H, s), 6.82 (1H, s), 7.24 (3H, m), 7.39 (2H, m), 7.56 (1H, t), 12.80 (1H, br s). |
| 31 | 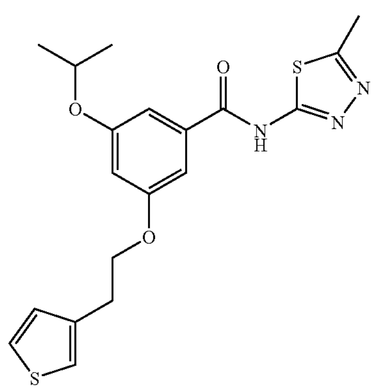 | 1b (HATU) | 404.40 | 402.37 | δ$_H$ (300 MHz, DMSO-d$_6$) 1.27 (6H, d), 2.63 (3H, s), 3.06 (2H, t), 4.25 (2H, t), 4.70 (1H, hept), 6.72 (1H, s), 7.12 (1H, d), 7.28 (3H, m), 7.47 (1H, m), 12.77 (1H, br s). |
| 32 | 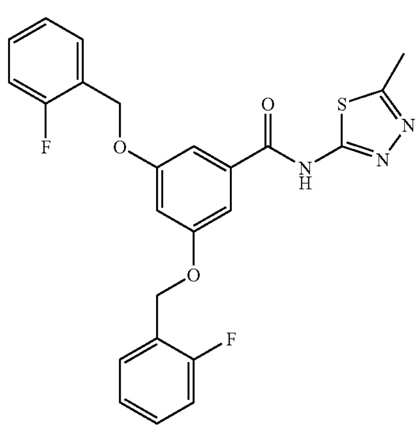 | 1b (HATU) | 468.39 | 466.37 | δ$_H$ (300 MHz, DMSO-d$_6$) 2.63 (3H, s), 5.23 (4H, s), 6.97 (1H, s), 7.24 (4H, m), 7.43 (4H, m), 7.57 (2H, t), 12.84 (1H, br s). |

| Example | Structure | Route | (M + H)+ | (M − H)− | NMR |
|---|---|---|---|---|---|
| 33 | (3-isopropoxy-5-(acetoxymethyl)benzamide linked to 1,3,4-thiadiazol-2-yl) | 1a | 336.44 | 334.40 | |

EXAMPLE II

By analogous methods to those described above the following compounds, Example numbers II$_1$ to II$_{166}$, were also made. Some compounds were prepared by Route 1b (multi-parallel synthesis), as described in Example T. For compounds made by Route 2a (hydrolysis of esters), the requisite starting materials may be prepared by Route 1 or 1b.

| Example | Structure | Route | (M + H)+ | (M − H)− | NMR |
|---|---|---|---|---|---|
| 1 | (3,5-bis(2-chlorobenzyloxy)-N-(thiazol-2-yl)benzamide) | 1 | 485, 487 | | 1H NMR d (d6-DMSO): 5.24 (4H, s); 6.93 (1H, s); 7.26 (1H, d); 7.36-7.43 (6H, m); 7.50 (2H, m); 7.55 (1H, d); 7.61 (2H, m); 12.60 (1H, br s). |
| 2 | (3,5-bis(2-chlorobenzyloxy)-N-(5-carboxythiazol-2-yl)benzamide) | 2a**** | | | 1H NMR d (d6-DMSO): 5.25 (4H, s); 7.0 (1H, s), 7.4 (6H, m), 7.5 (2H, m); 7.6 (2H, m); 8.2 (1H, d). |

-continued

| Example | Structure | Route | (M + H)+ | (M − H)− | NMR |
|---|---|---|---|---|---|
| 3 | 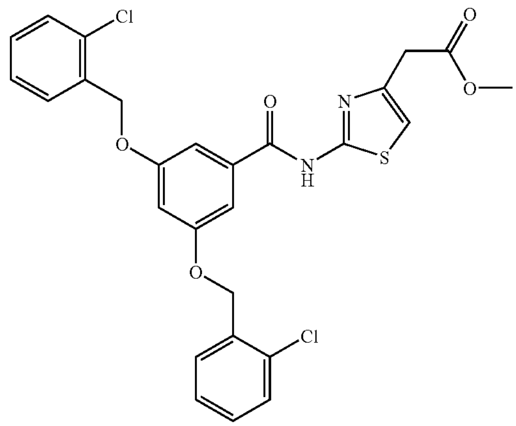 | 1 | | | 1H NMR d (d6-DMSO): 3.62 (3H, s); 3.76 (2H, s); 5.24 (4H, s); 6.94 (1H, m); 7.06 (1H, s); 7.38-7.47 (6H, m); 7.54 (2H, m); 7.63 (2H, m); 12.69 (1H, br s). |
| 4 | 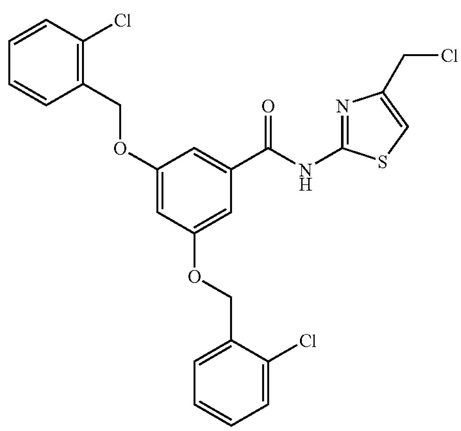 | 1 | | 531 | 1H NMR d (d6-DMSO): 4.77 (2H, s); 5.25 (4H, s); 6.94 (1H, m); 7.31 (1H, s); 7.36-7.48 (6H, m); 7.53 (2H, m); 7.63 (2H, m); 12.83 (1H, br s) (+0.4 eq. iPr2NEt). |
| 5 | 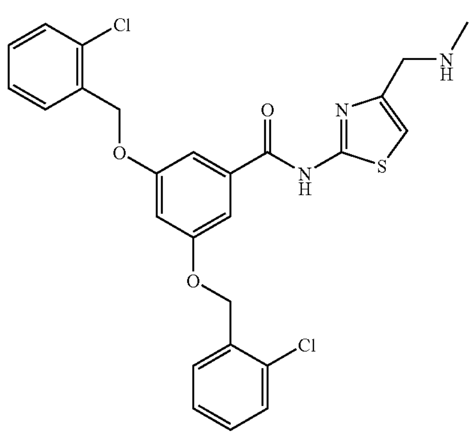 | 3 | | 528, 530 | 1H NMR d (d6-DMSO): 2.63 (3H, m); 4.16 (2H, m), 5.24 (4H, s), 6.99 (1H, s); 7.38-7.44 (7H, m); 7.52 (2H, m); 7.62 (2H, m); 9.06 (1H, br s); 12.75 (1H, br s). |

-continued

| Example | Structure | Route | (M + H)+ | (M − H)− | NMR |
|---|---|---|---|---|---|
| 6 | 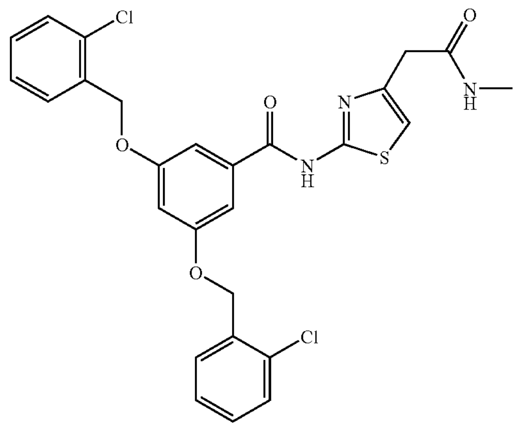 | 3 | | | 1H NMR d (d6-DMSO): 2.57 (3H, m); 3.48 (2H, m); 5.25 (4H, s); 6.95 (2H, m); 7.36-7.44 (6H, m); 7.53 (2H, m); 7.62 (2H, m); 7.83 (1H, m); 12.60 (1H, br s). |
| 7 | 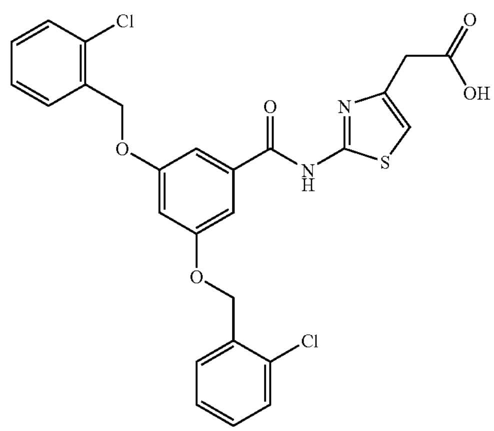 | 2a**** | | 497, 499 (—CO2) | 1H NMR d (d6-DMSO): 3.64 (2H, s); 5.26 (4H, s); 6.95 (1H, s); 7.04 (1H, s); 7.37-7.46 (6H, m); 7.54 (2H, m); 7.63 (2H, m); 12.40 (1H, br s); 12.68 (1H, br s) (•HCl). |
| 8 | 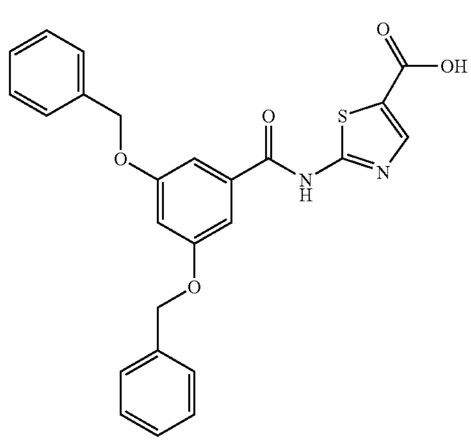 | 2a**** | | 459, 415 (—CO2) | 1H NMR d (d6-DMSO): 5.15 (4H, s); 6.9 (1H, s); 7.2-7.5 (12H, m); 8.1 (1H, s). |

-continued

| Example | Structure | Route | (M + H)+ | (M − H)− | NMR |
|---|---|---|---|---|---|
| 9 | 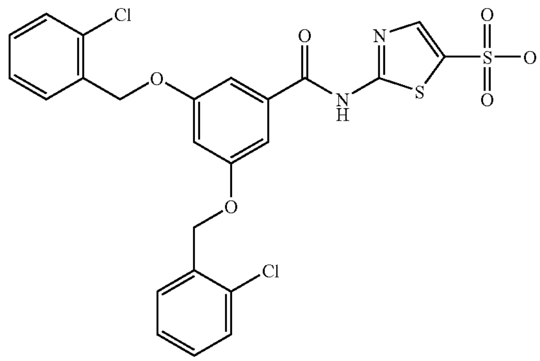 | 1 | | | 1H NMR d (d6-DMSO): (iPr2NEt salt) 1.24 (15H, m); 3.12 (2H, m); 3.80 (2H, m); 5.24 (4H, s); 6.93 (1H, m); 7.36-7.45 (7H, m); 7.51 (2H, m); 7.61 (2H, m); 12.56 (1H, br s). |
| 10 | 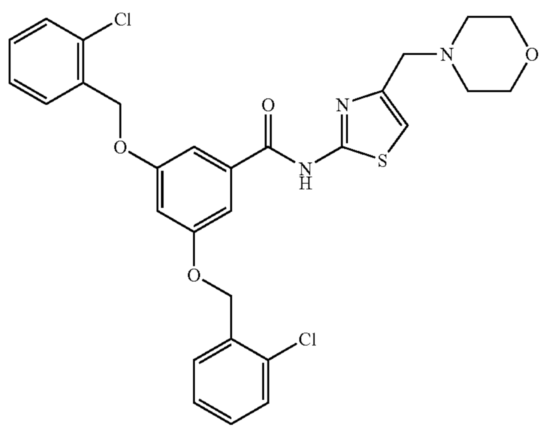 | 3 | | | 1H NMR d (d6-DMSO): 2.45 (4H, m); 3.55 (2H, s); 3.61 (4H, m); 5.29 (4H, s); 7.00 (1H, m); 7.11 (1H, s); 7.43-7.51 (6H, m); 7.58 (2H, m); 7.67 (2H, m); 12.66 (1H, br s). |
| 11 | 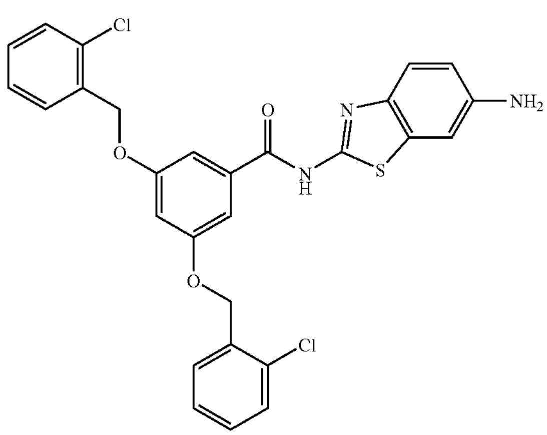 | 4 | 550, 552 | | 1H NMR d (d6-DMSO): 5.19 (2H, br s); 5.23 (4H, s); 6.72 (1H, dd); 6.93 (1H, m); 7.03 (1H, m); 7.35-7.44 (7H, m); 7.51 (2H, m); 7.61 (2H, m); 12.46 (1H, br s). |

| Example | Structure | Route | (M + H)+ | (M − H)− | NMR |
|---|---|---|---|---|---|
| 12 | 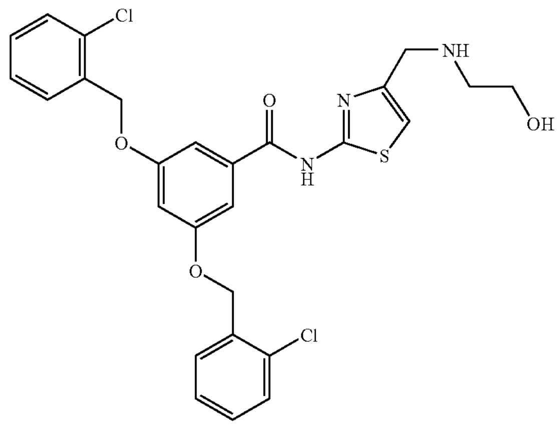 | 3 | 558, 560 | | 1H NMR d (d6-DMSO): 2.60 (2H, t); 3.45 (2H, t); 3.72 (2H, s); 5.22 (4H, s); 6.91 (1H, m); 6.96 (1H, s); 7.35-7.30 (7H, m); 7.50 (2H, m); 7.60 (2H, m). |
| 13 | 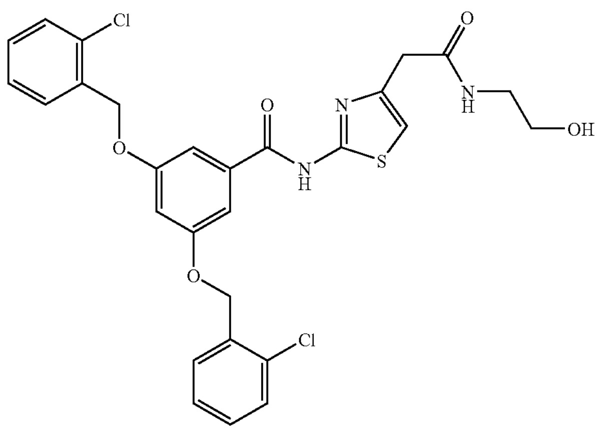 | 3 | 586, 588 | | 1H NMR d (d6-DMSO): 3.11 (2H, q); 3.37 (2H, q); 3.50 (2H, s); 3.61 (1H, t); 5.22 (4H, s); 6.92 (2H, m); 7.34-7.42 (6H, m); 7.49 (2H, m); 7.60 (2H, m); 7.88 (1H, br s). |
| 14 | 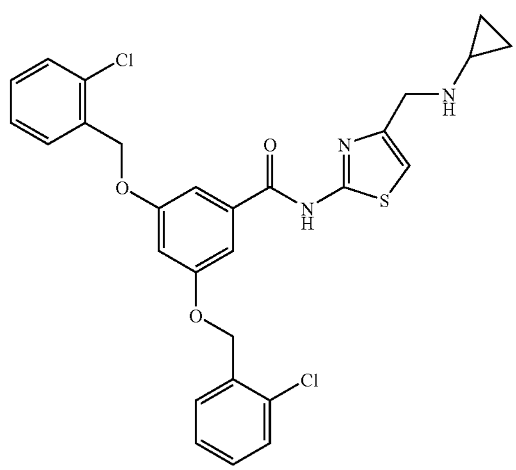 | 3 | 554, 556 | | 1H NMR d (d6-DMSO): 0.29 (2H, m); 0.40 (2H, m); 2.16 (1H, m); 3.79 (2H, s); 5.27 (4H, s); 6.98 (2H, m); 7.40-7.48 (7H, m); 7.56 (2H, m); 7.66 (2H, m). |
| 15 | 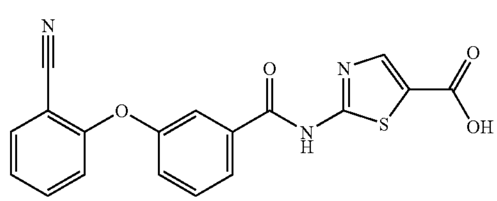 | 2b**** | 366 | 364 | 1H NMR d (d6-DMSO): 7.05 (1H, d); 7.35 (1H, t); 7.45 (1H, dd); 7.6-7.75 (2H, m); 7.85 (1H, m); 7.9-8.0 (2H, m); 8.15 (1H, s); 13.1 (2H, br s). |

-continued

| Example | Structure | Route | (M + H)+ | (M − H)− | NMR |
|---|---|---|---|---|---|
| 16 | 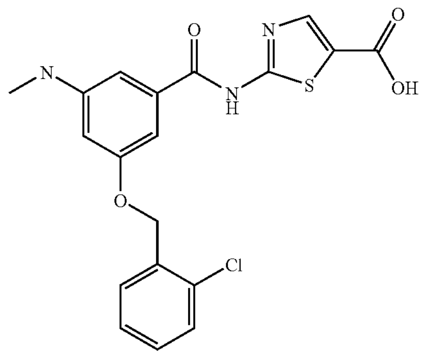 | 6 | | | 1H NMR d (d6-DMSO): 2.68 (3H, s); 3.81 (1H, s); 5.15 (2H, s); 6.38 (1H, s); 6.87 (1H, s); 7.00 (1H, s); 7.37 (2H, m); 7.49 (1H, m); 7.58 (1H, m); 8.10 (1H, s); 8.21 (1H, s). |
| 17 | 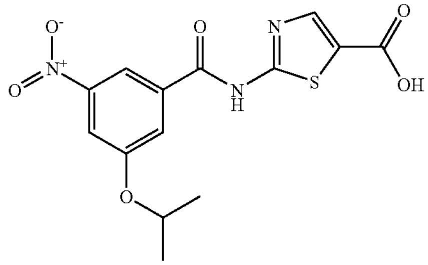 | 6 | | | 1H NMR d (d6-DMSO): 1.32 (6H, d); 4.88 (1H, m); 7.87 (1H, s); 8.05 (1H, s); 8.14 (1H, s); 8.45 (1H, s). |
| 18 | 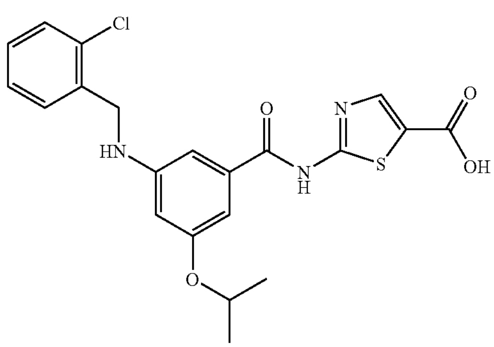 | 6 | | 400, 402 (—CO2) | 1H NMR d (d6-DMSO): 1.22 (6H, d); 4.36 (2H, m); 4.58 (1H, m); 6.24 (1H, s); 6.47 (1H, m); 6.84 (2H, m); 7.26 (3H, m); 7.37 (2H, m); 7.45 (1H, m); 7.76 (1H, br s). |
| 19 | 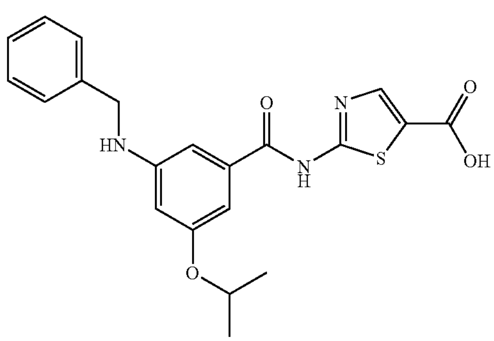 | 6 | | | 1H NMR d (d6-DMSO): 1.21 (6H, d); 4.28 (2H, m); 4.55 (1H, m); 6.26 (1H, s); 6.43 (1H, m); 6.83 (1H, s); 6.89 (1H, s); 7.20 (1H, m); 7.26-7.37 (4H, m); 7.74 (1H, br s). |

-continued

| Example | Structure | Route | (M + H)+ | (M − H)− | NMR |
|---|---|---|---|---|---|
| 20 | 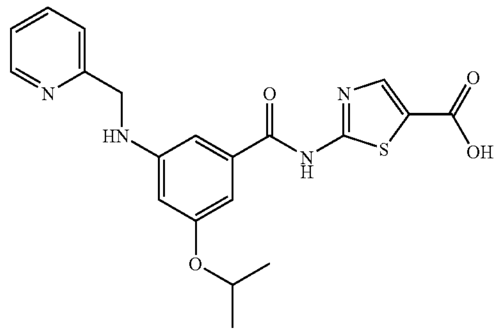 | 6 | | 367 (—CO2) | 1H NMR d (d6-DMSO): 1.23 (6H, d); 4.38 (2H, s); 4.60 (1H, m); 6.33 (1H, m); 6.89 (2H, m); 7.47 (1H, dd); 7.89 (1H, d); 8.10 (1H, s); 8.51 (1H, dd); 8.63 (1H, d). |
| 21 | 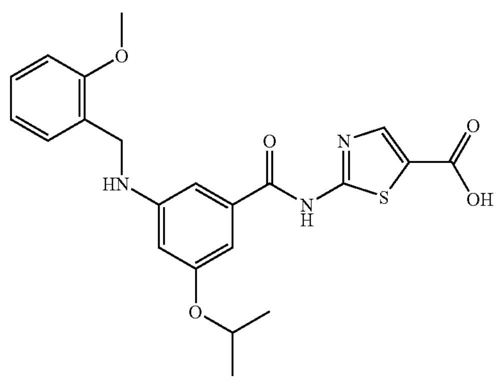 | 6 | | 396 (—CO2) | 1H NMR d (d6-DMSO): 1.21 (6H, d); 3.81 (3H, s); 4.24 (2H, m); 4.55 (1H, m); 6.26 (2H, m); 6.84 (3H, m); 6.97 (1H, m); 7.20 (2H, m). |
| 22 | 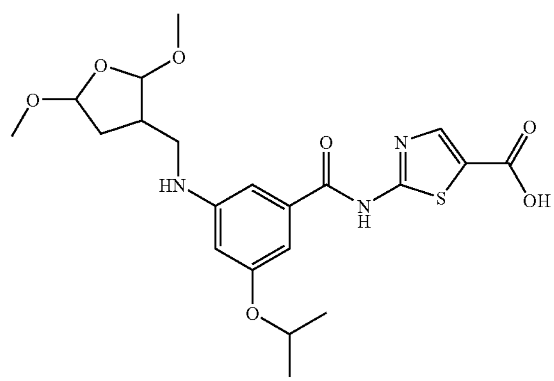 | 6 | | 464, 420 (—CO2) | |
| 23 | 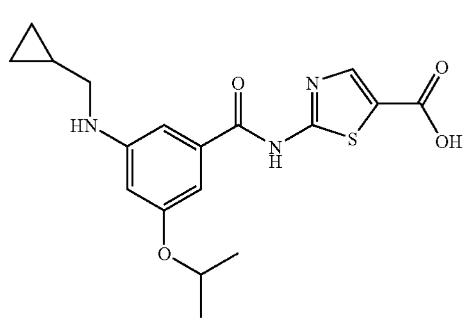 | 6 | | | 1H NMR d (d6-DMSO): 0.28 (2H, m); 0.52 (2H, m); 1.09 (1H, m); 1.32 (6H, d); 3.02 (2H, d); 4.69 (1H, m); 6.50 (1H, s); 6.99 (2H, s); 8.20 (1H, s). |

-continued
| Example | Structure | Route | (M + H)+ | (M − H)− | NMR |
|---|---|---|---|---|---|
| 24 | 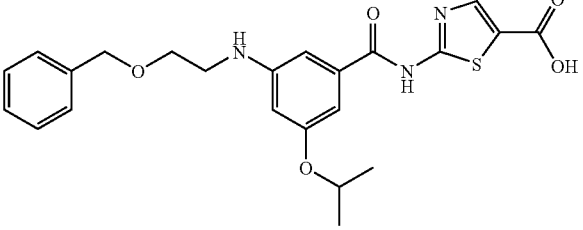 | 6 | | | 1H NMR d (d6-DMSO): 1.24 (6H, d); 3.29 (2H, m); 3.56 (2H, t); 4.50 (2H, s); 4.58 (1H, m); 6.37 (1H, m); 6.85 (1H, s); 6.90 (1H, s); 7.26 (2H, m); 7.13 (3H, m); 8.10 (1H, s). |
| 25 | 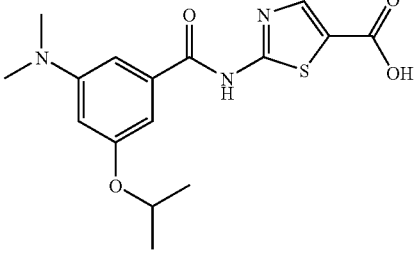 | 6 | | 348 | 1H NMR d (d6-DMSO): 1.27 (6H, d); 2.96 (6H, s); 4.69 (1H, m); 6.39 (1H, m); 6.97 (1H, s); 7.04 (1H, s); 8.13 (1H, s); 12.89 (1H, br s). |
| 26 | 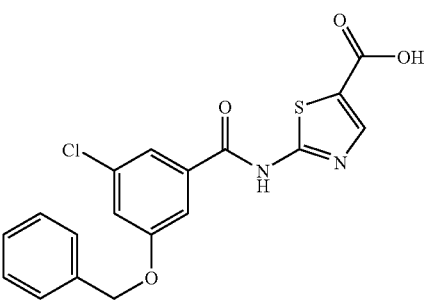 | 2a**** | 389, 391 | | 1H NMR d (d6-DMSO): 5.21 (2H, s); 7.29-7.49 (6H, m); 7.74 (2H, s); 8.13 (1H, s); 13.1 (1H, br s). |
| 27 | 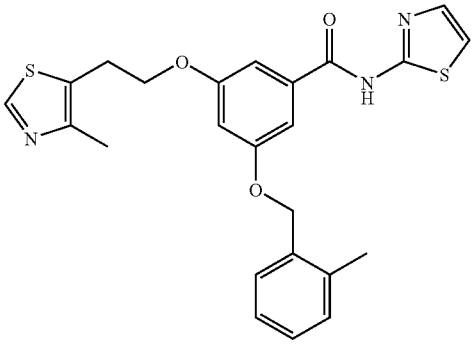 | 1 | | | 1H NMR d (d6-DMSO): 2.31 (3H, s); 2.35 (3H, s); 3.22 (2H, t); 4.21 (2H, t); 5.12 (2H, s); 6.79 (1H, m); 7.18-7.28 (4H, m); 7.30 (1H, m); 7.54 (1H, d); 8.82 (1H, s); 12.48 (1H, br s). |
| 28 | 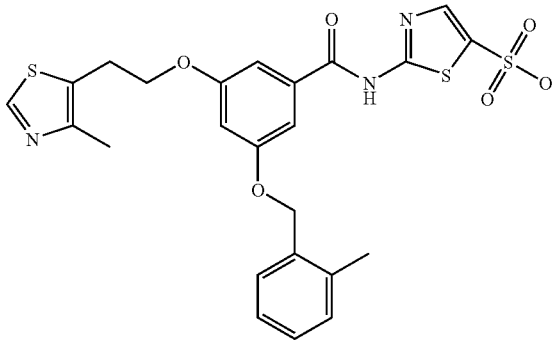 | 1 | | | 1H NMR d (d6-DMSO): 2.32 (3H, s); 2.37 (3H, s); 3.24 (2H, t); 4.22 (2H, t); 5.13 (2H, s); 6.80 (1H, m); 7.19 (3H, m); 7.29 (1H, s); 7.37-7.45 (3H, m); 9.06 (1H, s); 12.48 (1H, br s). |

-continued

| Example | Structure | Route | (M + H)+ | (M − H)− | NMR |
|---|---|---|---|---|---|
| 29 | 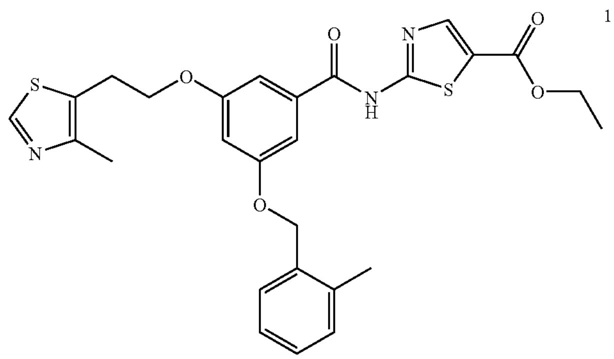 | 1 | | | 1H NMR d (d6-DMSO): 1.28 (3H, t); 2.32 (3H, s); 2.37 (3H, s); 3.24 (2H, t); 4.14-4.29 (4H, m); 5.13 (2H, s); 6.84 (1H, m); 7.21 (4H, m); 7.29 (1H, s); 7.38 (2H, m); 8.20 (1H, s); 8.81 (1H, s). |
| 30 | 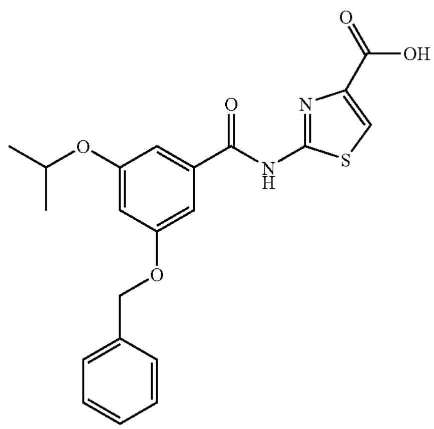 | 2a (1) | | | $^1$H NMR d (d$_6$-DMSO): 1.26 (d, 6H), 4.69 (m, 1H), 5.14 (s, 2H), 6.75 (s, 1H), 7.26-7.48 (m, 7H), 8.01 (s, 1H). |
| 31 | 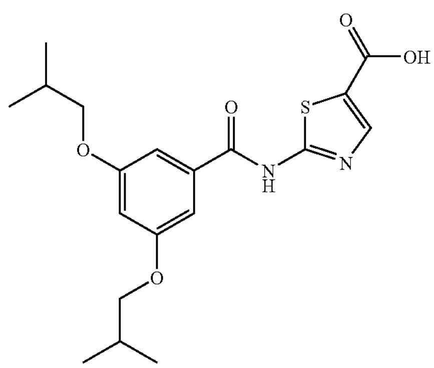 | 2a (1b) | | 391 | $^1$H NMR d (d$_6$-DMSO): 1.0 (d, 12H), 2.0 (m, 2H), 3.8 (d, 4H), 6.75 (s, 1H), 7.25 (d, 2H), 8.15 (s, 1H). |
| 32 | 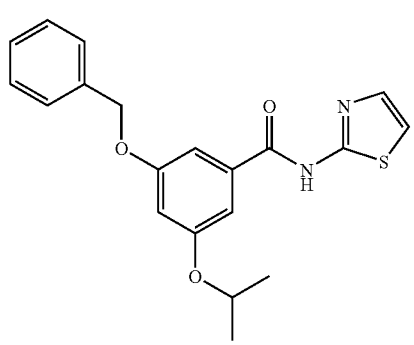 | 1 | | | $^1$H NMR δ (d$_6$-DMSO): 1.26 (d, 6H), 4.69 (m, 1H), 5.16 (s, 2H), 6.74 (s, 1H), 7.26 (d, 1H), 7.31-7.47 (m, 7H), 8.54 (d, 1H), 12.47 (bs, 1H). |

| Example | Structure | Route | (M + H)+ | (M − H)− | NMR |
|---------|-----------|-------|----------|----------|-----|
| 33 | 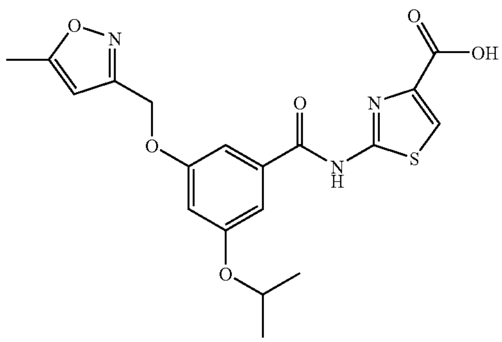 | 2a (1) | | | $^1$H NMR δ (d$_6$-DMSO): 1.26 (d, 6H), 2.38 (s, 3H), 4.69 (m, 1H), 5.18 (s, 2H), 6.31 (s, 1H), 6.76 (s, 1H), 7.30 (s, 1H), 7.35 (s, 1H), 8.00 (s, 1H). |
| 34 | 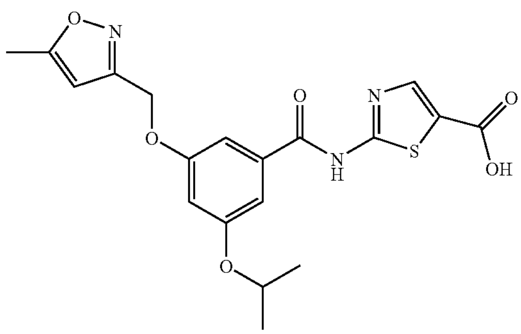 | 2a (1) | | | $^1$H NMR δ (d$_6$-DMSO): 1.26 (d, 6H), 2.39 (s, 3H), 4.70 (m, 1H), 5.20 (s, 2H), 6.31 (s, 1H), 6.79 (s, 1H), 7.27 (s, 1H), 7.32 (s, 1H), 8.12 (s, 1H). |
| 35 | 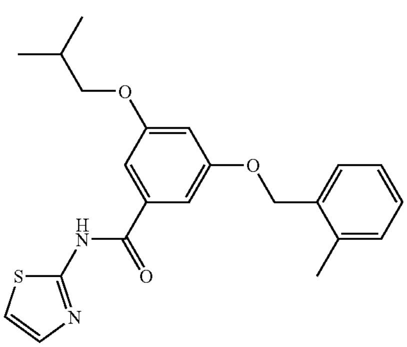 | 1b | 397 | | |
| 36 | 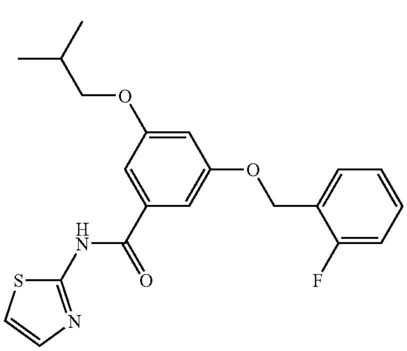 | 1b | 401 | | |

| Example | Structure | Route | (M + H)+ | (M − H)− | NMR |
|---|---|---|---|---|---|
| 37 | 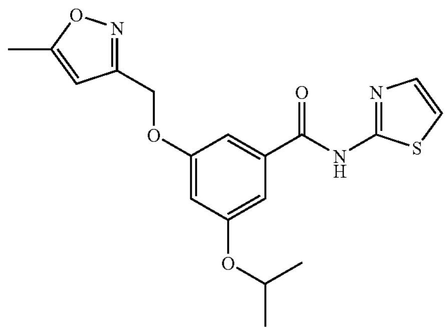 | 1 | | | ¹H NMR δ (d₆-DMSO): 1.27 (d, 6H), 2.39 (s, 3H), 4.69 (m, 1H), 5.18 (s, 2H), 6.31 (s, 1H), 6.76 (s, 1H), 7.26 (m, 2H), 7.32 (s, 1H), 8.53 (d, 1H). |
| 36a | 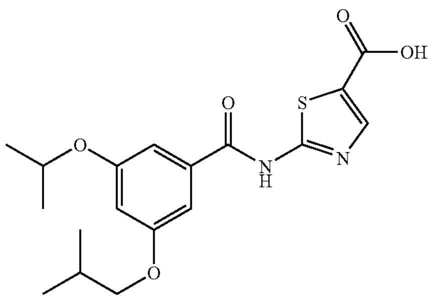 | 2a (1) | 379 | 377 | ¹H NMR δ (d₆-DMSO): 12.98 (bs, 1H), 8.12 (s, 1H), 7.24 (s, 1H), 6.66 (s, 1H), 4.70 (m, 1H), 3.79 (d, 2H), 2.01 (m, 1H), 1.28 (d, 6H), 0.98 (d, 6H). |
| 37a | 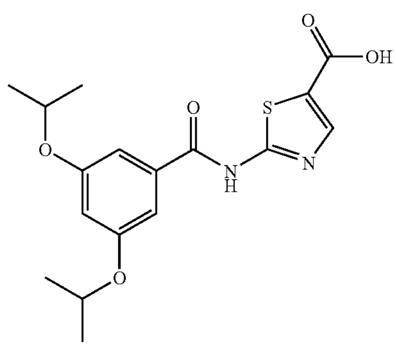 | 2a (1b) | 365 | | ¹H NMR d (d₆-DMSO): 1.25 (d, 12H), 4.7 (hept, 2H), 6.65 (s, 1H), 7.2 (s, 2H), 8.15 (s, 1H). |
| 38 | 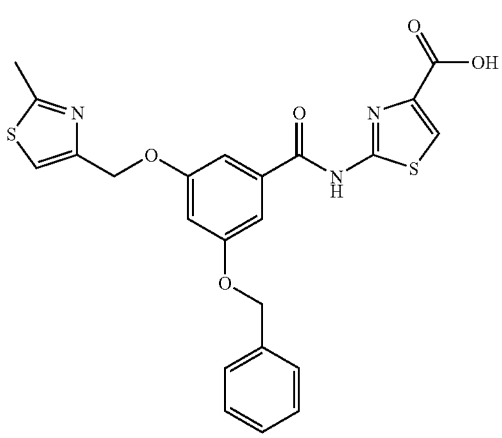 | 2a (1) | | | ¹H NMR δ (d₆-DMSO): 2.64 (s, 3H), 5.16 (s, 4H), 6.90 (s, 1H), 7.29-7.47 (m, 7H), 7.53 (s, 1H), 8.03 (m, 1H), 12.90 (bs, 1H). |

-continued

| Example | Structure | Route | (M + H)+ | (M − H)− | NMR |
|---|---|---|---|---|---|
| 39 | 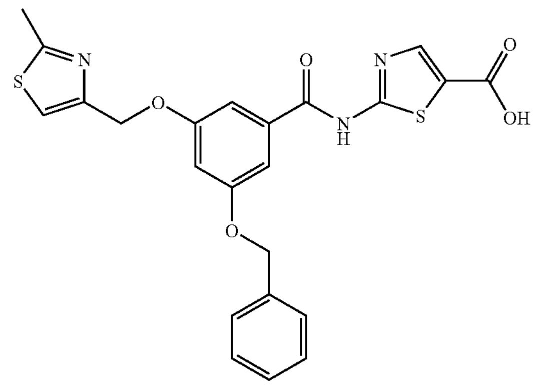 | 2a (1) | | | ¹H NMR δ (d₆-DMSO): 2.64 (s, 3H), 5.17 (s, 4H), 6.93 (s, 1H), 7.29-7.45 (m, 7H), 7.53 (s, 1H), 8.13 (m, 1H). |
| 40 | 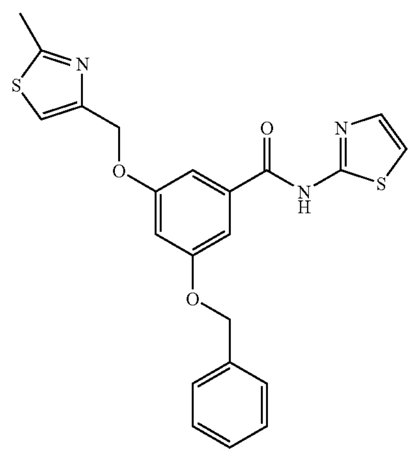 | 1 | | | ¹H NMR δ (d₆-DMSO): 2.64 (s, 3H), 5.14 (s, 4H), 6.90 (s, 1H), 7.26 (d, 1H), 7.31-7.47 (m, 7H), 7.49 (m, 1H), 7.55 (d, 1H), 12.56 (bs, 1H). |
| 41 | 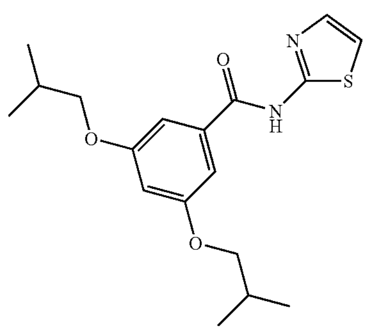 | 1b | | 349 | |
| 42 | 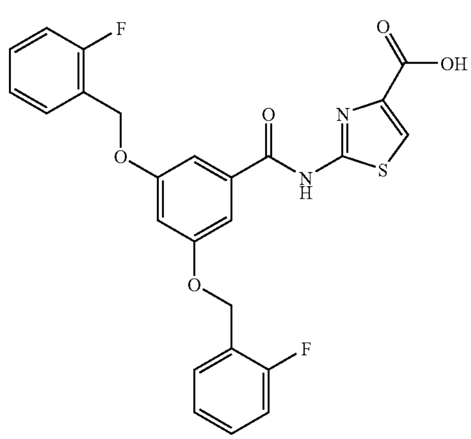 | 2a (1) | | | ¹H NMR δ (d₆-DMSO): 5.22 (s, 4H), 6.96 (s, 1H), 7.20-7.29 (m, 4H), 7.37-7.44 (m, 4H), 7.55 (m, 2H), 8.12 (s, 1H). |

| Example | Structure | Route | (M + H)+ | (M − H)− | NMR |
|---|---|---|---|---|---|
| 43 | 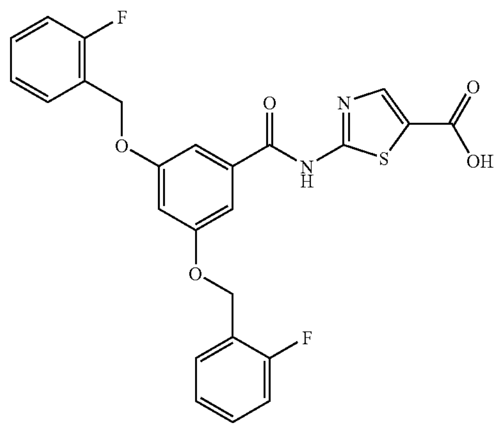 | 2a (1) | | | ¹H NMR δ (d₆-DMSO): 5.21 (s, 4H), 6.93 (s, 1H), 7.19-7.29 (m, 4H), 7.38-7.46 (m, 4H), 7.56 (m, 2H), 8.03 (s, 1H). |
| 44 | 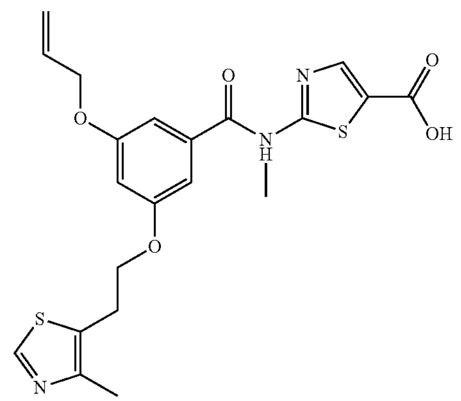 | 2a (1) | | | ¹H NMR δ (d₆-DMSO): 2.38 (s, 3H), 3.25 (t, 2H), 4.24 (t, 2H), 4.65 (d, 2H), 5.27 (d, 1H), 5.42 (d, 1H), 6.05 (m, 1H), 6.78 (s, 1H), 7.32 (s, 2H), 8.15 (s, 1H), 8.90 (s, 1H), 12.94 (br s, 1H). |
| 45 | 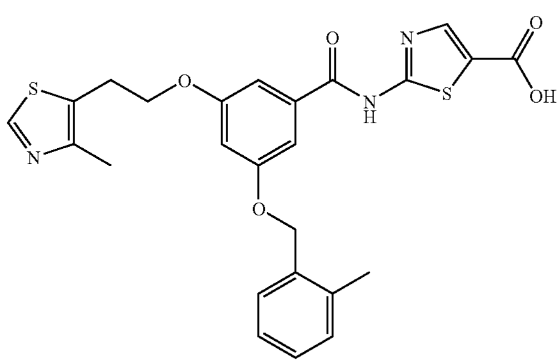 | 2a (1) | | | ¹H NMR δ (d₆-DMSO): 2.32 (s, 3H), 2.34 (s, 3H), 3.22 (t, 2H), 4.21 (t, 2H), 5.13 (s, 2H), 6.82 (s, 1H), 7.16-7.25 (m, 3H), 7.30 (1H, s), 7.39 (1H, m), 7.98 (s, 1H), 8.81 (s, 1H). |
| 46 | 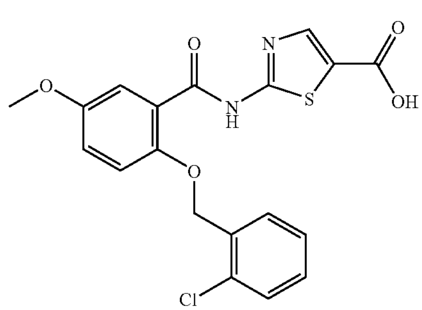 | 2a* | 419 | 417 | ¹H NMR δ (d₆-DMSO): 3.8 (s, 3H), 5.3 (s, 2H), 7.15 (dd, 1H), 7.2-7.4 (m, 4H), 7.5 (d, 1H), 7.6 (d, 1H), 8.0 (s, 1H). |

-continued

| Example | Structure | Route | (M + H)+ | (M − H)− | NMR |
|---|---|---|---|---|---|
| 47 | 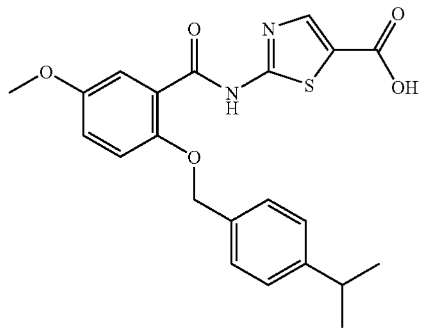 | 2a* | 427 | 425 | ¹H NMR δ (d₆-DMSO): 1.1 (d, 6H), 2.85 (hept, 1H), 3.75 (s, 3H), 5.2 (s, 2H), 7.0-7.3 (m, 6H), 7.4 (d, 1H), 8.0 (s, 1H). |
| 48 | 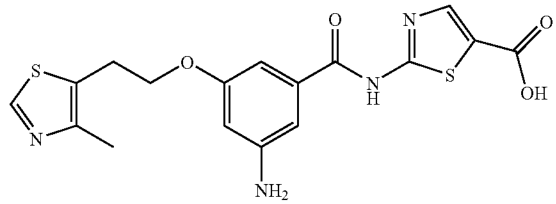 | 2a** | 405 | 403 | ¹H NMR δ (d₆-DMSO): 2.34 (s, 3H), 3.20 (t, 2H), 4.13 (t, 2H), 6.43 (s, 1H), 6.92 (s, 1H), 6.97 (s, 1H), 8.09 (s, 1H), 8.83 (s, 1H), 12.75 (bs, 1H) |
| 49 | 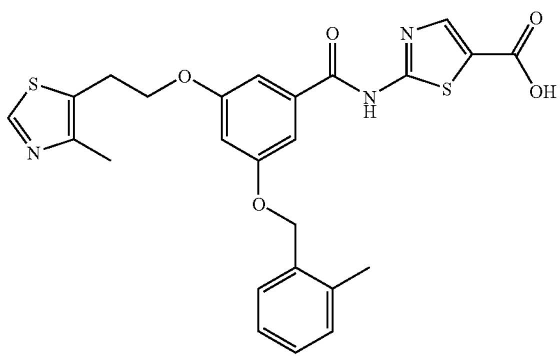 | 2a* | | | ¹H NMR δ (d₆-DMSO): 2.33 (s, 3H), 2.36 (2.36, 3H), 3.23 (t, 2H), 4.22 (t, 2H), 5.15 (s, 2H), 7.21 (s, 1H), 7.02-7.44 (m, 6H), 8.13 (s, 1H), 8.85 (s, 1H), 12.92 (bs, 1H) |
| 50 | 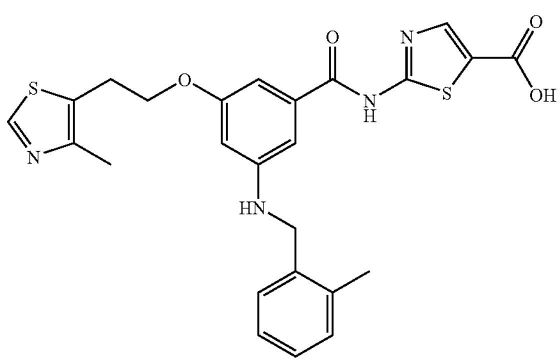 | 6** | | | ¹H NMR δ (d₆-DMSO): 2.32 (s, 3H), 2.34 (s, 3H), 3.19 (t, 2H), 4.12 (t, 2H), 4.25 (s, 2H), 6.37 (s, 1H), 6.92 (d, 2H), 7.08-7.21 (m, 3H), 7.25 (dd, 1H), 8.10 (s, 1H), 8.85 (s, 1H), 12.76 (bs, 1H) |
| 51 | 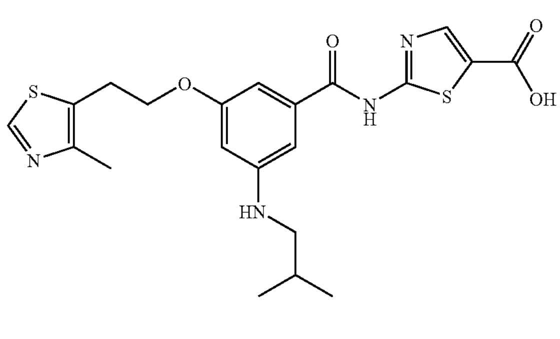 | 6** | | | |

-continued

| Example | Structure | Route | (M + H)+ | (M − H)− | NMR |
|---|---|---|---|---|---|
| 52 | 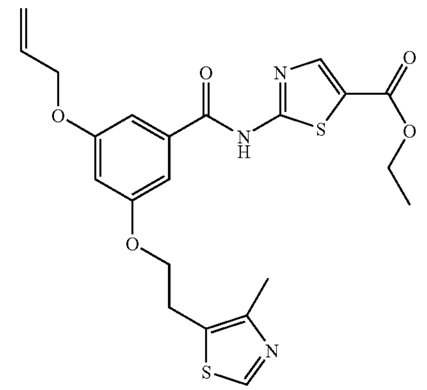 | 1 | | | ¹H NMR δ (d₆-DMSO): 1.28 (t, 3H), 2.35 (s, 3H), 3.22 (t, 2H), 4.11 (t, 2H), 4.27 (q, 2H), 4.63 (d, 2H), 5.26 (dd, 1H), 5.39 (d, 1H), 6.04 (m, 1H), 6.76 (t, 1H), 7.28 (d, 2H), 8.21 (s, 1H), 8.81 (s, 1H), 13.02 (bs, 1H) |
| 53 | 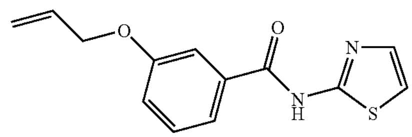 | 1b | 261 | 259 | ¹H NMR δ (CDCl₃): 4.58 (d, 2H), 5.31 (dd, 1H), 5.45 (dd, 1H), 6.04 (m, 1H), 6.95 (d, 1H) 7.11 (d, 1H), 7.18 (m, 1H), 7.41 (t, 1H), 7.55 (m, 2H), 12.09 (br s, 1H). |
| 54 | 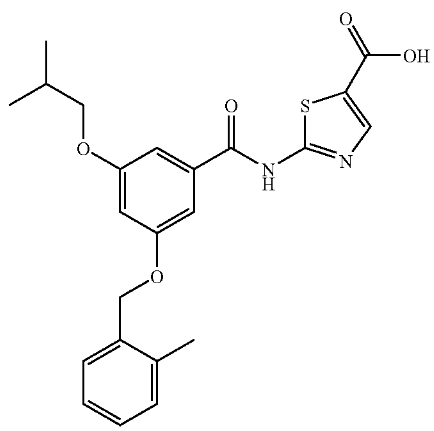 | 2a | 445 | | ¹H NMR δ (d₆-DMSO): 0.98 (d, 6H), 1.98-2.05 (m, 1H), 3.81 (d, 2H), 5.20 (s, 2H), 6.81 (s, 1H), 7.0-7.1 (m, 2H), 7.35 (s, 1H), 7.38-7.45 (m, 2H), 7.58 (t, 1H), 8.03 (s, 1H), 12.90 (br s, 1H). |
| 55 | 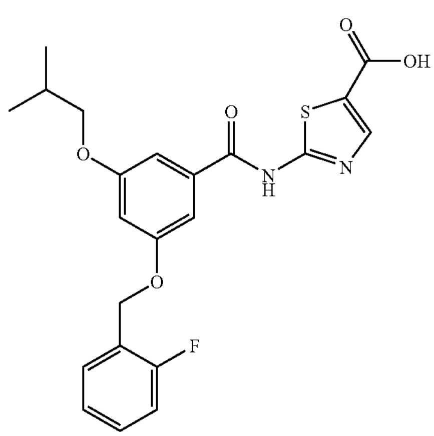 | 2a | 441 | | ¹H NMR δ (d₆-DMSO): 0.98 (d, 6H), 1.98-2.05 (m, 1H), 2.36 (s, 3H), 3.81 (d, 2H), 5.17 (s, 2H), 6.81 7.17-7.23 (m, 3H), 7.32 (s, 1H), 7.40 (ap d, 2H), 8.01 (s, 1H) |

-continued

| Example | Structure | Route | (M + H)+ | (M − H)− | NMR |
|---|---|---|---|---|---|
| 56 | 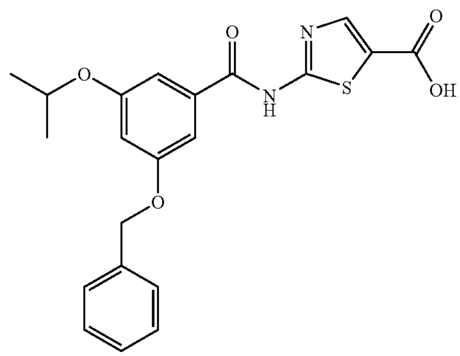 | 2a | | | ¹H NMR δ (d₆-DMSO): 1.27 (d, 6H), 4.71 (sept, 1H), 5.16 (d, 2H), 6.78 (d, 1H), 7.25-7.51 (m, 7H), 8.12 (s, 1H), 12.98 (bs, 1H) |
| 57 | 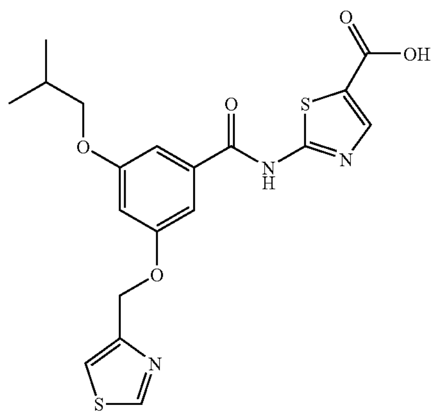 | 2a | 434 | 432 | ¹H NMR δ (d₆-DMSO): 0.98 (d, 6H), 1.98-2.05 (m, 1H), 3.81 (d, 2H), 5.26 (s, 2H), 6.83 (ap t, 1H), 7.30 (s, 1H), 7.39 (s, 1H), 7.79 (s, 1H), 8.12 (s, 1H), 9.1 (s, 1H). |
| 58 | 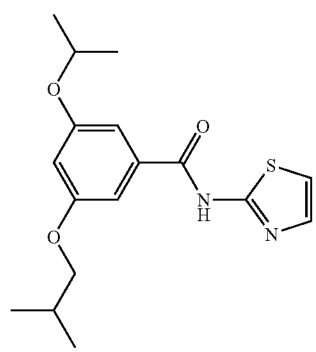 | 1b | 335 | | |
| 59 | 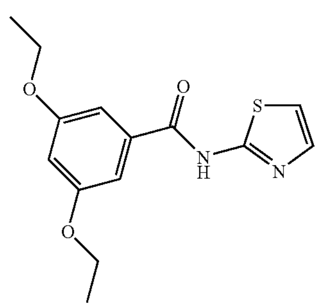 | 1b | 293 | | |

| Example | Structure | Route | (M + H)+ | (M − H)− | NMR |
|---|---|---|---|---|---|
| 60 | 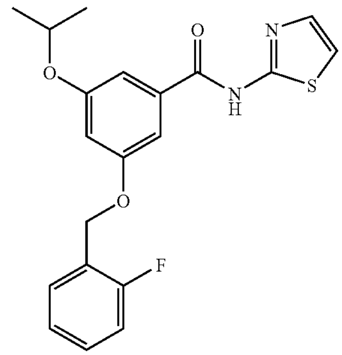 | 1 | | | $^1$H NMR δ (d$_6$-DMSO): 1.29 (d, 6H), 4.74 (sept, 1H), 5.22 (s, 2H), 6.79 (t, 1H), 7.19-7.32 (m, 4H), 7.37 (t, 1H), 7.43 (m, 1H), 7.56 (m, 2H), 12.61 (bs, 1H) |
| 61 | 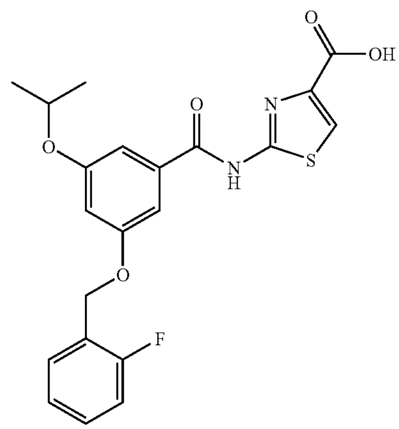 | 2a | | | $^1$H NMR δ (d$_6$-DMSO) 1.26 (d, 6H), 4.64-4.76 (m, 1H), 5.20 (s, 2H), 6.78 (s, 1H), 7.18-7.34 (m, 3H), 7.36-7.46 (m, 2H), 7.50-7.60 (m, 1H), 7.98 (s, 1H) |
| 62 | 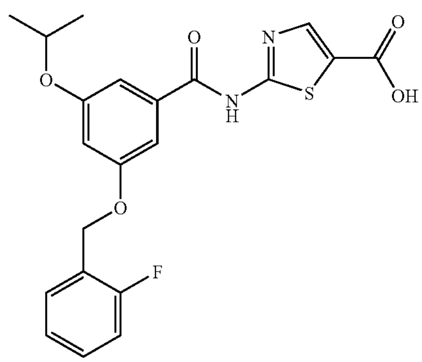 | 2a | | | $^1$H NMR δ (d$_6$-DMSO):): 1.27 (d, 6H), 4.71 (m, 1H), 5.20 (s, 2H), 6.78-6.84 (m, 1H), 7.18-7.31 (m, 3H), 7.34-7.49 (m, 2H), 7.52-7.61 (m, 1H), 8.12 (s, 1H), 12.98 (bs, 1H) |
| 63 | 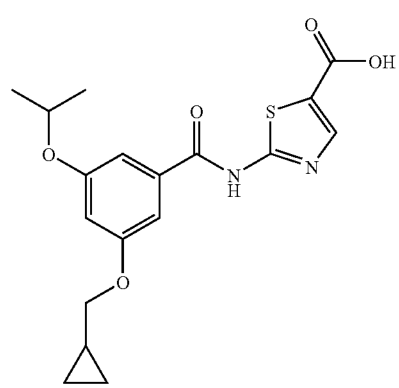 | 2a | 377 | | $^1$H NMR δ (d$_6$-DMSO): 0.0-0.2 (m, 2H), 0.22-0.3 (m, 2H), 0.98 (d, 6H), 3.59 (d, 2H), 4.35-4.42 (m, 1H), 6.4 (s, 1H), 6.93 (s, 2H), 7.82 (s, 1H). |

-continued

| Example | Structure | Route | (M + H)+ | (M − H)− | NMR |
|---|---|---|---|---|---|
| 64 | 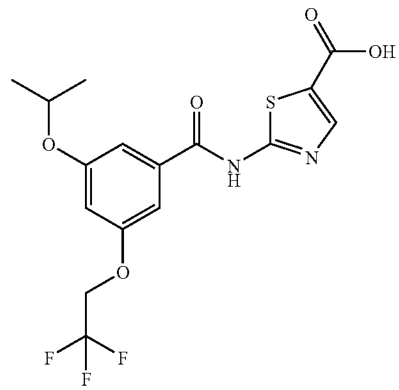 | 2a | 403 | | ¹H NMR δ (d₆-DMSO): 1.29 (d, 6H), 4.78 (m, 1H), 4.86 (q, 2H), 6.89 (ap t, 1H), 7.36 (ap t, 2H), 8.17 (s, 1H), 13.05 (bs) |
| 65 | 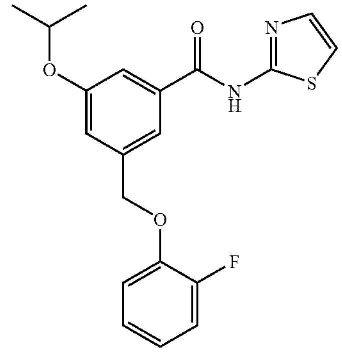 | 1*** | | | ¹H NMR δ (d₆-DMSO): 1.29 (d, 6H), 4.72 (m, 1H), 5.19 (s, 2H), 6.88-6.97 (m, 1H), 7.09 (m, 1H), 7.16-7.26 (m, 4H), 7.54 (d, 1H), 7.61 (s, 1H), 7.70 (s, 1H), 12.05 (bs, 1H). |
| 66 | 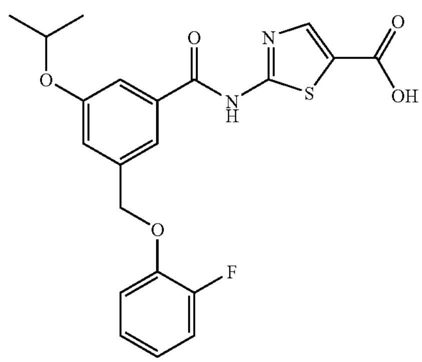 | 2a*** | | | ¹H NMR δ (d₆-DMSO): 1.29 (d, 6H), 4.74 (m, 1H), 5.18 (s, 2H), 6.87-6.97 (m, 1H), 7.11 (m, 1H), 7.16-7.26 (m, 3H), 7.63 (s, 1H), 7.71 (s, 1H), 8.11 (s, 1H). |
| 67 | 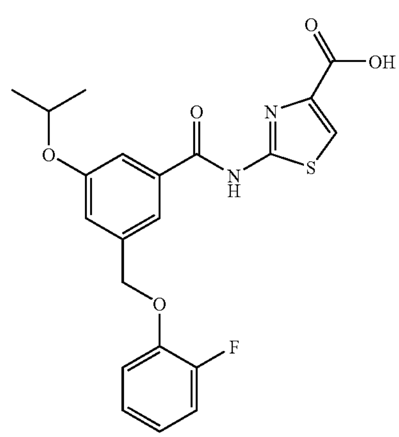 | 2a*** | | | ¹H NMR δ (d₆-DMSO): 1.29 (d, 6H), 4.74 (m, 1H), 5.18 (s, 2H), 6.89-6.97 (m, 1H), 7.09 (m, 1H), 7.17-7.26 (m, 3H), 7.66 (s, 1H), 7.74 (s, 1H), 7.99 (s, 1H). |

-continued

| Example | Structure | Route | (M + H)+ | (M − H)− | NMR |
|---------|-----------|-------|----------|----------|-----|
| 68 | 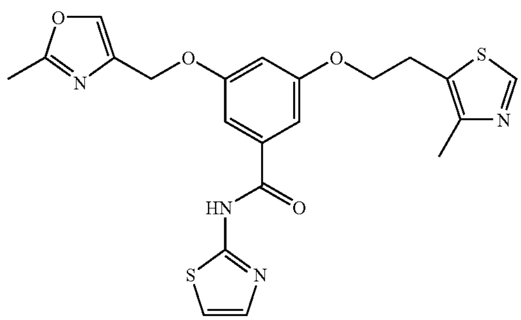 | 1b | 457 | | |
| 69 | 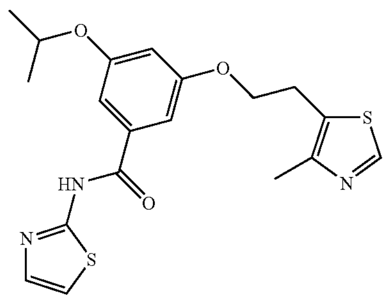 | 1b | 404 | | |
| 70 | 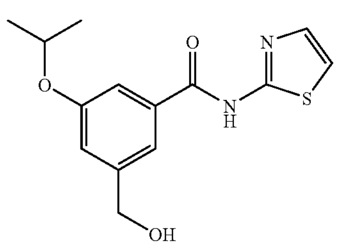 | 23 | | | ¹H NMR δ (d₆-DMSO): 1.28 (d, 6H), 4.51 (s, 2H), 4.71 (m, 1H), 7.05 (s, 1H), 7.25 (d, 1H), 7.50 (s, 1H), 7.53 (d, 1H), 7.58 (s, 1H), 12.50 (bs, 1H). |
| 71 | 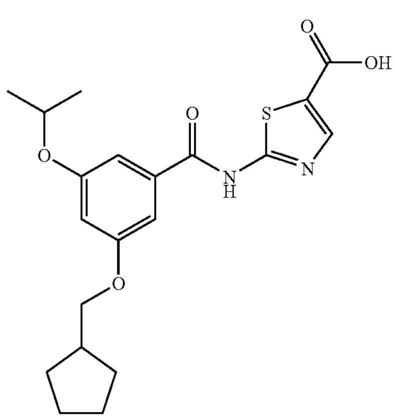 | 2a | 405 | 403 | ¹H NMR δ (d₆-DMSO): 1.14 (d, 6H), 1.3-1.4 (m, 2H), 1.42-1.62 (m, 4H), 1.65-1.82 (m, 2H), 3.9 (d, 2H), 4.62-4.78 (m, 1H), 6.68 (s, 1H), 7.22 (s, 2H), 8.12 (s, 1H). |

| Example | Structure | Route | (M + H)+ | (M − H)− | NMR |
|---|---|---|---|---|---|
| 72 | 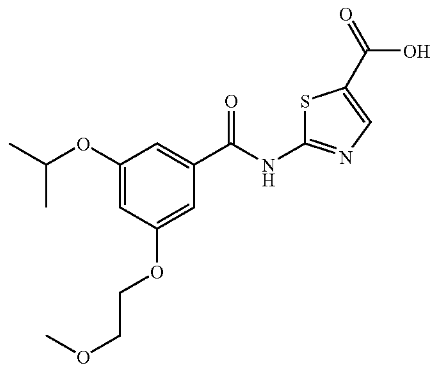 | 2a | 381 | 379 | ¹H NMR δ (d₆-DMSO): 1.25 (d, 6H), 3.3 (s, 3H), 3.7 (t, 2H), 4.15 (t, 2H), 4.6-4.8 (hept, 1H), 6.75 (t, 1H), 7.25 (d, 2H), 8.15 (s, 1H), 13.0 (bs, 2H). |
| 73 | 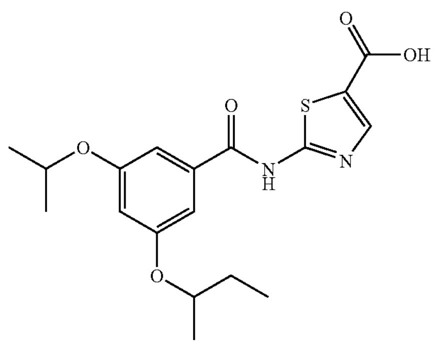 | 2a | 379 | 377 | ¹H NMR δ (d₆-DMSO): 3.85 (s, 3H), 5.25 (s, 2H) 6.9 (m, 1H) 7.2-7.35 (m, 3H), 7.4-7.5 (m, 2H), 7.6-7.7 (t of d, 1H), 8.15 (s, 1H), 13.0 (bs, 2H). |
| 74 | 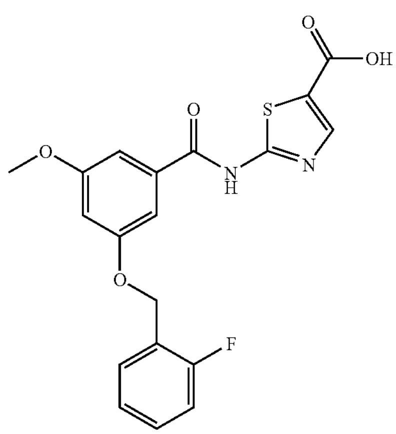 | 2a | 401 | | ¹H NMR δ (d₆-DMSO): 0.9 (t, 3H), 1.2-1.3 (d, 3H + d, 6H) 1.5-1.75 (m, 2H) 4.45 (hex, 1H), 4.75 (hept, 1H), 6.7 (t, 1H), 7.2 (d, 2H), 8.15 (s, 1H), 13.0 (bs, 2H). |
| 75 | 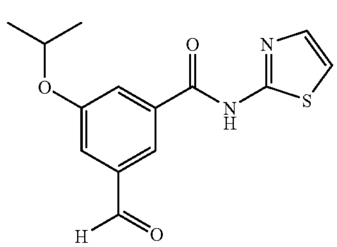 | 22 | | | ¹H NMR δ (d₆-DMSO): 1.31 (d, 6H), 4.82 (m, 1H), 7.26 (d, 1H), 7.56 (d, 1H), 7.59 (s, 1H), 7.94 (d, 1H), 8.15 (s, 1H), 10.00 (s, 1H), 12.77 (bs, 1H). |

| Example | Structure | Route | (M + H)+ | (M − H)− | NMR |
|---|---|---|---|---|---|
| 76 | 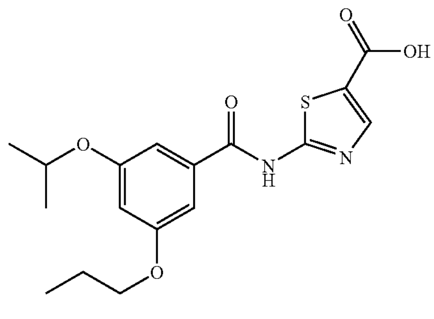 | 2a | | | ¹H NMR δ (d₆-DMSO): 0.97 (d, 3H), 1.26 (s, 6H), 1.72 (t, 2H), 3.85-4.20 (m, 2H), 4.56-4.83 (m, 1H), 6.69 (s, 1H), 7.00 (s, 1H), 7.26 (s, 1H), 8.11 (s, 1H) |
| 77 | 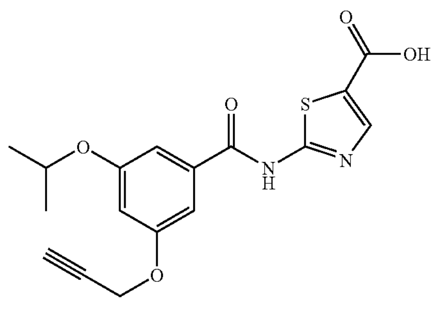 | 2a | 359 | | ¹H NMR δ (d₆-DMSO): 1.30 (d, 6H), 3.30 (s, 1H), 4.74 (m, 1H), 4.88 (s, 2H), 6.80 (s, 1H), 7.31 app d, 2H), 8.15 (s, 1H), 10.01 (bs, 1H) |
| 78 | 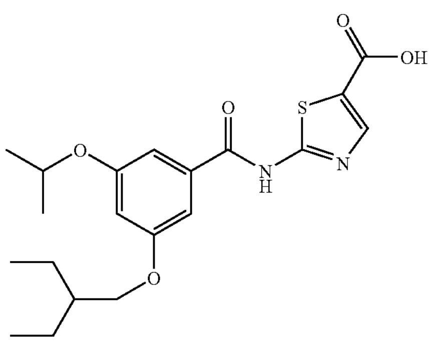 | 2a | 407 | 405 | ¹H NMR δ (d₆-DMSO): 0.91 (t, 6H), 1.29 (d, 6H), 1.37-1.53 (m, 4H), 1.56-1.70 (m, 1H), 3.30 (d, 2H), 4.73 (m, 1H) 6.72 (s, 1H), 7.26 (app d, 2H), 8.14 (s, 1H), 13.00 (bs, 1H) |
| 79 | 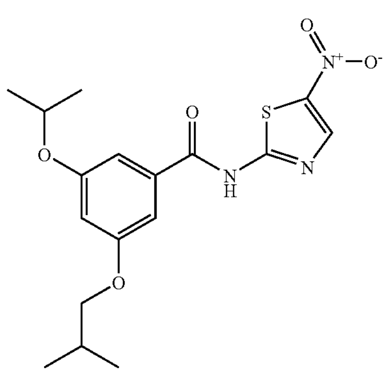 | 1 | 378 | | ¹H NMR δ (d₆-DMSO): 0.98 (d, 6H), 1.28 (d, 6H), 2.02 (m, 1H), 3.80 (d, 2H), 4.65 (m, 1H), 6.75 (ap t, 1H), 7.25 (ap d, 2H), 8.68 (s, 1H) |

| Example | Structure | Route | (M + H)+ | (M − H)− | NMR |
|---|---|---|---|---|---|
| 80 | 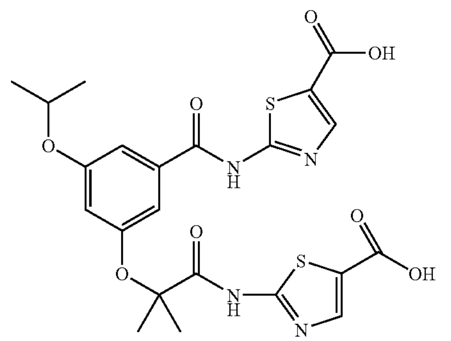 | 28 | 533 | | ¹H NMR δ (d₆-DMSO): 1.22 (d, 6H), 1.61 (s, 6H), 4.58-4.64 (m, 1H), 6.62 (s, 1H), 7.19 (s, 1H), 7.40 (s, 1H), 8.05 (s, 1H), 8.12 (s, 1H). |
| 81 | 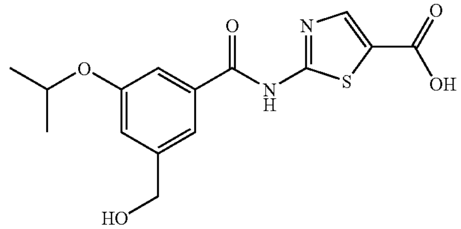 | 2a | | | ¹H NMR δ (d₆-DMSO): 1.29 (d, 6H), 4.50 (m, 2H), 4.71 (m, 1H), 5.26 (bs, 1H), 7.08 (s, 1H), 7.53 (s, 1H), 7.60 (s, 1H), 8.01 (s, 1H), 13.00 (bs, 1H). |
| 82 | 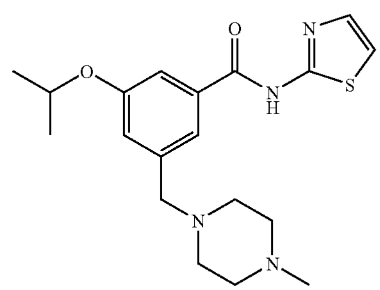 | 21 | | | ¹H NMR δ (d₆-DMSO): 1.32 (d, 6H), 2.80 (s, 3H), 3.37-3.63 (m, 4H), 3.95-4.10 (m, 4H), 4.39 (m, 2H), 4.76 (m, 1H), 7.29 (d, 1H), 7.53 (m, 3H), 7.68 (s, 1H), 7.79 (s, 1H), 12.77 (bs, 1H). |
| 83 | 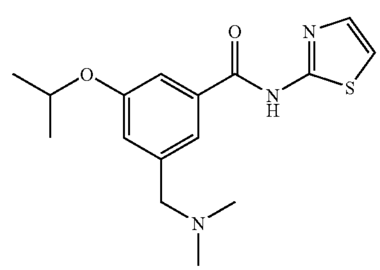 | 21 | | | ¹H NMR δ (d₆-DMSO): 1.31 (d, 6H), 2.71 (s, 6H), 4.26 (m, 2H), 4.76 (m, 1H), 7.29 (d, 1H), 7.42 (m, 1H), 7.55 (d, 1H), 7.70 (s, 1H), 10.66 (bs, 1H). |
| 84 | 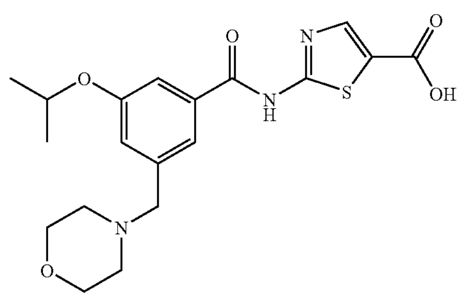 | 21 | | | ¹H NMR δ (d₆-DMSO): 1.31 (d, 6H), 3.03-3.16 (m, 4H), 3.71-3.95 (m, 4H), 4.34 (m, 2H), 4.77 (m, 1H), 7.47 (m, 1H), 7.72 (m, 2H), 8.13 (s, 1H). |

| Example | Structure | Route | (M + H)+ | (M − H)− | NMR |
|---|---|---|---|---|---|
| 85 | 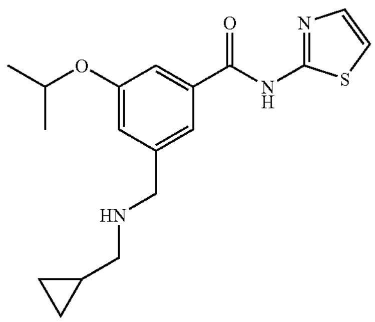 | 21 | | | ¹H NMR δ (d₆-DMSO): 0.41 (m, 2H), 0.60 (m, 2H), 1.14 (m, 1H), 1.35 (d, 6H), 2.85 (m, 2H), 4.19 (m, 2H), 4.81 (m, 1H), 7.32 (d, 1H), 7.46 (s, 1H), 7.60 (d, 1H), 7.72 (s, 1H), 7.80 (s, 1H), 9.35 (bs, 2H). |
| 86 | 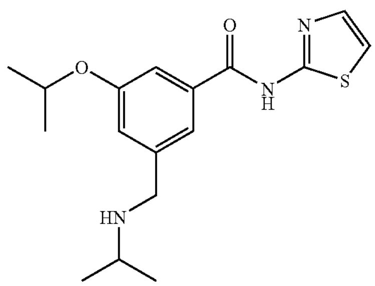 | 21 | | | ¹H NMR δ (d₆-DMSO): 1.27 (m, 12H), 3.26 (m, 2H), 4.14 (m, 2H), 4.76 (m, 1H), 7.26 (d, 1H), 7.45 (s, 1H), 7.55 (d, 1H), 7.68 (s, 1H), 7.76 (s, 1H), 9.18 (bs, 2H). |
| 87 | 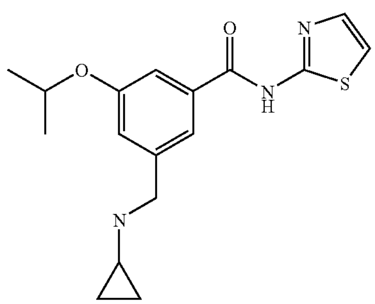 | 21 | | | ¹H NMR δ (d₆-DMSO): 0.72 (m, 2H), 0.89 (m, 2H), 1.32 (d, 6H), 2.66 (m, 1H), 4.21 (m, 2H), 4.75 (m, 1H), 7.26 (d, 1H), 7.42 (s, 1H), 7.55 (d, 1H), 7.68 (s, 1H), 7.76 (s, 1H), 9.53 (bs, 2H). |
| 88 | 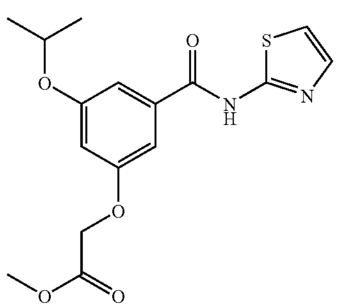 | 1 (See Ex 26) | 351 | 349 | ¹H NMR δ (d₆-DMSO): 1.27 (d, 6H), 3.70 (s, 3H), 4.71 (m, 1H), 4.86 (s, 2H), 6.99 (t, 1H), 7.23 (t, 1H), 7.26-7.27 (m, 2H), 12.53 (s, 1H) |
| 89 | 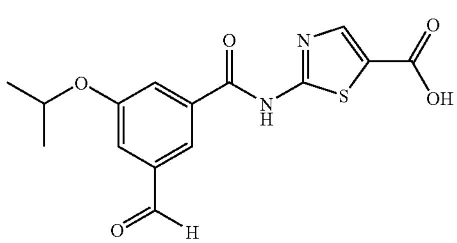 | 24 | | | ¹H NMR δ (d₆-DMSO): 1.32 (d, 6H), 4.79 (m, 1H), 7.62 (m, 1H), 7.92 (m, 1H), 8.13 (s, 1H), 8.18 (s, 1H), 10.03 (s, 1H). |

| Example | Structure | Route | (M + H)+ | (M − H)− | NMR |
|---|---|---|---|---|---|
| 90 | 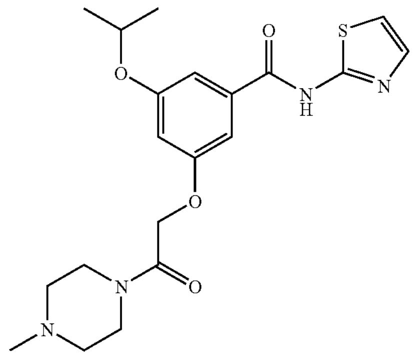 | 26 | 419 | 417 | ¹H NMR δ (d₆-DMSO): 1.28 (d, 6H), 2.18 (s, 3H), 2.24 (m, 2H), 2.32 (m, 2H), 3.44 (ap t, 4H), 4.65 (m, 1H), 4.85 (s, 2H), 6.68 (ap t, 1H), 7.19 (m, 1H), 7.24 (ap d, 2H), 7.55 (ap d, 1H), 12.45 (bs, 1H) |
| 91 | Z FORM | 25 | | | ¹H NMR δ (d₆-DMSO): 1.01 (d, 6H), 1.29 (d, 6H), 2.81 (m, 1H), 4.72 (m, 1H), 6.53 (dd, 1H), 6.29 (d, 1H), 6.97 (s, 1H), 7.50 (s, 1H), 7.53 (s, 1H), 8.11 (s, 1H), 8.18 (s, 1H). |
| 92 | 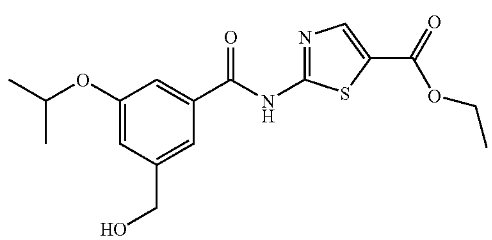 | 1 | | | ¹H NMR δ (d₆-DMSO): 1.29 (d, 9H), 4.28 (q, 2H), 4.53 (d, 2H), 4.71 (m, 1H), 5.26 (t, 1H (—OH)), 7.10 (s, 1H), 7.53 (s, 1H), 7.60 (s, 1H), 8.20 (s, 1H), 13.01 (bs, 1H). |
| 93 | 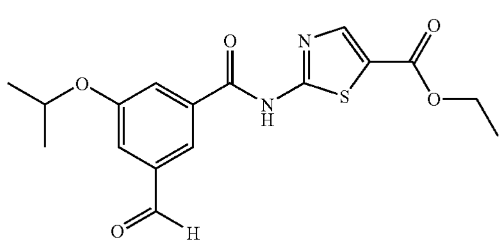 | 1 | | | ¹H NMR δ (d₆-DMSO): 1.34 (d, 3H), 1.39 (m, 6H), 4.30 (q, 2H), 4.84 (m, 1H), 7.58 (s, 1H), 7.97 (s, 1H), 8.17 (s, 1H), 8.26 (s, 1H), 10.09 (s, 1H). |
| 94 | 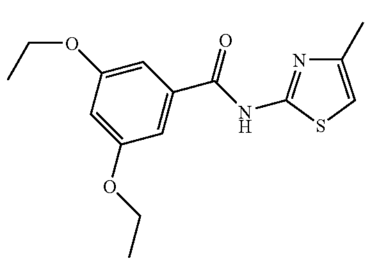 | 1a | 307 | | |

| Example | Structure | Route | (M + H)+ | (M − H)− | NMR |
|---|---|---|---|---|---|
| 95 | 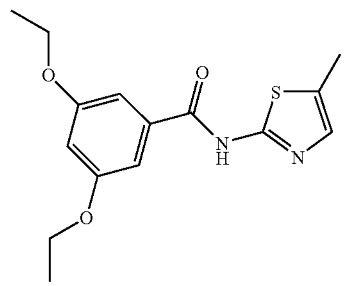 | 1a | 307 | | |
| 96 | 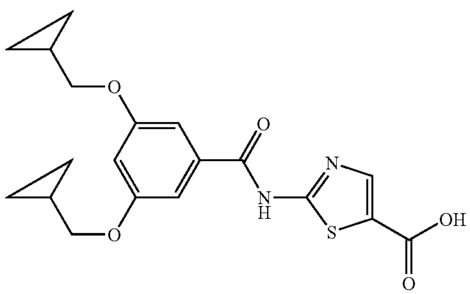 | 2a, 1c | 389 | 387 | δ$_H$ (300 MHz, DMSO-d$_6$)- 0.04-0.06 (4H, m); 0.22-0.35 (4H, m); 0.85-1.05 (2H, m); 3.54-4.64 (4H, d); 6.44 (1H, m); 6.93 (6.93-6.97 (2H, m); 7.84 (1H, s) |
| 97 | 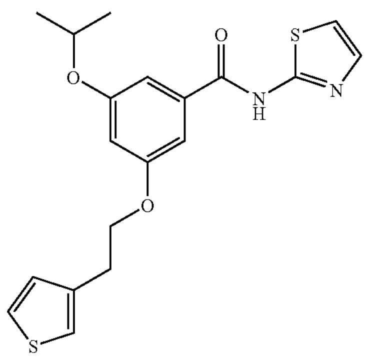 | 1b (HATU) | 389.38 | 387.34 | δ$_H$ (300 MHz, DMSO-d$_6$) 1.30 (6H, d), 3.08 (2H, t), 4.25 (2H, t), 4.73 (1H, hept), 6.70 (1H, s), 7.14 (1H, d), 7.3 (4H, m), 7.48 (1H, m), 7.57 (1H, d), 12.55 (1H, br s). |
| 98 | 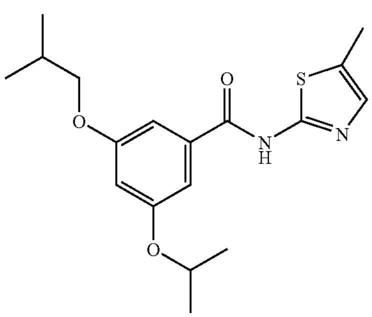 | 1a | 349 | | |
| 99 | 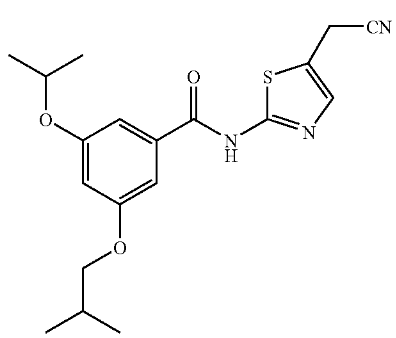 | 1b (HATU) | 374.43 | 372.39 | δ$_H$ (300 MHz, DMSO-d$_6$) 0.98 (6H, d), 1.27 (6H, d), 2.00 (1H, m), 3.80 (2H, d), 4.24 (2H, s), 4.70 (1H, hept), 6.66 (1H, t), 7.23 (2H, d), 7.46 (1H, s), 12.59 (1H, br s). |

-continued

| Example | Structure | Route | (M + H)+ | (M − H)− | NMR |
|---|---|---|---|---|---|
| 100 | 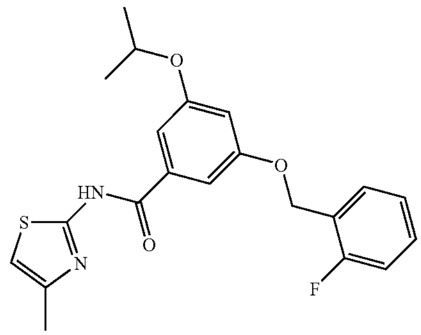 | 1a | 401 | | |
| 101 | 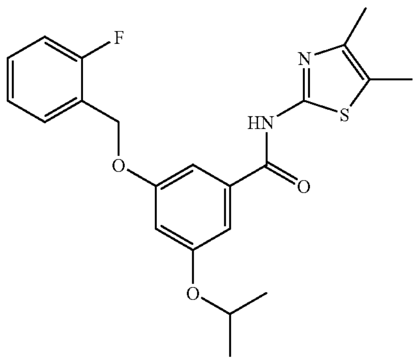 | 1a | 415 | | |
| 102 | 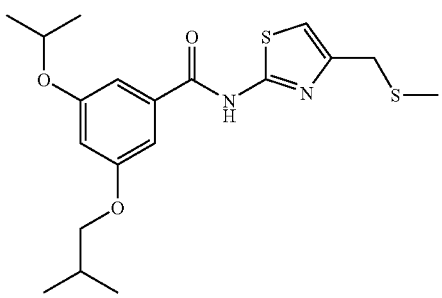 | 3 (e) (CM 1a) | 395.19 | 393.19 | δ$_H$ (300 MHz, CDCl$_3$) 1.02 (6H, d), 1.35 (6H, d), 2.08 (4H, m), 3.74 (4H, m), 4.60 (1H, hept), 6.64 (1H, m), 6.78 (1H, s), 7.00 (1H, m). |
| 103 | 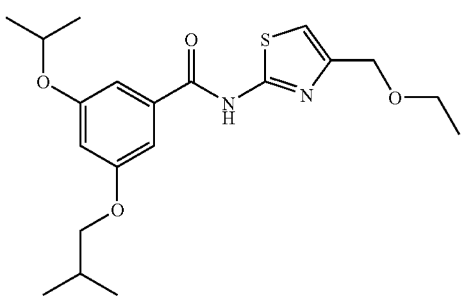 | 3 (e) (CM 1a) | 393.22 | 391.21 | δ$_H$ (300 MHz, CDCl$_3$) 1.02 (6H, d), 1.26 (3H, t), 1.35 (6H, d), 2.08 (1H, m), 3.60 (2H, q), 3.74 (d, 2H), 4.47 (2H, s), 4.58 (1H, hept), 6.64 (1H, m), 6.88 (1H, s), 7.02 (1H, m). |
| 104 | 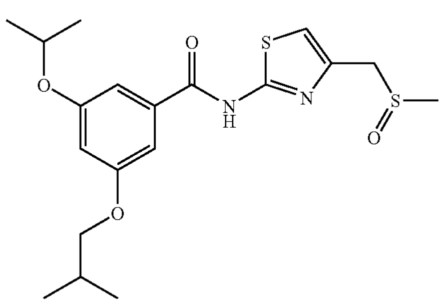 | | 411.42 | 409.38 | δ$_H$ (300 MHz, DMSO-d$_6$) 0.98 (6H, d), 1.27 (6H, d), 2.02 (1H, m), 2.55 (3H, s), 3.80 (2H, d), 4.14 (2H, s), 4.70 (1H, hept), 6.66 (1H, s), 7.23 (3H, m), 12.62 (1H, br s). |

| Example | Structure | Route | (M + H)+ | (M − H)− | NMR |
|---|---|---|---|---|---|
| 105 | 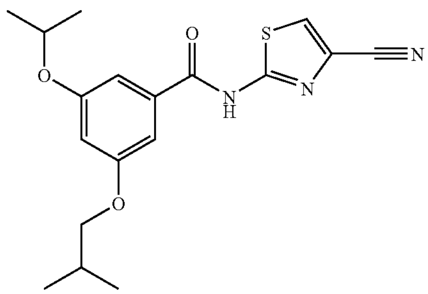 | 1a | 427.39 | 425.38 | δ$_H$ (300 MHz, CDCl$_3$) 1.02 (6H, d), 1.36 (6H, d), 2.08 (1H, m), 3.75 (2H, d), 4.60 (1H, hept), 6.68 (1H, m), 7.00 (2H, m), 7.69 (1H, s). |
| 106 | 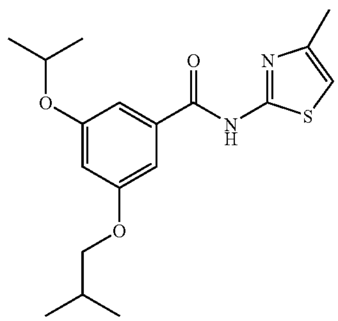 | 1b (HATU) | 349.45 | 347.43 | δ$_H$ (300 MHz, CDCl$_3$) 0.95 (6H, d), 1.25 (6H, d), 1.95-2.05 (1H, m), 2.2 (3H, s), 3.65 (2H, d), 6.7 (1H, m), 6.98 (1H, m), 7.02 (1H, m). |
| 107 | 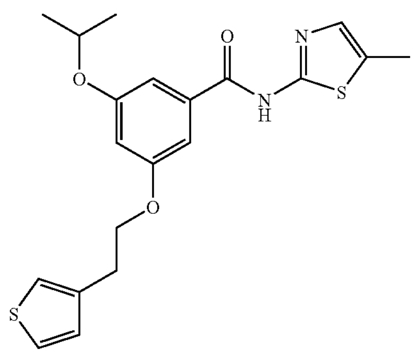 | 1b (HATU) | 403.39 | 401.37 | δ$_H$ (300 MHZ, DMSO-d$_6$) 1.25 (6H, d), 2.38 (3H, s), 3.05 (2H, t), 4.6-4.8 (1H, m), 7.05 (1H, d), 7.10-7.12 (3H, m), 7.15, (1H, m), 7.42-7.45 (1H, m) |
| 108 | 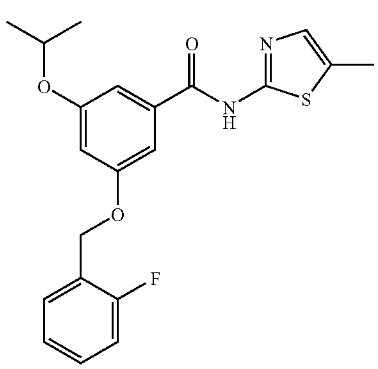 | 1b (HATU) | 401.42 | 399.39 | δ$_H$ (300 MHz, CDCl$_3$) 1.25 (6H, d) 2.3 (3H, s), 4.4-4.6 (1H, m) 5.05 (2H, s), 6.65 (1H, m), 6.85 (1H, s), 7.0-7.15 (4H, m) 7.2-7.3 (1H, m), 7.38-7.42 (1H, m). |

-continued

| Example | Structure | Route | (M + H)+ | (M − H)− | NMR |
|---|---|---|---|---|---|
| 109 | 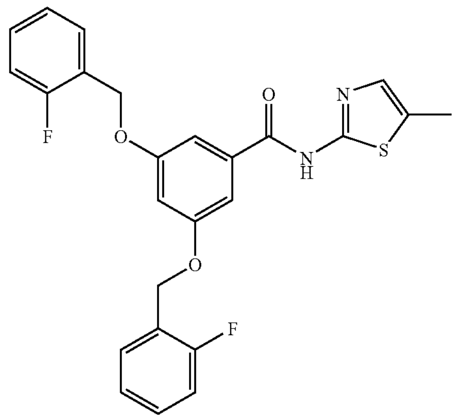 | 1b (HATU) | 467.38 | 465.37 | δ$_H$ (300 MHz, DMSO-d$_6$) 2.35 (3H, s), 5.2 (4H, s), 6.95 (1H, s), 7.2-7.3 (5H, m), 7.4-7.45 (4H, m), 7.5-7.6 (2H, m). |
| 110 | 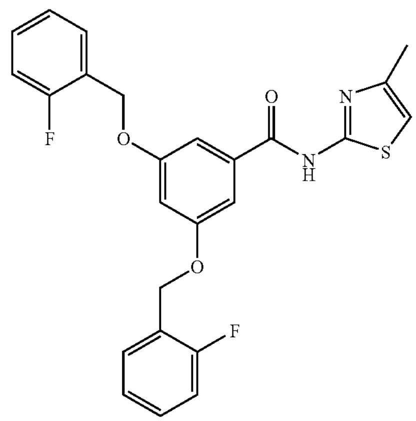 | 1b (HATU) | 467.37 | 465.38 | δ$_H$ (300 MHz, CDCl$_3$) 1.9 (3H, s), 4.95 (4H, s), 6.4 (1H, s), 6.9-7.1 (6H, m), 7.15-7.25 (2H, m), 7.3-7.4 (2H, m). |
| 111 | 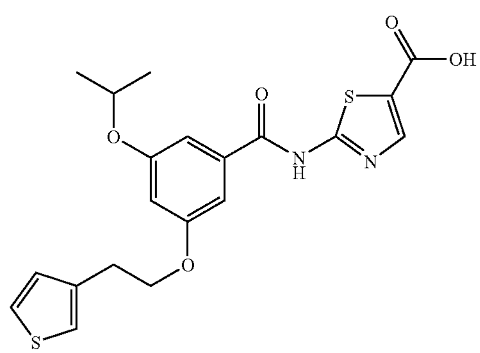 | 2a, 1a | 433 | 431 | δ$_H$ (500 MHz, DMSO-d$_6$) 1.27 (6H, d), 3.06 (2H, t), 4.25 (2H, t), 4.72 (1H, m), 6.71 (1H, s), 7.12 (1H, d), 7.23-7.32 (3H, br m), 7.46 (1H, m), 8.10 (1H, s). |
| 112 | 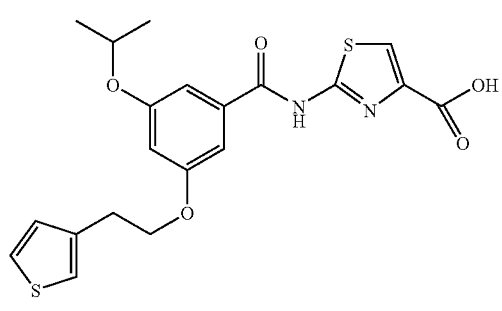 | 2a, 1a | 433 | 431 | δ$_H$ (500 MHz, DMSO-d$_6$) 1.28 (6H, d), 3.06 (2H, t), 4.24 (2H, t), 4.72 (1H, m), 6.69 (1H, s), 7.12 (1H, d), 7.27 (1H, s), 7.31 (2H, s), 7.47 (1H, m), 8.02 (1H, s). |

| Example | Structure | Route | (M + H)+ | (M − H)− | NMR |
|---|---|---|---|---|---|
| 113 | 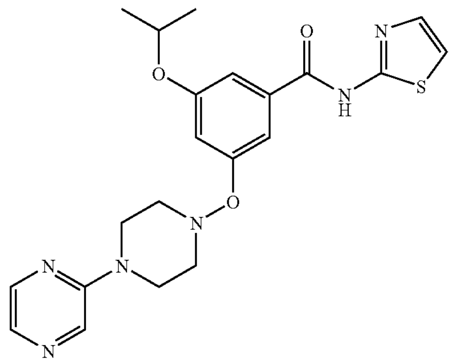 | 21 | 439.44 | 437.39 | δ$_H$ (300 MHz, DMSO-d$_6$) 1.25 (6H, d), 3.0-3.2 (2H, m), 3.3-3.55 (4H, m), 4.3-4.5 (4H, m), 4.75-4.85 (1H, m), 7.25 (1H, d), 7.55-7.6 (2H, m), 7.65 (1H, s), 7.75 (1H, s), 7.95 (1H, s), 8.1 (1H, s), 8.4 (1H, s). |
| 114 | 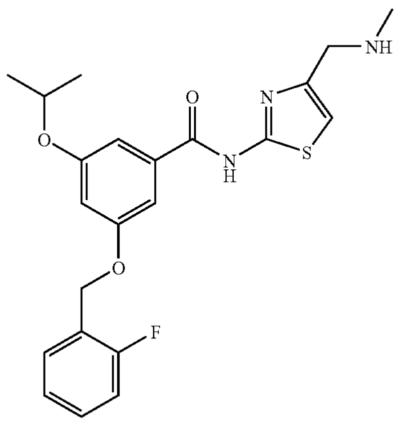 | 3 | 430.40 | 428.38 | δ$_H$ (300 MHz, CDCl$_3$) 1.25 (6H, d), 2.42 (3H, s), 3.82 (2H, s), 4.45-4.6 (1H, m), 5.05 (2H, s), 6.6 (1H, s), 6.95-7.15 (3H, m), 7.2-7.25 (2H, m), 7.35-7.45 (1H, m). |
| 115 | 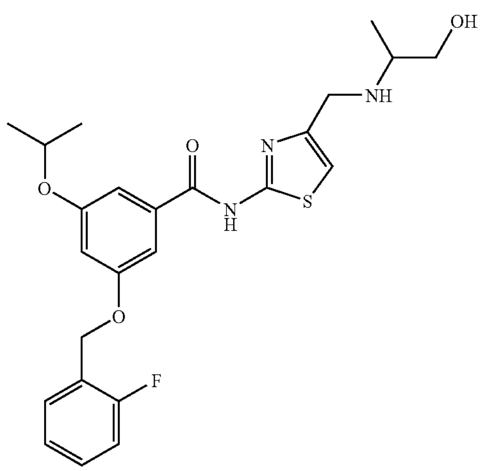 | 3 | 474.42 | 472.40 | |
| 116 | 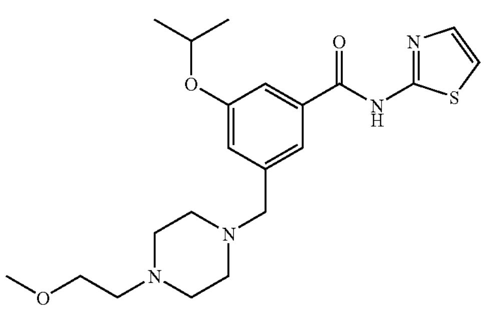 | 21 | 419.47 | 417.44 | δ$_H$ (300 MHz, DMSO-d$_6$) 1.25 (6H, d), 3.25 (3H, s), 3.3-3.75 (12H, m), 4.3-4.45 (2H, m), 4.75-4.8 (1H, m), 7.25 (1H, d), 7.5-7.6 (2H, m), 7.7 (1H, s), 7.8 (1H, s). |

| Example | Structure | Route | (M + H)+ | (M − H)− | NMR |
|---|---|---|---|---|---|
| 117 | 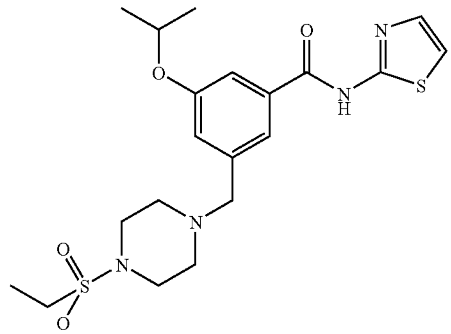 | 21 | 453.39 | 451.37 | |
| 118 | 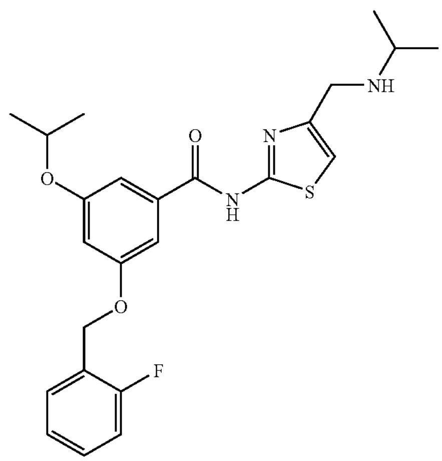 | 3 | 458.39 | 456.42 | |
| 119 | 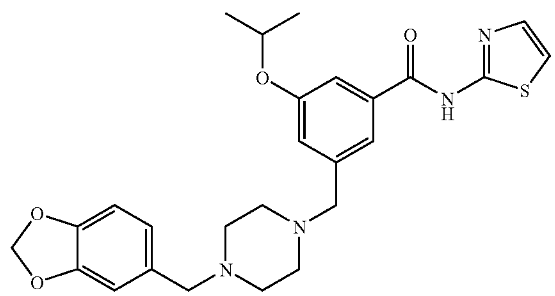 | 21 | 495.43 | | δ_H (300 MHz, DMSO-d_6) 1.25 (6H, d), 3.3-3.65 (8H, m), 4.2-4.5 (2H, m), 4.7-4.8 (1H, m), 6.05 (2H, s), 6.95 (1H, d), 7.05 (1H, d), 7.25 (2H, m), 7.55 (2H, m), 7.7 (1H, s), 7.8 (1H, s). |
| 120 | 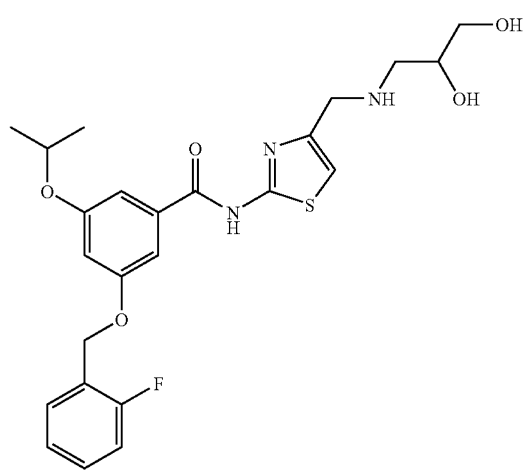 | 3 | 490.43 | 488.42 | |

-continued
| Example | Structure | Route | (M + H)+ | (M − H)− | NMR |
|---|---|---|---|---|---|
| 121 | 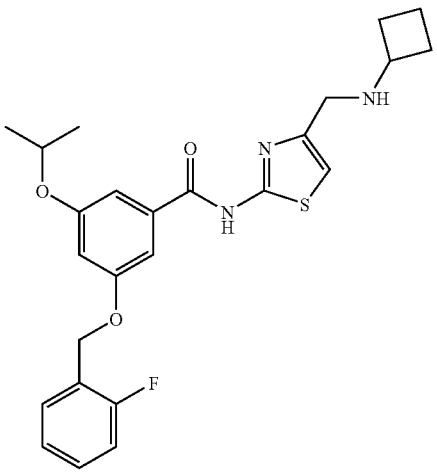 | 3 | 470.48 | 468.47 | |
| 122 | 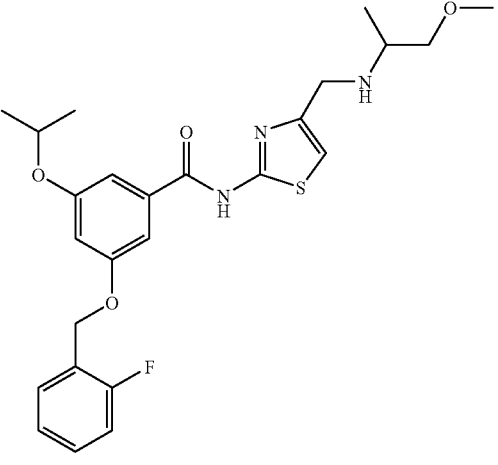 | 3 | 488.49 | 486.47 | |
| 123 | 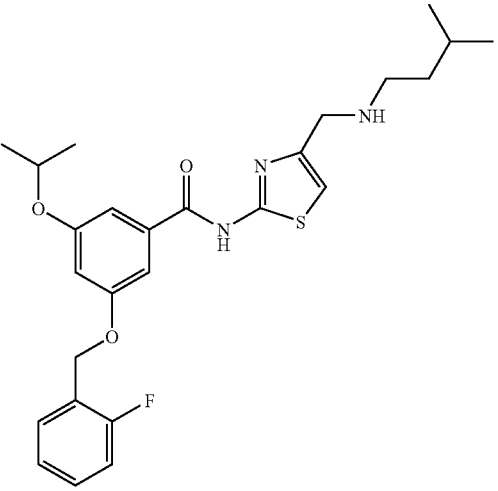 | 3 | 486.51 | 484.51 | |

-continued

| Example | Structure | Route | (M + H)+ | (M − H)− | NMR |
|---|---|---|---|---|---|
| 124 | 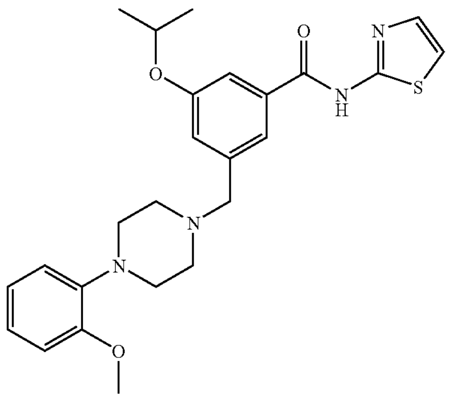 | 21 | 467.50 | 465.49 | |
| 125 | 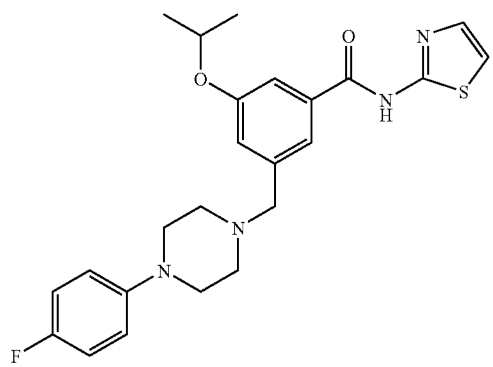 | 21 | 455.48<br>453.46 | | |
| 126 | 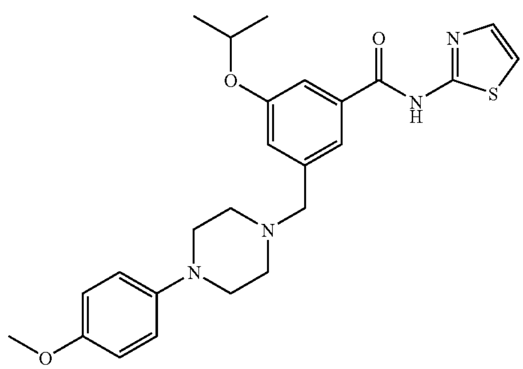 | 21 | 467.50 | 465.48 | |
| 127 | 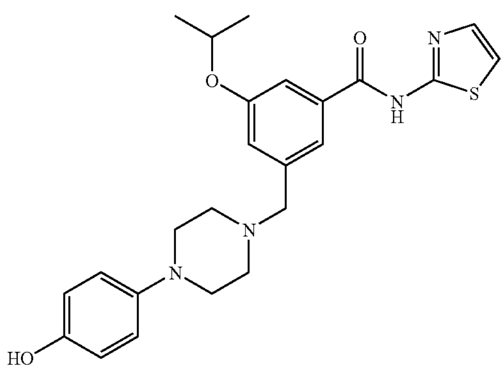 | 21 | 453.49 | 451.47 | |

| Example | Structure | Route | (M + H)+ | (M − H)− | NMR |
|---|---|---|---|---|---|
| 128 | 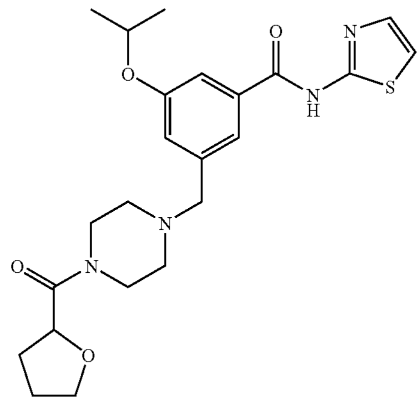 | 21 | 459.49 | 457.47 | |
| 129 | 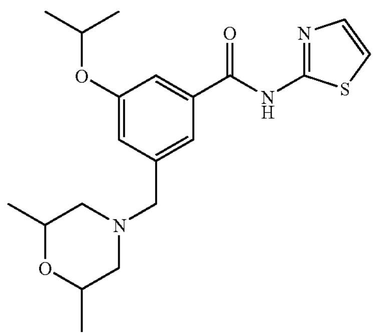 | 21 | 390.51 | 388.47 | |
| 130 | 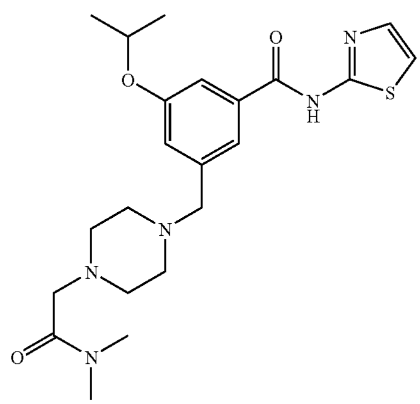 | 21 | 446.51 | 444.49 | |
| 131 | 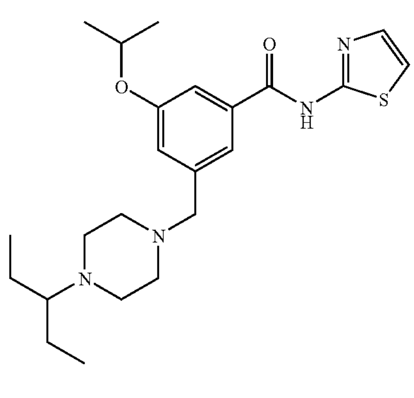 | 21 | 431.55 | 429.51 | |

-continued

| Example | Structure | Route | (M + H)+ | (M − H)− | NMR |
|---|---|---|---|---|---|
| 132 | 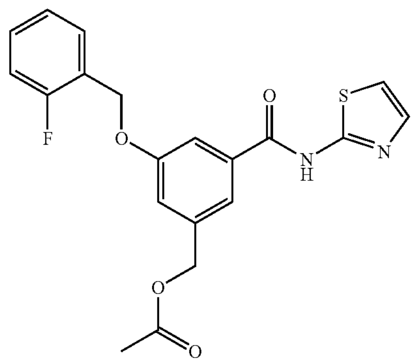 | 1b (HATU) | 401.37 | 399.33 | δ$_H$ (300 MHz, DMSO-d$_6$) 2.08 (3H, s), 5.12 (2H, s), 5.24 (2H, s), 7 23 (4H, m), 7.42 (1H, m), 7.56 (2H, m), 7.68 (1H, s), 7.76 (1H, s), 12.64 (1H, br s). |
| 133 | 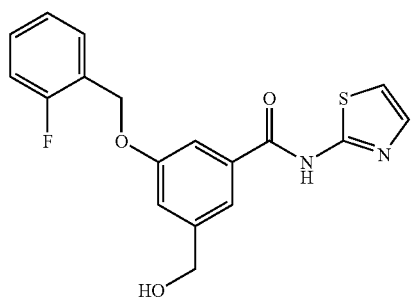 | 2a (f) | 359.43 | 357.39 | δ$_H$ (300 MHz, DMSO-d$_6$) 4.55 (2H, d), 5.23 (2H, s), 7.23 (4H, m), 7.42 (1H, m), 7.56 (2H, m), 7.68 (2H, m), 12.56 (1H, br s). |
| 134 | 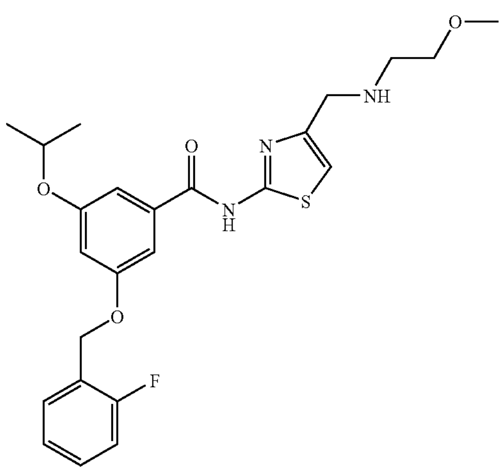 | 3 | 474.48 | 472.47 | |
| 135 | 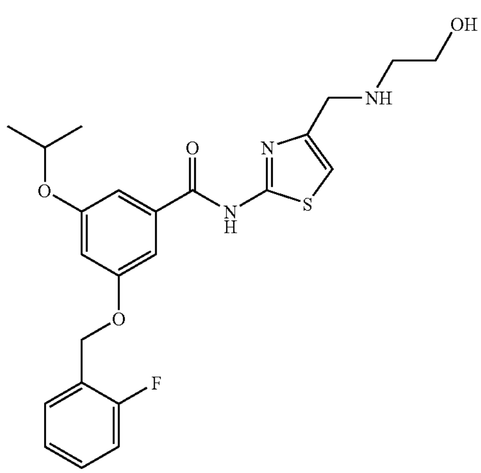 | 3 | 460.46 | 458.43 | |

-continued

| Example | Structure | Route | (M + H)+ | (M − H)− | NMR |
|---|---|---|---|---|---|
| 136 | 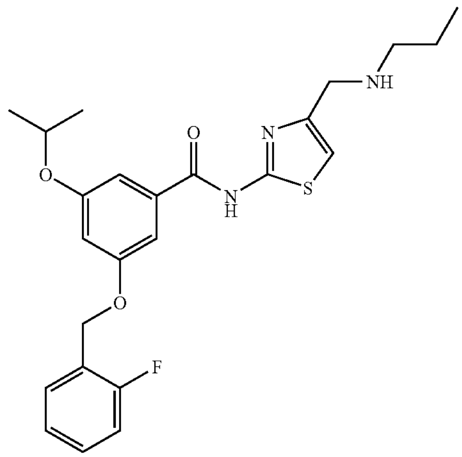 | 3 | 458.48 | 456.47 | |
| 137 | 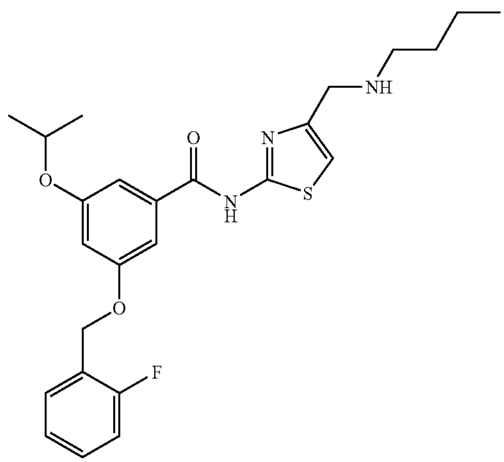 | 3 | 472.51 | 470.49 | |
| 138 | 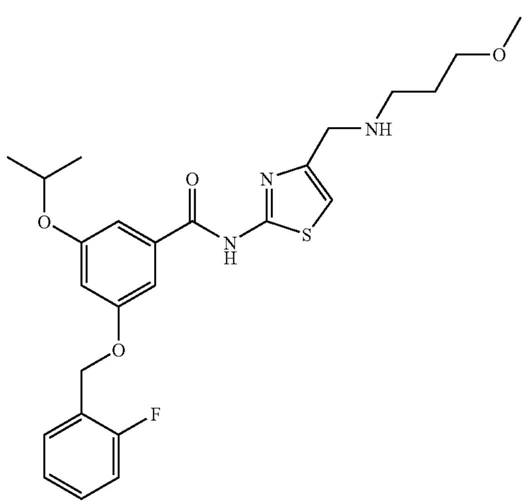 | 3 | 488.51 | 486.52 | |

| Example | Structure | Route | (M + H)+ | (M − H)− | NMR |
|---------|-----------|-------|----------|----------|-----|
| 139 | 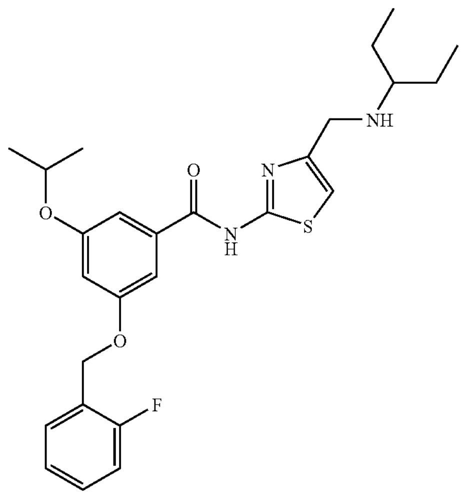 | 3 | 486.49 | 484.47 | |
| 140 | 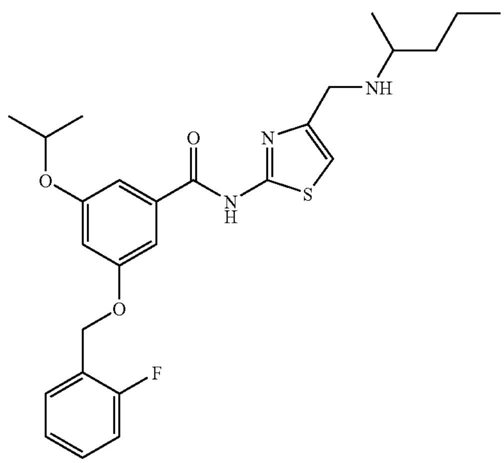 | 3 | 486.50 | 484.49 | |
| 141 | 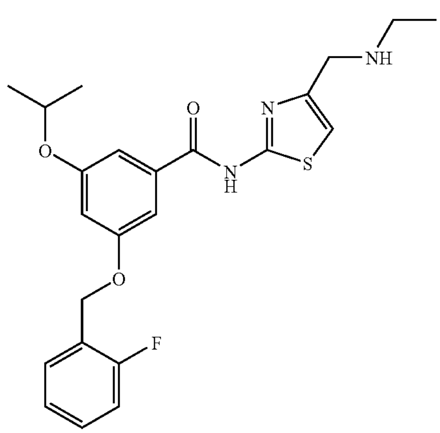 | 3 | 444.45 | 442.41 | |

-continued

| Example | Structure | Route | (M + H)+ | (M − H)− | NMR |
|---|---|---|---|---|---|
| 142 | 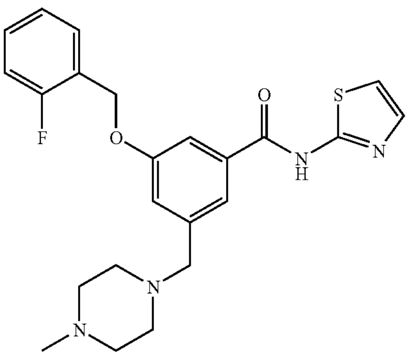 | 21 | 441.43 | 439.42 | δ_H (300 MHZ, DMSO-d₆) 2.82 (3H, s), 3.49 (8H, m), 4.54 (1H, d), 5.24 (3H, m), 7.30 (3H, m), 7.45 (2H, m), 7.59 (2H, m), 7.81 (2H, m), 12.65 (1H, br s). |
| 143 | 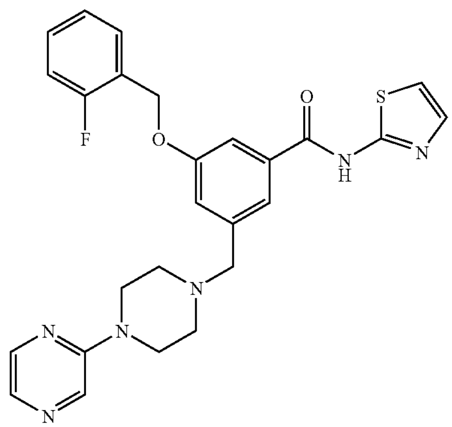 | 21 | 505.45 | 503.38 | δ_H (300 MHZ, DMSO-d₆) 3.15 (2H, m), 3.45 (2H, m), 4.25 (4H, m), 4.52 (1H, d), 5.25 (3H, m), 7.27 (3H, m), 7.45 (1H, m), 7.62 (3H, m), 7.90 (3H, m), 8.16 (1H, s), 8.42 (1H, s), 12.70 (1H, br s). |
| 144 | 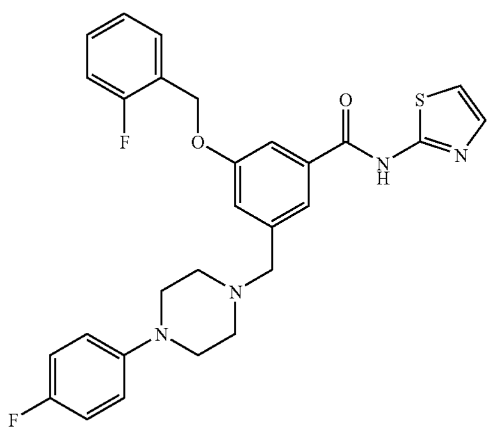 | 21 | 521.43 | | δ_H (300 MHz, DMSO-d₆) 3.33 (8H, m), 4.52 (1H, d), 5.27 (3H, m), 7.03 (5H, m), 7.28 (3H, m), 7.45 (1H, m), 7.65 (3H, m), 7.89 (1H, m), 9.20 (1H, br s), 12.69 (1H, br s). |
| 145 | 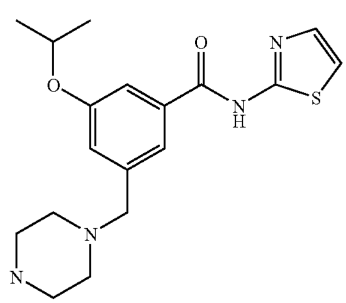 | 21 | 361.50 | 359.46 | δ_H (300 MHz, CDCl₃) 1.36 (6H, d), 2.56 (4H, m), 3.04 (4H, m), 3.53 (2H, s), 4.61 (1H, hept), 6.95 (1H, d), 7.07 (1H, m), 7.24 (1H, m) 7.44 (2H, m). |

| Example | Structure | Route | (M + H)+ | (M − H)− | NMR |
|---|---|---|---|---|---|
| 146 | 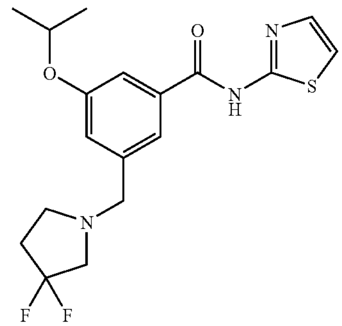 | 21 | 382.12 | 380.13 | ¹H NMR δ (CDCl₃): 1.37 (d, 6H), 2.3 (m, 2H), 2.7 (m, 2H), 2.7 (m, 2H), 2.85 (m, 2H), 4.6 (m, 1H), 6.95 (m, 1H), 7.1 (m, 1H), 7.2 (m, 1H), 7.4 (m, 2H) |
| 147 | 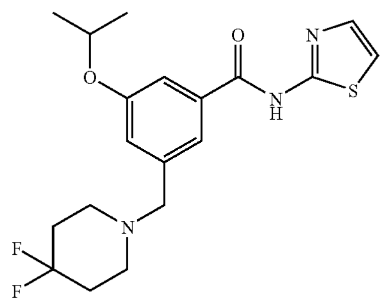 | 21 | 396.45 | 394.4 | ¹H NMR δ (CDCl₃): 1.37 (d, 6H), 1.95 (m, 4H), 2.5 (m, 4H), 3.55 (s, 2H), 4.6 (m, 1H), 7.0 (d, 1H), 7.1 (m, 1H), 7.6 (m, 1H) |
| 148 | 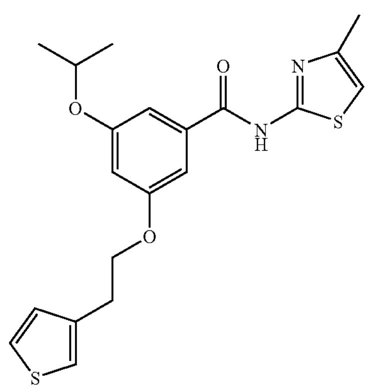 | 1b (HATU) | 382.12 | 380.13 | ¹H NMR δ (CDCl₃): 1.37 (d, 6H), 2.3 (m, 2H), 2.7 (m, 2H), 2.7 (m, 2H), 2.85 (m, 2H), 4.6 (m, 1H), 6.95 (m, 1H), 7.1 (m, 1H), 7.2 (m, 1H), 7.4 (m, 2H) |
| 149 | 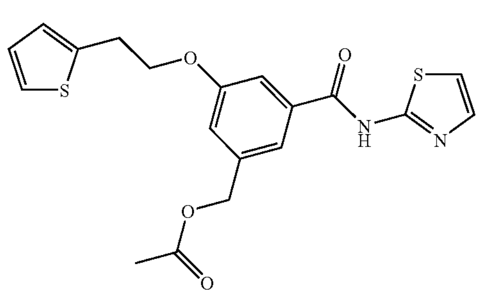 | 1b (HATU) | 403.39 | 401.36 | δ$_H$ (300 MHz, DMSO-d₆) 2.09 (3H, s), 3.26 (2H, t), 4.30 (2H, t), 5.08 (2H, s), 6.98 (2H, m), 7.17 (1H, s), 7.26 (1H, d), 7.35 (1H, m), 7.54 (1H, d), 7.64 (2H, br s), 12.62 (1H, br s). |

| Example | Structure | Route | (M + H)+ | (M − H)− | NMR |
|---|---|---|---|---|---|
| 150 | 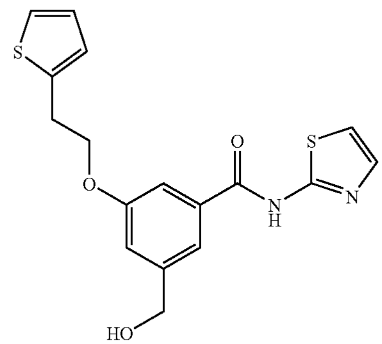 | 2a (g) | 361.41 | 359.58 | |
| 151 | 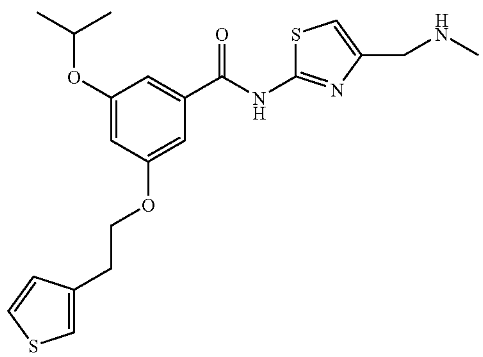 | 3 | 432.40 | 430.37 | |
| 152 | 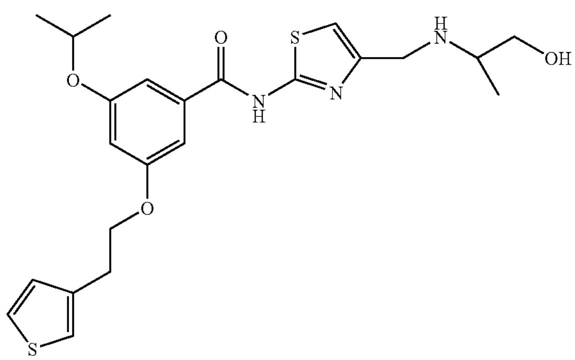 | 3 | 476.48 | 474.47 | |
| 153 | 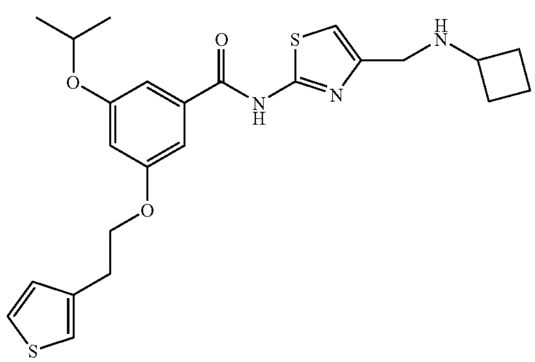 | 3 | 472.48 | 470.45 | |

-continued

| Example | Structure | Route | (M + H)+ | (M − H)− | NMR |
|---|---|---|---|---|---|
| 154 | 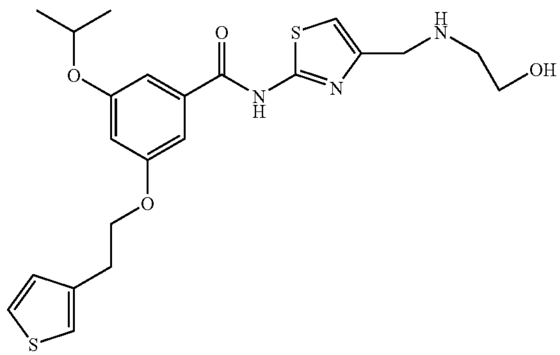 | 3 | 462.45 | 460.43 | |
| 155 | 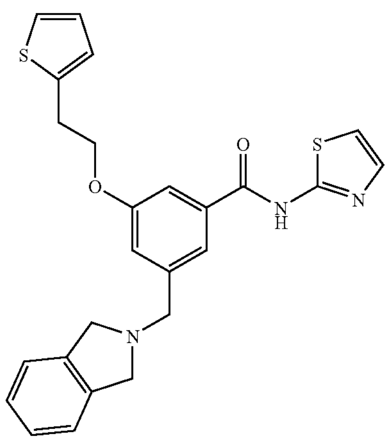 | 21 | 462.41 | 460.38 | |
| 156 | 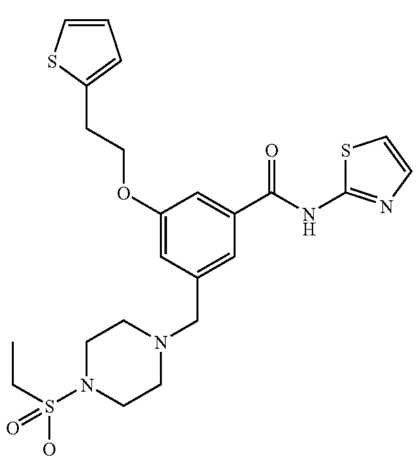 | 21 | 521.42 | 519.40 | |

| Example | Structure | Route | (M + H)+ | (M − H)− | NMR |
|---|---|---|---|---|---|
| 157 | 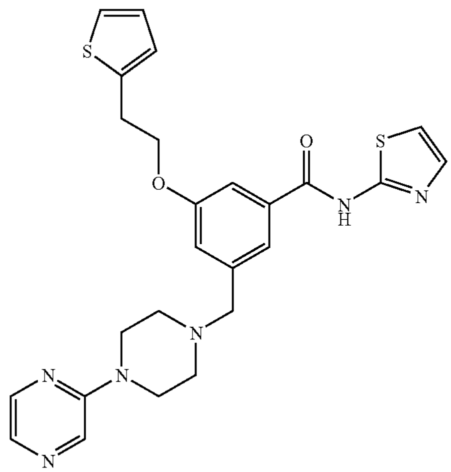 | 21 | 507.48 | | |
| 158 | 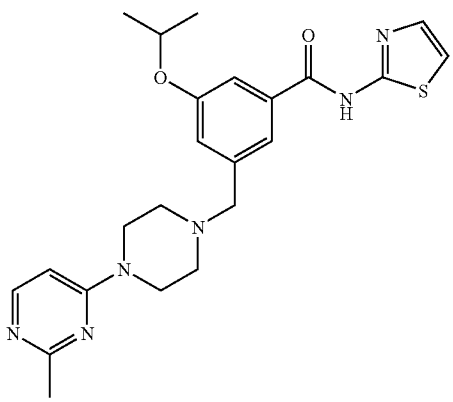 | 21 | 453.52 | 451.49 | ¹H NMR δ (CDCl₃): 1.35 (d, 6H), 2.5 ((m, 2H), 3.65 (m, 4H), 4.65 (m, 1H), 6.3 (d, 1H), 6.95 (d, 1H), 7.1 (m, 1H), 7.35 (d, 1H), 7.5 (m, 1H), 7.58 (s, 1H), 8.1 (d, 1H) |
| 159 | 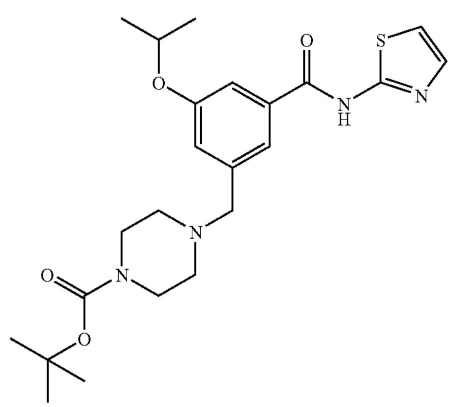 | 21 | 461.49 | 459.48 | |

-continued
| Example | Structure | Route | (M + H)+ | (M − H)− | NMR |
|---|---|---|---|---|---|
| 160 | 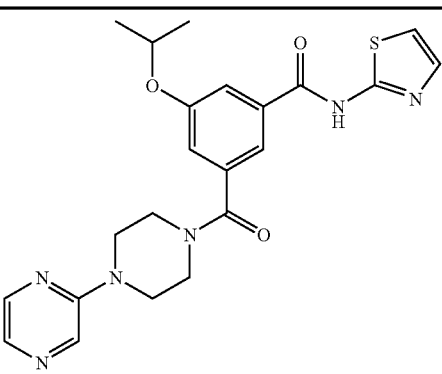 | 1b (HATU) (h) | 453.44 | 451.40 | |
| 161 | 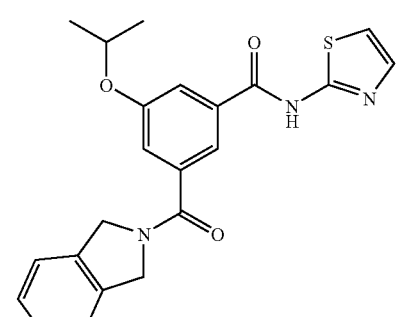 | 1b (HATU) (h) | 406.40 | | |
| 162 | 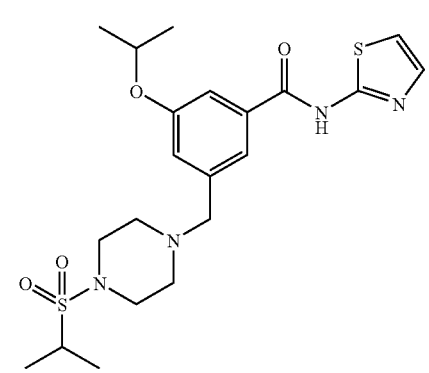 | 21 (i) | 467.50 | 465.49 | |

-continued

| Example | Structure | Route | (M + H)+ | (M − H)− | NMR |
|---------|-----------|-------|----------|----------|-----|
| 163 | 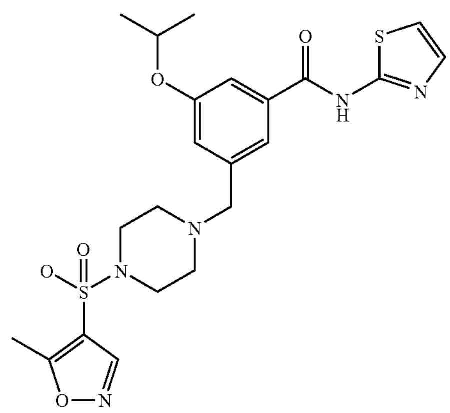 | 21 (i) | 506.47 | 504.46 | |
| 164 | 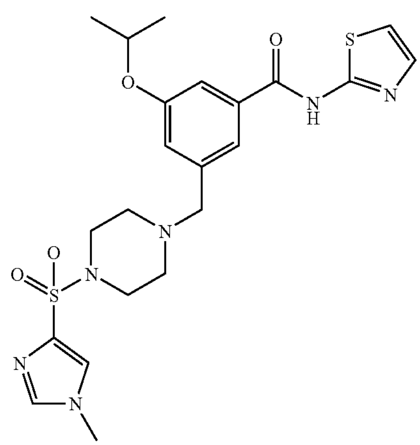 | 21 (i) | 505.46 | 503.43 | |
| 165 | 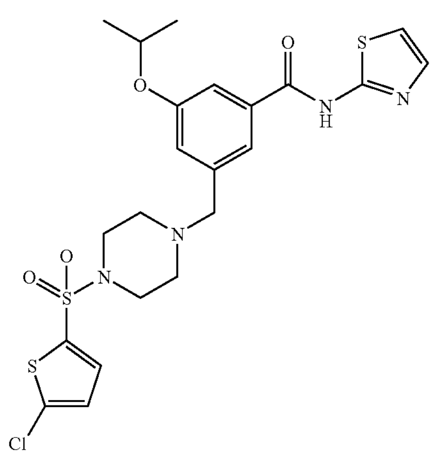 | 21 (i) | 541.39 | 539.35 | |

| Example | Structure | Route | (M + H)+ | (M − H)− | NMR |
|---|---|---|---|---|---|
| 166 | 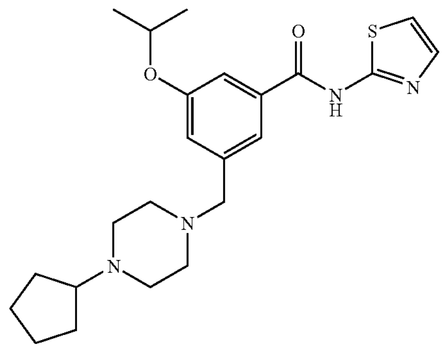 | 21 | 429.54 | 427.51 | |

Notes:
*Final products prepared by hydrolysis method 2a; requisite starting materials prepared according to generic alkylation methodology followed by coupling (Route 1).
**Final products prepared by reductive amination method 6 method; requisite starting materials prepared according to generic alkylation methodology followed by coupling (Route 1) and hydrolysis (Route 2a).
***Final products prepared by hydrolysis (Route 2a) or acid chloride coupling (Route 1); requisite starting materials prepared according to generic alkylation methodology followed by coupling (Route 1).
****For Examples II$_2$, II$_7$, II$_8$, II$_{15}$ and II$_{26}$, the ester intermediates were prepared by route 1:

$^1$HNMR δ (d$_6$-DMSO): 1.3 (3H, t); 4.3 (2H, q); 5.25 (4H,s); 7.0 (1H, t); 7.4 (6H,m); 7.5 (2H, m); 7.6 (2H, m); 8.2 (1H, s).

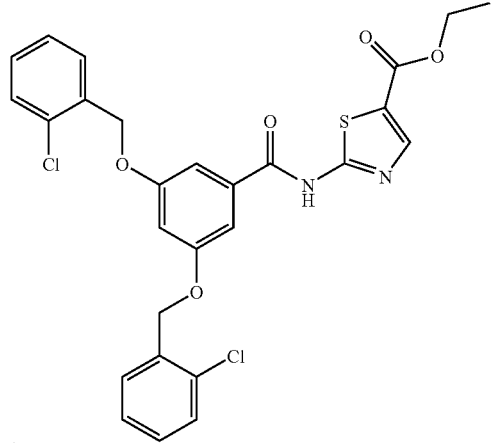

exemplified as Example II$_3$.

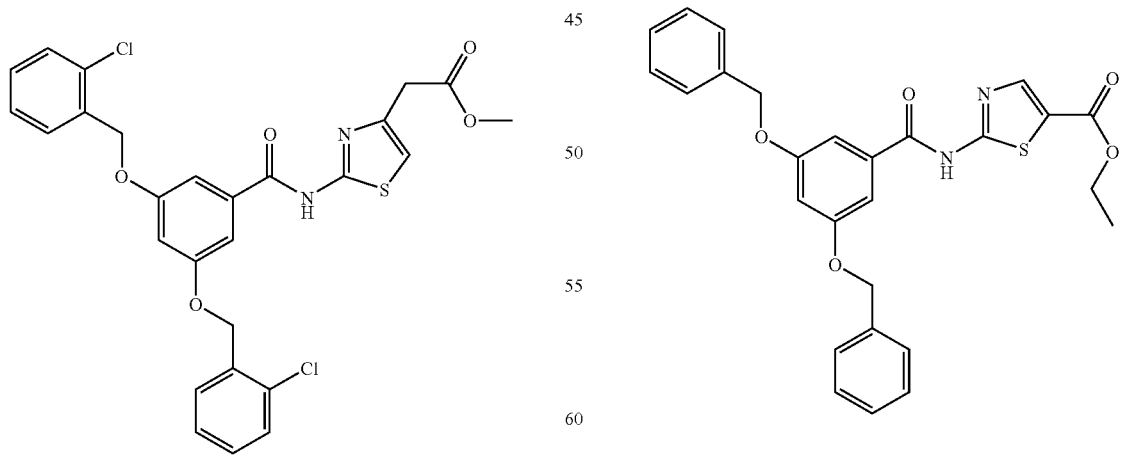

$^1$H NMR δ (d$_6$-DMSO): 1.3 (3H, t); 4.3 (2H, q); 5.2 (4H, s); 6.95 (1H, t); 7.2-7.5 (12H, m); 8.2 (1H, s); 13.05 (1H, br s); the spectrum also contains signals due to trace amounts of 2-aminothiazole.

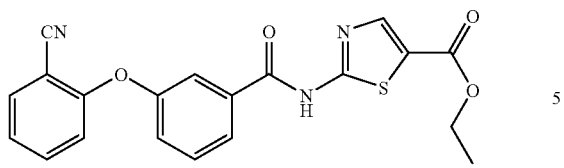
not characterised.
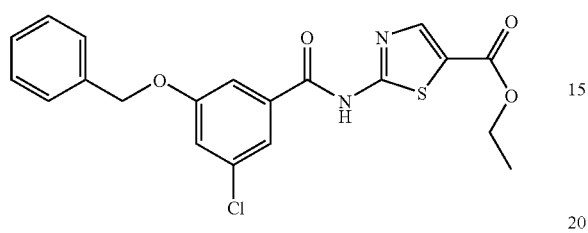
MH+=389, 391
M−H=387, 389
EXAMPLE JJ
By analogous methods to those described above the following compounds, Example numbers $JJ_1$ to $JJ_{57}$, were also made.
| Example | Structure | Route | (M + H)+ | (M − H)− | NMR |
|---|---|---|---|---|---|
| 1 | 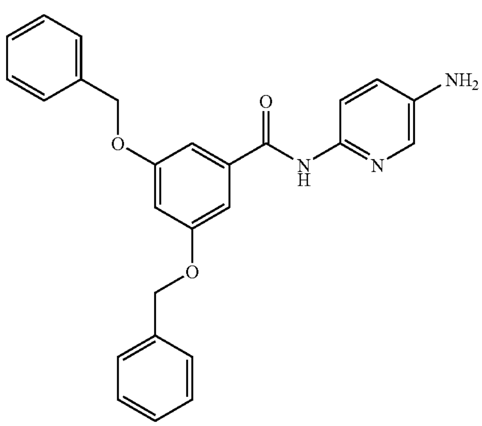 | 7 | 426.19 | 424.25 | 1H NMR d (d6-DMSO): 5.17 (m, 6H), 6.80 (s, 1H), 7.00 (d, 1H), 7.26 to 7.46 (m, 12H), 7.71 (s, 1H), 7.78 (d, 1H), 10.28 (brs, 1H) |
| 2 | 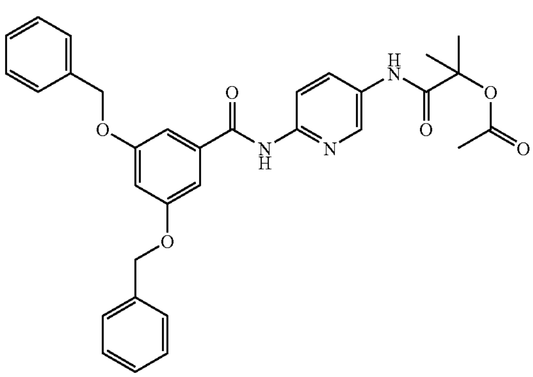 | 8 | | 552.22 | 1H NMR d (d6-DMSO): 1.55 (s, 6H), 2.08 (s, 3H), 5.18 (s, 4H), 6.85 (s, 1H), 7.29 to 7.50 (m, 12H), 7.98 (dd, 1H), 8.13 (d, 1H), 8.61 (s, 1H), 9.70 (s, 1H), 10.72 (s, 1H) |

-continued

| Example | Structure | Route | (M + H)+ | (M − H)− | NMR |
|---|---|---|---|---|---|
| 3 | 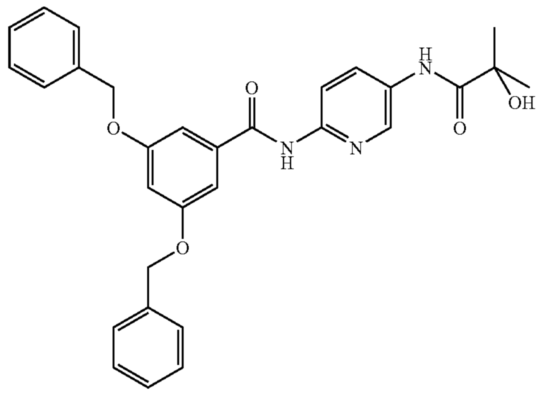 | 9 | 512.16 | 510.22 | 1H NMR d (d6-DMSO): 1.35 (s, 6H), 5.18 (s, 4H), 6.88 (s, 1H), 7.28 to 7.48 (m, 12H), 8.08 (d, 1H), 8.22 (d, 1H), 8.82 (s, 1H), 9.90 (s, 1H), 10.96 (s, 1H) |
| 4 | 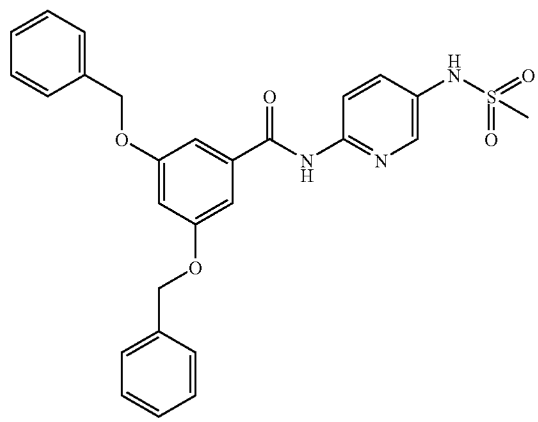 | 8 | | 502.49 | 1H NMR d (d6-DMSO): 3.02 (s, 3H), 5.17 (s, 4H), 6.86 (s, 1H), 7.29 to 7.58 (m, 12H), 7.70 (d, 1H), 8.13 (d, 1H), 8.24 (s, 1H), 9.83 (s, 1H), 10.83 (s, 1H) |
| 5 | 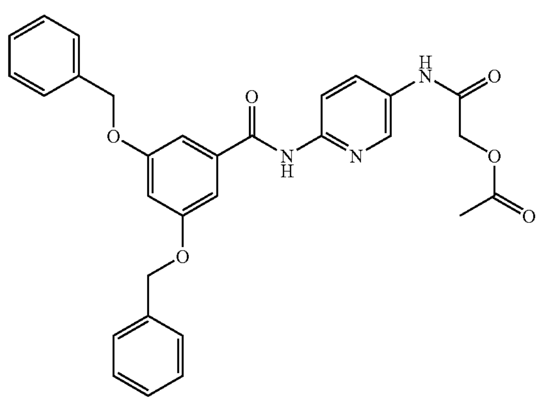 | 8 | 526.41 | 524.45 | 1H NMR d (d6-DMSO): 2.13 (s, 3H), 4.65 (s, 2H), 5.18 (s, 4H), 6.84 (s, 1H), 7.27 to 7.48 (m, 12H), 7.96 (d, 1H), 8.13 (d, 1H), 8.61 (s, 1H), 10.24 (s, 1H), 10.73 (s, 1H) |
| 6 | 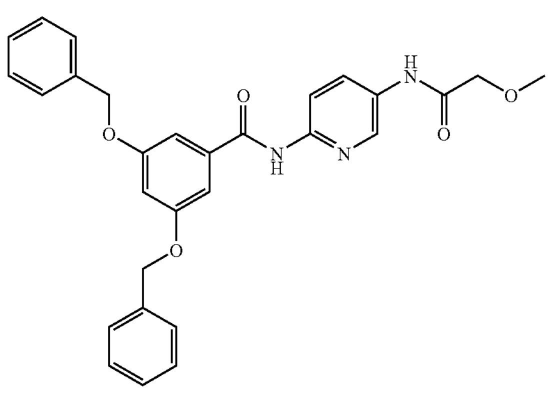 | 8 | 498.55 | 496.55 | 1H NMR d (d6-DMSO): 3.39 (s, 3H), 4.01 (s, 1H), 5.18, (s, 4H), 6.85 (s, 1H), 7.28 to 7.50 (m, 12H), 8.07 (m, 2H), 8.67 (s, 1H), 9.95 (s, 1H), 10.71 (s, 1H) |

-continued

| Example | Structure | Route | (M + H)+ | (M − H)− | NMR |
|---|---|---|---|---|---|
| 7 | 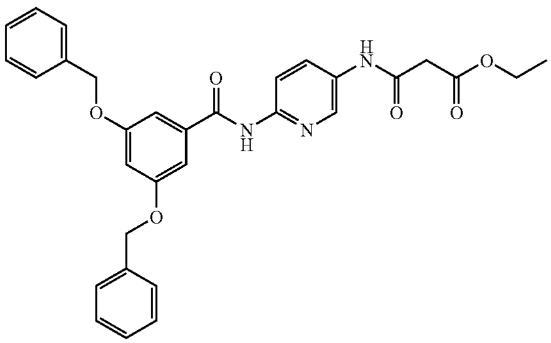 | 8 | 540.58 | 538.63 | 1H NMR d (d6-DMSO): 1.20 (t, 3H), 3.47 (s, 2H), 4.11 (q, 2H), 5.17 (s, 4H), 6.83 (s, 1H), 7.28 to 7.48 (m, 12H), 7.95 (d, 1H), 8.13 (d, 1H), 8.60 (s, 1H), 10.35 (s, 1H), 10.73 (s, 1H) |
| 8 | 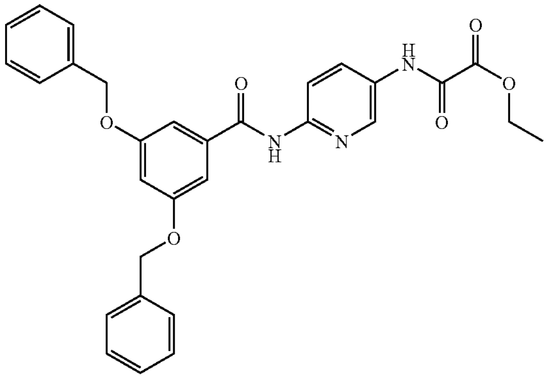 | 8 | 526.53 | 524.61 | 1H NMR d (d6-DMSO): 1.30 (t, 3H), 4.30 (q, 2H), 5.17 (s, 4H), 6.86 (s, 1H), 7.28 to 7.50 (m, 12H), 8.14 (s, 2H), 8.74 (s, 1H), 10.78 (s, 1H), 10.97 (s, 1H) |
| 9 | 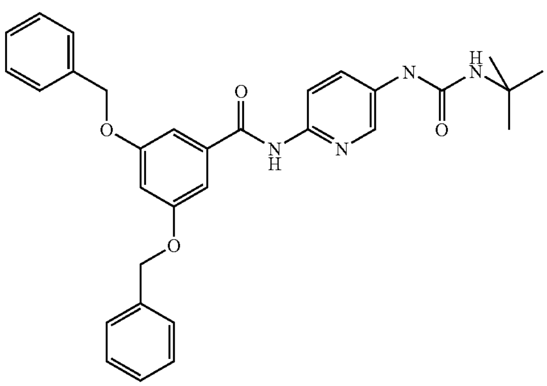 | 10 | 525.61 | 523.66 | 1H NMR d (d6-DMSO): 1.30 (s, 9H), 5.18 (s, 4H), 6.09 (s, 1H), 6.85 (s, 1H), 7.32-7.50 (m, 12H), 7.78 (dd, 1H), 8.04 (d, 1H), 8.38 (s, 1H), 8.44 (s, 1H), 10.65 (s, 1H) |
| 10 | 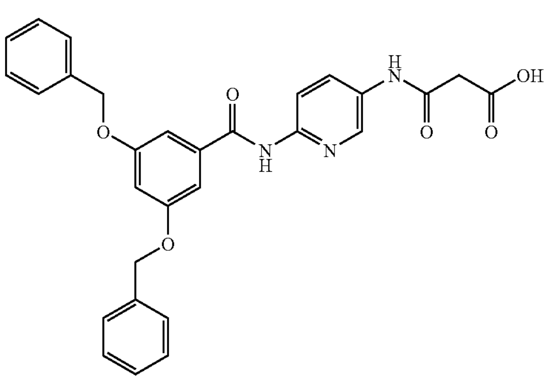 | 9 | 512.4 | | 1H NMR d (d6-DMSO): 3.41 (s, 2H), 5.17 (s, 4H), 6.90 (s, 1H), 7.29 to 7.54 (m, 12H), 8.03 (d, 1H), 8.13 (d, 1H), 8.70 (s, 1H), 10.50 (s, 1H), 10.85 (s, 1H) |

-continued

| Example | Structure | Route | (M + H)+ | (M − H)− | NMR |
|---|---|---|---|---|---|
| 11 | 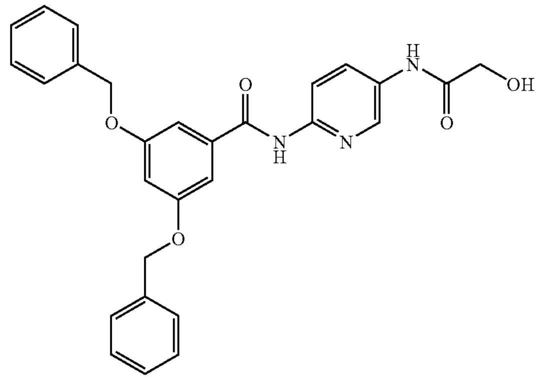 | 9 | 484.4 | | 1H NMR d (d6-DMSO): 4.04 (s, 2H), 5.20 (s, 4H), 6.89 (s, 1H), 7.30 to 7.51 (m, 12 H), 8.12 (d, 1H), 8.22 (d, 1H), 8.81 (s, 1H), 10.05 (s, 1H), 11.00 (s, 1H) |
| 12 | 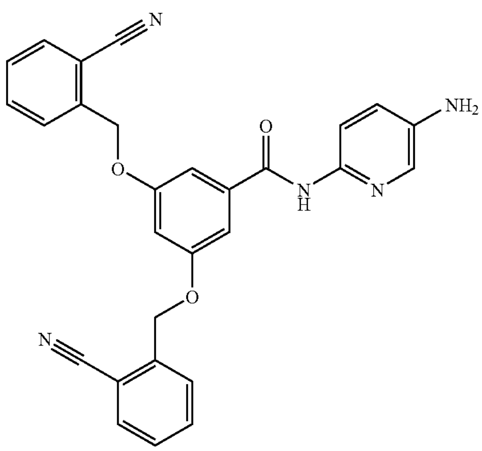 | 7 | 476.36 | | 1H NMR d (d6-DMSO): 5.14 (s, 2H), 5.32 (s, 4H), 6.90 (s, 1H), 7.01 (dd, 1H), 7.35 (s, 2H), 7.59 (m, 2H), 7.80 (m, 6H), 7.90 (d, 2H), 10.38 (s, 1H) + 0.1 EtOAc |
| 13 | 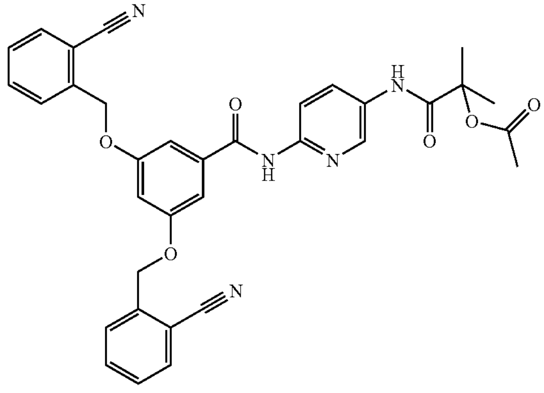 | 8 | 604.29 | 602.3 | 1H NMR d (d6-DMSO): 1.55 (s, 6H), 2.07 (s, 3H), 5.33 (s, 4H), 6.95 (s, 1H), 7.40 (s, 2H), 7.56 (m, 2H), 7.73 (m, 4H), 7.90 (d, 2H), 7.98 (dd, 1H), 8.13 (d, 1H), 8.63 (s, 1H), 9.71 (s, 1H), 10.82 (s, 1H) |

-continued

| Example | Structure | Route | (M + H)+ | (M − H)− | NMR |
|---|---|---|---|---|---|
| 14 | 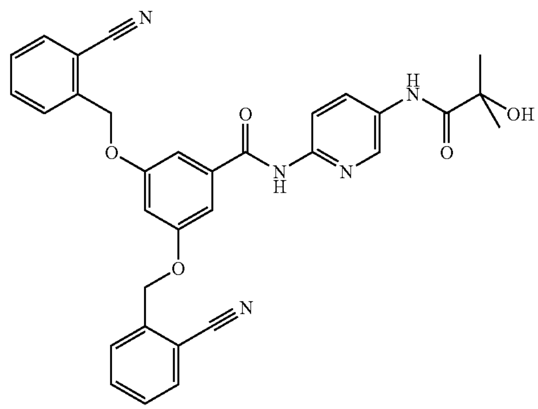 | 9 | 562.28 | 560.27 | 1H NMR d (d6-DMSO): 1.34 (s, 6H), 5.32 (s, 4H), 6.97 (s, 1H), 7.40 (s, 2H), 7.57 (m, 2H), 7.75 (m, 4H), 7.90 (d, 2H), 8.09 (d, 1H), 8.21 (dd, 1H), 8.82 (s, 1H), 9.90 (s, 1H), 10.99 (s, 1H) |
| 15 | 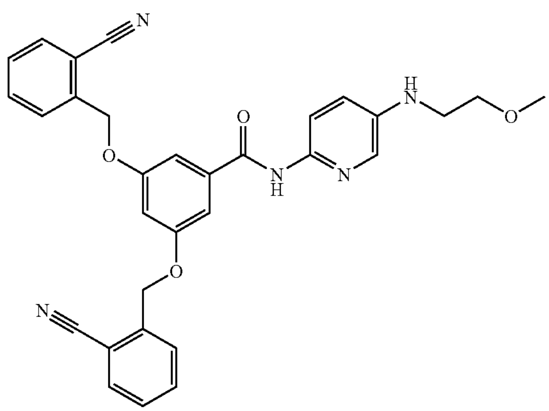 | 11 | 534.41 | | 1H NMR d (d6-DMSO): 3.22 (t, 2H), 3.28 (2, 3H), 3.50 (t, 2H), 5.31 (s, 4H), 6.92 (s, 1H), 7.12 (dd, 1H), 7.34 (s, 2H), 7.57 (m, 2H), 7.75 (m, 5H), 7.82 (d, 1H), 7.91 (d, 2H), 10.49 (brs, 1H) |
| 16 | 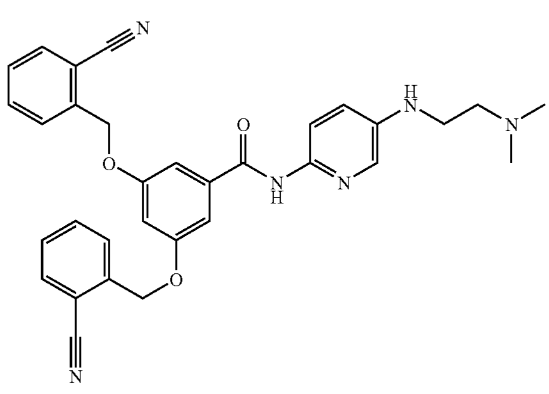 | 11 | 547.86 | | 1H NMR d (d6-DMSO): 2.20 (s, 6H), 3.12 (m, 2H), 5.32 (s, 4H), 5.51 (br s, 1H), 6.89 (s, 1H), 7.06 (dd, 1H), 7.37 (s, 2H), 7.57 (m, 2H), 7.74 (m, 5H), 7.83 (d, 1H), 7.92 (d, 2H), 10.41 (s, 1H), and 2H under DMSO or water |

| Example | Structure | Route | (M + H)+ | (M − H)− | NMR |
|---|---|---|---|---|---|
| 17 | 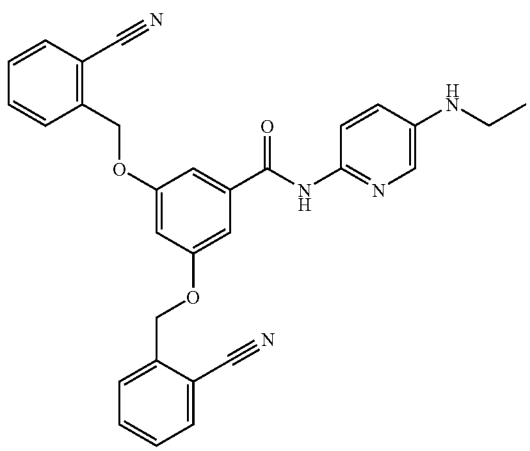 | 11 | 504.54 | | 1H NMR d (d6-DMSO): 1.15 (t, 3H), 3.06 (quartet, 2H), 5.32 (s, 4H), 6.90 (s, 1H), 7.00 (dd, 1H), 7.35 (s, 2H), 7.57 (m, 2H), 7.73 (m, 5H), 7.85 (d, 1H), 7.92 (d, 2H), 10.41 (s, 1H) |
| 18 | 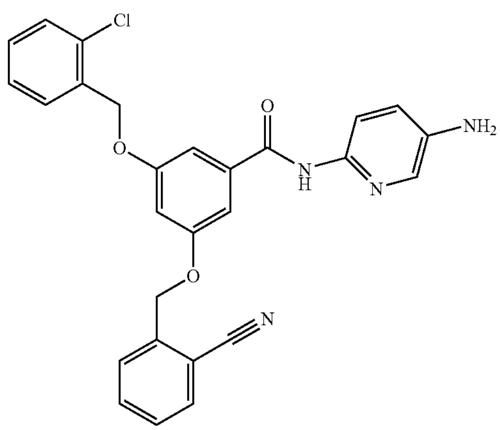 | 12 | 485.5 | 483.5 | 1H NMR d (d6-DMSO): 5.13 (s, 2H), 5.18 (s, 2H), 5.31 (s, 1H), 6.88 (s, 1H), 7.00 (dd, 1H), 7.32 (s, 2H), 7.40 (m, 3H), 7.50 (s, 1H), 7.58 (m, 1H), 7.74 (m, 3H), 7.80 (d, 1H), 7.90 (d, 1H), 10.33 (s, 1H) |
| 19 | 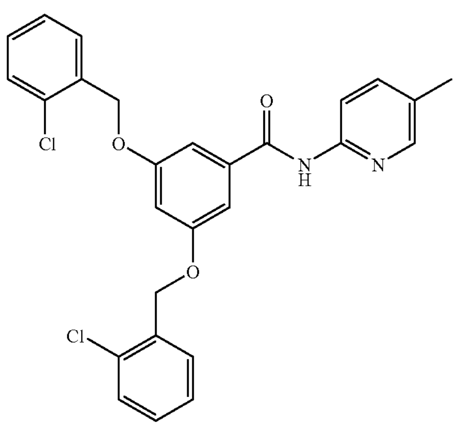 | 1 | 493, 495 | | 1H NMR d (d6-DMSO): 2.35 (3H, s); 5.31 (4H, s); 6.98 (1H, t); 7.43-7.48 (6H, m); 7.58-7.61 (2H, m); 7.65-7.71 (3H, m); 8.14 (1H, d); 8.29 (1H, s); 10.84 (1H, s) |
| 20 | 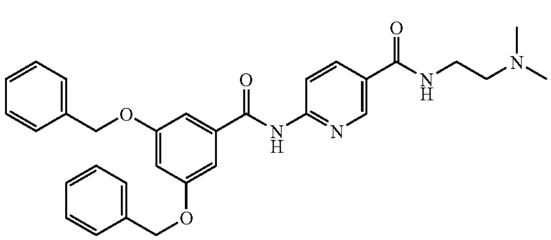 | 13 | 525 | | 1H NMR d (d6-DMSO): 3.10 (2H, m); 3.30 (6H, s); 3.60 (2H, m); 5.19 (4H, s); 6.89 (1H, s); 7.31-7.48 (12H, m); 8.29 (2H, m); 8.92 (1H, s); 11.05 (1H, s |

-continued

| Example | Structure | Route | (M + H)+ | (M − H)− | NMR |
|---|---|---|---|---|---|
| 21 | 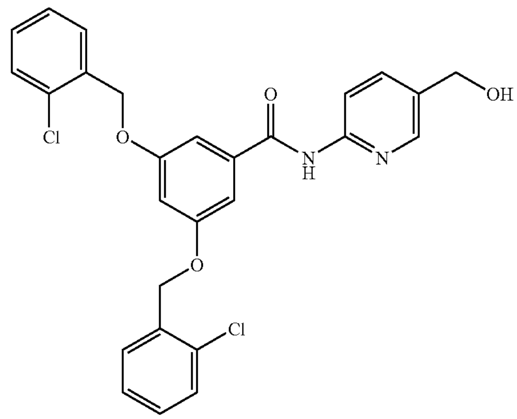 | 14 | 509 | | 1H NMR d (d6-DMSO): 4.5 (1H, d), 5.25 (s, 4H), 6.9 (s, 1H), 7.40 (m, 6H), 7.5 (m, 2H). 7.6 (m, 2H) 7.75 (dd, 1H), 8.10 (d, 1H), 8.3 (s, 1H), 10.8 (br s, 1H); |
| 22 | 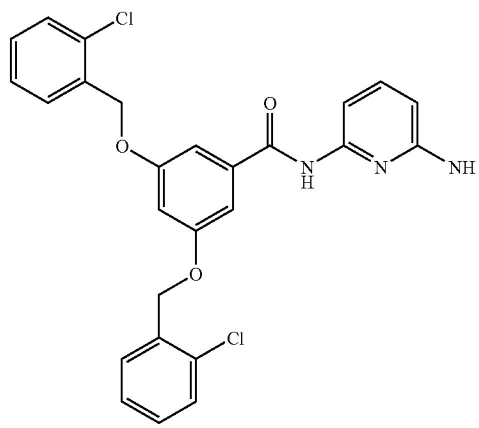 | 1 | 494/ 496 | | 1H NMR d (d6-DMSO): 5.25 (4H, s); 5.65 (2H, s); 6.23 (1H, d); 6.85 (1H, s); 7.05-7.15 (3H, m); 7.18-7.22 (5H, m); 7.45-7.55 (2H, m); 7.58-7.62 (2H, m); 10.16 (1H, brs). |
| 23 | 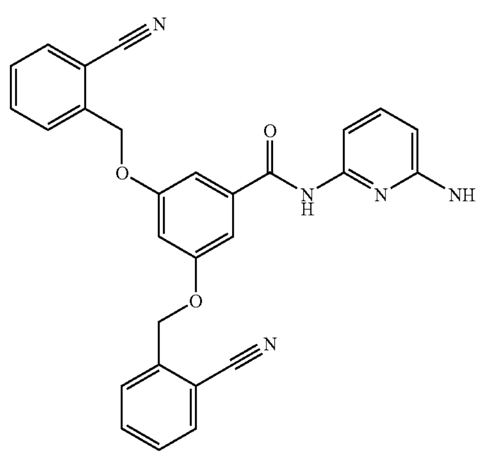 | 1 | 476 | | 1H NMR d (d6-DMSO): 5.25 (4H, s); 5.75 (2H, s); 6.22 (1H, d); 6.90 (1H, s); 7.25-7.41 (4H, m); 7.50-7.60 (2H, m); 7.70-7.80 (4H, m); 7.90 (2H, d); 10.19 (1H, br s). |

| Example | Structure | Route | (M + H)+ | (M − H)− | NMR |
|---|---|---|---|---|---|
| 24 | 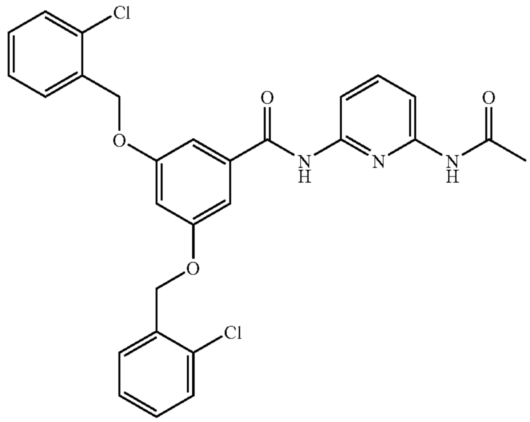 | 15 | 536/538 | | 1H NMR d (d6-DMSO): 3.25 (3H, s); 5.20 (4H, s); 6.9 (1H, t); 7.25 (2H, d); 7.35-7.40 (4H, m); 7.4-7.55 (2H, m); 7.58-7.63 (2H, m); 7.68-7.72 (1H, m); 7.75-7.80 (2H, d); 10.14 (1H, br s); 10.36 (1H, br s). |
| 25 | 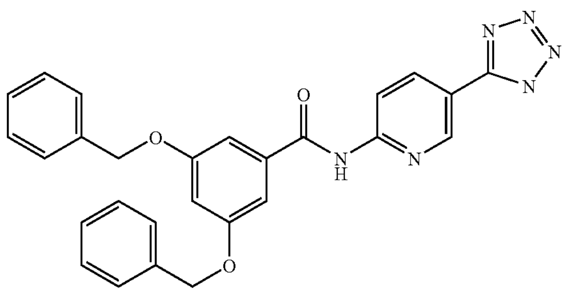 | 16 | 479 | 477 | 1H NMR d (d6-DMSO): 5.19 (4H, s); 6.88 (1H, s); 7.26-7.48 (12H, m); 8.40 (1H, d); 8.46 (1H, dd); 9.04 (1H, s); 11.13 (1H, br s). |
| 26 | 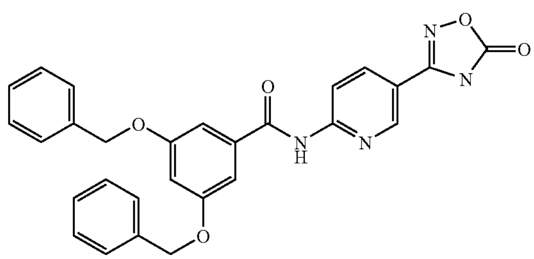 | 17 | 495 | 493 | 1H NMR d (d6-DMSO): 5.19 (4H, s); 6.87 (1H, s); 7.28-7.46 (12H, m); 8.21 (1H, dd); 8.38 (1H, d); 8.79 (1H, s); 11.14 (1H, br s). |
| 27 | 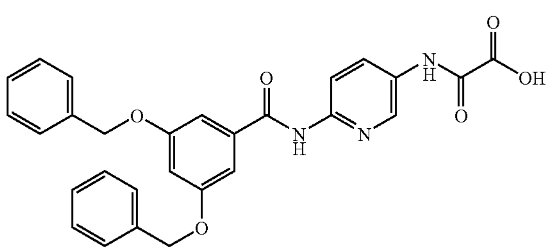 | 18 | 498 | | 1H NMR d (d6-DMSO): 5.18 (4H, s); 6.88 (1H, s); 7.30-7.50 (12H, m); 8.17 (2H, s); 8.79 (1H, s); 10.79 (1H, s); 10.93 (1H, br s). |
| 28 | 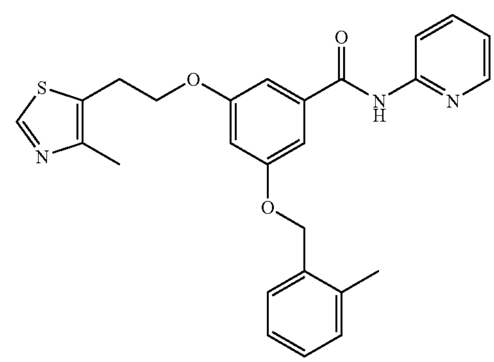 | 1 | 460 | | 1H NMR δ (d6-DMSO): 2.32 (s, 3H), 2.36 (s, 3H), 3.23 (t, 2H), 4.22 (t, 2H), 5.13 (s, 2H), 6.78 (m, 1H), 7.11-7.24 (brm, 5H), 7.30 (m, 1H), 7.41 (d, 1H), 7.83 (m, 1H), 8.14 (d, 1H), 8.37 (m, 1H), 8.82 (s, 1H), 10.74 (brs, 1H) |

| Example | Structure | Route | (M + H)+ | (M − H)− | NMR |
|---|---|---|---|---|---|
| 29 | 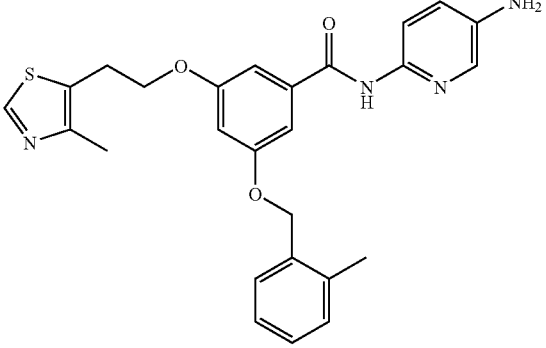 | 7 | 475 | | ¹H NMR δ (d₆-DMSO): 2.32 (s, 3H), 2.36 (s, 3H), 3.22 (t, 2H), 4.20 (t, 2H), 5.11 (s, 4H), 6.72 (m, 1H), 7.00 (m, 1H), 7.15-7.28 (brm, 5H), 7.41 (d, 1H), 7.73 (m, 2H), 8.82 (s, 1H), 10.29 (brs, 1H). |
| 30 | 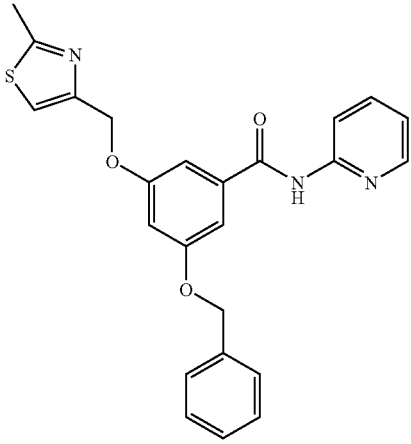 | 1 | | | ¹H NMR δ(d₆-DMSO): 2.66 (s, 3H), 5.15 (s, 4H), 6.88 (m, 1H), 7.14 (m, 1H), 7.39-7.47 (brm, 7H), 7.52 (s, 1H), 7.83 (m, 1H), 8.15 (d, 1H), 8.38 (m, 1H), 10.72 (brs, 1H). |
| 31 | 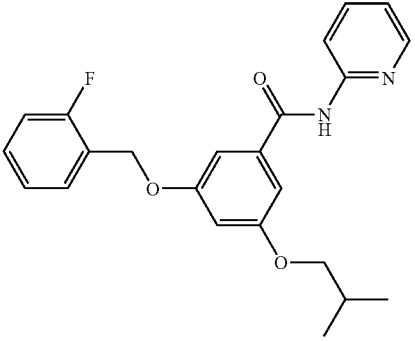 | 1b | 395 | | |
| 32 | 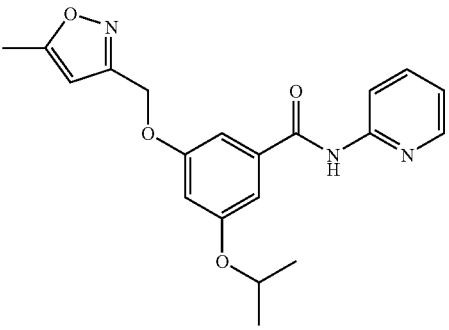 | 1 | | | ¹H NMR δ(d₆-DMSO): 1.28 (d, 6H), 2.39 (s, 3H), 4.72 (m, 1H), 5.20 (s, 2H), 6.33 (s, 1H), 6.72 (s, 1H), 7.14 (m, 1H), 7.20 (s, 1H), 7.27 (s, 1H), 7.82 (m, 1H), 8.13 (d, 1H), 8.36 (d, 1H), 10.72 (brs, 1H). |

| Example | Structure | Route | (M + H)+ | (M − H)− | NMR |
|---|---|---|---|---|---|
| 33 | 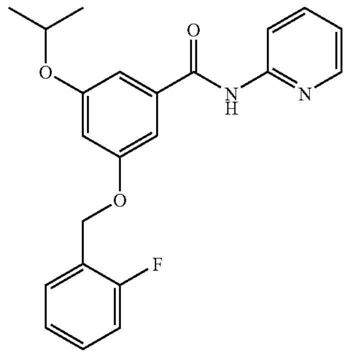 | 1 | | | ¹H NMR δ(d₆-DMSO): 1.27 (d, 6H), 4.71 (m, 1H), 5.21 (s, 2H), 6.73 (t, 1H), 7.12-7.29 (brm, 5H), 7.22 (m, 1H), 7.56 (m, 1H), 7.83 (m, 1H), 8.14 (d, 1H), 8.35 (m, 1H), 10.72 (brs, 1H). |
| 34 | 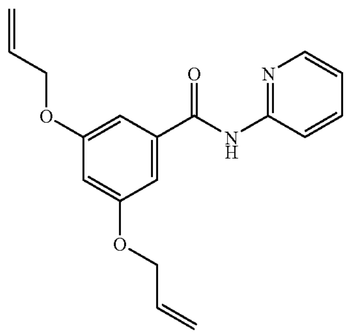 | 1b | 311 | | |
| 35 | 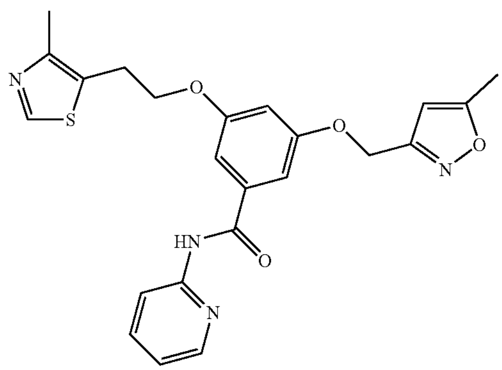 | 1b | 451 | | |
| 36 | 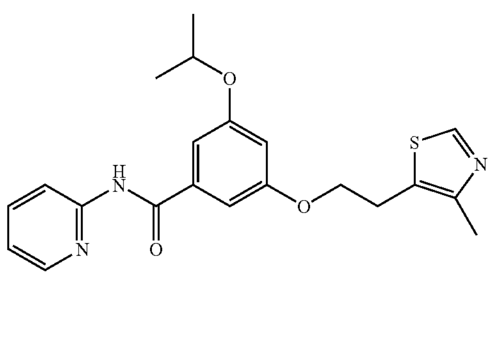 | 1b | 398 | | |

-continued

| Example | Structure | Route | (M + H)+ | (M − H)− | NMR |
|---|---|---|---|---|---|
| 37 | 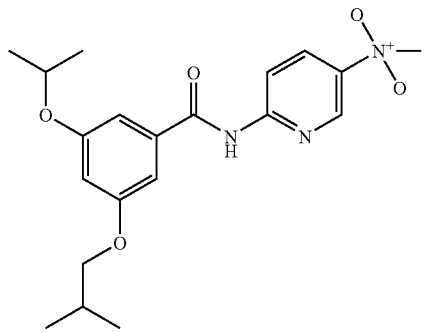 | 1 | 374 | 372 | ¹H NMR δ(d₆-DMSO): 0.98 (d, 6H), 1.27 (d, 6H), 2.01 (m, 1H), 3.60 (d, 2H), 4.71 (m, 1H), 6.67 (ap t, 1H), 7.17 (ap d, 2H), 8.39 (d, 1H), 8.63 (dd, 1H), 9.20 (d, 1H), 11.43 (bs, 1H) |
| 38 | 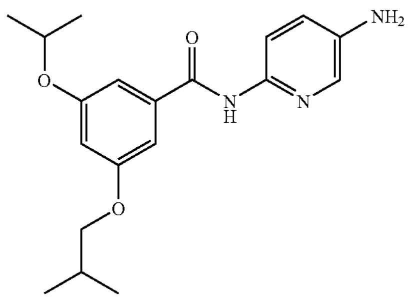 | 7b | 344 | | ¹H NMR δ(d₆-DMSO): 0.97 (d, 6H), 1.26 (d, 6H), 2.00 (m, 1H), 3.78 (d, 2H), 4.69 (m, 1H), 5.12 (s, 2H), 6.58 (t, 1H), 6.99 (dd, 1H), 7.1 (ap d, 2H), 7.73-7.78 (m, 2H), 10.24 (bs, 1H) |
| 39 | 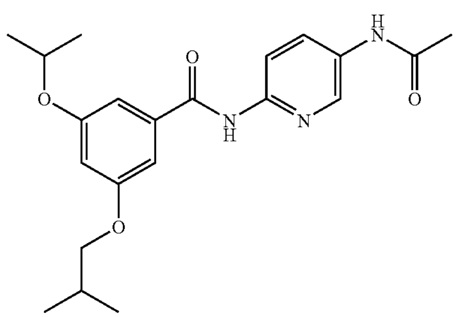 | 15 | 386 | | ¹H NMR δ(d₆-DMSO): 0.98 (d, 6H), 1.26 (d, 6H), 2.01 (m, 1H), 2.05 (s, 3H), 3.79 (d, 2H), 4.70 (m, 1H), 6.61 (apt, 1H), 7.14 (ap d, 2H), 7.95 (dd, 1H), 8.08 (d, 1H), 7.59 (ap d, 1H), 10.07 (bs, 1H) |
| 40 | 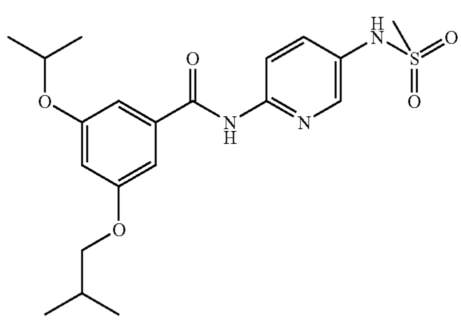 | 15 | 422 | 420 | ¹H NMR δ(d₆-DMSO): 0.97 (d, 6H), 1.26 (d, 6H), 2.03 (m, 1H), 3.01 (s, 3H), 3.79 (d, 2H), 4.70 (m, 1H), 6.63 (apt, 1H), 7.14 (ap d, 2H), 7.70 (dd, 1H), 8.12 (d, 1H), 8.34 (ap d, 1H), (9.83, s, 1H), 10.81 (bs, 1H) |
| 41 | 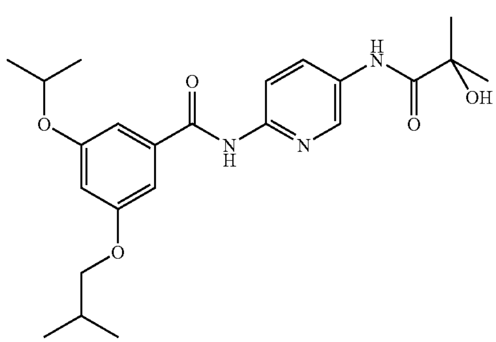 | 9 | M + H 430 M − H 428 | | ¹H NMR δ (d₆-DMSO): 0.98 (d, 6H), 1.27 (d, 6H), 1.35 (s, 6H), 2.01 (m, 1H), 3.79 (d, 2H), 4.70 (m, 1H), 5.71 (s, 1H), 6.61 (s, 1H), 7.15 (s, 2H), 8.06-8.15 (m, 2H), 8.76 (ap d, 1H), 9.78 (s, 1H), 10.65 (bs, 1H) |

| Example | Structure | Route | (M + H)+ | (M − H)− | NMR |
|---|---|---|---|---|---|
| 42 | 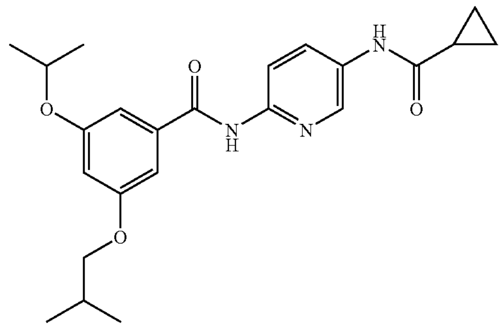 | 15 | 412 (M + HCOOH)+ 456 | | ¹H NMR δ(d₆-DMSO): 0.79-0.82 (m, 4H), 0.98 (d, 6H), 1.26 (d, 6H), 1.77 (m, 1H), 2.01 (m, 1H), 4.70 (h, 1H), 6.11 (ap t, 1H), 7.14 (ap d, 2H), 7.95 (dd, 1H), 8.08 (d, 1H), 8.62 (ap d, 1H), 10.33 (bs, 1H), 10.64 (bs, 1H) |
| 43 | 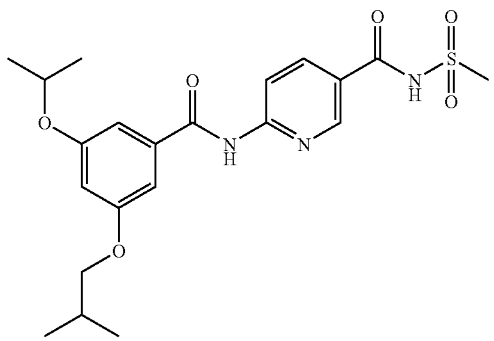 | 27 | M + H 450 | M − H 448 | ¹H NMR δ(d₆-DMSO): 0.98 (d, 6H), 1.27 (d, 6H), 2.01 (m., 1H), 3.37 (s, 3H), 3.80 (d, 2H), 4.71 (m, 1H), 6.65 (ap t, 1H), 7.17 (s, 2H), 8.27-8.35 (m, 2H), 8.91 (m, 1H), 11.13 (bs, 1H) |
| 44 | 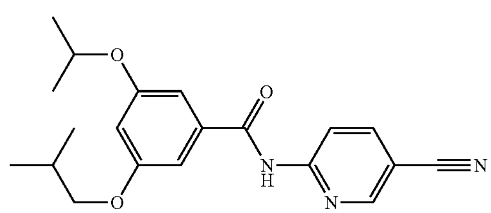 | 1c | 352 | | δ$_H$ (300 MHz, DMSO-d₆) 0.94-1.02 (6H, d); 1.24-1.34 (6H, d); 1095-2.10 (1H, m); 3.76-3.84 (2H, d); 4.64-4.77 (1H, m); 6.64-6.70 (1H, m); 7.14-7.17 (2H, m); 8.25-8.36 (2H, m); 8.85 (1H, m); 11.21 (1H, s) |
| 45 | 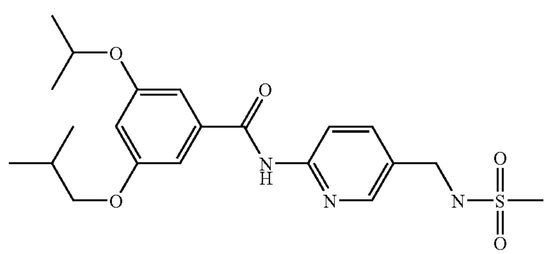 | 8 (a) 7c | | | δ$_H$ (300 MHz, DMSO-d₆) 0.94-1.03 (6H, d); 1.26-1.30 (6H, d); 1.95-2.08 (1H, m); 2.90 (3H, s); 3.75-3.84 (2H, d); 4.04-4.26 (2H, d + H₂O); 4.65-4.77 (1H, m); 6.64 (1H, m); 7.15 (2H, m); 7.50-7.62 (1H, broad t); 7.80-7.90 (1H, d of m); 8.08-8.16 (1H, app d); 8.35 (1H, m); 10.84 (1H, m) |
| 46 | 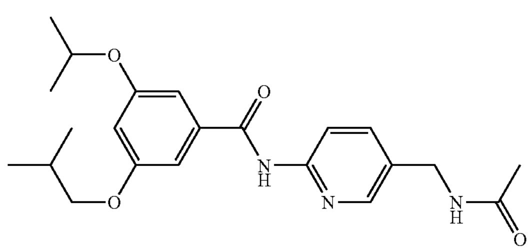 | 8 (a) 7c | | | δ$_H$ (300 MHz, DMSO-d₆) 0.94-1.02 (6H, d); 1.24-1.30 (6H, d); 1.84 (3H, s); 1.95-2.07 (1H, m); 3.75-3.83 (2H, d), 4.18-4.27 (2H, d); 4.64-4.76 (1H, m); 6.62 (1H, m); 7.15 (2H, m); 7.63-7.73 (1H, app d of m); 8.05-8.13 (1H, app d); 8.27 (1H,s); 8.30-8.38 (1H, app broad t); 10.69 (1H, s) |

-continued
| Example | Structure | Route | (M + H)+ | (M − H)− | NMR |
|---|---|---|---|---|---|
| 46a | 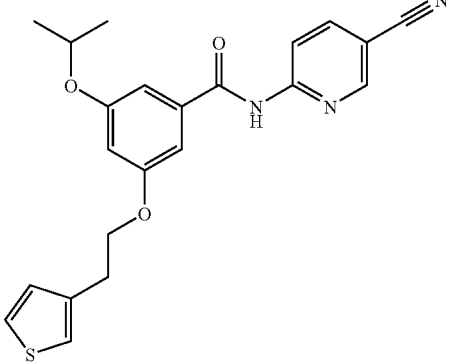 | 1a | 408 | 406 | δ$_H$ (300 MHz, DMSO-d$_6$) 1.26 (d, 6H), 3.05 (t, 2H), 4.25 (t, 2H), 4.72 (sept, 1H), 6.68 (s, 1H), 7.12 (d, 1H), 7.16 (s, 1H), 7.19 (s, 1H), 7.33 (s, 1H), 7.47 (dd, 1H), 8.30 (m, 2H), 8.83 (s, 1H), 11.23 (bs, 1H) |
| 47 | 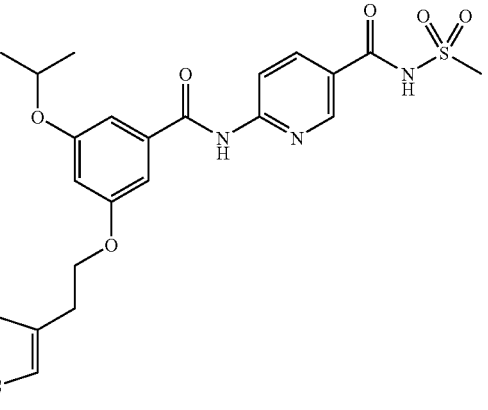 | 27 | 504 | | δ$_H$ (300 MHz, DMSO-d$_6$) 1.27 (d, 6H), 3.06 (t, 2H), 3.38 (s, 3H), 4.25 (t, 2H), 4.71 (sept, 1H), 6.68 (t, 1H), 7.11 (dd, 1H), 7.12 (s, 1H), 7.17 (s, 1H), 7.31 (d, 1H), 7.46 (dd, 1H), 8.29 (d, 1H), 8.34 (dd, 1H), 8.92 (d, 1H), 11.14 (bs, 1H) |
| 48 | 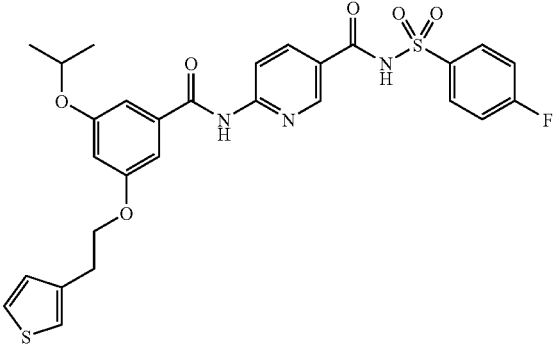 | 27 | 584 | 582 | δ$_H$ (300 MHz, DMSO-d$_6$) 1.25 (d, 6H), 3.04 (t, 2H), 4.23 (t, 2H), 4.69 (sept, 1H), 6.67 (s, 1H), 7.11 (d, 1H), 7.15 (s, 1H), 7.20 (s, 1H), 7.31 (d, 1H), 7.46 (m, 3H), 8.07 (dd, 2H), 8.26 (s, 2H), 8.86 (s, 1H), 11.13 (bs, 1H) |
| 49 | 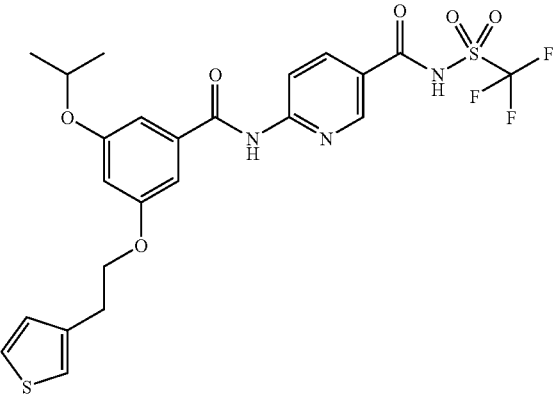 | 27 | 556 | | δ$_H$ (300 MHz, DMSO-d$_6$) 1.27 (d, 6H), 3.04 (t, 2H), 4.23 (t, 2H), 4.71 (sept, 1H), 6.64 (s, 1H), 7.11 (d, 1H), 7.18 (s, 1H), 7.22 (s, 1H), 7.32 (s, 1H), 7.46 (dd, 1H), 8.19 (m, 2H), 8.82 (d, 1H), 10.93 (bs, 1H) |

| Example | Structure | Route | (M + H)+ | (M − H)− | NMR |
|---|---|---|---|---|---|
| 50 | 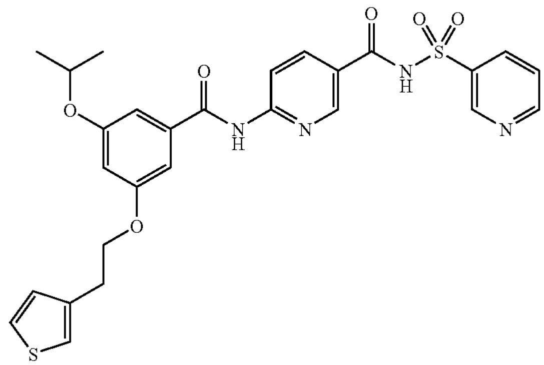 | 27 | 567 | | δ$_H$ (300 MHz, DMSO-d$_6$) 1.26 (d, 6H), 3.04 (t, 2H), 4.24 (t, 2H), 4.70 (sept, 1H), 6.64 (t, 1H), 7.11 (dd, 1H), 7.16 (s, 1H), 7.21 (s, 1H), 7.30 (m, 1H), 7.46 (m, 1H), 8.16 (m, 3H), 8.62 (d, 1H), 8.83 (s, 1H), 8.98 (s, 1H), 10.90 (bs, 1H) |
| 51 | 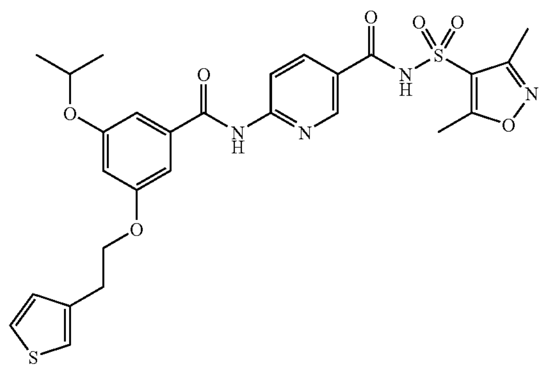 | 27 | 585 | 583 | δ$_H$ (300 MHz, DMSO-d$_6$) 1.27 (d, 6H), 2.39 (s, 3H), 2.68 (s, 3H), 3.06 (t, 2H), 4.26 (t, 2H), 4.73 (sept, 1H), 6.69 (t, 1H), 7.12 (d, 1H), 7.17 (s, 1H), 7.22 (s, 1H), 7.33 (m, 1H), 7.49 (m, 1H), 8.28 (m, 2H), 8.89 (s, 1H), 11.10 (bs, 1H) |
| 52 | 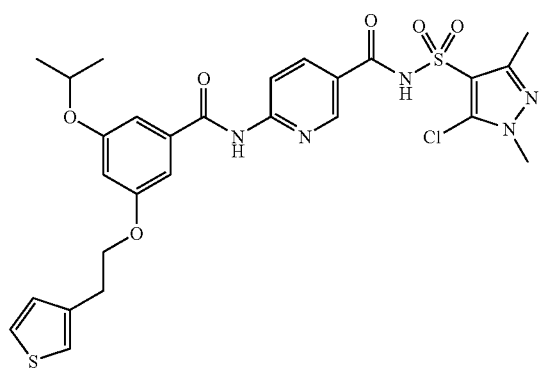 | 27 | 618/ 620 (1xCl) | 616/ 618 (1xCl) | δ$_H$ (300 MHz, DMSO-d$_6$) 1.28 (d, 6H), 2.40 (s, 3H), 3.08 (t, 2H), 3.79 (s, 3H), 4.25 (t, 2H), 4.71 (sept, 1H), 6.68 (s, 1H), 7.12 (d, 1H), 7.18 (s, 1H), 7.22 (s, 1H), 7.34 (m, 1H), 7.39 (s, 1H), 7.48 (dd, 1H), 8.30 (m, 2H), 8.92 (s, 1H), 11.15 (bs, 1H) |
| 53 | 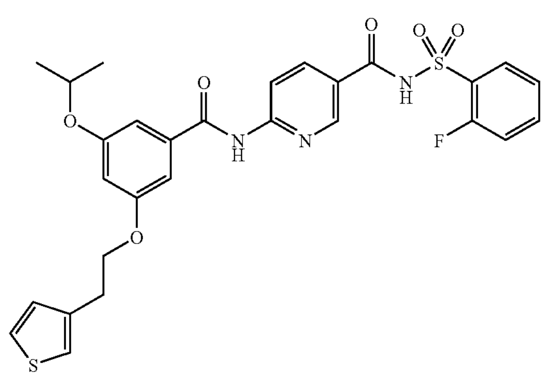 | 27 | 584 | | δ$_H$ (300 MHz, DMSO-d$_6$) 1.26 (d, 6H), 3.04 (t, 2H), 4.24 (t, 2H), 4.70 (sept, 1H), 6.66 (t, 1H), 7.12 (dd, 1H), 7.18 (s, 1H), 7.22 (s, 1H), 7.30 (m, 1H), 7.37 (m, 1H), 7.45 (dd, 1H), 7.67 (m, 1H), 7.78 (dt, 1H), 7.96 (dt, 1H), 8.822 (s, 2H), 8.86 (s, 1H), 11.08 (bs, 1H) |

| Example | Structure | Route | (M + H)+ | (M − H)− | NMR |
|---|---|---|---|---|---|
| 54 | 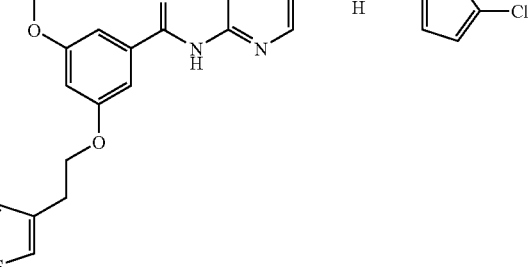 | 27 | 606 | 604 | δ$_H$ (300 MHz, DMSO-d$_6$) 1.26 (d, 6H), 3.04 (t, 2H), 4.25 (t, 2H), 4.71 (sept, 1H), 6.64 (t, 1H), 7.00 (d, 1H), 7.12 (dd, 1H), 7.16 (s, 1H), 7.22 (s, 1H), 7.32 (m, 2H), 7.46 (dd, 1H), 8.14 (d, 1H), 8.22 (dd, 1H), 8.83 (t, 1H), 10.87 (bs, 1H) |
| 55 | 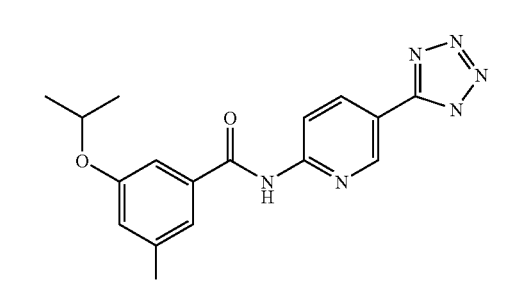 | 16 | 451 | 449 | δ$_H$ (300 MHz, DMSO-d$_6$) 1.28 (d, 6H), 3.06 (t, 2H), 4.26 (t, 2H), 4.72 (sept, 1H), 6.65 (s, 1H), 7.12 (d, 1H), 7.18 (s, 1H), 7.23 (s, 1H), 7.32 (s, 1H), 7.47 (m, 1H), 8.23 (d, 1H), 8.32 (dd, 1H), 8.95 (s, 1H), 10.81 (bs, 1H) |
| 56 | 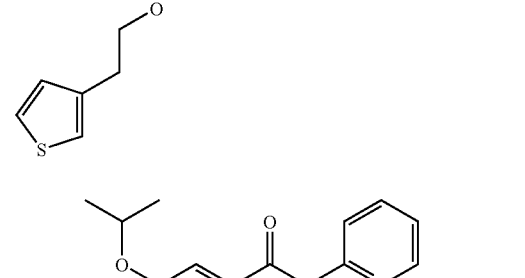 | 1a | 329.48 | 327.46 | |
| 57 | 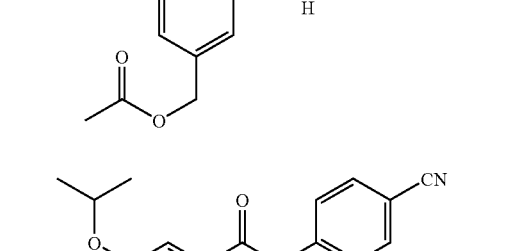 | 1a | 354.46 | 352.43 | |

Notes:

* Final products prepared by hydrolysis method 2a; requisite starting materials prepared according to generic alkylation methodology followed by coupling (Route 1).

** Final products prepared by reductive amination method 6 method; requisite starting materials prepared according to generic alkylation methodology followed by coupling (Route 1) and hydrolysis (Route 2a).

*** Final products prepared by hydrolysis (Route 2a) or acid chloride coupling (Route 1); requisite starting materials prepared according to generic alkylation methodology followed by coupling (Route 1).

EXAMPLE KK

By analogous methods to those described above the following compounds, Example numbers KK$_1$ to KK$_7$, were also made.

| Example | Structure | Route | (M + H)+ | (M − H)− | NMR |
|---|---|---|---|---|---|
| 1 | 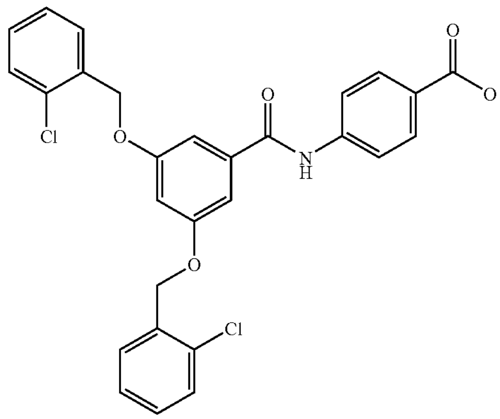 | 2b * | 522 | 520 | 1H NMR d (d6-DMSO): 5.20 (4H, s); 6.95 (1H, s); 7.25 (2H, s); 7.30-7.5 (4H, m); 7.5 (2H, m); 7.6 (2H, m); 7.8-8.0 (4H, s). |
| 2 | 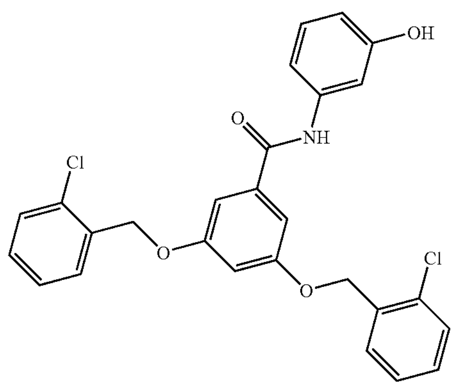 | 1 | | 494 | No data |
| 3 | 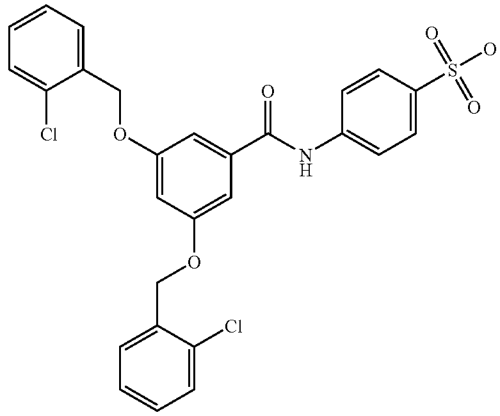 | 1 | | 445/ 558 | NMR not right |

-continued

| Example | Structure | Route | (M + H)+ | (M − H)− | NMR |
|---|---|---|---|---|---|
| 4 | 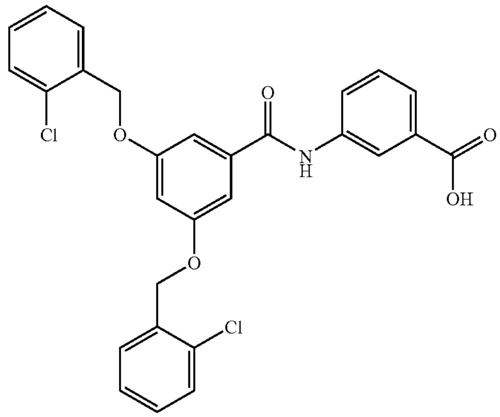 | 2b | 522 | | 1H NMR d (d6-DMSO): 5.25 (4H, s); 6.95 (1H, s); 7.25 (2H, s); 7.35-7.55 (7H, m); 7.6-7.7 (3H, m); 8.05 (1H, d); 8.4 (1H, s); 10.3 (1H, br s); 12.9 (1H, br s). |
| 5 | 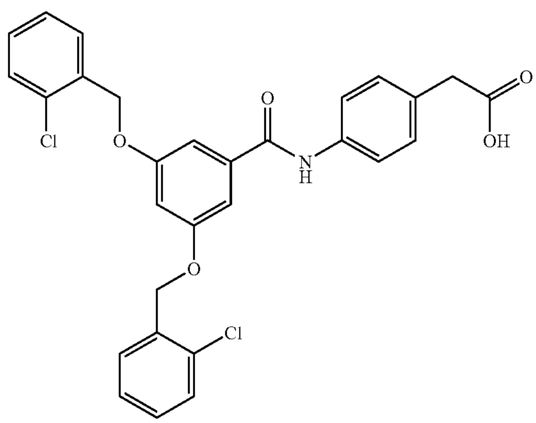 | 2b * | 536 | 534 | 1H NMR d (d6-DMSO): 3.4 (2H, s); 5.2 (4H, s); 6.95 (1H, s); 7.2 (4H, m); 7.4 (4H, m); 7.5 (2H, m); 7.6-7.7 (4H, m); 10.1 (1H, br s). |
| 6 | 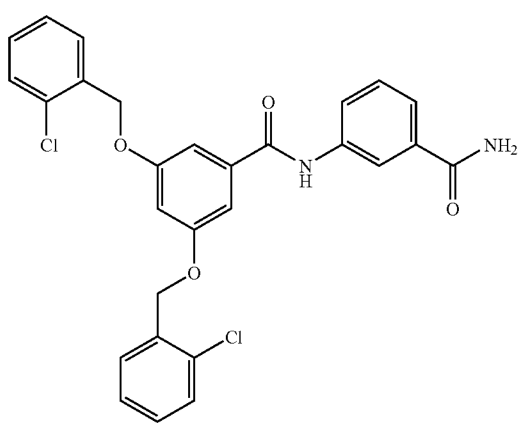 | 1 | | 519 | 1H NMR d (d6-DMSO): 5.2 (4H, s); 6.95 (1H, m); 7.25 (2H, m); 7.4 (5H, m); 7.5 (2H, m); 7.55-7.65 (4H, m); 7.9 (2H, m); 8.2 (1H, s); 10.3 (1H, br s). |

| Example | Structure | Route | (M + H)+ | (M − H)− | NMR |
|---|---|---|---|---|---|
| 7 | 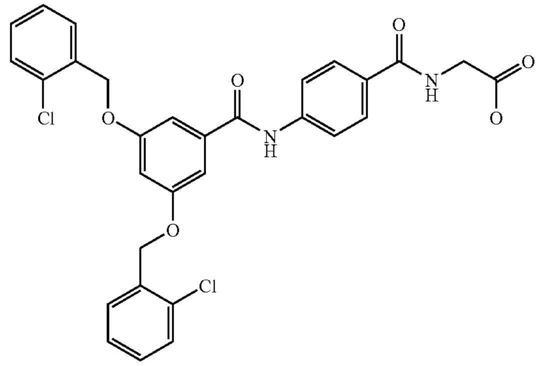 | 1 | | 577 | V. poor spectrum |
\* For Examples KK₁ and KK₅, the ester intermediates were prepared by route 1:
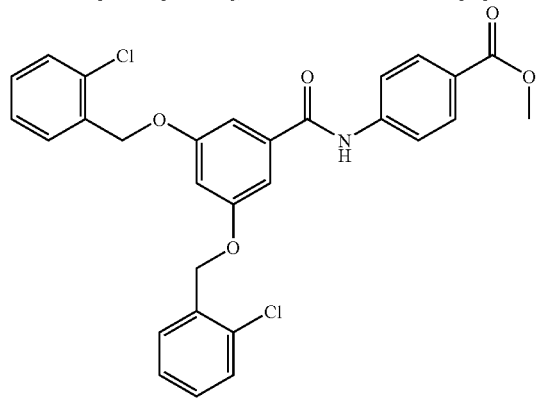
¹H NMR δ (d₆-DMSO): 3.8 (3H, s); 5.25 (4H, s); 6.95 (1H, t); 7.25 (2H, d); 7.4 (4H, m); 7.5 (2H, m); 7.6 (2H, m); 8.0 (4H, q); 10.6 (1H, br s).
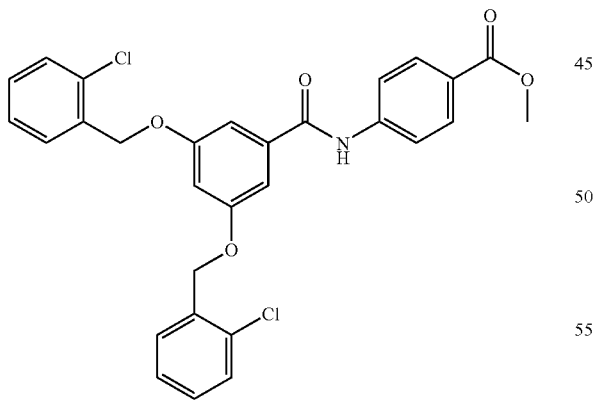
¹H NMR δ (d₆-DMSO): 1.2 (3H, t); 3.6 (2H, s); 4.1 (2H, q); 5.25 (4H, s); 6.95 (1H, t); 7.2 (4H, m); 7.4 (4H, m); 7.5 (2H, m); 7.6 (2H, m); 7.7 (2H, m); 10.15 (1H, br s).

EXAMPLE LL

By analogous methods to those described above the following compounds, Example numbers $LL_1$ to $LL_3$, were also made.

| Example | Structure | Route | (M + H)+ | (M − H)− | NMR |
|---|---|---|---|---|---|
| 1 | 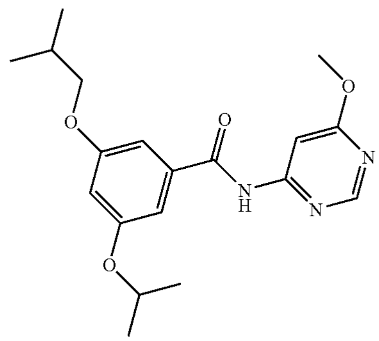 | 1a | 360 | | |
| 2 | 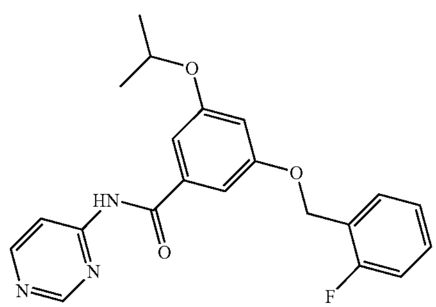 | 1a | 382 | | |
| 3 | 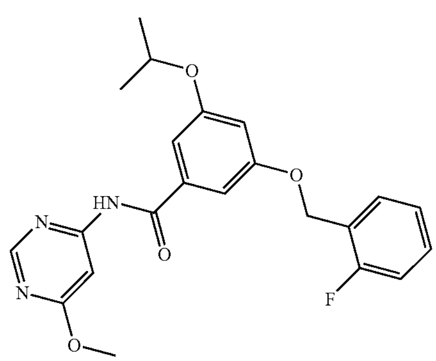 | 1a | 412 | | |

EXAMPLE MM

By analogous methods to those described above the following compounds, Example numbers MM$_1$ to MM$_2$, were also made.

| Example | Structure | Route | (M + H)+ | (M − H) | NMR |
|---|---|---|---|---|---|
| 1 | 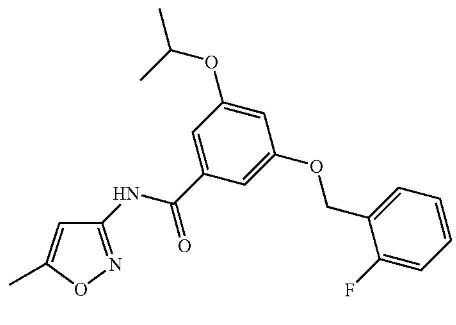 | 1a | 385 | | |
| 2 | 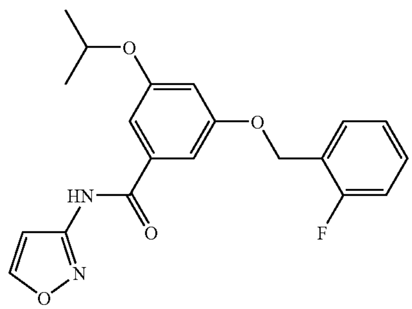 | 1a | 371 | | |

Biological Tests:

The biological effects of the compounds of formula (I) or (IA) or (IB) may be tested in the following way:

(1) Enzymatic activity of GLK may be measured by incubating GLK, ATP and glucose. The rate of product formation may be determined by coupling the assay to a G-6-P dehydrogenase, NADP/NADPH system and measuring the increase in optical density at 340 nm (Matschinsky et al 1993).

(2) A GLK/GLKRP binding assay for measuring the binding interactions between GLK and GLKRP. The method may be used to identify compounds which modulate GLK by modulating the interaction between GLK and GLKRP. GLKRP and GLK are incubated with an inhibitory concentration of F-6-P, optionally in the presence of test compound, and the extent of interaction between GLK and GLKRP is measured. Compounds which either displace F-6-P or in some other way reduce the GLK/GLKRP interaction will be detected by a decrease in the amount of GLK/GLKRP complex formed. Compounds which promote F-6-P binding or in some other way enhance the GLK/GLKRP interaction will be detected by an increase in the amount of GLK/GLKRP complex formed. A specific example of such a binding assay is described below GLK/GLKRP Scintillation Proximity Assay The compounds A to S (described in Examples A to S) and 1 to 118 (described in Examples T to Y) were found to have an activity of at least 40% activity at 10 μm when tested in the GLK/GLKRP scintillation proximity assay described below.

Recombinant human GLK and GLKRP were used to develop a "mix and measure" 96 well SPA (scintillation proximity assay) as described in WO01/20327 (the contents of which are incorporated herein by reference). GLK (Biotinylated) and GLKRP are incubated with streptavidin linked SPA beads (Amersham) in the presence of an inhibitory concentration of radiolabelled [3H]F-6-P (Amersham Custom Synthesis TRQ8689), giving a signal. Compounds which either displace the F-6-P or in some other way disrupt the GLK/GLKRP binding interaction will cause this signal to be lost.

Binding assays were performed at room temperature for 2 hours. The reaction mixtures contained 50 mM Tris-HCl (pH 7.5), 2 mM ATP, 5 mM MgCl$_2$, 0.5 mM DTT, recombinant biotinylated GLK (0.1 mg), recombinant GLKRP (0.1 mg), 0.05 mCi [3H] F-6-P (Amersham) to give a final volume of 100 ml. Following incubation, the extent of GLK/GLKRP complex formation was determined by addition of 0.1 mg/well avidin linked SPA beads (Amersham) and scintillation counting on a Packard TopCount NXT.

(3) A F-6-P/GLKRP binding assay for measuring the binding interaction between GLKRP and F-6-P. This method may be used to provide further information on the mechanism of action of the compounds. Compounds identified in the GLK/GLKRP binding assay may modulate the interaction of GLK and GLKRP either by displacing F-6-P or by modifying the GLK/GLKRP interaction in some other way. For example, protein-protein interactions are generally known to occur by interactions through multiple binding sites. It is thus possible that a compound which modifies the interaction between GLK and GLKRP could act by binding to one or more of several different binding sites.

The F-6-P/GLKRP binding assay identifies only those compounds which modulate the interaction of GLK and GLKRP by displacing F-6-P from its binding site on GLKRP.

GLKRP is incubated with test compound and an inhibitory concentration of F-6-P, in the absence of GLK, and the extent of interaction between F-6-P and GLKRP is measured. Compounds which displace the binding of F-6-P to GLKRP may be detected by a change in the amount of GLKRP/F-6-P complex formed. A specific example of such a binding assay is described below F-6-P/GLKRP Scintillation Proximity Assay Recombinant human GLKRP was used to develop a "mix and measure" 96 well scintillation proximity assay) as described in WO01/20327 (the contents of which are incorporated herein by reference). FLAG-tagged GLKRP is incubated with protein A coated SPA beads (Amersham) and an anti-FLAG antibody in the presence of an inhibitory concentration of radiolabelled [3H]F-6-P. A signal is generated. Compounds which displace the F-6-P will cause this signal to be lost. A combination of this assay and the GLK/GLKRP binding assay will allow the observer to identify compounds which disrupt the GLK/GLKRP binding interaction by displacing F-6-P.

Binding assays were performed at room temperature for 2 hours. The reaction mixtures contained 50 mM Tris-HCl (pH 7.5), 2 mM ATP, 5 mM $MgCl_2$, 0.5 mM DTT, recombinant FLAG tagged GLKRP (0.1 mg), Anti-Flag M2 Antibody (0.2 mg) (IBI Kodak), 0.05 mCi [3H] F-6-P (Amersham) to give a final volume of 100 ml. Following incubation, the extent of F-6-P/GLKRP complex formation was determined by addition of 0.1 mg/well protein A linked SPA beads (Amersham) and scintillation counting on a Packard TopCount NXT.

Production of Recombinant GLK and GLKRP:

Preparation of mRNA

Human liver total mRNA was prepared by polytron homogenisation in 4M guanidine isothiocyanate, 2.5 mM citrate, 0.5% Sarkosyl, 100 mM b-mercaptoethanol, followed by centrifugation through 5.7M CsCl, 25 mM sodium acetate at 135,000 g (max) as described in Sambrook J, Fritsch E F & Maniatis T, 1989.

Poly $A^+$ mRNA was prepared directly using a FastTrack™ mRNA isolation kit (Invitrogen).

PCR Amplification of GLK and GLKRP cDNA Sequences

Human GLK and GLKRP cDNA was obtained by PCR from human hepatic mRNA using established techniques described in Sambrook, Fritsch & Maniatis, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in E. coli using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

E. Coli transformations were generally carried out by electroporation. 400 ml cultures of strains DH5a or BL21(DE3) were grown in L-broth to an OD 600 of 0.5 and harvested by centrifugation at 2,000 g. The cells were washed twice in ice-cold deionised water, resuspended in 1 ml 10% glycerol and stored in aliquots at −70° C. Ligation mixes were desalted using Millipore V Series™ membranes (0.0025 mm) pore size). 40 ml of cells were incubated with 1 ml of ligation mix or plasmid DNA on ice for 10 minutes in 0.2 cm electroporation cuvettes, and then pulsed using a Gene Pulser™ apparatus (BioRad) at 0.5 $kVcm^{-1}$, 250 mF, 250 ?. Transformants were selected on L-agar supplemented with tetracyline at 10 mg/ml or ampicillin at 100 mg/ml.

Expression

GLK was expressed from the vector pTB375NBSE in E. coli BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in E. coli BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

Biotinylation of GLK:

GLK was biotinylated by reaction with biotinamidocaproate N-hydroxysuccinimide ester (biotin-NHS) purchased from Sigma-Aldrich (cat no. B2643). Briefly, free amino groups of the target protein (GLK) are reacted with biotin-NHS at a defined molar ratio forming stable amide bonds resulting in a product containing covalently bound biotin. Excess, non-conjugated biotin-NHS is removed from the product by dialysis. Specifically, 7.5 mg of GLK was added to 0.31 mg of biotin-NHS in 4 mL of 25 mM HEPES pH7.3, 0.15M KCl, 1 mM dithiothreitol, 1 mM EDTA, 1 mM $MgCl_2$ (buffer A). This reaction mixture was dialysed against 100 mL of buffer A containing a further 22 mg of biotin-NHS. After 4 hours excess biotin-NHS was removed by extensive dialysis against buffer A.

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium | 1.5 |

-continued

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml | |
|---|---|---|
| Compound X | 40 | mg |
| Ethanol | 300 | μl |
| Water | 300 | μl |
| 1-Dodecylazacycloheptan-2-one | 50 | μl |
| Propylene glycol | to 1 | ml |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

REFERENCES

1. Printz, R. L., Magnuson, M. A. and Granner, D. K. (1993) Annual Review of Nutrition 13, 463-96
2. DeFronzo, R. A. (1988) Diabetes 37, 667-87
3. Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4. Bell, G. I., Pilkis, S. J., Weber, I. T. and Polonsky, K. S. (1996) Annual Review of Physiology 58, 171-86
5. Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6. Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
7. Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30
8. Caro, J. F., Triester, S., Patel, V. K., Tapscott, E. B., Frazier, N. L. and Dohm, G. L. (1995) Hormone & Metabolic Research 27, 19-22
9. Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10. Shiota, M., Postic, C., Fujimoto, Y., Jetton, T. L., Dixon, K., Pan, D., Grimsby, J., Grippo, J. F., Magnuson, M. A. and Chemington, A. D. (2001) Diabetes 50, 622-9
11. Ferre, T., Pujol, A., Riu, E., Bosch, F. and Valera, A. (1996) Proceedings of the National Academy of Sciences of the United States of America 93, 7225-30
12. Seoane, J., Barbera, A., Telemaque-Potts, S., Newgard, C. B. and Guinovart, J. J. (1999) Journal of Biological Chemistry 274, 31833-8
13. Moore, M. C., Davis, S. N., Mann, S. L. and Chemington, A. D. (2001) Diabetes Care 24, 1882-7
14. Alvarez, E., Roncero, I., Chowen, J. A., Vazquez, P. and Blazquez, E. (2002) Journal of Neurochemistry 80, 45-53
15. Lynch, R. M., Tompkins, L. S., Brooks, H. L., Dunn-Meynell, A. A. and Levin, B. E. (2000) Diabetes 49, 693-700
16. Roncero, I., Alvarez, E., Vazquez, P. and Blazquez, E. (2000) Journal of Neurochemistry 74, 1848-57
17. Yang, X. J., Kow, L. M., Funabashi, T. and Mobbs, C. V. (1999) Diabetes 48, 1763-1772
18. Schuit, F. C., Huypens, P., Heimberg, H. and Pipeleers, D. G. (2001) Diabetes 50, 1-11
19. Levin, B. E. (2001) International Journal of Obesity 25
20. Alvarez, E., Roncero, I., Chowen, J. A., Thorens, B. and Blazquez, E. (1996) Journal of Neurochemistry 66, 920-7
21. Mobbs, C. V., Kow, L. M. and Yang, X. J. (2001) American Journal of Physiology—Endocrinology & Metabolism 281, E649-54
22. Levin, B. E., Dunn-Meynell, A. A. and Routh, V. H. (1999) American Journal of Physiology 276, R1223-31
23. Spanswick, D., Smith, M. A., Groppi, V. E., Logan, S. D. and Ashford, M. L. (1997) Nature 390, 521-5
24. Spanswick, D., Smith, M. A., Mirshamsi, S., Routh, V. H. and Ashford, M. L. (2000) Nature Neuroscience 3, 757-8
25. Levin, B. E. and Dunn-Meynell, A. A. (1997) Brain Research 776, 146-53
26. Levin, B. E., Govek, E. K. and Dunn-Meynell, A. A. (1998) Brain Research 808, 317-9

27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20

The invention claimed is:

1. A method for the treatment of type 2 diabetes, comprising administering a compound of Formula (I) or a salt thereof,

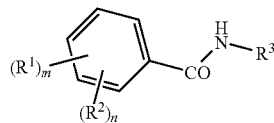

Formula (I)

wherein
m is 0, 1, or 2;
n is 0, 1, 2, 3, or 4; and
n+m>0;
each $R^1$ is independently selected from OH, —$(CH_2)_{1-4}$OH, —$CH_{3-a}F_a$, —$(CH_2)_{1-4}CH_{3-a}F_a$, —$OCH_{3-a}F_a$, halo, $C_{1-6}$alkyl, $C_{2-6}$alkenyl, $C_{2-6}$alkynyl, $NH_2$, —NH—$C_{1-4}$alkyl, —N-di-($C_{1-4}$alkyl), CN, formyl, phenyl, and heterocyclyl optionally substituted with $C_{1-6}$alkyl;
each $R^2$ is the group Y—X—;
each X and $X^1$ is a linker independently selected from —O—Z—, —O—Z—O—Z—, —C(O)O—Z—, —OC(O)—Z—, —S—Z—, —SO—Z—, —$SO_2$—Z—, —N($R^6$)—Z—, —N($R^6$)$SO_2$—Z—, —$SO_2$N($R^6$)—Z—, —$(CH_2)_{1-4}$—, —CH=CH—Z—, —C≡C—Z—, —N($R^6$)CO—Z—, —CON($R^6$)—Z—, —C(O)N($R^6$)S(O)$_2$—Z—, —S(O)$_2$N($R^6$)C(O)—Z—, —C(O)—Z—, —Z—, —C(O)—Z—O—Z—, —N($R^6$)—C(O)—Z—O—Z—, —O—Z—N($R^6$)—Z—, —O—C(O)—Z—O—Z—, and a direct bond;
each Z is independently selected from a direct bond, $C_{2-6}$alkenylene, and a group of the formula —$(CH_2)_p$—C($R^{6a}$)$_2$—$(CH_2)_q$—;
each Y is independently selected from aryl-$Z^1$—, heterocyclyl-$Z^1$—, $C_{3-7}$ cycloalkyl-$Z^1$—, $C_{1-6}$alkyl, $C_{2-6}$alkenyl, $C_{2-6}$alkynyl, —$(CH_2)_{1-4}CH_{3-a}F_a$, and —CH(OH)$CH_{3-a}F_a$; wherein Y is optionally substituted with up to three $R^4$ groups;
each $R^4$ is independently selected from halo, —$CH_{3-a}F_a$, CN, $NH_2$, $C_{1-6}$alkyl, —$OC_{1-6}$alkyl, —COOH, —C(O)$OC_{1-6}$alkyl, OH, phenyl optionally substituted with $C_{1-6}$alkyl or —C(O)$OC_{1-6}$alkyl; and $R^5$—$X^1$—;
$R^5$ is selected from hydrogen, $C_{1-6}$alkyl, —$CH_{3-a}F_a$, phenyl, naphthyl, heterocyclyl, and $C_{3-7}$cycloalkyl; wherein $R^5$ is optionally substituted with one or more substituents independently selected from halo, $C_{1-6}$alkyl, —$OC_{1-6}$alkyl, —$CH_{3-a}F_a$, CN, OH, $NH_2$, COOH, and —C(O)$OC_{1-6}$alkyl;
each $Z^1$ is independently selected from a direct bond, $C_{2-6}$alkenylene, and a group of the formula —$(CH_2)_p$—C($R^{6a}$)$_2$—$(CH_2)_q$—;
$R^3$ is selected from phenyl and a heterocyclyl, and $R^3$ is optionally substituted with one or more $R^7$ groups;
$R^6$ is independently selected from hydrogen, $C_{1-6}$alkyl, and —$C_{2-4}$alkyl-O—$C_{1-4}$alkyl;

$R^{6a}$ is independently selected from hydrogen, halo, $C_{1-6}$alkyl, and —$C_{2-4}$alkyl-O—$C_{1-4}$alkyl;
each $R^7$ is independently selected from $C_{1-6}$alkyl, $C_{2-6}$alkenyl, $C_{2-6}$alkynyl, $(CH_2)_{0-3}$aryl, $(CH_2)_{0-3}$heterocyclyl, $(CH_2)_{0-3}C_{3-7}$cycloalkyl, OH, $C_{1-6}$alkyl-OH, halo, $C_{1-6}$alkyl-halo, $OC_{1-6}$alkyl, $(CH_2)_{0-3}S(O)_{0-2}R^8$, SH, $SO_3H$, thioxo, $NH_2$, CN, $(CH_2)_{0-3}NHSO_2R^8$, $(CH_2)_{0-3}COOH$, $(CH_2)_{0-3}$—O—$(CH_2)_{0-3}R^8$, $(CH_2)_{0-3}C(O)(CH_2)_{0-3}R^8$, $(CH_2)_{0-3}C(O)OR^8$, $(CH_2)_{0-3}C(O)NH_2$, $(CH_2)_{0-3}C(O)NH(CH_2)_{0-3}R^8$, $(CH_2)_{0-3}NH(CH_2)_{0-3}R^8$, $(CH_2)_{0-3}NHC(O)(CH_2)_{0-3}R^8$, $(CH_2)_{0-3}C(O)NHSO_2$—$R^8$ and $(CH_2)_{0-3}SO_2NHC(O)$—$R^8$; wherein any alkyl chain, cycloalkyl ring, or heterocyclyl ring within $R^7$ is optionally substituted with one or more substituents independently selected from $C_{1-4}$alkyl, OH, halo, CN, $NH_2$, N—$C_{1-4}$alkylamino, N,N-di-$C_{1-4}$alkylamino, and $OC_{1-4}$alkyl;
$R^8$ is selected from hydrogen, $C_{1-6}$alkyl, aryl, heterocyclyl, $C_{3-7}$cycloalkyl, OH, $C_{1-6}$alkyl-OH, COOH, C(O)$OC_{1-6}$alkyl, N($R^6$)$C_{1-6}$ alkyl, $OC_{1-6}$alkyl, $C_{0-6}$alkylOC(O)$C_{1-6}$ alkyl, and C(OH)($C_{1-6}$alkyl)$C_{1-6}$alkyl; wherein any alkyl chain or aryl, heterocyclyl, or cycloalkyl ring within $R^8$ is optionally substituted with one or more substituents independently selected from $C_{1-4}$alkyl, OH, halo, CN, $NH_2$, —NH—$C_{1-4}$alkyl, —N-di-($C_{1-4}$alkyl), and $OC_{1-4}$alkyl;
each a is independently 1, 2, or 3;
p is 0, 1, 2, or 3;
q is 0, 1, 2, or 3; and
p+q<4;
provided that when $R^3$ is pyridine, then $R^7$ is other than COOH or COO$C_{1-6}$ alkyl.

2. The method of claim 1, wherein the compound of Formula (I) or a salt thereof is administered as a pharmaceutical composition, together with a pharmaceutically acceptable diluent or carrier.

3. The method of claim 1, wherein for the compound of Formula (I) or a salt thereof,
each $R^1$ is independently selected from OH, formyl, $CH_{3-a}F_aOCH_{3-a}F_a$, halo, $C_{1-6}$alkyl, $NH_2$, CN, $(CH_2)_{1-4}$OH, and a heterocyclyl optionally substituted with $C_{1-6}$alkyl.

4. The method of claim 1, wherein for the compound of Formula (I) or a salt thereof,
each $R^2$ is the group Y—X—;
each X is independently selected from —Z—, —CH=CH—Z—, —O—Z—, —C(O)—Z—, —C(O)O—Z—, —OC(O)—Z—, —C(O)—Z—O—Z—, —O—C(O)—Z—O—Z—, —S—Z—, —SO—Z—, —$SO_2$—Z—, —N($R^6$)—Z—, —N($R^6$)CO—Z—, —CON($R^6$)—Z—, —N($R^6$)—C(O)—Z—O—Z—, —$SO_2$N($R^6$)—Z—, —N($R^6$)$SO_2$—Z—, and —O—Z—N($R^6$)—Z—;
each Y is independently selected from $C_{1-6}$alkyl, $C_{2-6}$alkenyl, aryl-$Z^1$—, heterocyclyl-$Z^1$—, $C_{3-7}$cycloalkyl $(CH_2)_{0-2}$, and —$(CH_2)_{1-4}CH_{3-a}F_a$; wherein each Y is independently optionally substituted with $R^4$.

5. The method according to claim 1, wherein for the compound of Formula (I) or a salt thereof,
each $R^4$ is independently selected from halo, $CH_{3-a}F_a$, $OCH_{3-a}F_a$, CN, $C_{1-6}$alkyl, $OC_{1-6}$alkyl, COOH, C(O)$OC_{1-6}$alkyl, $(CH_2)_{0-3}$COOH, $O(CH_2)_{0-3}$COOH, CO-phenyl, $CONH_2$, CONH-phenyl, $SO_2NH_2$, $SO_2C_{1-6}$alkyl, OH, and phenyl optionally substituted with one or more $R^5$ groups selected from $C_{1-6}$alkyl, and C(O)$OC_{1-6}$alkyl.

6. The method according to claim 1, wherein for the compound of Formula (I) or a salt thereof, R³ is a nitrogen-containing heterocyclyl, optionally substituted with one or more R⁷ groups.

7. The method according to claim 6, wherein for the compound of Formula (I) or a salt thereof,
R³ is selected from thiazole, benzothiazole, thiadiazole, pyridine, pyrazine, pyridazine, pyrazole, imidazole, pyrimidine, oxazole, and indole.

8. The method according to claim 1, wherein for the compound of Formula (I) or a salt thereof,
R³ is unsubstituted or is substituted with one R⁷ group.

9. The method according to claim 1, wherein for the compound of Formula (I) or a salt thereof,
each R⁷ is independently selected from OH, CN, NH$_2$, SO$_3$H, thioxo, halo, C$_{1-4}$alkyl, C$_{1-4}$alkyl-OH, O—C$_{1-4}$alkyl, C$_{1-4}$alkyl-halo, (CH$_2$)$_{0-1}$COOH, (CH$_2$)$_{0-1}$C(O)OR⁸, (CH$_2$)$_{0-1}$NH(CH$_2$)$_{0-2}$R⁸, (CH$_2$)$_{0-1}$NHC(O)(CH$_2$)$_{0-2}$R⁸, (CH$_2$)$_{0-1}$C(O)NH(CH$_2$)$_{0-2}$R⁸, —(CH$_2$)$_{0-2}$S(O)$_{0-2}$ R⁸, —(CH$_2$)$_{0-1}$N(R⁶)SO$_2$R⁸, (CH$_2$)$_{0-1}$C(O)N(R⁶)S(O)$_2$R⁸, and (CH$_2$)$_{0-1}$heterocyclyl.

10. The method according to claim 1, wherein for the compound of Formula (I) or a salt thereof,
Y is phenyl-Z¹—, optionally substituted with halo or C$_{1-6}$alkyl.

11. The method according to claim 1, wherein for the compound of Formula (I) or a salt thereof,
each R² is the group Y—X—, Z within the definition of X is a direct bond and Z¹ within the definition of Y is a group of the formula —(CH$_2$)$_p$—C(R$^{6a}$)$_2$—(CH$_2$)$_q$—.

* * * * *